US 11,104,892 B2

(12) United States Patent
Collier et al.

(10) Patent No.: US 11,104,892 B2
(45) Date of Patent: Aug. 31, 2021

(54) COMPOSITIONS AND METHODS FOR TREATMENT OF PAIN

(71) Applicants: President and Fellows of Harvard College, Cambridge, MA (US); Massachusetts Institute of Technology, Cambridge, MA (US)

(72) Inventors: R. John Collier, Wellesley, MA (US); Isaac Chiu, Brookline, MA (US); Bradley L. Pentelute, Cambridge, MA (US)

(73) Assignees: President and Fellows of Harvard College, Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/884,893

(22) Filed: May 27, 2020

(65) Prior Publication Data
US 2020/0362325 A1 Nov. 19, 2020

Related U.S. Application Data

(62) Division of application No. 15/755,543, filed as application No. PCT/US2016/049099 on Aug. 26, 2016, now Pat. No. 10,704,035.

(60) Provisional application No. 62/210,610, filed on Aug. 27, 2015.

(51) Int. Cl.
*C12N 9/52* (2006.01)
*C07K 14/33* (2006.01)
*C12N 9/50* (2006.01)
*C07K 14/32* (2006.01)
*A61P 29/00* (2006.01)

(52) U.S. Cl.
CPC ............ *C12N 9/52* (2013.01); *A61P 29/00* (2018.01); *C07K 14/32* (2013.01); *C07K 14/33* (2013.01); *C12N 9/50* (2013.01); *C07K 2319/01* (2013.01); *C07K 2319/55* (2013.01)

(58) Field of Classification Search
CPC ...... A61K 2039/55522; A61K 39/0011; A61K 39/07; A61K 45/06
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,223,409 A | 6/1993 | Ladner et al. | |
| 5,354,556 A | 10/1994 | Sparks et al. | |
| 5,591,767 A | 1/1997 | Mohr et al. | |
| 5,639,476 A | 6/1997 | Oshlack et al. | |
| 5,674,533 A | 10/1997 | Santos et al. | |
| 5,733,566 A | 3/1998 | Lewis | |
| 5,908,626 A | 6/1999 | Chang et al. | |
| 6,365,185 B1 | 4/2002 | Ritschel et al. | |
| 9,079,952 B2 | 7/2015 | Collier et al. | |
| 9,234,011 B2 | 1/2016 | Rummel | |
| 9,243,301 B2 | 1/2016 | Foster et al. | |
| 10,704,035 B2 | 7/2020 | Collier et al. | |
| 2003/0049264 A1 | 3/2003 | Foster et al. | |
| 2003/0104578 A1 | 6/2003 | Ballance | |
| 2003/0202989 A1 | 10/2003 | Collier et al. | |
| 2005/0143560 A1 | 6/2005 | McIntosh et al. | |
| 2005/0214903 A1 | 9/2005 | Olivera et al. | |
| 2007/0166332 A1 | 7/2007 | Steward et al. | |
| 2009/0004224 A1 | 1/2009 | Steward et al. | |
| 2012/0087969 A1 | 4/2012 | Favreau et al. | |
| 2012/0220539 A1 | 8/2012 | McIntosh et al. | |
| 2012/0277166 A1 | 11/2012 | Lewis et al. | |
| 2013/0336974 A1 | 12/2013 | Collier et al. | |
| 2014/0056870 A1 | 2/2014 | James et al. | |
| 2014/0147429 A1 | 5/2014 | Chaddock et al. | |
| 2014/0378654 A1 | 12/2014 | Leppla et al. | |
| 2015/0044210 A1 | 2/2015 | Mechaly et al. | |
| 2015/0267186 A1 | 9/2015 | Collier et al. | |

(Continued)

FOREIGN PATENT DOCUMENTS

| | | |
|---|---|---|
| JP | 2014-516526 A | 7/2014 |
| JP | 2015-509501 A | 3/2015 |
| WO | WO-92/06204 A1 | 4/1992 |

(Continued)

OTHER PUBLICATIONS

Ahmed, S. et al., Identification of residues surrounding the active site of type A botulinum neurotoxin important for substrate recognition and catalytic activity, Protein J, 27(3):151-62 (2008).

(Continued)

*Primary Examiner* — Padmavathi Baskar
(74) *Attorney, Agent, or Firm* — Choate, Hall & Stewart LLP; Brenda Herschbach Jarrell; Stephanie L. Schonewald

(57) ABSTRACT

Embodied herein are engineered fusion proteins that bind and target nociceptor neurons, compositions comprising these engineered fusion proteins, and methods for treatment of pain using these engineered fusion proteins or compositions containing the engineered fusion proteins. The engineered fusion proteins contain domains derived from protein toxins such as the anthrax toxin, clostridial botulinum family of toxins, disulphide-containing toxins, and AB component type toxins.

24 Claims, 10 Drawing Sheets

Specification includes a Sequence Listing.

(56) References Cited

U.S. PATENT DOCUMENTS

| | | | |
|---|---|---|---|
| 2018/0244731 A1 | 8/2018 | Collier et al. | |
| 2018/0251740 A1 | 9/2018 | Collier et al. | |

FOREIGN PATENT DOCUMENTS

| | | |
|---|---|---|
| WO | WO01/14570 A1 | 3/2001 |
| WO | WO-06/096515 A2 | 9/2006 |
| WO | WO-2007/106115 A1 | 9/2007 |
| WO | WO-08/008803 A2 | 1/2008 |
| WO | WO-08/008805 A2 | 1/2008 |
| WO | WO-2012/096926 A2 | 7/2012 |
| WO | WO-2012/156743 A1 | 11/2012 |
| WO | WO-2013/126690 A1 | 8/2013 |
| WO | WO-2013/177231 A1 | 11/2013 |
| WO | WO-2014/088928 A1 | 6/2014 |
| WO | WO-2015/166242 A1 | 11/2015 |
| WO | WO-2017/035507 A1 | 3/2017 |
| WO | WO-2017/035508 A1 | 3/2017 |

OTHER PUBLICATIONS

Alewood, P. et al., Marine Toxins as Sources of Drug Leads, Australian Journal of Chemistry, 56:769-774 (2003).
Ashkenazi, A. and Chamow, S., Immunoadhesins as research tools and therapeutic agents, Curr Opin Immunol, 9(2):195-200 (1997).
Bergeron, Z.L. and Bingham, J.P., Scorpion toxins specific for potassium (K+) channels: a historical overview of peptide bioengineering, Toxins (Basel), 4(11):1082-119 (2012).
Bitter, G.A. et al., Expression and secretion vectors for yeast, Methods Enzymol, 153:516-44 (1987).
Blanke, S.R. et al., Fused polycationic peptide mediates delivery of diphtheria toxin A chain to the cytosol in the presence of anthrax protective antigen, Proc Natl Acad Sci USA, 93(16):8437-42 (1996).
Blaustein, R. et al., The N-terminal half of the heavy chain of botulinum type A neurotoxin forms channels in planar phospholipid bilayers, FEBS Letts, 226(1):115-120 (1987).
Bowie, J. and Sauer, R., Identifying determinants of folding and activity for a protein of unknown structure, Proc Natl Acad Sci USA, 86(7):2152-6 (1989).
Carlsson, J. et al., Protein thiolation and reversible protein-protein conjugation. N-Succinimidyl 3-(2-pyridyldithio)propionate, a new heterobifunctional reagent, Biochem J, 173(3):723-37 (1978).
Chen, S. and Barbieri, J., Engineering botulinum neurotoxin to extend therapeutic intervention, Proc Natl Acad Sci USA, 106(23):9180-4 (2009).
Chothia, C. and Lesk, A., Canonical structures for the hypervariable regions of immunoglobulins, J Mol Biol, 196(4):901-17 (1987).
Chung, H. et al., Probing the role of loop 2 in Ras function with unnatural amino acids, Proc Natl Acad Sci USA, 90(21):10145-9 (1993).
Chung, H. et al., Probing the structure and mechanism of Ras protein with an expanded genetic code, Science, 259(5096):806-9 (1993).
Craik, D.J. et al., The cystine knot motif in toxins and implications for drug design, Toxicon, 39(1):43-60 (2001).
Cunningham,B. and Wells, J. High-resolution epitope mapping of hGH-receptor interactions by alanine-scanning mutagenesis, Science, 244(4908):1081-5 (1989).
Daly, N.L. and Craik, D.J., Bioactive cystine knot proteins, Curr Opin Chem Biol, 15(3):362-8 (2011).
De Vos, A. et al., Human growth hormone and extracellular domain of its receptor: crystal structure of the complex, Science, 255(5042):306-12 (1992).
De Wildt, R. et al., Characterization of human variable domain antibody fragments against the U1 RNA-associated A protein, selected from a synthetic and patient-derived combinatorial V gene library, Eur J Immunol, 26(3):629-39 (1996).
Derbyshire, K. et al., A simple and efficient procedure for saturation mutagenesis using mixed oligodeoxynucleotides, Gene, 1986;46(2-3):145-52.
Dineen, S. et al., The Adnectin CT-322 is a novel VEGF receptor 2 inhibitor that decreases tumor burden in an orthotopic mouse model of pancreatic cancer, BMC Cancer, 8(352): 10 pages (2008).
Duesbery, N.S. et al., Proteolytic inactivation of MAP-kinase-kinase by anthrax lethal factor, Science, 280(5364):734-7 (1998).
Duggan, M. et al., Inhibition of release of neurotransmitters from rat dorsal root ganglia by a novel conjugate of a Clostridium botulinum toxin A endopeptidase fragment and Erythrina cristagalli lectin, J Biol Chem, 277(38):34846-52 (2002).
Ellman, J. et al., Biosynthetic method for introducing unnatural amino acids site-specifically into proteins, Methods Enzymol, 202:301-36 (1991).
Franklin, S.E., and Mayfield, S.P., Recent developments in the production of human therapeutic proteins in eukaryotic algae, Expert Opin Biol Ther, 5(2):225-35 (2005).
Fuhrmann, M., Production of antigens in Chlamydomonas reinhardtii: green microalgae as a novel source of recombinant proteins, Methods Mol Med, 94:191-5 (2004).
Gohar, Ofra, Contribution of Ion Channels in Pain Sensation, Modulator, 19:9-13 (2005).
Green, N. et al., Immunogenic structure of the influenza virus hemagglutinin, Cell, 28(3):477-87 (1982).
Griesbeck, C. et al,. Chlamydomonas reinhardtii: a protein expression system for pharmaceutical and biotechnological proteins, Mol Biotechnol, 34(2):213-23 (2006).
Grishin, E., Polypeptide neurotoxins from spider venoms, Eur J Biochem, 264(2):276-80 (1999).
Herzig, V. et al., ArachnoServer 2.0, an updated online resource for spider toxin sequences and structures, Nucleic Acids Res, 39(Database issue):D653-7 (2010).
Holliger, P. Expression of antibody fragments in Pichia pastoris, Methods Mol Biol, 178:349-57 (2002).
Inouye, S. and Inouye, M., Up-promoter mutations in the Ipp gene of *Escherichia coli*, Nucleic Acids Res, 13(9):3101-10 (1985).
International Search Report for PCT/US16/49099, 6 pages (dated Jan. 19, 2017).
International Search Report for PCT/US16/49106, 6 pages (dated Dec. 28, 2016).
Kielian, M. et al., Mechanisms of mutations inhibiting fusion and infection by Semliki Forest virus, J Cell Biol, 134(4):863-72 (1996).
Kihara, A. and Pastan, I., Analysis of sequences required for the cytotoxic action of a chimeric toxin composed of Pseudomonas exotoxin and transforming growth factor alpha, Bioconjug Chem, 5(6):532-8 (1994).
King, G.F. et al., A rational nomenclature for naming peptide toxins from spiders and other venomous animals, Toxicon, 52(2):264-76 (2008).
King, G.F., Venoms as a platform for human drugs: translating toxins into therapeutics, Expert Opin Biol Ther, 11(11):1469-84 (2011).
Kohler, G., Immunoglobulin chain loss in hybridoma lines, Proc Natl Acad Sci USA, 77(4):2197-9 (1980).
Koide, H. et al., Receptor-binding affinities of human epidermal growth factor variants having unnatural amino acid residues in position 23, Biochemistry, 33(23):7470-6 (1994).
Kolmar, H., Alternative binding proteins: biological activity and therapeutic potential of cystine-knot miniproteins, FEBS J, 275(11):2684-90 (2008).
Leipold, E. et al., Molecular interaction of delta-conotoxins with voltage-gated sodium channels, FEBS Lett, 579(18):3881-4 (2005).
Leppla, S.H., Anthrax toxin edema factor: a bacterial adenylate cyclase that increases cyclic AMP concentrations of eukaryotic cells, Proc Natl Acad Sci USA, 79(10):3162-6 (1982).
Levy, I. and Shoseyov, O., Cellulose-binding domains: biotechnological applications, Biotechnol Adv, 20(3-4):191-213 (2002).
Li, R.A. and Tomaselli, G.F., Using the deadly mu-conotoxins as probes of voltage-gated sodium channels, Toxicon, 44(2):117-22 (2004).
Liang, S. et al., An overview of peptide toxins from the venom of the Chinese bird spider *Selenocosmia huwena* Wang [=*Ornithoctonus huwena* (Wang)], Toxicon, 43(5):575-85 (2004).

(56) References Cited

OTHER PUBLICATIONS

Liao, X. et al., Delivery of antibody mimics into mammalian cells via anthrax toxin protective antigen, Chembiochem, 15(16):2458-66 (2014).

Logan, J. and Shenk, T., Adenovirus tripartite leader sequence enhances translation of mRNAs late after infection, Proc Natl Acad Sci USA, 81(12):3655-9 (1984).

London, E., Diptheria toxin: membrane interaction and membrane translocation, Biochem. Byophys. Acta., 1112:25-51 (1992).

Lowman, H. et al., Selecting high-affinity binding proteins by monovalent phage display, Biochemistry, 30(45):10832-8 (1991).

Manuell, A.L. et al., Robust expression of a bioactive mammalian protein in Chlamydomonas chloroplast, Plant Biotechnol J, 5(3):402-12 (2007).

Mayfield, S.P. and Franklin, S.E., Expression of human antibodies in eukaryotic micro-algae, Vaccine, 23(15):1828-32 (2005).

Means, G.E. and Feeney, R.E., Chemical modifications of proteins: history and applications, Bioconjug Chem, 1(1):2-12 (1990).

Mechaly, A. et al., Changing the receptor specificity of anthrax toxin, MBio., 3(3) e00088-12 (2012).

Milne, J. et al., Protective antigen-binding domain of anthrax lethal factor mediates translocation of a heterologous protein fused to its amino- or carboxy-terminus, Mol Microbiol, 15(4):661-6 (1995).

Milne, J.C. et al., Anthrax protective antigen forms oligomers during intoxication of mammalian cells, J Biol Chem, 269(32):20607-12 (1994).

Murata, M. et al., pH-dependent membrane fusion and vesiculation of phospholipid large unilamellar vesicles induced by amphiphilic anionic and cationic peptides, Biochemistry, 31(7):1986-92 (1992).

Ner, S. et al., A simple and efficient procedure for generating random point mutations and for codon replacements using mixed oligodeoxynucleotides, DNA, 7(2):127-34 (1988).

Nielsen, K.J. et al., Structure-activity relationships of omega-conotoxins at N-type voltage-sensitive calcium channels, J Mol Recognit, 13(2):55-70 (2000).

No Author Listed, GeneCards ANTXR2, Anthrax Toxin Receptor 2 [online], 13 pages, Apr. 27, 2015, <http://web.archive.org/web/20150427232202/http://www.genecards.org/cgi-bin/carddisp.pl?gene=ANTXR2>, [retrieved Oct. 18, 2016].

Nord, K. et al., Binding proteins selected from combinatorial libraries of an alpha-helical bacterial receptor domain, Nat Biotechnol, 15(8):772-7 (1997).

O'Keefe, D. et al., pH-dependent insertion of proteins into membranes: B-chain mutation of diphtheria toxin that inhibits membrane translocation, Glu-349-Lys, Proc Natl Acad Sci USA, 89(13):6202-6 (1992).

Palker, T.J., et al., A conserved region at the COOH terminus of human immunodeficiency virus gp120 envelope protein contains an immunodominant epitope, Proc Natl Acad Sci USA, 84(8):2479-83 (1987).

Picard-Maureau, M. et al., Foamy virus envelope glycoprotein-mediated entry involves a pH-dependent fusion process, J Virol, 77(8):4722-30 (2003).

Plank, C. et al., The influence of endosome-disruptive peptides on gene transfer using synthetic virus-like gene transfer systems, J. Biol. Chem., 269(17):12918-24 (1994).

Pohler, J. et al., Gene structure and extracellular secretion of Neisseria gonorrhoeae IgA protease, Nature, 325(6103):458-62 (1987).

Prior, T. et al., Translocation mediated by domain II of Pseudomonas exotoxin A: transport of barnase into the cytosol. Biochemistry, 31(14):3555-9 (1992).

Proudfoot, N.J., Transcriptional interference and termination between duplicated alpha-globin gene constructs suggests a novel mechanism for gene regulation, Nature, 322(6079):562-5 (1986).

Reidhaar-Olson, J. and Sauer, R., Combinatorial cassette mutagenesis as a probe of the informational content of protein sequences, Science, 241(4861):53-7 (1988).

Robertson, S. et al., A General and Efficient Route for Chemical Aminoacylation of Transfer RNAs, J. Am. Chem. Soc., 113:2722 (1991).

Rosovitz, M.J. et al., Alanine-scanning mutations in domain 4 of anthrax toxin protective antigen reveal residues important for binding to the cellular receptor and to a neutralizing monoclonal antibody, J Biol Chem, 278(33):30936-44 (2003).

Rummel, et al., The $H_{cc}$-domain of botulinum neurotoxins A and B exhibits a singular ganglioside binding site displaying serotype specific carbohydrate interaction, Molecular Microbiol, 51(3):631-634 (2004).

Ruther, U. and Muller-Hill, B., Easy identification of cDNA clones, EMBO J, 2(10):1791-4 (1983).

Saez, N.J. et al,. Spider-venom peptides as therapeutics, Toxins (Basel), 2(12):2851-71 (2010).

Seth, S, et al., Activation of fusion by the SER virus F protein: a low-pH-dependent paramyxovirus entry process, J Virol, 77(11):6520-7 (2003).

Shone, C. et al., A 50-kDa fragment from teh $NH_2$-terminus of the heavy subunit of *Clostridium botulinum* type A neurotoxin forms channels in lipid vesicles, Eur. J. Biochem, 167(1):175-180 (1987).

Silverman et al., Multivalent avimer proteins evolved by exon shuffling of a family of human receptor domains, Nat Biotechnol, 23:1556-1661 (2005).

Silverman, J. et al., Mutational analysis of the helical hairpin region of diphtheria toxin transmembrane domain, J Biol Chem, 269(36):22524-32 (1994).

Skerra, A., Alternative binding proteins: anticalins—harnessing the structural plasticity of the lipocalin ligand pocket to engineer novel binding activities, FEBS J, 275(11):2677-83 (2008).

Smith, L.J. et al., Human interleukin 4. The solution structure of a four-helix bundle protein, J Mol Biol, 224(4):899-904 (1992).

Szeto, T.H., et al., Isolation and pharmacological characterisation of delta-atracotoxin-Hv1b, a vertebrate-selective sodium channel toxin, FEBS Lett, 470(3):293-9 (2000).

Turcatti, G. et al., Probing the structure and function of the tachykinin neurokinin-2 receptor through biosynthetic incorporation of fluorescent amino acids at specific sites, J Biol Chem, 271(33):19991-8 (1996).

Turton et al., Botulinum and Tetanus Neurotoxins: structure, function and therapeutic utility, Trends Biochem. Sci., 27(11 ): 552-558 (2002).

Van Heeke, G., and Schuster, S., Expression of human asparagine synthetase in *Escherichia coli*, J Biol Chem, 264(10):5503-9 (1989).

Vetter, I. et al., Venomics: a new paradigm for natural products-based drug discovery, Amino Acids, 40(1):15-28 (2011).

Vitale, G. et al., Anthrax lethal factor cleaves the N-terminus of MAPKKs and induces tyrosine/threonine phosphorylation of MAPKs in cultured macrophages, Biochem Biophys Res Commun, 248(3):706-11 (1998).

Vodkin, M.H. and Leppla, S.H., Cloning of the protective antigen gene of Bacillus anthracis, Cell, 34(2):693-7 (1983).

Wagner, E. et al., Influenza virus hemagglutinin HA-2 N-terminal fusoqenic peptides augment gene transfer by transferrin-polylysine-DNA complexes: toward a synthetic virus-like gene-transfer vehicle, Proc Natl Acad Sci USA, 89(17):7934-8 (1992).

Ward, E. et al., Binding activities of a repertoire of single immunoglobulin variable domains secreted from *Escherichia coli*, Nature, 341(6242):544-6 (1989).

Wlodawer, A. et al., Crystal structure of human recombinant interleukin-4 at 2.25 A resolution, FEBS Lett, 309(1):59-64 (1992).

Written Opinion for PCT/US16/49099, 13 pages (dated Jan. 19, 2017).

Written Opinion for PCT/US16/49106, 11 pages (dated Dec. 28, 2016).

Wynn, R. and Richards, F., Unnatural amino acid packing mutants of *Escherichia coli* thioredoxin produced by combined mutagenesis/chemical modification techniques, Protein Sci, 2(3):395-403 (1993).

Yao, Y. et al., Membrane fusion activity of vesicular stomatitis virus glycoprotein G is induced by low pH but not by heat or denaturant, Virology, 310(2):319-32 (2003).

(56) References Cited

OTHER PUBLICATIONS

Yeh, P. et al., Design of yeast-secreted albumin derivatives for human therapy: biological and antiviral properties of a serum albumin-CD4 genetic conjugate, PNAS, 89(5):1904-1908 (1992).

Zahnd, et al., Selection and characterization of Her2 binding-designed ankyrin repeat proteins, J Biol Chem., 281:35167-75 (2006).

Zhu, S. et al., Evolutionary origin of inhibitor cystine knot peptides, FASEB J, 17(12):1765-7 (2003).

Zornetta, I. et al., The first non Clostridial botulinum-like toxin cleaves VAMP within the juxtamembrane domain, Scientific Reports, 6(30257), 7 pages (2016).

PA + LFn-DTA

- ● 0 nM PA
- ○ 10 nM PA

X-axis: Concentration of LFn-DTA (M), ranging from $10^{-14}$ to $10^{-7}$
Y-axis: Protein synthesis (%), ranging from 0 to 200

Figure 7A

BoTX Light chain — BoTX Translocation Domain — Linker peptide — PA-derived (A with -S-S- disulfide; B = L = Linker; C = PA-derived)

A: Botulinum Neurotoxin Light chain and part of the heavy chain required for pore-formation and translocation
1. BoNT/A (a.a. 1-872)
2. BoNT/A (a.a. 1-842)
3. BoNT/B (a.a. 1-863)

B: Linker

C:
1. PA domain 4 (PA a.a. 596-735)
2. PA mutant for furin cleavage site

Figure 7B

TTX Light chain — TTX Translocation Domain — Linker peptide — PA-derived (A with -S-S- disulfide; B = L = Linker; C = PA-derived)

A: Tetanus Toxin (TeNT) light chain (or chain A) and part of the Heavy chain (or chain B) responsible for translocation

B: Linker

C:
1. PA domain 4 (PA a.a. 596-735)
2. PA mutant for furin cleavage site

[Native PA]

A. PA (Native form, non-mutated)

B

[BoTX Light Chain / catalytic domain]

B: Botulinum Toxin Light chains
1. BoNT/A LC (a.a. 1-448)
2. BoNT/B LC (a.a. 1-441)
3. BoNT/C LC (a.a. 1-449)
4. BoNT/D LC (a.a. 1-442)
5. BoNT/E LC (a.a. 1-422)
6. BoNT/F LC (a.a. 1-436)
7. BoNT/G LC (a.a. 1-442)

C

[Linker peptide]

C: Linker

D

[PA-binding domain]

D:
1. LFn
2. EFn

[Native PA]

A. PA (Native form, non-mutated)

B

[TTX Light Chain / catalytic domain/ other toxins]

B: Other Toxin enzyme domains
1. Tetanus Toxin Catalytic Domain
2. Diptheria Toxin-A and B
3. Exotoxin A and B
4. Shiga toxin A and B
5. Cholera Toxin A and B
6. Ricin toxin

C

[Linker peptide]

C: Linker

D

[PA-binding domain]

D:
1. LFn
2. EFn

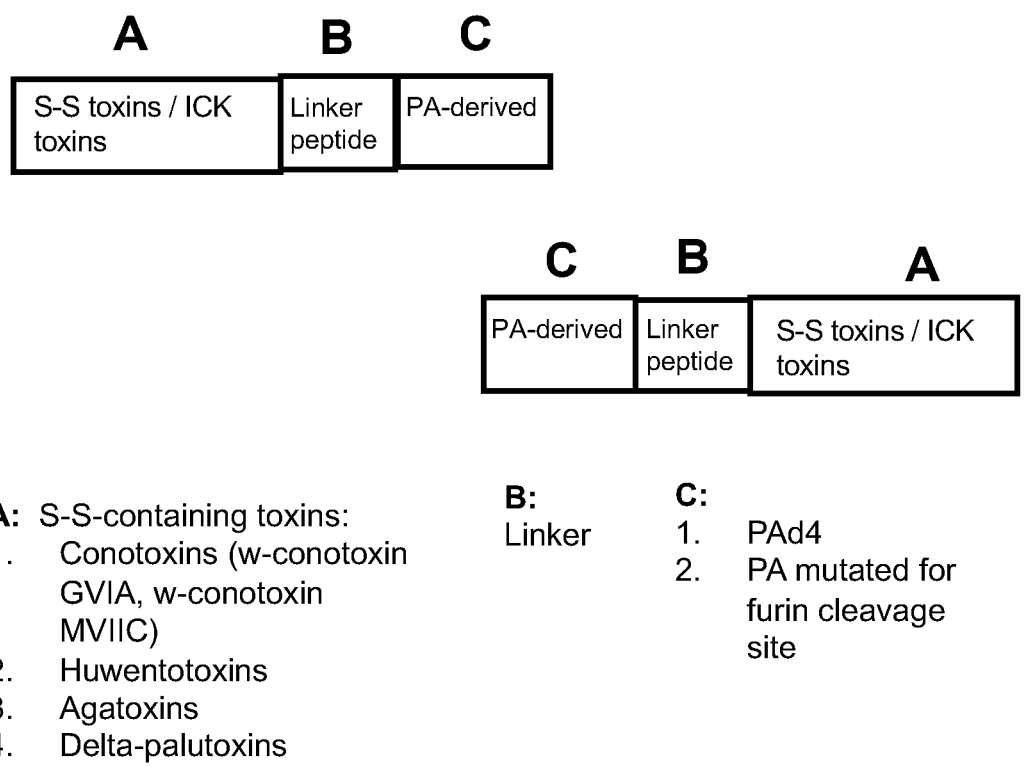

SEQUENCE LISTING

<160> NUMBER OF SEQ ID NOS: 148

<210> SEQ ID NO 1
<211> LENGTH: 764
<212> TYPE: PRT
<213> ORGANISM: Bacillus anthracis

<400> SEQUENCE: 1

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys

-continued

```
                20                  25                  30
Gln Glu Asn Arg Leu Leu Asn Glu Ser Glu Ser Ser Gln Gly Leu
             35                  40                  45
Leu Gly Tyr Tyr Phe Ser Asp Leu Asn Phe Gln Ala Pro Met Val Val
 50                  55                  60
Thr Ser Ser Thr Thr Gly Asp Leu Ser Ile Pro Ser Ser Glu Leu Glu
 65                  70                  75                  80
Asn Ile Pro Ser Glu Asn Gln Tyr Phe Gln Ser Ala Ile Trp Ser Gly
                 85                  90                  95
Phe Ile Lys Val Lys Lys Ser Asp Glu Tyr Thr Phe Ala Thr Ser Ala
                100                 105                 110
Asp Asn His Val Thr Met Trp Val Asp Gln Glu Val Ile Asn Lys
             115                 120                 125
Ala Ser Asn Ser Asn Lys Ile Arg Leu Glu Lys Gly Arg Leu Tyr Gln
 130                 135                 140
Ile Lys Ile Gln Tyr Gln Arg Glu Asn Pro Thr Glu Lys Gly Leu Asp
 145                 150                 155                 160
Phe Lys Leu Tyr Trp Thr Asp Ser Gln Asn Lys Lys Glu Val Ile Ser
                165                 170                 175
Ser Asp Asn Leu Gln Leu Pro Glu Leu Lys Gln Lys Ser Ser Asn Ser
            180                 185                 190
Arg Lys Lys Arg Ser Thr Ser Ala Gly Pro Thr Val Pro Asp Arg Asp
            195                 200                 205
Asn Asp Gly Ile Pro Asp Ser Leu Glu Val Glu Gly Tyr Thr Val Asp
 210                 215                 220
Val Lys Asn Lys Arg Thr Phe Leu Ser Pro Trp Ile Ser Asn Ile His
 225                 230                 235                 240
Glu Lys Lys Gly Leu Thr Lys Tyr Lys Ser Ser Pro Glu Lys Trp Ser
                245                 250                 255
Thr Ala Ser Asp Pro Tyr Ser Asp Phe Glu Lys Val Thr Gly Arg Ile
                260                 265                 270
Asp Lys Asn Val Ser Pro Glu Ala Arg His Pro Leu Val Ala Ala Tyr
            275                 280                 285
Pro Ile Val His Val Asp Met Glu Asn Ile Ile Leu Ser Lys Asn Glu
            290                 295                 300
Asp Gln Ser Thr Gln Asn Thr Asp Ser Gln Thr Arg Thr Ile Ser Lys
 305                 310                 315                 320
Asn Thr Ser Thr Ser Arg Thr His Thr Ser Glu Val His Gly Asn Ala
                325                 330                 335
Glu Val His Ala Ser Phe Phe Asp Ile Gly Gly Ser Val Ser Ala Gly
            340                 345                 350
Phe Ser Asn Ser Asn Ser Ser Thr Val Ala Ile Asp His Ser Leu Ser
            355                 360                 365
Leu Ala Gly Glu Arg Thr Trp Ala Glu Thr Met Gly Leu Asn Thr Ala
            370                 375                 380
Asp Thr Ala Arg Leu Asn Ala Asn Ile Arg Tyr Val Asn Thr Gly Thr
 385                 390                 395                 400
Ala Pro Ile Tyr Asn Val Leu Pro Thr Thr Ser Leu Val Leu Gly Lys
                405                 410                 415
Asn Gln Thr Leu Ala Thr Ile Lys Ala Lys Glu Asn Gln Leu Ser Gln
            420                 425                 430
Ile Leu Ala Pro Asn Asn Tyr Tyr Pro Ser Lys Asn Leu Ala Pro Ile
            435                 440                 445
```

```
Ala Leu Asn Ala Gln Asp Asp Phe Ser Ser Thr Pro Ile Thr Met Asn
    450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
        515                 520                 525

Leu Val Glu Arg Arg Ile Ala Ala Val Asn Pro Ser Asp Pro Leu Glu
    530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
            580                 585                 590

Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
    690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
        755                 760

<210> SEQ ID NO 2
<211> LENGTH: 560
<212> TYPE: PRT
<213> ORGANISM: Corynebacterium diphtheriae

<400> SEQUENCE: 2

Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
```

-continued

```
                50                  55                  60
Ser Gly Thr Gln Gly Asn Tyr Asp Asp Asp Trp Lys Gly Phe Tyr Ser
 65                  70                  75                  80

Thr Asp Asn Lys Tyr Asp Ala Ala Gly Tyr Ser Val Asp Asn Glu Asn
                 85                  90                  95

Pro Leu Ser Gly Lys Ala Gly Val Val Lys Val Thr Tyr Pro Gly
                100                 105                 110

Leu Thr Lys Val Leu Ala Leu Lys Val Asp Asn Ala Glu Thr Ile Lys
                115                 120                 125

Lys Glu Leu Gly Leu Ser Leu Thr Glu Pro Leu Met Glu Gln Val Gly
                130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Val Glu Tyr Ile Asn
                165                 170                 175

Asn Trp Glu Gln Ala Lys Ala Leu Ser Val Glu Leu Glu Ile Asn Phe
                180                 185                 190

Glu Thr Arg Gly Lys Arg Gly Gln Asp Ala Met Tyr Glu Tyr Met Ala
                195                 200                 205

Gln Ala Cys Ala Gly Asn Arg Val Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Lys Ala Lys Gln Tyr Leu
                260                 265                 270

Glu Glu Phe His Gln Thr Ala Leu Glu His Pro Glu Leu Ser Glu Leu
                275                 280                 285

Lys Thr Val Thr Gly Thr Asn Pro Val Phe Ala Gly Ala Asn Tyr Ala
                290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
                340                 345                 350

Ile Val Ala Gln Ser Ile Ala Leu Ser Ser Leu Met Val Ala Gln Ala
                355                 360                 365

Ile Pro Leu Val Gly Glu Leu Val Asp Ile Gly Phe Ala Ala Tyr Asn
370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr Gln Pro Phe Leu His
                405                 410                 415

Asp Gly Tyr Ala Val Ser Trp Asn Thr Val Glu Asp Ser Ile Ile Arg
                420                 425                 430

Thr Gly Phe Gln Gly Glu Ser Gly His Asp Ile Lys Ile Thr Ala Glu
                435                 440                 445

Asn Thr Pro Leu Pro Ile Ala Gly Val Leu Leu Pro Thr Ile Pro Gly
                450                 455                 460

Lys Leu Asp Val Asn Lys Ser Lys Thr His Ile Ser Val Asn Gly Arg
465                 470                 475                 480
```

```
Lys Ile Arg Met Arg Cys Arg Ala Ile Asp Gly Asp Val Thr Phe Cys
            485                 490                 495

Arg Pro Lys Ser Pro Val Tyr Val Gly Asn Gly Val His Ala Asn Leu
            500                 505                 510

His Val Ala Phe His Arg Ser Ser Glu Lys Ile His Ser Asn Glu
            515                 520                 525

Ile Ser Ser Asp Ser Ile Gly Val Leu Gly Tyr Gln Lys Thr Val Asp
            530                 535                 540

His Thr Lys Val Asn Ser Lys Leu Ser Leu Phe Phe Glu Ile Lys Ser
545                 550                 555                 560

<210> SEQ ID NO 3
<211> LENGTH: 638
<212> TYPE: PRT
<213> ORGANISM: Pseudomonas aeruginosa

<400> SEQUENCE: 3

Met His Leu Thr Pro His Trp Ile Pro Leu Val Ala Ser Leu Gly Leu
1               5                   10                  15

Leu Ala Gly Gly Ser Phe Ala Ser Ala Ala Glu Glu Ala Phe Asp Leu
            20                  25                  30

Trp Asn Glu Cys Ala Lys Ala Cys Val Leu Asp Leu Lys Asp Gly Val
            35                  40                  45

Arg Ser Ser Arg Met Ser Val Asp Pro Ala Ile Ala Asp Thr Asn Gly
        50                  55                  60

Gln Gly Val Leu His Tyr Ser Met Val Leu Gly Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
            115                 120                 125

Pro Ile Gly His Glu Lys Pro Ser Asn Ile Lys Val Phe Ile His Glu
            130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190

Ser His Ala Gly Val Ser Val Val Met Ala Gln Ala Gln Pro Arg Arg
            195                 200                 205

Glu Lys Arg Trp Ser Glu Trp Ala Ser Gly Lys Val Leu Cys Leu Leu
            210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255

Pro Ala Lys His Asp Leu Asp Ile Lys Pro Thr Val Ile Ser His Arg
            260                 265                 270

Leu His Phe Pro Glu Gly Gly Ser Leu Ala Ala Leu Thr Ala His Gln
            275                 280                 285

Ala Cys His Leu Pro Leu Glu Thr Phe Thr Arg His Arg Gln Pro Arg
```

```
            290                 295                 300
Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
            325                 330                 335

Ile Arg Asn Ala Leu Ala Ser Pro Gly Ser Gly Asp Leu Gly Glu
            340                 345                 350

Ala Ile Arg Glu Gln Pro Glu Gln Ala Arg Leu Ala Leu Thr Leu Ala
            355                 360                 365

Ala Ala Glu Ser Glu Arg Phe Val Arg Gln Gly Thr Gly Asn Asp Glu
            370                 375                 380

Ala Gly Ala Ala Ser Ala Asp Val Val Ser Leu Thr Cys Pro Val Ala
385                 390                 395                 400

Ala Gly Glu Cys Ala Gly Pro Ala Asp Ser Gly Asp Ala Leu Leu Glu
                405                 410                 415

Arg Asn Tyr Pro Thr Gly Ala Glu Phe Leu Gly Asp Gly Asp Ile
            420                 425                 430

Ser Phe Ser Thr Arg Gly Thr Gln Asn Trp Thr Val Glu Arg Leu Leu
            435                 440                 445

Gln Ala His Arg Gln Leu Glu Glu Arg Gly Tyr Val Phe Val Gly Tyr
            450                 455                 460

His Gly Thr Phe Leu Glu Ala Ala Gln Ser Ile Val Phe Gly Val
465                 470                 475                 480

Arg Ala Arg Ser Gln Asp Leu Asp Ala Ile Trp Arg Gly Phe Tyr Ile
                485                 490                 495

Ala Gly Asp Pro Ala Leu Ala Tyr Gly Tyr Ala Gln Asp Gln Glu Pro
            500                 505                 510

Asp Ala Arg Gly Arg Ile Arg Asn Gly Ala Leu Leu Arg Val Tyr Val
            515                 520                 525

Pro Arg Ser Ser Leu Pro Gly Phe Tyr Arg Thr Gly Leu Thr Leu Ala
            530                 535                 540

Ala Pro Glu Ala Ala Gly Glu Val Glu Arg Leu Ile Gly His Pro Leu
545                 550                 555                 560

Pro Leu Arg Leu Asp Ala Ile Thr Gly Pro Glu Glu Gly Gly Arg
            565                 570                 575

Leu Glu Thr Ile Leu Gly Trp Pro Leu Ala Glu Arg Thr Val Val Ile
            580                 585                 590

Pro Ser Ala Ile Pro Thr Asp Pro Arg Asn Val Gly Gly Asp Leu Asp
            595                 600                 605

Pro Ser Ser Ile Pro Asp Lys Glu Gln Ala Ile Ser Ala Leu Pro Asp
            610                 615                 620

Tyr Ala Ser Gln Pro Gly Lys Pro Pro Arg Glu Asp Leu Lys
625                 630                 635

<210> SEQ ID NO 4
<211> LENGTH: 1296
<212> TYPE: PRT
<213> ORGANISM: Clostridium botulinum

<400> SEQUENCE: 4

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30
```

```
Val Lys Ala Phe Lys Ile His Asn Lys Ile Trp Val Ile Pro Glu Arg
         35                  40                  45

Asp Thr Phe Thr Asn Pro Glu Glu Gly Asp Leu Asn Pro Pro Glu
 50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
             85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
            130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Glu
            210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
            290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
```

```
            450                 455                 460
Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
            595                 600                 605

Gln Leu Val Tyr Asp Phe Thr Asp Glu Thr Ser Glu Val Ser Thr Thr
610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
            850                 855                 860

Thr Phe Thr Glu Tyr Ile Lys Asn Ile Ile Asn Thr Ser Ile Leu Asn
865                 870                 875                 880
```

-continued

```
Leu Arg Tyr Glu Ser Asn His Leu Ile Asp Leu Ser Arg Tyr Ala Ser
            885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
            915                 920                 925

Lys Asn Ala Ile Val Tyr Asn Ser Met Tyr Glu Asn Phe Ser Thr Ser
        930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
            965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
            995                 1000                1005

Asp Tyr Ile Asn Arg Trp Ile Phe Val Thr Ile Thr Asn Asn Arg
            1010                1015                1020

Leu Asn Asn Ser Lys Ile Tyr Ile Asn Gly Arg Leu Ile Asp Gln
            1025                1030                1035

Lys Pro Ile Ser Asn Leu Gly Asn Ile His Ala Ser Asn Asn Ile
            1040                1045                1050

Met Phe Lys Leu Asp Gly Cys Arg Asp Thr His Arg Tyr Ile Trp
            1055                1060                1065

Ile Lys Tyr Phe Asn Leu Phe Asp Lys Glu Leu Asn Glu Lys Glu
            1070                1075                1080

Ile Lys Asp Leu Tyr Asp Asn Gln Ser Asn Ser Gly Ile Leu Lys
            1085                1090                1095

Asp Phe Trp Gly Asp Tyr Leu Gln Tyr Asp Lys Pro Tyr Tyr Met
            1100                1105                1110

Leu Asn Leu Tyr Asp Pro Asn Lys Tyr Val Asp Val Asn Asn Val
            1115                1120                1125

Gly Ile Arg Gly Tyr Met Tyr Leu Lys Gly Pro Arg Gly Ser Val
            1130                1135                1140

Met Thr Thr Asn Ile Tyr Leu Asn Ser Ser Leu Tyr Arg Gly Thr
            1145                1150                1155

Lys Phe Ile Ile Lys Lys Tyr Ala Ser Gly Asn Lys Asp Asn Ile
            1160                1165                1170

Val Arg Asn Asn Asp Arg Val Tyr Ile Asn Val Val Val Lys Asn
            1175                1180                1185

Lys Glu Tyr Arg Leu Ala Thr Asn Ala Ser Gln Ala Gly Val Glu
            1190                1195                1200

Lys Ile Leu Ser Ala Leu Glu Ile Pro Asp Val Gly Asn Leu Ser
            1205                1210                1215

Gln Val Val Val Met Lys Ser Lys Asn Asp Gln Gly Ile Thr Asn
            1220                1225                1230

Lys Cys Lys Met Asn Leu Gln Asp Asn Asn Gly Asn Asp Ile Gly
            1235                1240                1245

Phe Ile Gly Phe His Gln Phe Asn Asn Ile Ala Lys Leu Val Ala
            1250                1255                1260

Ser Asn Trp Tyr Asn Arg Gln Ile Glu Arg Ser Ser Arg Thr Leu
            1265                1270                1275
```

Gly Cys Ser Trp Glu Phe Ile Pro Val Asp Asp Gly Trp Gly Glu
        1280                1285                1290

Arg Pro Leu
        1295

<210> SEQ ID NO 5
<211> LENGTH: 1315
<212> TYPE: PRT
<213> ORGANISM: Clostridium tetani

<400> SEQUENCE: 5

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Ser Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Ile Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

```
Ser Ile Met Tyr Gly Phe Thr Glu Ile Glu Leu Gly Lys Lys Phe Asn
        355                 360                 365
Ile Lys Thr Arg Leu Ser Tyr Phe Ser Met Asn His Asp Pro Val Lys
        370                 375                 380
Ile Pro Asn Leu Leu Asp Asp Thr Ile Tyr Asn Asp Thr Glu Gly Phe
385                 390                 395                 400
Asn Ile Glu Ser Lys Asp Leu Lys Ser Glu Tyr Lys Gly Gln Asn Met
                405                 410                 415
Arg Val Asn Thr Asn Ala Phe Arg Asn Val Asp Gly Ser Gly Leu Val
                420                 425                 430
Ser Lys Leu Ile Gly Leu Cys Lys Lys Ile Ile Pro Pro Thr Asn Ile
            435                 440                 445
Arg Glu Asn Leu Tyr Asn Arg Thr Ala Ser Leu Thr Asp Leu Gly Gly
    450                 455                 460
Glu Leu Cys Ile Lys Ile Lys Asn Glu Asp Leu Thr Phe Ile Ala Glu
465                 470                 475                 480
Lys Asn Ser Phe Ser Glu Pro Phe Gln Asp Glu Thr Val Ser Tyr
                485                 490                 495
Asn Thr Lys Asn Lys Pro Leu Asn Phe Asn Tyr Ser Leu Asp Lys Ile
            500                 505                 510
Ile Leu Asp Tyr Asn Leu Gln Ser Lys Ile Thr Leu Pro Asn Asp Arg
        515                 520                 525
Thr Thr Pro Val Thr Lys Gly Ile Pro Tyr Ala Pro Lys Tyr Lys Ser
    530                 535                 540
Asn Ala Ala Ser Thr Ile Glu Ile His Asn Ile Asp Asp Asn Thr Ile
545                 550                 555                 560
Tyr Gln Tyr Leu Tyr Ala Gln Lys Ser Pro Thr Thr Leu Gln Arg Ile
                565                 570                 575
Thr Met Thr Asn Ser Val Asp Asp Ala Leu Ile Asn Ser Thr Lys Ile
            580                 585                 590
Tyr Ser Tyr Phe Pro Ser Val Ile Ser Lys Val Asn Gln Gly Ala Gln
        595                 600                 605
Gly Ile Leu Phe Leu Gln Trp Val Arg Asp Ile Asp Asp Phe Thr
    610                 615                 620
Asn Glu Ser Ser Gln Lys Thr Thr Ile Asp Lys Ile Ser Asp Val Ser
625                 630                 635                 640
Thr Ile Val Pro Tyr Ile Gly Pro Ala Leu Asn Ile Val Lys Gln Gly
                645                 650                 655
Tyr Glu Gly Asn Phe Ile Gly Ala Leu Glu Thr Thr Gly Val Val Leu
            660                 665                 670
Leu Leu Glu Tyr Ile Pro Glu Ile Thr Leu Pro Val Ile Ala Ala Leu
        675                 680                 685
Ser Ile Ala Glu Ser Ser Thr Gln Lys Glu Lys Ile Ile Lys Thr Ile
    690                 695                 700
Asp Asn Phe Leu Glu Lys Arg Tyr Glu Lys Trp Ile Glu Val Tyr Lys
705                 710                 715                 720
Leu Ile Lys Ala Lys Trp Leu Gly Thr Val Asn Thr Gln Phe Gln Lys
                725                 730                 735
Arg Ser Tyr Gln Met Tyr Arg Ser Leu Glu Tyr Gln Val Asp Ala Ile
            740                 745                 750
Lys Lys Ile Ile Asp Tyr Glu Tyr Lys Ile Tyr Ser Gly Pro Asp Lys
        755                 760                 765
```

```
Glu Gln Ile Ala Asp Glu Ile Asn Asn Leu Lys Asn Lys Leu Glu Glu
    770                 775                 780
Lys Ala Asn Lys Ala Met Ile Asn Ile Asn Ile Phe Met Arg Glu Ser
785                 790                 795                 800
Ser Arg Ser Phe Leu Val Asn Gln Met Ile Asn Glu Ala Lys Lys Gln
                805                 810                 815
Leu Leu Glu Phe Asp Thr Gln Ser Lys Asn Ile Leu Met Gln Tyr Ile
                820                 825                 830
Lys Ala Asn Ser Lys Phe Ile Gly Ile Thr Glu Leu Lys Lys Leu Glu
                835                 840                 845
Ser Lys Ile Asn Lys Val Phe Ser Thr Pro Ile Pro Phe Ser Tyr Ser
    850                 855                 860
Lys Asn Leu Asp Cys Trp Val Asp Asn Glu Glu Asp Ile Asp Val Ile
865                 870                 875                 880
Leu Lys Lys Ser Thr Ile Leu Asn Leu Asp Ile Asn Asn Asp Ile Ile
                885                 890                 895
Ser Asp Ile Ser Gly Phe Asn Ser Ser Val Ile Thr Tyr Pro Asp Ala
                900                 905                 910
Gln Leu Val Pro Gly Ile Asn Gly Lys Ala Ile His Leu Val Asn Asn
                915                 920                 925
Glu Ser Ser Glu Val Ile Val His Lys Ala Met Asp Ile Glu Tyr Asn
    930                 935                 940
Asp Met Phe Asn Asn Phe Thr Val Ser Phe Trp Leu Arg Val Pro Lys
945                 950                 955                 960
Val Ser Ala Ser His Leu Glu Gln Tyr Gly Thr Asn Glu Tyr Ser Ile
                965                 970                 975
Ile Ser Ser Met Lys Lys Tyr Ser Leu Ser Ile Gly Ser Gly Trp Ser
                980                 985                 990
Val Ser Leu Lys Gly Asn Asn Leu Ile Trp Thr Leu Lys Asp Ser Ala
            995                 1000                1005
Gly Glu Val Arg Gln Ile Thr Phe Ser Asp Leu Ser Asp Lys Phe
    1010                1015                1020
Asn Ala Tyr Leu Ala Asn Lys Trp Val Phe Ile Thr Ile Thr Asn
    1025                1030                1035
Asp Arg Leu Ser Ser Ala Asn Leu Tyr Ile Asn Gly Val Leu Met
    1040                1045                1050
Lys Asn Ala Glu Ile Thr Gly Leu Gly Ala Ile Arg Glu Asp Asn
    1055                1060                1065
Asn Ile Thr Leu Lys Leu Asp Arg Cys Asn Asn Asn Asn Gln Tyr
    1070                1075                1080
Val Ser Ile Asp Lys Phe Arg Ile Phe Cys Lys Ala Leu Asn Pro
    1085                1090                1095
Lys Glu Ile Glu Lys Leu Tyr Thr Ser Tyr Leu Ser Ile Thr Phe
    1100                1105                1110
Leu Arg Asp Phe Trp Gly Asn Pro Leu Arg Tyr Asp Thr Glu Tyr
    1115                1120                1125
Tyr Leu Ile Pro Val Ala Ser Ser Ser Lys Asp Val Gln Leu Lys
    1130                1135                1140
Asn Ile Thr Asp Tyr Met Tyr Leu Thr Asn Ala Pro Ser Tyr Thr
    1145                1150                1155
Asn Gly Lys Leu Asn Ile Tyr Tyr Arg Arg Leu Tyr Ser Gly Leu
    1160                1165                1170
Lys Phe Ile Ile Lys Arg Tyr Thr Pro Asn Asn Glu Ile Asp Ser
```

-continued

```
                1175                1180                1185

Phe Val Lys Ser Gly Asp Phe Ile Lys Leu Tyr Val Ser Tyr Asn
                    1190                1195                1200

Asn Asn Glu His Ile Val Gly Tyr Pro Lys Asp Gly Asn Ala Phe
                    1205                1210                1215

Asn Asn Leu Asp Arg Ile Leu Arg Val Gly Tyr Asn Ala Pro Gly
                    1220                1225                1230

Ile Pro Leu Tyr Lys Lys Met Glu Ala Val Lys Leu Arg Asp Leu
                    1235                1240                1245

Lys Thr Tyr Ser Val Gln Leu Lys Leu Tyr Asp Asp Lys Asn Ala
                    1250                1255                1260

Ser Leu Gly Leu Val Gly Ile Arg Asn Gly Gln Ile Gly Asn Asp
                    1265                1270                1275

Pro Asn Arg Asp Ile Leu Ile Ala Ser Asn Trp Tyr Phe Asn His
                    1280                1285                1290

Leu Lys Asp Lys Thr Leu Thr Cys Asp Trp Tyr Phe Val Pro Thr
                    1295                1300                1305

Asp Glu Gly Trp Thr Asn Asp
                    1310                1315

<210> SEQ ID NO 6
<211> LENGTH: 800
<212> TYPE: PRT
<213> ORGANISM: Bacillus anthracis

<400> SEQUENCE: 6

Met Thr Arg Asn Lys Phe Ile Pro Asn Lys Phe Ser Ile Ile Ser Phe
1               5                   10                  15

Ser Val Leu Leu Phe Ala Ile Ser Ser Ser Gln Ala Ile Glu Val Asn
                20                  25                  30

Ala Met Asn Glu His Tyr Thr Glu Ser Asp Ile Lys Arg Asn His Lys
            35                  40                  45

Thr Glu Lys Asn Lys Thr Glu Lys Glu Lys Phe Lys Asp Ser Ile Asn
        50                  55                  60

Asn Leu Val Lys Thr Glu Phe Thr Asn Glu Thr Leu Asp Lys Ile Gln
65                  70                  75                  80

Gln Thr Gln Asp Leu Leu Lys Lys Ile Pro Lys Asp Val Leu Glu Ile
                85                  90                  95

Tyr Ser Glu Leu Gly Gly Glu Ile Tyr Phe Thr Asp Ile Asp Leu Val
                100                 105                 110

Glu His Lys Glu Leu Gln Asp Leu Ser Glu Glu Lys Asn Ser Met
            115                 120                 125

Asn Ser Arg Gly Glu Lys Val Pro Phe Ala Ser Arg Phe Val Phe Glu
        130                 135                 140

Lys Lys Arg Glu Thr Pro Lys Leu Ile Ile Asn Ile Lys Asp Tyr Ala
145                 150                 155                 160

Ile Asn Ser Glu Gln Ser Lys Glu Val Tyr Tyr Glu Ile Gly Lys Gly
                165                 170                 175

Ile Ser Leu Asp Ile Ile Ser Lys Asp Lys Ser Leu Asp Pro Glu Phe
            180                 185                 190

Leu Asn Leu Ile Lys Ser Leu Ser Asp Asp Ser Asp Ser Ser Asp Leu
            195                 200                 205

Leu Phe Ser Gln Lys Phe Lys Glu Lys Leu Glu Leu Asn Asn Lys Ser
        210                 215                 220
```

Ile Asp Ile Asn Phe Ile Lys Glu Asn Leu Thr Glu Phe Gln His Ala
225                 230                 235                 240

Phe Ser Leu Ala Phe Ser Tyr Tyr Phe Ala Pro Asp His Arg Thr Val
            245                 250                 255

Leu Glu Leu Tyr Ala Pro Asp Met Phe Glu Tyr Met Asn Lys Leu Glu
        260                 265                 270

Lys Gly Gly Phe Glu Lys Ile Ser Glu Ser Leu Lys Lys Glu Gly Val
    275                 280                 285

Glu Lys Asp Arg Ile Asp Val Leu Lys Gly Glu Lys Ala Leu Lys Ala
290                 295                 300

Ser Gly Leu Val Pro Glu His Ala Asp Ala Phe Lys Lys Ile Ala Arg
305                 310                 315                 320

Glu Leu Asn Thr Tyr Ile Leu Phe Arg Pro Val Asn Lys Leu Ala Thr
                325                 330                 335

Asn Leu Ile Lys Ser Gly Val Ala Thr Lys Gly Leu Asn Val His Gly
            340                 345                 350

Lys Ser Ser Asp Trp Gly Pro Val Ala Gly Tyr Ile Pro Phe Asp Gln
    355                 360                 365

Asp Leu Ser Lys Lys His Gly Gln Gln Leu Ala Val Glu Lys Gly Asn
370                 375                 380

Leu Glu Asn Lys Lys Ser Ile Thr Glu His Glu Gly Glu Ile Gly Lys
385                 390                 395                 400

Ile Pro Leu Lys Leu Asp His Leu Arg Ile Glu Glu Leu Lys Glu Asn
                405                 410                 415

Gly Ile Ile Leu Lys Gly Lys Lys Glu Ile Asp Asn Gly Lys Lys Tyr
            420                 425                 430

Tyr Leu Leu Glu Ser Asn Asn Gln Val Tyr Glu Phe Arg Ile Ser Asp
    435                 440                 445

Glu Asn Asn Glu Val Gln Tyr Lys Thr Lys Glu Gly Lys Ile Thr Val
450                 455                 460

Leu Gly Glu Lys Phe Asn Trp Arg Asn Ile Glu Val Met Ala Lys Asn
465                 470                 475                 480

Val Glu Gly Val Leu Lys Pro Leu Thr Ala Asp Tyr Asp Leu Phe Ala
                485                 490                 495

Leu Ala Pro Ser Leu Thr Glu Ile Lys Lys Gln Ile Pro Gln Lys Glu
            500                 505                 510

Trp Asp Lys Val Val Asn Thr Pro Asn Ser Leu Glu Lys Gln Lys Gly
    515                 520                 525

Val Thr Asn Leu Leu Ile Lys Tyr Gly Ile Glu Arg Lys Pro Asp Ser
530                 535                 540

Thr Lys Gly Thr Leu Ser Asn Trp Gln Lys Gln Met Leu Asp Arg Leu
545                 550                 555                 560

Asn Glu Ala Val Lys Tyr Thr Gly Tyr Thr Gly Gly Asp Val Val Asn
                565                 570                 575

His Gly Thr Glu Gln Asp Asn Glu Glu Phe Pro Glu Lys Asp Asn Glu
            580                 585                 590

Ile Phe Ile Ile Asn Pro Glu Gly Glu Phe Ile Leu Thr Lys Asn Trp
    595                 600                 605

Glu Met Thr Gly Arg Phe Ile Glu Lys Asn Ile Thr Gly Lys Asp Tyr
610                 615                 620

Leu Tyr Tyr Phe Asn Arg Ser Tyr Asn Lys Ile Ala Pro Gly Asn Lys
625                 630                 635                 640

Ala Tyr Ile Glu Trp Thr Asp Pro Ile Thr Lys Ala Lys Ile Asn Thr

```
                    645                 650                 655
Ile Pro Thr Ser Ala Glu Phe Ile Lys Asn Leu Ser Ser Ile Arg Arg
                660                 665                 670

Ser Ser Asn Val Gly Val Tyr Lys Asp Ser Gly Asp Lys Asp Glu Phe
            675                 680                 685

Ala Lys Lys Glu Ser Val Lys Lys Ile Ala Gly Tyr Leu Ser Asp Tyr
        690                 695                 700

Tyr Asn Ser Ala Asn His Ile Phe Ser Gln Glu Lys Lys Arg Lys Ile
705                 710                 715                 720

Ser Ile Phe Arg Gly Ile Gln Ala Tyr Asn Glu Ile Glu Asn Val Leu
                725                 730                 735

Lys Ser Lys Gln Ile Ala Pro Glu Tyr Lys Asn Tyr Phe Gln Tyr Leu
            740                 745                 750

Lys Glu Arg Ile Thr Asn Gln Val Gln Leu Leu Leu Thr His Gln Lys
        755                 760                 765

Ser Asn Ile Glu Phe Lys Leu Leu Tyr Lys Gln Leu Asn Phe Thr Glu
770                 775                 780

Asn Glu Thr Asp Asn Phe Glu Val Phe Gln Lys Ile Ile Asp Glu Lys
785                 790                 795                 800

<210> SEQ ID NO 7
<211> LENGTH: 809
<212> TYPE: PRT
<213> ORGANISM: Bacillus anthracis

<400> SEQUENCE: 7

Met Asn Ile Lys Lys Glu Phe Ile Lys Val Ile Ser Met Ser Cys Leu
1               5                   10                  15

Val Thr Ala Ile Thr Leu Ser Gly Pro Val Phe Ile Pro Leu Val Gln
            20                  25                  30

Gly Ala Gly Gly His Gly Asp Val Gly Met His Val Lys Glu Lys Glu
        35                  40                  45

Lys Asn Lys Asp Glu Asn Lys Arg Lys Asp Glu Glu Arg Asn Lys Thr
    50                  55                  60

Gln Glu Glu His Leu Lys Glu Ile Met Lys His Ile Val Lys Ile Glu
65                  70                  75                  80

Val Lys Gly Glu Glu Ala Val Lys Lys Glu Ala Ala Glu Lys Leu Leu
                85                  90                  95

Glu Lys Val Pro Ser Asp Val Leu Glu Met Tyr Lys Ala Ile Gly Gly
            100                 105                 110

Lys Ile Tyr Ile Val Asp Gly Asp Ile Thr Lys His Ile Ser Leu Glu
        115                 120                 125

Ala Leu Ser Glu Asp Lys Lys Lys Ile Lys Asp Ile Tyr Gly Lys Asp
    130                 135                 140

Ala Leu Leu His Glu His Tyr Val Tyr Ala Lys Glu Gly Tyr Glu Pro
145                 150                 155                 160

Val Leu Val Ile Gln Ser Ser Glu Asp Tyr Val Glu Asn Thr Glu Lys
                165                 170                 175

Ala Leu Asn Val Tyr Tyr Glu Ile Gly Lys Ile Leu Ser Arg Asp Ile
            180                 185                 190

Leu Ser Lys Ile Asn Gln Pro Tyr Gln Lys Phe Leu Asp Val Leu Asn
        195                 200                 205

Thr Ile Lys Asn Ala Ser Asp Ser Asp Gly Gln Asp Leu Leu Phe Thr
    210                 215                 220
```

```
Asn Gln Leu Lys Glu His Pro Thr Asp Phe Ser Val Glu Phe Leu Glu
225                 230                 235                 240

Gln Asn Ser Asn Glu Val Gln Glu Val Phe Ala Lys Ala Phe Ala Tyr
            245                 250                 255

Tyr Ile Glu Pro Gln His Arg Asp Val Leu Gln Leu Tyr Ala Pro Glu
        260                 265                 270

Ala Phe Asn Tyr Met Asp Lys Phe Asn Glu Gln Glu Ile Asn Leu Ser
        275                 280                 285

Leu Glu Glu Leu Lys Asp Gln Arg Met Leu Ser Arg Tyr Glu Lys Trp
        290                 295                 300

Glu Lys Ile Lys Gln His Tyr Gln His Trp Ser Asp Ser Leu Ser Glu
305                 310                 315                 320

Glu Gly Arg Gly Leu Leu Lys Lys Leu Gln Ile Pro Ile Glu Pro Lys
            325                 330                 335

Lys Asp Asp Ile Ile His Ser Leu Ser Gln Glu Lys Glu Leu Leu
            340                 345                 350

Lys Arg Ile Gln Ile Asp Ser Ser Asp Phe Leu Ser Thr Glu Glu Lys
            355                 360                 365

Glu Phe Leu Lys Lys Leu Gln Ile Asp Ile Arg Asp Ser Leu Ser Glu
        370                 375                 380

Glu Glu Lys Glu Leu Leu Asn Arg Ile Gln Val Asp Ser Ser Asn Pro
385                 390                 395                 400

Leu Ser Glu Lys Glu Lys Glu Phe Leu Lys Lys Leu Lys Leu Asp Ile
                405                 410                 415

Gln Pro Tyr Asp Ile Asn Gln Arg Leu Gln Asp Thr Gly Gly Leu Ile
            420                 425                 430

Asp Ser Pro Ser Ile Asn Leu Asp Val Arg Lys Gln Tyr Lys Arg Asp
        435                 440                 445

Ile Gln Asn Ile Asp Ala Leu Leu His Gln Ser Ile Gly Ser Thr Leu
450                 455                 460

Tyr Asn Lys Ile Tyr Leu Tyr Glu Asn Met Asn Ile Asn Asn Leu Thr
465                 470                 475                 480

Ala Thr Leu Gly Ala Asp Leu Val Asp Ser Thr Asp Asn Thr Lys Ile
            485                 490                 495

Asn Arg Gly Ile Phe Asn Glu Phe Lys Lys Asn Phe Lys Tyr Ser Ile
            500                 505                 510

Ser Ser Asn Tyr Met Ile Val Asp Ile Asn Glu Arg Pro Ala Leu Asp
        515                 520                 525

Asn Glu Arg Leu Lys Trp Arg Ile Gln Leu Ser Pro Asp Thr Arg Ala
530                 535                 540

Gly Tyr Leu Glu Asn Gly Lys Leu Ile Leu Gln Arg Asn Ile Gly Leu
545                 550                 555                 560

Glu Ile Lys Asp Val Gln Ile Ile Lys Gln Ser Glu Lys Glu Tyr Ile
            565                 570                 575

Arg Ile Asp Ala Lys Val Val Pro Lys Ser Lys Ile Asp Thr Lys Ile
            580                 585                 590

Gln Glu Ala Gln Leu Asn Ile Asn Gln Glu Trp Asn Lys Ala Leu Gly
        595                 600                 605

Leu Pro Lys Tyr Thr Lys Leu Ile Thr Phe Asn Val His Asn Arg Tyr
        610                 615                 620

Ala Ser Asn Ile Val Glu Ser Ala Tyr Leu Ile Leu Asn Glu Trp Lys
625                 630                 635                 640

Asn Asn Ile Gln Ser Asp Leu Ile Lys Lys Val Thr Asn Tyr Leu Val
```

```
            645                 650                 655
Asp Gly Asn Gly Arg Phe Val Phe Thr Asp Ile Thr Leu Pro Asn Ile
            660                 665                 670

Ala Glu Gln Tyr Thr His Gln Asp Glu Ile Tyr Glu Gln Val His Ser
            675                 680                 685

Lys Gly Leu Tyr Val Pro Glu Ser Arg Ser Ile Leu Leu His Gly Pro
            690                 695                 700

Ser Lys Gly Val Glu Leu Arg Asn Asp Ser Glu Gly Phe Ile His Glu
705                 710                 715                 720

Phe Gly His Ala Val Asp Asp Tyr Ala Gly Tyr Leu Leu Asp Lys Asn
                    725                 730                 735

Gln Ser Asp Leu Val Thr Asn Ser Lys Lys Phe Ile Asp Ile Phe Lys
            740                 745                 750

Glu Glu Gly Ser Asn Leu Thr Ser Tyr Gly Arg Thr Asn Glu Ala Glu
            755                 760                 765

Phe Phe Ala Glu Ala Phe Arg Leu Met His Ser Thr Asp His Ala Glu
            770                 775                 780

Arg Leu Lys Val Gln Lys Asn Ala Pro Lys Thr Phe Gln Phe Ile Asn
785                 790                 795                 800

Asp Gln Ile Lys Phe Ile Ile Asn Ser
                805

<210> SEQ ID NO 8
<211> LENGTH: 71
<212> TYPE: PRT
<213> ORGANISM: Conus magus

<400> SEQUENCE: 8

Met Lys Leu Thr Cys Val Val Ile Val Ala Val Leu Leu Thr Ala
1               5                   10                  15

Cys Gln Leu Ile Thr Ala Asp Asp Ser Arg Gly Thr Gln Lys His Arg
            20                  25                  30

Ala Leu Arg Ser Thr Thr Lys Leu Ser Met Ser Thr Arg Cys Lys Gly
            35                  40                  45

Lys Gly Ala Lys Cys Ser Arg Leu Met Tyr Asp Cys Cys Thr Gly Ser
        50                  55                  60

Cys Arg Ser Gly Lys Cys Gly
65                  70

<210> SEQ ID NO 9
<211> LENGTH: 34
<212> TYPE: PRT
<213> ORGANISM: Conus geographus

<400> SEQUENCE: 9

Ala Cys Ser Gly Arg Gly Ser Arg Cys Pro Pro Gln Cys Cys Met Gly
1               5                   10                  15

Leu Arg Cys Gly Arg Gly Asn Pro Gln Lys Cys Ile Gly Ala His Glu
            20                  25                  30

Asp Val

<210> SEQ ID NO 10
<211> LENGTH: 31
<212> TYPE: PRT
<213> ORGANISM: Conus eburneus

<400> SEQUENCE: 10
```

```
Leu Asn Lys Arg Cys Ala Gly Ile Gly Ser Phe Cys Gly Leu Pro Gly
1               5                   10                  15

Leu Val Asp Cys Cys Ser Gly Arg Cys Phe Ile Val Cys Leu Pro
            20                  25                  30
```

<210> SEQ ID NO 11
<211> LENGTH: 293
<212> TYPE: PRT
<213> ORGANISM: Shigella dysenteriae

<400> SEQUENCE: 11

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65              70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
                260                 265                 270

Asn Lys Ile Leu Trp Asp Ser Ser Thr Leu Gly Ala Ile Leu Met Arg
            275                 280                 285

Arg Thr Ile Ser Ser
        290
```

<210> SEQ ID NO 12
<211> LENGTH: 69
<212> TYPE: PRT
<213> ORGANISM: Shigella dysenteriae

<400> S

```
Thr Pro Asp Cys Val Thr Gly Lys Val Glu Tyr Thr Lys Tyr Asn Asp
1               5                   10                  15

Asp Asp Thr Phe Thr Val Lys Val Gly Asp Lys Glu Leu Phe Thr Asn
            20                  25                  30

Arg Trp Asn Leu Gln Ser Leu Leu Ser Ala Gln Ile Thr Gly Met
        35                  40                  45

Thr Val Thr Ile Lys Thr Asn Ala Cys His Asn Gly Gly Phe Ser
    50                  55                  60

Glu Val Ile Phe Arg
65
```

<210> SEQ ID NO 13
<211> LENGTH: 613
<212> TYPE: PRT
<213> ORGANISM: Pseudomonas aeruginosa

<400> SEQUENCE: 13

```
Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300
```

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
            325                 330                 335

Arg Leu Ala Leu Thr Leu Ala Ala Glu Ser Glu Arg Phe Val Arg
        340                 345                 350

Gln Gly Thr Gly Asn Asp Glu Ala Gly Ala Asn Ala Asp Val Val
            355                 360                 365

Ser Leu Thr Cys Pro Val Ala Ala Gly Glu Cys Ala Gly Pro Ala Asp
370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
                435                 440                 445

Ser Ile Val Phe Gly Gly Val Arg Ala Arg Ser Gln Asp Leu Asp Ala
450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
            515                 520                 525

Arg Leu Ile Gly His Pro Leu Pro Leu Arg Leu Asp Ala Ile Thr Gly
            530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
                580                 585                 590

Ala Ile Ser Ala Leu Pro Asp Tyr Ala Ser Gln Pro Gly Lys Pro Pro
                595                 600                 605

Arg Glu Asp Leu Lys
        610

<210> SEQ ID NO 14
<211> LENGTH: 194
<212> TYPE: PRT
<213> ORGANISM: Vibrio cholerae

<400> SEQUENCE: 14

Asn Asp Asp Lys Leu Tyr Arg Ala Asp Ser Arg Pro Pro Asp Glu Ile
1               5                   10                  15

Lys Gln Ser Gly Gly Leu Met Pro Arg Gly Gln Ser Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg His Asp Asp Gly Tyr Val Ser Thr Ser Ile 50                  55                  60
Ser Leu Arg Ser Ala His Leu Val Gly Gln Thr Ile Leu Ser Gly His
 65                  70                  75                  80

Ser Thr Tyr Tyr Leu Tyr Val Leu Ala Thr Ala Pro Asn Met Phe Asn
                 85                  90                  95

Val Asn Asp Val Leu Gly Ala Tyr Ser Pro His Pro Asp Glu Gln Glu
            100                 105                 110

Val Ser Ala Leu Gly Gly Ile Pro Tyr Ser Gln Ile Tyr Gly Trp Tyr
        115                 120                 125

Arg Val His Phe Gly Val Leu Asp Glu Gln Leu His Arg Asn Arg Gly
    130                 135                 140

Tyr Arg Asp Arg Tyr Tyr Ser Asn Leu Asp Ile Ala Pro Ala Ala Asp
145                 150                 155                 160

Gly Tyr Gly Leu Ala Gly Phe Pro Pro Glu His Arg Ala Trp Arg Glu
                165                 170                 175

Glu Pro Trp Ile His His Ala Pro Pro Gly Cys Gly Asn Ala Pro Arg
            180                 185                 190

Ser Ser

<210> SEQ ID NO 15
<211> LENGTH: 46
<212> TYPE: PRT
<213> ORGANISM: Vibrio cholerae

<400> SEQUENCE: 15

Met Ser Asn Thr Cys Asp Glu Lys Thr Gln Ser Leu Gly Val Lys Phe
 1               5                  10                  15

Leu Asp Glu Tyr Gln Ser Lys Val Lys Arg Gln Ile Phe Ser Gly Tyr
                20                  25                  30

Gln Ser Asp Ile Asp Thr His Asn Arg Ile Lys Asp Glu Leu
            35                  40                  45

<210> SEQ ID NO 16
<211> LENGTH: 103
<212> TYPE: PRT
<213> ORGANISM: Vibrio cholerae

<400> SEQUENCE: 16

Thr Pro Gln Asn Ile Thr Asp Leu Cys Ala Glu Tyr His Asn Thr Gln
 1               5                  10                  15

Ile Tyr Thr Leu Asn Asp Lys Ile Phe Ser Tyr Thr Glu Ser Leu Ala
                20                  25                  30

Gly Lys Arg Glu Met Ala Ile Ile Thr Phe Lys Asn Gly Ala Ile Phe
            35                  40                  45

Gln Val Glu Val Pro Ser Ser Gln His Ile Asp Ser Gln Lys Lys Ala
        50                  55                  60

Ile Glu Arg Met Lys Asp Thr Leu Arg Ile Ala Tyr Leu Thr Glu Ala
 65                  70                  75                  80

Lys Val Glu Lys Leu Cys Thr Trp Asn Asn Lys Thr Pro His Ala Ile
                85                  90                  95

Ala Ala Ile Ser Met Ala Asn
            100

<210> SEQ ID NO 17
<211> LENGTH: 456
<212> TYPE: PRT
<213> ORGANISM: Clostridium tetani

<400> SEQUENCE: 17

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
            85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
            115                 120                 125

Asp Thr Asn Ser Asn Ser Val Ser Phe Asn Leu Leu Glu Gln Asp Pro
130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
            195                 200                 205

Val Ile Glu Asn Ile Thr Ser Leu Thr Ile Gly Lys Ser Lys Tyr Phe
210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
            275                 280                 285

Asn Asp Leu Tyr Glu Lys Thr Leu Asn Asp Tyr Lys Ala Ile Ala Asn
            290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
            355                 360                 365

Ile Lys Thr Arg Leu Ser Tyr Phe Ser Met Asn His Asp Pro Val Lys
            370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met

```
                405                 410                 415
Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr
    450                 455

<210> SEQ ID NO 18
<211> LENGTH: 267
<212> TYPE: PRT
<213> ORGANISM: Ricinus communis

<400> SEQUENCE: 18

Ile Phe Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
            20                  25                  30

Thr Thr Gly Ala Asp Val Arg His Glu Ile Pro Val Leu Pro Asn Arg
        35                  40                  45

Val Gly Leu Pro Ile Asn Gln Arg Phe Ile Leu Val Glu Leu Ser Asn
    50                  55                  60

His Ala Glu Leu Ser Val Thr Leu Ala Leu Asp Val Thr Asn Ala Tyr
65                  70                  75                  80

Val Val Gly Tyr Arg Ala Gly Asn Ser Ala Tyr Phe Phe His Pro Asp
                85                  90                  95

Asn Gln Glu Asp Ala Glu Ala Ile Thr His Leu Phe Thr Asp Val Gln
            100                 105                 110

Asn Arg Tyr Thr Phe Ala Phe Gly Gly Asn Tyr Asp Arg Leu Glu Gln
        115                 120                 125

Leu Ala Gly Asn Leu Arg Glu Asn Ile Glu Leu Gly Asn Gly Pro Leu
    130                 135                 140

Glu Glu Ala Ile Ser Ala Leu Tyr Tyr Tyr Ser Thr Gly Gly Thr Gln
145                 150                 155                 160

Leu Pro Thr Leu Ala Arg Ser Phe Ile Ile Cys Ile Gln Met Ile Ser
                165                 170                 175

Glu Ala Ala Arg Phe Gln Tyr Ile Glu Gly Glu Met Arg Thr Arg Ile
            180                 185                 190

Arg Tyr Asn Arg Arg Ser Ala Pro Asp Pro Ser Val Ile Thr Leu Glu
        195                 200                 205

Asn Ser Trp Gly Arg Leu Ser Thr Ala Ile Gln Glu Ser Asn Gln Gly
    210                 215                 220

Ala Phe Ala Ser Pro Ile Gln Leu Gln Arg Arg Asn Gly Ser Lys Phe
225                 230                 235                 240

Ser Val Tyr Asp Val Ser Ile Leu Ile Pro Ile Ile Ala Leu Met Val
                245                 250                 255

Tyr Arg Cys Ala Pro Pro Ser Ser Gln Phe
            260                 265

<210> SEQ ID NO 19
<211> LENGTH: 262
<212> TYPE: PRT
<213> ORGANISM: Ricinus communis

<400> SEQUENCE: 19

Ala Asp Val Cys Met Asp Pro Glu Pro Ile Val Arg Ile Val Gly Arg
```

```
            1               5                  10                 15
        Asn Gly Leu Cys Val Asp Val Arg Asp Gly Arg Phe His Asn Gly Asn
                        20                 25                 30

Ala Ile Gln Leu Trp Pro Cys Lys Ser Asn Thr Asp Ala Asn Gln Leu
                        35                 40                 45

Trp Thr Leu Lys Arg Asp Asn Thr Ile Arg Ser Asn Gly Lys Cys Leu
                    50                 55                 60

Thr Thr Tyr Gly Tyr Ser Pro Gly Val Tyr Val Met Ile Tyr Asp Cys
        65                 70                 75                 80

Asn Thr Ala Ala Thr Asp Ala Thr Arg Trp Gln Ile Trp Asp Asn Gly
                        85                 90                 95

Thr Ile Ile Asn Pro Arg Ser Ser Leu Val Leu Ala Ala Thr Ser Gly
                       100                105                110

Asn Ser Gly Thr Thr Leu Thr Val Gln Thr Asn Ile Tyr Ala Val Ser
                       115                120                125

Gln Gly Trp Leu Pro Thr Asn Asn Thr Gln Pro Phe Val Thr Thr Ile
                   130                135                140

Val Gly Leu Tyr Gly Leu Cys Leu Gln Ala Asn Ser Gly Gln Val Trp
        145                150                155                160

Ile Glu Asp Cys Ser Ser Glu Lys Ala Glu Gln Trp Ala Leu Tyr
                       165                170                175

Ala Asp Gly Ser Ile Arg Pro Gln Gln Asn Arg Asp Asn Cys Leu Thr
                       180                185                190

Ser Asp Ser Asn Ile Arg Glu Thr Val Val Lys Ile Leu Ser Cys Gly
                       195                200                205

Pro Ala Ser Ser Gly Gln Arg Trp Met Phe Lys Asn Asp Gly Thr Ile
                   210                215                220

Leu Asn Leu Tyr Ser Gly Leu Val Leu Asp Val Arg Ala Ser Asp Pro
        225                230                235                240

Ser Leu Lys Gln Ile Ile Leu Tyr Pro Leu His Gly Asp Pro Asn Gln
                       245                250                255

Ile Trp Leu Pro Leu Phe
                   260

<210> SEQ ID NO 20
<211> LENGTH: 448
<212> TYPE: PRT
<213> ORGANISM: Clostridium botulinum

<400> SEQUENCE: 20

Met Pro Phe Val Asn Lys Gln Phe Asn Tyr Lys Asp Pro Val Asn Gly
        1               5                  10                 15

Val Asp Ile Ala Tyr Ile Lys Ile Pro Asn Val Gly Gln Met Gln Pro
                        20                 25                 30

Val Lys Ala Phe Lys Ile His Asn Lys Ile Trp Val Ile Pro Glu Arg
                        35                 40                 45

Asp Thr Phe Thr Asn Pro Glu Glu Gly Asp Leu Asn Pro Pro Pro Glu
                    50                 55                 60

Ala Lys Gln Val Pro Val Ser Tyr Tyr Asp Ser Thr Tyr Leu Ser Thr
        65                 70                 75                 80

Asp Asn Glu Lys Asp Asn Tyr Leu Lys Gly Val Thr Lys Leu Phe Glu
                        85                 90                 95

Arg Ile Tyr Ser Thr Asp Leu Gly Arg Met Leu Leu Thr Ser Ile Val
                       100                105                110
```

-continued

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
            165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Glu
            210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
            245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
            290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
            325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

<210> SEQ ID NO 21
<211> LENGTH: 430
<212> TYPE: PRT
<213> ORGANISM: Clostridium botulinum

<400> SEQUENCE: 21

Met Pro Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro
            20                  25                  30

Val Lys Ala Phe Lys Ile His Asn Lys Ile Trp Val Ile Pro Glu Arg
        35                  40                  45

-continued

Asp Thr Phe Thr Asn Pro Glu Glu Gly Asp Leu Asn Pro Pro Glu
 50                  55                  60
Ala Lys Gln Val Pro Val Ser Tyr Tyr Asp Ser Thr Tyr Leu Ser Thr
 65                  70                  75                  80
Asp Asn Glu Lys Asp Asn Tyr Leu Lys Gly Val Thr Lys Leu Phe Glu
                 85                  90                  95
Arg Ile Tyr Ser Thr Asp Leu Gly Arg Met Leu Leu Thr Ser Ile Val
            100                 105                 110
Arg Gly Ile Pro Phe Trp Gly Gly Ser Thr Ile Asp Thr Glu Leu Lys
        115                 120                 125
Val Ile Asp Thr Asn Cys Ile Asn Val Ile Gln Pro Asp Gly Ser Tyr
    130                 135                 140
Arg Ser Glu Glu Leu Asn Leu Val Ile Ile Gly Pro Ser Ala Asp Ile
145                 150                 155                 160
Ile Gln Phe Glu Cys Lys Ser Phe Gly His Glu Val Leu Asn Leu Thr
                165                 170                 175
Arg Asn Gly Tyr Gly Ser Thr Gln Tyr Ile Arg Phe Ser Pro Asp Phe
            180                 185                 190
Thr Phe Gly Phe Glu Glu Ser Leu Glu Val Asp Thr Asn Pro Leu Leu
        195                 200                 205
Gly Ala Gly Lys Phe Ala Thr Asp Pro Ala Val Thr Leu Ala His Glu
    210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                245                 250                 255
Glu Val Ser Phe Glu Glu Leu Arg Thr Phe Gly Gly His Asp Ala Lys
            260                 265                 270
Phe Ile Asp Ser Leu Gln Glu Asn Glu Phe Arg Leu Tyr Tyr Tyr Asn
        275                 280                 285
Lys Phe Lys Asp Ile Ala Ser Thr Leu Asn Lys Ala Lys Ser Ile Val
    290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
            340                 345                 350
Asn Phe Val Lys Phe Phe Lys Val Leu Asn Arg Lys Thr Tyr Leu Asn
        355                 360                 365
Phe Asp Lys Ala Val Phe Lys Ile Asn Ile Val Pro Lys Val Asn Tyr
    370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys
            420                 425                 430

<210> SEQ ID NO 22
<211> LENGTH: 441
<212> TYPE: PRT
<213> ORGANISM: Clostridium botulinum

```
<400> SEQUENCE: 22

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415
```

-continued

Asn Lys Gln Ala Tyr Glu Glu Ile Ser Lys Glu His Leu Ala Val Tyr
            420                 425                 430

Lys Ile Gln Met Cys Lys Ser Val Lys
            435                 440

<210> SEQ ID NO 23
<211> LENGTH: 437
<212> TYPE: PRT
<213> ORGANISM: Clostridium botulinum

<400> SEQUENCE: 23

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu

```
            340                 345                 350
Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Val Lys Ile Lys
        370                 375             380

Asn Leu Leu Asp Asn Glu Ile Tyr Thr Ile Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys
            435

<210> SEQ ID NO 24
<211> LENGTH: 449
<212> TYPE: PRT
<213> ORGANISM: Clostridium botulinum

<400> SEQUENCE: 24

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270
```

Phe Gly Gly Pro Thr Ile Asp Leu Ile Pro Lys Ser Ala Arg Lys Tyr
            275                 280                 285

Phe Glu Glu Lys Ala Leu Asp Tyr Tyr Arg Ser Ile Ala Lys Arg Leu
            290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
            325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
            355                 360                 365

Val Gln Asn Arg Lys Ile Tyr Leu Ser Asn Val Tyr Thr Pro Val Thr
            370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
            405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
            435                 440                 445

Lys

<210> SEQ ID NO 25
<211> LENGTH: 442
<212> TYPE: PRT
<213> ORGANISM: Clostridium botulinum

<400> SEQUENCE: 25

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
            35                  40                  45

Arg Phe Ser Ser Asp Thr Asn Pro Ser Leu Ser Lys Pro Pro Arg Pro
50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
            85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
            115                 120                 125

Phe Thr Arg His Thr Thr Asn Ile Ala Val Glu Lys Phe Glu Asn Gly
            130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
            165                 170                 175

Gln Gln Ser Asn Pro Ser Phe Glu Gly Phe Gly Thr Leu Ser Ile Leu
            180                 185                 190

```
Lys Val Ala Pro Glu Phe Leu Leu Thr Phe Ser Asp Val Thr Ser Asn
            195                 200                 205

Gln Ser Ser Ala Val Leu Gly Lys Ser Ile Phe Cys Met Asp Pro Val
        210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
            245                 250                 255

Phe Phe Ser Gln Asp Gly Pro Asn Val Gln Phe Glu Glu Leu Tyr Thr
        260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
            325                 330                 335

Thr Gly Asn Phe Val Val Asn Ile Asp Lys Phe Asn Ser Leu Tyr Ser
        340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
            405                 410                 415

Arg Asn Pro Ala Leu Gln Lys Leu Ser Ser Glu Ser Val Val Asp Leu
        420                 425                 430

Phe Thr Lys Val Cys Leu Arg Leu Thr Lys
        435                 440

<210> SEQ ID NO 26
<211> LENGTH: 422
<212> TYPE: PRT
<213> ORGANISM: Clostridium botulinum

<400> SEQUENCE: 26

Met Pro Thr Ile Asn Ser Phe Asn Tyr Asn Asp Pro Val Asn Asn Arg
1               5                   10                  15

Thr Ile Leu Tyr Ile Lys Pro Gly Gly Cys Gln Gln Phe Tyr Lys Ser
            20                  25                  30

Phe Asn Ile Met Lys Asn Ile Trp Ile Ile Pro Glu Arg Asn Val Ile
        35                  40                  45

Gly Thr Ile Pro Gln Asp Phe Leu Pro Pro Thr Ser Leu Lys Asn Gly
    50                  55                  60

Asp Ser Ser Tyr Tyr Asp Pro Asn Tyr Leu Gln Ser Asp Gln Glu Lys
65                  70                  75                  80

Asp Lys Phe Leu Lys Ile Val Thr Lys Ile Phe Asn Arg Ile Asn Asp
            85                  90                  95

Asn Leu Ser Gly Arg Ile Leu Leu Glu Glu Leu Ser Lys Ala Asn Pro
        100                 105                 110

Tyr Leu Gly Asn Asp Asn Thr Pro Asp Gly Asp Phe Ile Ile Asn Asp
        115                 120                 125
```

Ala Ser Ala Val Pro Ile Gln Phe Ser Asn Gly Ser Gln Ser Ile Leu
            130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Lys Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg
            420

<210> SEQ ID NO 27
<211> LENGTH: 436
<212> TYPE: PRT
<213> ORGANISM: Clostridium botulinum

<400> SEQUENCE: 27

Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asn Pro Ser Asp Phe Asp Pro Pro Ala Ser
50                  55                  60

Leu Lys Asn Gly Ser Ser Ala Tyr Tyr Asp Pro Asn Tyr Leu Thr Thr

```
                 65                  70                  75                  80
Asp Ala Glu Lys Asp Arg Tyr Leu Lys Thr Thr Ile Lys Leu Phe Lys
                 85                  90                  95
Arg Ile Asn Ser Asn Pro Ala Gly Lys Val Leu Leu Gln Glu Ile Ser
                100                 105                 110
Tyr Ala Lys Pro Tyr Leu Gly Asn Asp His Thr Pro Ile Asp Glu Phe
                115                 120                 125
Ser Pro Val Thr Arg Thr Thr Ser Val Asn Ile Lys Leu Ser Thr Asn
130                 135                 140
Val Glu Ser Ser Met Leu Leu Asn Leu Leu Val Leu Gly Ala Gly Pro
145                 150                 155                 160
Asp Ile Phe Glu Ser Cys Cys Tyr Pro Val Arg Lys Leu Ile Asp Pro
                165                 170                 175
Asp Val Val Tyr Asp Pro Ser Asn Tyr Gly Phe Gly Ser Ile Asn Ile
                180                 185                 190
Val Thr Phe Ser Pro Glu Tyr Glu Tyr Thr Phe Asn Asp Ile Ser Gly
                195                 200                 205
Gly His Asn Ser Ser Thr Glu Ser Phe Ile Ala Asp Pro Ala Ile Ser
                210                 215                 220
Leu Ala His Glu Leu Ile His Ala Leu His Gly Leu Tyr Gly Ala Arg
225                 230                 235                 240
Gly Val Thr Tyr Glu Glu Thr Ile Glu Val Lys Gln Ala Pro Leu Met
                245                 250                 255
Ile Ala Glu Lys Pro Ile Arg Leu Glu Glu Phe Leu Thr Phe Gly Gly
                260                 265                 270
Gln Asp Leu Asn Ile Ile Thr Ser Ala Met Lys Glu Lys Ile Tyr Asn
                275                 280                 285
Asn Leu Leu Ala Asn Tyr Glu Lys Ile Ala Thr Arg Leu Ser Glu Val
                290                 295                 300
Asn Ser Ala Pro Pro Glu Tyr Asp Ile Asn Glu Tyr Lys Asp Tyr Phe
305                 310                 315                 320
Gln Trp Lys Tyr Gly Leu Asp Lys Asn Ala Asp Gly Ser Tyr Thr Val
                325                 330                 335
Asn Glu Asn Lys Phe Asn Glu Ile Tyr Lys Lys Leu Tyr Ser Phe Thr
                340                 345                 350
Glu Ser Asp Leu Ala Asn Lys Phe Lys Val Lys Cys Arg Asn Thr Tyr
                355                 360                 365
Phe Ile Lys Tyr Glu Phe Leu Lys Val Pro Asn Leu Leu Asp Asp Asp
370                 375                 380
Ile Tyr Thr Val Ser Glu Gly Phe Asn Ile Gly Asn Leu Ala Val Asn
385                 390                 395                 400
Asn Arg Gly Gln Ser Ile Lys Leu Asn Pro Lys Ile Ile Asp Ser Ile
                405                 410                 415
Pro Asp Lys Gly Leu Val Glu Lys Ile Val Lys Phe Cys Lys Ser Val
                420                 425                 430
Ile Pro Arg Lys
            435

<210> SEQ ID NO 28
<211> LENGTH: 442
<212> TYPE: PRT
<213> ORGANISM: Clostridium botulinum
<220> FEATURE:
<221> NAME/KEY: MOD_RES
<222> LOCATION: (7)..(7)
```

<223> OTHER INFORMATION: Any amino acid

<400> SEQUENCE: 28

```
Met Pro Val Asn Ile Lys Xaa Phe Asn Tyr Asn Asp Pro Ile Asn Asn
1               5                   10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
                100                 105                 110

Val Asp Ala Ile Pro Tyr Leu Gly Asn Ala Ser Thr Pro Pro Asp Lys
            115                 120                 125

Phe Ala Ala Asn Val Ala Asn Val Ser Ile Asn Lys Lys Ile Ile Gln
130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
                180                 185                 190

Ile Arg Phe Cys Pro Ser Cys Leu Asn Val Phe Asn Asn Val Gln Glu
                195                 200                 205

Asn Lys Asp Thr Ser Ile Phe Ser Arg Arg Ala Tyr Phe Ala Asp Pro
            210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
                260                 265                 270

Gly Gly His Asp Pro Ser Val Ile Ser Pro Ser Thr Asp Met Asn Ile
            275                 280                 285

Tyr Asn Lys Ala Leu Gln Asn Phe Gln Asp Ile Ala Asn Arg Leu Asn
290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
        355                 360                 365

Arg Tyr Ser Tyr Phe Ser Glu Tyr Leu Pro Pro Ile Lys Thr Glu Lys
    370                 375                 380

Leu Leu Asp Asn Thr Ile Tyr Thr Gln Asn Glu Gly Phe Asn Ile Ala
385                 390                 395                 400
```

```
Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
            420                 425                 430

Ile Ala Met Cys Lys Pro Val Met Tyr Lys
            435                 440

<210> SEQ ID NO 29
<211> LENGTH: 872
<212> TYPE: PRT
<213> ORGANISM: Clostridium botulinum

<400> SEQUENCE: 29

Met Pro Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335
```

```
Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
                355                 360                 365

Phe Asp Lys Ala Val Phe Lys Ile Asn Ile Val Pro Lys Val Asn Tyr
                370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Lys Gly Tyr Asn Lys
                435                 440                 445

Ala Leu Asn Asp Leu Cys Ile Lys Val Asn Asn Trp Asp Leu Phe Phe
                450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
                500                 505                 510

Glu Asn Ile Ser Ile Glu Asn Leu Ser Ser Asp Ile Ile Gly Gln Leu
                515                 520                 525

Glu Leu Met Pro Asn Ile Glu Arg Phe Pro Asn Gly Lys Lys Tyr Glu
                530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
                580                 585                 590

Lys Val Asn Lys Ala Thr Glu Ala Ala Met Phe Leu Gly Trp Val Glu
                595                 600                 605

Gln Leu Val Tyr Asp Phe Thr Asp Glu Thr Ser Glu Val Ser Thr Thr
                610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Asn Lys
                675                 680                 685

Val Leu Thr Val Gln Thr Ile Asp Asn Ala Leu Ser Lys Arg Asn Glu
                690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
                740                 745                 750
```

```
Gln Tyr Thr Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn
865                 870

<210> SEQ ID NO 30
<211> LENGTH: 842
<212> TYPE: PRT
<213> ORGANISM: Clostridium botulinum

<400> SEQUENCE: 30

Met Pro Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
                100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255
```

```
Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
            290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
            325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
            450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
            485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
            530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
            565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Met Phe Leu Gly Trp Val Glu
            595                 600                 605

Gln Leu Val Tyr Asp Phe Thr Asp Glu Thr Ser Glu Val Ser Thr Thr
            610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
            645                 650                 655

Ile Phe Ser Gly Ala Val Ile Leu Leu Glu Phe Ile Pro Glu Ile Ala
            660                 665                 670
```

```
Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
        690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Met Lys Glu Ala Leu
        725                 730                 735

Glu Asn Gln Ala Glu Ala Thr Lys Ala Ile Ile Asn Tyr Gln Tyr Asn
                740                 745                 750

Gln Tyr Thr Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
        770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn
        835                 840

<210> SEQ ID NO 31
<211> LENGTH: 863
<212> TYPE: PRT
<213> ORGANISM: Clostridium botulinum

<400> SEQUENCE: 31

Met Pro Val Thr Ile Asn Phe Asn Tyr Asn Asp Pro Ile Asp Asn
1               5                   10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
        50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
                100                 105                 110

Ile Asn Gly Ile Pro Tyr Leu Gly Asp Arg Arg Val Pro Leu Glu Glu
            115                 120                 125

Phe Asn Thr Asn Ile Ala Ser Val Thr Val Asn Lys Leu Ile Ser Asn
        130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
            165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
            195                 200                 205
```

```
Asn Lys Gly Ala Ser Ile Phe Asn Arg Arg Gly Tyr Phe Ser Asp Pro
            210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
                275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
                340                 345                 350

Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Pro Val Lys Ile Lys
370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
            435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
                580                 585                 590

Trp Val Lys Gln Ile Val Asn Asp Phe Val Ile Glu Ala Asn Lys Ser
            595                 600                 605

Asn Thr Met Asp Lys Ile Ala Asp Ile Ser Leu Ile Val Pro Tyr Ile
610                 615                 620
```

-continued

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
            645                 650                 655

Glu Leu Leu Ile Pro Val Val Gly Ala Phe Leu Leu Glu Ser Tyr Ile
        660                 665                 670

Asp Asn Lys Asn Lys Ile Ile Lys Thr Ile Asp Asn Ala Leu Thr Lys
    675                 680                 685

Arg Asn Glu Lys Trp Ser Asp Met Tyr Gly Leu Ile Val Ala Gln Trp
690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
            725                 730                 735

Arg Tyr Asn Ile Tyr Ser Glu Lys Glu Lys Ser Asn Ile Asn Ile Asp
        740                 745                 750

Phe Asn Asp Ile Asn Ser Lys Leu Asn Glu Gly Ile Asn Gln Ala Ile
    755                 760                 765

Asp Asn Ile Asn Asn Phe Ile Asn Gly Cys Ser Val Ser Tyr Leu Met
770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
            805                 810                 815

Leu Ile Gly Ser Ala Glu Tyr Glu Lys Ser Lys Val Asn Lys Tyr Leu
        820                 825                 830

Lys Thr Ile Met Pro Phe Asp Leu Ser Ile Tyr Thr Asn Asp Thr Ile
    835                 840                 845

Leu Ile Glu Met Phe Asn Lys Tyr Asn Ser Glu Ile Leu Asn Asn
850                 855                 860

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Ser Ser Arg
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Ser Ser Ser
1

<210> SEQ ID NO 34
<211> LENGTH: 29
<212> TYPE: PRT
<213> ORGANISM: Bacillus anthracis

```
<400> SEQUENCE: 34

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala
            20                  25

<210> SEQ ID NO 35
<211> LENGTH: 141
<212> TYPE: PRT
<213> ORGANISM: Bacillus anthracis

<400> SEQUENCE: 35

Arg Phe His Tyr Asp Arg Asn Asn Ile Ala Val Gly Ala Asp Glu Ser
1               5                   10                  15

Val Val Lys Glu Ala His Arg Glu Val Ile Asn Ser Ser Thr Glu Gly
            20                  25                  30

Leu Leu Leu Asn Ile Asp Lys Asp Ile Arg Lys Ile Leu Ser Gly Tyr
        35                  40                  45

Ile Val Glu Ile Glu Asp Thr Glu Gly Leu Lys Glu Val Ile Asn Asp
    50                  55                  60

Arg Tyr Asp Met Leu Asn Ile Ser Ser Leu Arg Gln Asp Gly Lys Thr
65                  70                  75                  80

Phe Ile Asp Phe Lys Lys Tyr Asn Asp Lys Leu Pro Leu Tyr Ile Ser
                85                  90                  95

Asn Pro Asn Tyr Lys Val Asn Val Tyr Ala Val Thr Lys Glu Asn Thr
            100                 105                 110

Ile Ile Asn Pro Ser Glu Asn Gly Asp Thr Ser Thr Asn Gly Ile Lys
        115                 120                 125

Lys Ile Leu Ile Phe Ser Lys Lys Gly Tyr Glu Ile Gly
    130                 135                 140

<210> SEQ ID NO 36
<211> LENGTH: 141
<212> TYPE: PRT
<213> ORGANISM: Bacillus anthracis

<400> SEQUENCE: 36

Arg Phe His Tyr Asp Arg Asn Asn Ile Ala Val Gly Ala Asp Glu Ser
1               5                   10                  15

Val Val Lys Glu Ala His Arg Glu Val Ile Asn Ser Ser Thr Glu Gly
            20                  25                  30

Leu Leu Leu Asn Ile Asp Lys Asp Ile Arg Lys Ile Leu Ser Gly Tyr
        35                  40                  45

Ile Val Glu Ile Glu Asp Thr Glu Gly Leu Lys Glu Val Ile Asn Asp
    50                  55                  60

Arg Tyr Asp Met Leu Asn Ile Ser Ser Leu Arg Gln Asp Gly Lys Thr
65                  70                  75                  80

Phe Ile Asp Phe Lys Lys Tyr Asn Asp Lys Leu Pro Leu Tyr Ile Ser
                85                  90                  95

Asn Pro Asn Tyr Lys Val Asn Val Tyr Ala Val Thr Lys Glu Asn Thr
            100                 105                 110

Ile Ile Asn Pro Ser Glu Asn Gly Asp Thr Ser Thr Asn Gly Ile Lys
        115                 120                 125

Lys Ile Leu Ile Phe Ser Lys Lys Gly Tyr Glu Ile Gly
    130                 135                 140
```

```
<210> SEQ ID NO 37
<211> LENGTH: 140
<212> TYPE: PRT
<213> ORGANISM: Bacillus anthracis

<400> SEQUENCE: 37

Phe His Tyr Asp Arg Asn Asn Ile Ala Val Gly Ala Asp Glu Ser Val
1               5                   10                  15

Val Lys Glu Ala His Arg Glu Val Ile Asn Ser Ser Thr Glu Gly Leu
            20                  25                  30

Leu Leu Asn Ile Asp Lys Asp Ile Arg Lys Ile Leu Ser Gly Tyr Ile
        35                  40                  45

Val Glu Ile Glu Asp Thr Glu Gly Leu Lys Glu Val Ile Asn Asp Arg
    50                  55                  60

Tyr Asp Met Leu Asn Ile Ser Ser Leu Arg Gln Asp Gly Lys Thr Phe
65                  70                  75                  80

Ile Asp Phe Lys Lys Tyr Asn Asp Lys Leu Pro Leu Tyr Ile Ser Asn
                85                  90                  95

Pro Asn Tyr Lys Val Asn Val Tyr Ala Val Thr Lys Glu Asn Thr Ile
            100                 105                 110

Ile Asn Pro Ser Glu Asn Gly Asp Thr Ser Thr Asn Gly Ile Lys Lys
        115                 120                 125

Ile Leu Ile Phe Ser Lys Lys Gly Tyr Glu Ile Gly
    130                 135                 140

<210> SEQ ID NO 38
<211> LENGTH: 140
<212> TYPE: PRT
<213> ORGANISM: Bacillus anthracis

<400> SEQUENCE: 38

Phe His Tyr Asp Arg Asn Asn Ile Ala Val Gly Ala Asp Glu Ser Val
1               5                   10                  15

Val Lys Glu Ala His Arg Glu Val Ile Asn Ser Ser Thr Glu Gly Leu
            20                  25                  30

Leu Leu Asn Ile Asp Lys Asp Ile Arg Lys Ile Leu Ser Gly Tyr Ile
        35                  40                  45

Val Glu Ile Glu Asp Thr Glu Gly Leu Lys Glu Val Ile Asn Asp Arg
    50                  55                  60

Tyr Asp Met Leu Asn Ile Ser Ser Leu Arg Gln Asp Gly Lys Thr Phe
65                  70                  75                  80

Ile Asp Phe Lys Lys Tyr Asn Asp Lys Leu Pro Leu Tyr Ile Ser Asn
                85                  90                  95

Pro Asn Tyr Lys Val Asn Val Tyr Ala Val Thr Lys Glu Asn Thr Ile
            100                 105                 110

Ile Asn Pro Ser Glu Asn Gly Asp Thr Ser Thr Asn Gly Ile Lys Lys
        115                 120                 125

Ile Leu Ile Phe Ser Lys Lys Gly Tyr Glu Ile Gly
    130                 135                 140

<210> SEQ ID NO 39
<211> LENGTH: 85
<212> TYPE: PRT
<213> ORGANISM: Bacillus anthracis

<400> SEQUENCE: 39

Gly Leu Lys Glu Val Ile Asn Asp Arg Tyr Asp Met Leu Asn Ile Ser
1               5                   10                  15
```

Ser Leu Arg Gln Asp Gly Lys Thr Phe Ile Asp Phe Lys Lys Tyr Asn
            20                  25                  30

Asp Lys Leu Pro Leu Tyr Ile Ser Asn Pro Asn Tyr Lys Val Asn Val
            35                  40                  45

Tyr Ala Val Thr Lys Glu Asn Thr Ile Ile Asn Pro Ser Glu Asn Gly
 50                  55                  60

Asp Thr Ser Thr Asn Gly Ile Lys Lys Ile Leu Ile Phe Ser Lys Lys
 65                  70                  75                  80

Gly Tyr Glu Ile Gly
            85

<210> SEQ ID NO 40
<211> LENGTH: 85
<212> TYPE: PRT
<213> ORGANISM: Bacillus anthracis

<400> SEQUENCE: 40

Gly Leu Lys Glu Val Ile Asn Asp Arg Tyr Asp Met Leu Asn Ile Ser
1               5                   10                  15

Ser Leu Arg Gln Asp Gly Lys Thr Phe Ile Asp Phe Lys Lys Tyr Asn
            20                  25                  30

Asp Lys Leu Pro Leu Tyr Ile Ser Asn Pro Asn Tyr Lys Val Asn Val
            35                  40                  45

Tyr Ala Val Thr Lys Glu Asn Thr Ile Ile Asn Pro Ser Glu Asn Gly
 50                  55                  60

Asp Thr Ser Thr Asn Gly Ile Lys Lys Ile Leu Ile Phe Ser Lys Lys
 65                  70                  75                  80

Gly Tyr Glu Ile Gly
            85

<210> SEQ ID NO 41
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Phe His Tyr Asp Arg Asn Asn Ile Ala Val Gly Ala Asp Glu Ser Val
1               5                   10                  15

Val Lys Glu Ala His Arg Glu Val Ile Asn Ser Ser Thr Glu Gly Leu
            20                  25                  30

Leu Leu Asn Ile Asp Lys Asp Ile Arg Lys Ile Leu Ser Gly Tyr Ile
            35                  40                  45

Val Glu Ile Glu Asp Thr Glu
     50                  55

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Val Glu Ile Glu Asp Thr Glu
1               5

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Lys Asp Ile Arg Lys Ile Leu Ser Gly Tyr Ile Val Glu Ile Glu Asp
1               5                   10                  15

Thr Glu

<210> SEQ ID NO 44
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Ser Thr Glu Gly Leu Leu Leu Asn Ile Asp Lys Asp Ile Arg Lys Ile
1               5                   10                  15

Leu Ser Gly Tyr Ile Val Glu Ile Glu Asp Thr Glu
                20                  25

<210> SEQ ID NO 45
<211> LENGTH: 46
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

Val Gly Ala Asp Glu Ser Val Val Lys Glu Ala His Arg Glu Val Ile
1               5                   10                  15

Asn Ser Ser Thr Glu Gly Leu Leu Leu Asn Ile Asp Lys Asp Ile Arg
                20                  25                  30

Lys Ile Leu Ser Gly Tyr Ile Val Glu Ile Glu Asp Thr Glu
            35                  40                  45

<210> SEQ ID NO 46
<211> LENGTH: 140
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

Phe His Tyr Asp Arg Asn Asn Ile Ala Val Gly Ala Asp Glu Ser Val
1               5                   10                  15

Val Lys Glu Ala His Arg Glu Val Ile Asn Ser Ser Thr Glu Gly Leu
                20                  25                  30

Leu Leu Asn Ile Asp Lys Asp Ile Arg Lys Ile Leu Ser Gly Tyr Ile
            35                  40                  45

Val Glu Ile Glu Asp Thr Glu Gly Leu Lys Glu Val Ile Asn Asp Arg
        50                  55                  60

Tyr Asp Met Leu Asn Ile Ser Ser Leu Arg Gln Asp Gly Lys Thr Phe
65                  70                  75                  80

```
Ile Asp Phe Lys Lys Tyr Asn Asp Lys Leu Pro Leu Tyr Ile Ser Asn
             85                  90                  95

Pro Asn Tyr Lys Val Asn Val Tyr Ala Val Thr Lys Glu Asn Thr Ile
            100                 105                 110

Ile Asn Pro Ser Glu Asn Gly Asp Thr Ser Thr Asn Gly Ile Lys Lys
            115                 120                 125

Ile Leu Ile Phe Ser Lys Lys Gly Tyr Glu Ile Gly
            130                 135                 140

<210> SEQ ID NO 47
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Val Glu Ile Glu Asp Thr Glu Gly Leu Lys Glu Val Ile Asn Asp Arg
1               5                   10                  15

Tyr Asp Met Leu Asn Ile Ser Ser Leu Arg Gln Asp Gly Lys Thr Phe
            20                  25                  30

Ile Asp Phe Lys Lys Tyr Asn Asp Lys Leu Pro Leu Tyr Ile Ser Asn
            35                  40                  45

Pro Asn Tyr Lys Val Asn Val Tyr Ala Val Thr Lys Glu Asn Thr Ile
50                  55                  60

Ile Asn Pro Ser Glu Asn Gly Asp Thr Ser Thr Asn Gly Ile Lys Lys
65                  70                  75                  80

Ile Leu Ile Phe Ser Lys Lys Gly Tyr Glu Ile Gly
            85                  90

<210> SEQ ID NO 48
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Lys Asp Ile Arg Lys Ile Leu Ser Gly Tyr Ile Val Glu Ile Glu Asp
1               5                   10                  15

Thr Glu Gly Leu Lys Glu Val Ile Asn Asp Arg Tyr Asp Met Leu Asn
            20                  25                  30

Ile Ser Ser Leu Arg Gln Asp Gly Lys Thr Phe Ile Asp Phe Lys Lys
            35                  40                  45

Tyr Asn Asp Lys Leu Pro Leu Tyr Ile Ser Asn Pro Asn Tyr Lys Val
            50                  55                  60

Asn Val Tyr Ala Val Thr Lys Glu Asn Thr Ile Ile Asn Pro Ser Glu
65                  70                  75                  80

Asn Gly Asp Thr Ser Thr Asn Gly Ile Lys Lys Ile Leu Ile Phe Ser
                85                  90                  95

Lys Lys Gly Tyr Glu Ile Gly
            100

<210> SEQ ID NO 49
<211> LENGTH: 113
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 49

Ser Thr Glu Gly Leu Leu Asn Ile Asp Lys Asp Ile Arg Lys Ile
1               5                   10                  15

Leu Ser Gly Tyr Ile Val Glu Ile Glu Asp Thr Glu Gly Leu Lys Glu
                20                  25                  30

Val Ile Asn Asp Arg Tyr Asp Met Leu Asn Ile Ser Ser Leu Arg Gln
            35                  40                  45

Asp Gly Lys Thr Phe Ile Asp Phe Lys Tyr Asn Asp Lys Leu Pro
        50                  55                  60

Leu Tyr Ile Ser Asn Pro Asn Tyr Lys Val Asn Val Tyr Ala Val Thr
65              70                  75                  80

Lys Glu Asn Thr Ile Ile Asn Pro Ser Glu Asn Gly Asp Thr Ser Thr
                85                  90                  95

Asn Gly Ile Lys Lys Ile Leu Ile Phe Ser Lys Lys Gly Tyr Glu Ile
            100                 105                 110

Gly

<210> SEQ ID NO 50
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Val Gly Ala Asp Glu Ser Val Val Lys Glu Ala His Arg Glu Val Ile
1               5                   10                  15

Asn Ser Ser Thr Glu Gly Leu Leu Leu Asn Ile Asp Lys Asp Ile Arg
                20                  25                  30

Lys Ile Leu Ser Gly Tyr Ile Val Glu Ile Glu Asp Thr Glu Gly Leu
            35                  40                  45

Lys Glu Val Ile Asn Asp Arg Tyr Asp Met Leu Asn Ile Ser Ser Leu
        50                  55                  60

Arg Gln Asp Gly Lys Thr Phe Ile Asp Phe Lys Lys Tyr Asn Asp Lys
65              70                  75                  80

Leu Pro Leu Tyr Ile Ser Asn Pro Asn Tyr Lys Val Asn Val Tyr Ala
                85                  90                  95

Val Thr Lys Glu Asn Thr Ile Ile Asn Pro Ser Glu Asn Gly Asp Thr
            100                 105                 110

Ser Thr Asn Gly Ile Lys Lys Ile Leu Ile Phe Ser Lys Lys Gly Tyr
        115                 120                 125

Glu Ile Gly
    130

<210> SEQ ID NO 51
<211> LENGTH: 27
<212> TYPE: PRT
<213> ORGANISM: Conus sp.
<220> FEATURE:
<221> NAME/KEY: MOD_RES
<222> LOCATION: (4)..(4)
<223> OTHER INFORMATION: Hyp
<220> FEATURE:
<221> NAME/KEY: MOD_RES
<222> LOCATION: (10)..(10)
<223> OTHER INFORMATION: Hyp

```
<220> FEATURE:
<221> NAME/KEY: MOD_RES
<222> LOCATION: (21)..(21)
<223> OTHER INFORMATION: Hyp

<400> SEQUENCE: 51

Cys Lys Ser Xaa Gly Ser Ser Cys Ser Xaa Thr Ser Tyr Asn Cys Cys
1               5                   10                  15

Arg Ser Cys Asn Xaa Tyr Thr Lys Arg Cys Tyr
            20                  25

<210> SEQ ID NO 52
<211> LENGTH: 26
<212> TYPE: PRT
<213> ORGANISM: Conus sp.

<400> SEQUENCE: 52

Cys Lys Gly Lys Gly Ala Pro Cys Arg Lys Thr Met Tyr Asp Cys Cys
1               5                   10                  15

Ser Gly Ser Cys Gly Arg Arg Gly Lys Cys
            20                  25

<210> SEQ ID NO 53
<211> LENGTH: 48
<212> TYPE: PRT
<213> ORGANISM: Unknown
<220> FEATURE:
<223> OTHER INFORMATION: Description of Unknown:
      Omega-Agatoxin IVA polypeptide

<400> SEQUENCE: 53

Lys Lys Lys Cys Ile Ala Lys Asp Tyr Gly Arg Cys Lys Trp Gly Gly
1               5                   10                  15

Thr Pro Cys Cys Arg Gly Arg Gly Cys Ile Cys Ser Ile Met Gly Thr
            20                  25                  30

Asn Cys Glu Cys Lys Pro Arg Leu Ile Met Glu Gly Leu Gly Leu Ala
        35                  40                  45

<210> SEQ ID NO 54
<211> LENGTH: 48
<212> TYPE: PRT
<213> ORGANISM: Unknown
<220> FEATURE:
<223> OTHER INFORMATION: Description of Unknown:
      Omega-Agatoxin TK polypeptide

<400> SEQUENCE: 54

Glu Asp Asn Cys Ile Ala Glu Asp Tyr Gly Lys Cys Thr Trp Gly Gly
1               5                   10                  15

Thr Lys Cys Cys Arg Gly Arg Pro Cys Arg Cys Ser Met Ile Gly Thr
            20                  25                  30

Asn Cys Glu Cys Thr Pro Arg Leu Ile Met Glu Gly Leu Ser Phe Ala
        35                  40                  45

<210> SEQ ID NO 55
<211> LENGTH: 35
<212> TYPE: PRT
<213> ORGANISM: Unknown
<220> FEATURE:
<223> OTHER INFORMATION: Description of Unknown:
      Chinese bird spider polypeptide

<400> SEQUENCE: 55

Glu Cys Leu Glu Ile Phe Lys Ala Cys Asn Pro Ser Asn Asp Gln Cys
```

```
                1               5                  10                  15
Cys Lys Ser Ser Lys Leu Val Cys Ser Arg Lys Thr Arg Trp Cys Lys
                20                  25                  30

Tyr Gln Ile
        35

<210> SEQ ID NO 56
<211> LENGTH: 30
<212> TYPE: PRT
<213> ORGANISM: Pseudomonas aeruginosa

<400> SEQUENCE: 56

Tyr Cys Gln Lys Trp Met Trp Thr Cys Asp Ser Glu Arg Lys Cys Cys
1               5                  10                  15

Glu Gly Met Val Cys Arg Leu Trp Cys Lys Lys Lys Leu Trp
                20                  25                  30

<210> SEQ ID NO 57
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(24)
<223> OTHER INFORMATION: This sequence may encompass 1-8 'Gly Gly Ser'
      repeating units wherein some positions may be absent
<220> FEATURE:
<223> OTHER INFORMATION: See specification as filed for detailed
      description of substitutions and preferred embodiments

<400> SEQUENCE: 57

Gly Gly Ser Gly Gly Ser Gly Gly Ser Gly Gly Ser Gly Gly Ser Gly
1               5                  10                  15

Gly Ser Gly Gly Ser Gly Gly Ser
                20

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Gly Ser Gly Gly Ser
1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Lys Lys Lys Lys Lys Lys
1               5

<210> SEQ ID NO 60
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 60

Lys Lys Lys Lys Lys Lys Lys Lys
1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

His His His His His His
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

His His His His His His His His
1               5

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Arg Arg Arg Arg Arg
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Arg Arg Arg Arg Arg Arg Arg
1               5

<210> SEQ ID NO 65
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Phe His Tyr Asp Arg Asn Asn Ile Ala Val Gly Ala Asp Glu Ser Val
1               5                   10                  15
```

```
Val Lys Glu Ala His Arg Glu Val Ile Asn Ser Ser Thr Glu Gly Leu
         20                  25                  30

Leu Leu Asn Ile Asp Lys Asp Ile Arg Lys Ile Leu Ser Gly Tyr Ile
         35                  40                  45

Val Glu Ile Glu Asp Thr Glu
         50                  55

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Val Glu Ile Glu Asp Thr Glu
1               5

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Lys Asp Ile Arg Lys Ile Leu Ser Gly Tyr Ile Val Glu Ile Glu Asp
1               5                   10                  15

Thr Glu

<210> SEQ ID NO 68
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Thr Glu Gly Leu Leu Leu Asn Ile Asp Lys Asp Ile Arg Lys Ile
1               5                   10                  15

Leu Ser Gly Tyr Ile Val Glu Ile Glu Asp Thr Glu
            20                  25

<210> SEQ ID NO 69
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Glu Val Lys Gln Glu Asn Arg Leu Leu Asn Glu Ser Glu Ser
1               5                   10

<210> SEQ ID NO 70
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 70

Val Gly Ala Asp Glu Ser Val Val Lys Glu Ala His Arg Glu Val Ile
1               5                   10                  15

Asn Ser Ser Thr Glu Gly Leu Leu Asn Ile Asp Lys Asp Ile Arg
            20                  25                  30

Lys Ile Leu Ser Gly Tyr Ile Val Glu Ile Glu Asp Thr Glu
        35                  40                  45

<210> SEQ ID NO 71
<211> LENGTH: 7
<212> TYPE: PRT
<213> ORGANISM: Clostridium botulinum

<400> SEQUENCE: 71

Glu Ala Asn Gln Arg Ala Thr
1               5

<210> SEQ ID NO 72
<211> LENGTH: 7
<212> TYPE: PRT
<213> ORGANISM: Clostridium botulinum

<400> SEQUENCE: 72

Gly Ala Ser Gln Phe Glu Thr
1               5

<210> SEQ ID NO 73
<211> LENGTH: 7
<212> TYPE: PRT
<213> ORGANISM: Clostridium botulinum

<400> SEQUENCE: 73

Ala Asn Gln Arg Ala Thr Lys
1               5

<210> SEQ ID NO 74
<211> LENGTH: 7
<212> TYPE: PRT
<213> ORGANISM: Clostridium botulinum

<400> SEQUENCE: 74

Asp Thr Lys Lys Ala Val Lys
1               5

<210> SEQ ID NO 75
<211> LENGTH: 7
<212> TYPE: PRT
<213> ORGANISM: Clostridium botulinum

<400> SEQUENCE: 75

Arg Asp Gln Lys Leu Ser Glu
1               5

<210> SEQ ID NO 76
<211> LENGTH: 7
<212> TYPE: PRT
<213> ORGANISM: Clostridium botulinum

<400> SEQUENCE: 76

Gln Ile Asp Arg Ile Met Glu
1               5

```
<210> SEQ ID NO 77
<211> LENGTH: 7
<212> TYPE: PRT
<213> ORGANISM: Clostridium botulinum

<400> SEQUENCE: 77

Glu Arg Asp Gln Lys Leu Ser
1               5

<210> SEQ ID NO 78
<211> LENGTH: 7
<212> TYPE: PRT
<213> ORGANISM: Clostridium botulinum

<400> SEQUENCE: 78

Glu Thr Ser Ala Ala Lys Ile
1               5

<210> SEQ ID NO 79
<211> LENGTH: 7
<212> TYPE: PRT
<213> ORGANISM: Clostridium tetani

<400> SEQUENCE: 79

Gly Ala Ser Gln Phe Glu Thr
1               5

<210> SEQ ID NO 80
<211> LENGTH: 7
<212> TYPE: PRT
<213> ORGANISM: Unknown
<220> FEATURE:
<223> OTHER INFORMATION: Description of Unknown:
      IgA protease peptide

<400> SEQUENCE: 80

Ser Thr Pro Pro Thr Pro Ser
1               5

<210> SEQ ID NO 81
<211> LENGTH: 7
<212> TYPE: PRT
<213> ORGANISM: Unknown
<220> FEATURE:
<223> OTHER INFORMATION: Description of Unknown:
      Antarease peptide

<400> SEQUENCE: 81

Ile Lys Arg Lys Tyr Trp Trp
1               5

<210> SEQ ID NO 82
<211> LENGTH: 7
<212> TYPE: PRT
<213> ORGANISM: Clostridium botulinum

<400> SEQUENCE: 82

Glu Ala Asn Gln Arg Ala Thr
1               5

<210> SEQ ID NO 83
<211> LENGTH: 7
<212> TYPE: PRT
<213> ORGANISM: Clostridium botulinum

<400> SEQUENCE: 83
```

```
Ala Asn Gln Arg Ala Thr Lys
1               5

<210> SEQ ID NO 84
<211> LENGTH: 7
<212> TYPE: PRT
<213> ORGANISM: Clostridium botulinum

<400> SEQUENCE: 84

Glu Ala Asn Gln Arg Ala Thr
1               5

<210> SEQ ID NO 85
<211> LENGTH: 7
<212> TYPE: PRT
<213> ORGANISM: Clostridium botulinum

<400> SEQUENCE: 85

Phe Ala Asn Gln Arg Ala Thr
1               5

<210> SEQ ID NO 86
<211> LENGTH: 7
<212> TYPE: PRT
<213> ORGANISM: Clostridium botulinum

<400> SEQUENCE: 86

Glu Ala Asn Gln Arg Ala Thr
1               5

<210> SEQ ID NO 87
<211> LENGTH: 7
<212> TYPE: PRT
<213> ORGANISM: Clostridium botulinum

<400> SEQUENCE: 87

Glu Ala Asn Gln Arg Ala Ile
1               5

<210> SEQ ID NO 88
<211> LENGTH: 7
<212> TYPE: PRT
<213> ORGANISM: Clostridium botulinum

<400> SEQUENCE: 88

Glu Ala Asn Lys Ala Thr Lys
1               5

<210> SEQ ID NO 89
<211> LENGTH: 7
<212> TYPE: PRT
<213> ORGANISM: Clostridium botulinum

<400> SEQUENCE: 89

Glu Ala Asn Lys His Ala Thr
1               5

<210> SEQ ID NO 90
<211> LENGTH: 7
<212> TYPE: PRT
<213> ORGANISM: Clostridium botulinum

<400> SEQUENCE: 90

Glu Ala Asn Lys His Ala Asn
1               5
```

<210> SEQ ID NO 91
<211> LENGTH: 7
<212> TYPE: PRT
<213> ORGANISM: Clostridium botulinum

<400> SEQUENCE: 91

Asp Glu Ala Asn Gln Arg Ala
1               5

<210> SEQ ID NO 92
<211> LENGTH: 7
<212> TYPE: PRT
<213> ORGANISM: Clostridium botulinum

<400> SEQUENCE: 92

Glu Ala Asn Gln Arg Ala Thr
1               5

<210> SEQ ID NO 93
<211> LENGTH: 7
<212> TYPE: PRT
<213> ORGANISM: Clostridium botulinum

<400> SEQUENCE: 93

Ala Asn Gln Arg Ala Thr Lys
1               5

<210> SEQ ID NO 94
<211> LENGTH: 7
<212> TYPE: PRT
<213> ORGANISM: Clostridium botulinum

<400> SEQUENCE: 94

Asn Gln Arg Ala Thr Lys Met
1               5

<210> SEQ ID NO 95
<211> LENGTH: 7
<212> TYPE: PRT
<213> ORGANISM: Clostridium botulinum

<400> SEQUENCE: 95

Ala Asn Gln Arg Ala Ile Lys
1               5

<210> SEQ ID NO 96
<211> LENGTH: 7
<212> TYPE: PRT
<213> ORGANISM: Clostridium botulinum

<400> SEQUENCE: 96

Ala Asn Gln Arg Ala His Gln
1               5

<210> SEQ ID NO 97
<211> LENGTH: 7
<212> TYPE: PRT
<213> ORGANISM: Clostridium botulinum

<400> SEQUENCE: 97

Asp Thr Lys Lys Ala Val Lys
1               5

```
<210> SEQ ID NO 98
<211> LENGTH: 7
<212> TYPE: PRT
<213> ORGANISM: Clostridium botulinum

<400> SEQUENCE: 98

Lys Thr Lys Lys Ala Val Lys
1               5

<210> SEQ ID NO 99
<211> LENGTH: 7
<212> TYPE: PRT
<213> ORGANISM: Clostridium botulinum

<400> SEQUENCE: 99

Glu Thr Lys Lys Ala Ile Lys
1               5

<210> SEQ ID NO 100
<211> LENGTH: 7
<212> TYPE: PRT
<213> ORGANISM: Clostridium botulinum

<400> SEQUENCE: 100

Glu Thr Lys Arg Ala Met Lys
1               5

<210> SEQ ID NO 101
<211> LENGTH: 7
<212> TYPE: PRT
<213> ORGANISM: Clostridium botulinum

<400> SEQUENCE: 101

Asp Thr Lys Lys Ala Val Arg
1               5

<210> SEQ ID NO 102
<211> LENGTH: 7
<212> TYPE: PRT
<213> ORGANISM: Clostridium botulinum

<400> SEQUENCE: 102

Asp Thr Lys Lys Ala Leu Lys
1               5

<210> SEQ ID NO 103
<211> LENGTH: 7
<212> TYPE: PRT
<213> ORGANISM: Clostridium botulinum

<400> SEQUENCE: 103

Asp Thr Lys Lys Ala Met Lys
1               5

<210> SEQ ID NO 104
<211> LENGTH: 7
<212> TYPE: PRT
<213> ORGANISM: Clostridium botulinum

<400> SEQUENCE: 104

Glu Ser Lys Lys Ala Val Lys
1               5

<210> SEQ ID NO 105
<211> LENGTH: 7
```

```
<212> TYPE: PRT
<213> ORGANISM: Clostridium botulinum

<400> SEQUENCE: 105

Glu Thr Lys Lys Ala Met Lys
1               5

<210> SEQ ID NO 106
<211> LENGTH: 7
<212> TYPE: PRT
<213> ORGANISM: Clostridium botulinum

<400> SEQUENCE: 106

Glu Thr Lys Lys Ala Val Lys
1               5

<210> SEQ ID NO 107
<211> LENGTH: 7
<212> TYPE: PRT
<213> ORGANISM: Clostridium botulinum

<400> SEQUENCE: 107

Gln Ile Asp Arg Ile Met Glu
1               5

<210> SEQ ID NO 108
<211> LENGTH: 7
<212> TYPE: PRT
<213> ORGANISM: Clostridium botulinum

<400> SEQUENCE: 108

Gln Ile Gln Lys Ile Thr Glu
1               5

<210> SEQ ID NO 109
<211> LENGTH: 7
<212> TYPE: PRT
<213> ORGANISM: Clostridium botulinum

<400> SEQUENCE: 109

Gln Ile Asp Arg Ile Val Glu
1               5

<210> SEQ ID NO 110
<211> LENGTH: 7
<212> TYPE: PRT
<213> ORGANISM: Clostridium botulinum

<400> SEQUENCE: 110

Gln Phe Asp Arg Ile Met Asp
1               5

<210> SEQ ID NO 111
<211> LENGTH: 7
<212> TYPE: PRT
<213> ORGANISM: Clostridium botulinum

<400> SEQUENCE: 111

Gln Phe Asp Arg Ile Met Glu
1               5

<210> SEQ ID NO 112
<211> LENGTH: 7
<212> TYPE: PRT
<213> ORGANISM: Clostridium botulinum
```

```
<400> SEQUENCE: 112

Gln Leu Asp Arg Ile His Asp
1               5

<210> SEQ ID NO 113
<211> LENGTH: 7
<212> TYPE: PRT
<213> ORGANISM: Clostridium botulinum

<400> SEQUENCE: 113

Gln Ile Asp Arg Ile Met Asp
1               5

<210> SEQ ID NO 114
<211> LENGTH: 7
<212> TYPE: PRT
<213> ORGANISM: Clostridium botulinum

<400> SEQUENCE: 114

Gln Val Asp Arg Ile Gln Gln
1               5

<210> SEQ ID NO 115
<211> LENGTH: 7
<212> TYPE: PRT
<213> ORGANISM: Clostridium botulinum

<400> SEQUENCE: 115

Gly Ala Ser Gln Phe Glu Thr
1               5

<210> SEQ ID NO 116
<211> LENGTH: 7
<212> TYPE: PRT
<213> ORGANISM: Clostridium botulinum

<400> SEQUENCE: 116

Ala Gly Ala Ser Gln Phe Glu
1               5

<210> SEQ ID NO 117
<211> LENGTH: 7
<212> TYPE: PRT
<213> ORGANISM: Clostridium botulinum

<400> SEQUENCE: 117

Gly Ala Ser Gln Phe Glu Ser
1               5

<210> SEQ ID NO 118
<211> LENGTH: 7
<212> TYPE: PRT
<213> ORGANISM: Clostridium botulinum

<400> SEQUENCE: 118

Gln Ala Ser Gln Phe Glu Ser
1               5

<210> SEQ ID NO 119
<211> LENGTH: 7
<212> TYPE: PRT
<213> ORGANISM: Clostridium botulinum

<400> SEQUENCE: 119
```

Gly Ala Ser Gln Gly Glu Thr
1               5

<210> SEQ ID NO 120
<211> LENGTH: 7
<212> TYPE: PRT
<213> ORGANISM: Clostridium botulinum

<400> SEQUENCE: 120

Gly Ala Ser Gln Phe Glu Gln
1               5

<210> SEQ ID NO 121
<211> LENGTH: 7
<212> TYPE: PRT
<213> ORGANISM: Clostridium botulinum

<400> SEQUENCE: 121

Gln Ala Ser Gln Phe Glu Ala
1               5

<210> SEQ ID NO 122
<211> LENGTH: 7
<212> TYPE: PRT
<213> ORGANISM: Clostridium botulinum

<400> SEQUENCE: 122

Gly Ala Ser Gln Phe Gln Gln
1               5

<210> SEQ ID NO 123
<211> LENGTH: 7
<212> TYPE: PRT
<213> ORGANISM: Clostridium botulinum

<400> SEQUENCE: 123

Gly Ala Ser Gln Phe Glu Ala
1               5

<210> SEQ ID NO 124
<211> LENGTH: 7
<212> TYPE: PRT
<213> ORGANISM: Clostridium botulinum

<400> SEQUENCE: 124

Arg Asp Gln Lys Leu Ser Glu
1               5

<210> SEQ ID NO 125
<211> LENGTH: 7
<212> TYPE: PRT
<213> ORGANISM: Clostridium botulinum

<400> SEQUENCE: 125

Arg Asp Gln Lys Ile Ser Glu
1               5

<210> SEQ ID NO 126
<211> LENGTH: 7
<212> TYPE: PRT
<213> ORGANISM: Clostridium botulinum

<400> SEQUENCE: 126

Lys Asp Gln Lys Leu Ala Glu

```
1               5

<210> SEQ ID NO 127
<211> LENGTH: 7
<212> TYPE: PRT
<213> ORGANISM: Clostridium botulinum

<400> SEQUENCE: 127

Glu Arg Asp Gln Lys Leu Ser
1               5

<210> SEQ ID NO 128
<211> LENGTH: 7
<212> TYPE: PRT
<213> ORGANISM: Clostridium botulinum

<400> SEQUENCE: 128

Val Leu Glu Arg Asp Gln Lys
1               5

<210> SEQ ID NO 129
<211> LENGTH: 7
<212> TYPE: PRT
<213> ORGANISM: Clostridium botulinum

<400> SEQUENCE: 129

Glu Arg Asp Gln Lys Ile Ser
1               5

<210> SEQ ID NO 130
<211> LENGTH: 7
<212> TYPE: PRT
<213> ORGANISM: Clostridium botulinum

<400> SEQUENCE: 130

Glu Arg Asp Gln Ala Leu Ser
1               5

<210> SEQ ID NO 131
<211> LENGTH: 7
<212> TYPE: PRT
<213> ORGANISM: Clostridium botulinum

<400> SEQUENCE: 131

Glu Lys Asp Gln Lys Leu Ala
1               5

<210> SEQ ID NO 132
<211> LENGTH: 7
<212> TYPE: PRT
<213> ORGANISM: Clostridium botulinum

<400> SEQUENCE: 132

Glu Ser Ser Ala Ala Lys Ile
1               5

<210> SEQ ID NO 133
<211> LENGTH: 7
<212> TYPE: PRT
<213> ORGANISM: Clostridium botulinum

<400> SEQUENCE: 133

Glu Thr Ser Ala Ala Lys Ile
1               5
```

<210> SEQ ID NO 134
<211> LENGTH: 7
<212> TYPE: PRT
<213> ORGANISM: Clostridium botulinum

<400> SEQUENCE: 134

Glu Ser Ser Ala Ala Lys Leu
1               5

<210> SEQ ID NO 135
<211> LENGTH: 7
<212> TYPE: PRT
<213> ORGANISM: Clostridium botulinum

<400> SEQUENCE: 135

Glu Thr Ser Ala Ala Lys Leu
1               5

<210> SEQ ID NO 136
<211> LENGTH: 7
<212> TYPE: PRT
<213> ORGANISM: Clostridium tetani

<400> SEQUENCE: 136

Gly Ala Ser Gln Phe Glu Thr
1               5

<210> SEQ ID NO 137
<211> LENGTH: 7
<212> TYPE: PRT
<213> ORGANISM: Clostridium tetani

<400> SEQUENCE: 137

Gly Ala Ser Gln Gly Glu Thr
1               5

<210> SEQ ID NO 138
<211> LENGTH: 7
<212> TYPE: PRT
<213> ORGANISM: Clostridium tetani

<400> SEQUENCE: 138

Gly Ala Ser Gln Phe Glu Gln
1               5

<210> SEQ ID NO 139
<211> LENGTH: 7
<212> TYPE: PRT
<213> ORGANISM: Clostridium tetani

<400> SEQUENCE: 139

Gln Ala Ser Gln Phe Glu Ala
1               5

<210> SEQ ID NO 140
<211> LENGTH: 7
<212> TYPE: PRT
<213> ORGANISM: Clostridium tetani

<400> SEQUENCE: 140

Gly Ala Ser Gln Phe Glu Ser
1               5

<210> SEQ ID NO 141

```
<211> LENGTH: 7
<212> TYPE: PRT
<213> ORGANISM: Clostridium tetani

<400> SEQUENCE: 141

Gln Ala Ser Gln Phe Glu Ser
1               5

<210> SEQ ID NO 142
<211> LENGTH: 7
<212> TYPE: PRT
<213> ORGANISM: Clostridium tetani

<400> SEQUENCE: 142

Gly Ala Ser Gln Phe Gln Gln
1               5

<210> SEQ ID NO 143
<211> LENGTH: 7
<212> TYPE: PRT
<213> ORGANISM: Clostridium tetani

<400> SEQUENCE: 143

Gly Ala Ser Gln Phe Glu Ala
1               5

<210> SEQ ID NO 144
<211> LENGTH: 7
<212> TYPE: PRT
<213> ORGANISM: Unknown
<220> FEATURE:
<223> OTHER INFORMATION: Description of Unknown:
      IgA protease peptide

<400> SEQUENCE: 144

Ser Thr Pro Pro Thr Pro Ser
1               5

<210> SEQ ID NO 145
<211> LENGTH: 7
<212> TYPE: PRT
<213> ORGANISM: Unknown
<220> FEATURE:
<223> OTHER INFORMATION: Description of Unknown:
      Antarease peptide

<400> SEQUENCE: 145

Ile Lys Arg Lys Tyr Trp Trp
1               5

<210> SEQ ID NO 146
<211> LENGTH: 23
<212> TYPE: PRT
<213> ORGANISM: Influenza virus

<400> SEQUENCE: 146

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 147
<211> LENGTH: 40
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-8 'Gly Gly Gly
      Gly Ser' repeating units wherein some positions may be absent
<220> FEATURE:
<223> OTHER INFORMATION: See specification as filed for detailed
      description of substitutions and preferred embodiments

<400> SEQUENCE: 147

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 148
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Gly Gly Gly Ser
1               5
```

COMPOSITIONS AND METHODS FOR TREATMENT OF PAIN

CROSS REFERENCE TO RELATED APPLICATION

This application is a divisional application of U.S. application Ser. No. 15/755,543, filed on Feb. 26, 2018, which is the National Stage of International Application No. PCT/US2016/049099, filed Aug. 26, 2016, which claims benefit under 35 U.S.C. § 119(e) of the U.S. provisional application No. 62/210,610 filed Aug. 27, 2015, the contents of which is/are incorporated herein by reference in its entirety.

SEQUENCE LISTING

The instant application contains a Sequence Listing which has been submitted electronically in ASCII format and is hereby incorporated by reference in its entirety. The ASCII copy, created on Aug. 26, 2016, is named 002806-084951-PCT SL.txt and is 165,499 bytes in size.

FIELD OF THE INVENTION

We describe novel compositions and methods for treatment of pain.

BACKGROUND OF THE INVENTION

Pain in chronic disease conditions including osteoarthritis, rheumatoid arthritis, muscle spasticity, and cancer is a major socioeconomic burden, for which few effective treatments are available.

Current chronic pain therapies such as opioids are mostly ineffective or have major off-target effects such as addictiveness due to action on other neuronal subtypes.

Nociceptor sensory neurons mediate the detection of harmful/injurious stimuli, and their aberrant activation produces chronic pain. These neurons are dysregulated in muscle spasticity that may contribute to overactive sensorimotor reflexes, and also innervate joints affected in osteoarticular conditions to mediate pain.

SUMMARY OF THE INVENTION

The present invention provides novel compositions and methods for treatment of pain. The invention is based, at least in part, on our discovery that pain-sensing nociceptor neurons specifically express high levels of ANTXR2 (also known as CMG2), a receptor for anthrax toxin, while this receptor is not substantially expressed by other neuron subtypes. By using the endosomal delivery mechanisms inherent to anthrax toxin, we can specifically deliver molecular cargo into nociceptors that would result in pain-specific block without causing other neurological side effects. For examples, the molecular cargoes can be intracellularly acting toxins that inhibit or block cell signaling pathways in vivo or inhibit or block the release of synaptic neurotransmitters.

Accordingly, we provide, in one aspect, a fusion protein comprising: (a) a botulinum neurotoxin (BTx) or a tetanus neurotoxin (TTx), and (b) an anthrax toxin protective antigen (PA), or a C-terminal receptor-binding domain of PA, wherein part (a) and (b) are linked or fused together. The term "fusion protein" is used interchangeably with the term "chimeric protein" and the term "engineered fusion protein" herein.

In one embodiment, the BTx or TTx comprises a BTx or TTx enzymatic moiety and translocation peptide or domain.

In one embodiment, the BTx moiety or translocation peptide/domain is selected from the BTx light chain and heavy chain domains of any one of BTx/A, BTx/B, BTx/C, BTx/D, BTx/E, BTx/F, BTx/G, and a non-Clostridial botulinum-like toxin. The back slash followed by an alphabet (/A, /B, /C, etc) denotes the various serotypes within the *Clostridium botulinum* family.

In one embodiment, the BTx or TTx enzymatic moiety or translocation peptide/domain is selected from the enzymatic moieties and translocation domain of the Btx or TTx toxins provided in Table 1.

In another aspect, provided herein is a fusion protein comprising: (a) a non-cytotoxic protease, which protease is capable of cleaving a SNARE protein in a nociceptor neuron; and (b) a protein capable of binding to an anthrax toxin protective antigen (PA) or a fragment thereof, wherein the PA or PA fragment thereof binds a receptor expressed on the nociceptor neuron. In other words, the fusion protein here cleaves a SNARE protein.

In one embodiment, the non-cytotoxic protease comprises a clostridial neurotoxin L-chain. In one embodiment, the clostridial neurotoxin is botulinum neurotoxin (BTx) or tetanus neurotoxin (TTx).

In one embodiment, the BTx is selected from any one of BTx/A, BTx/B, BTx/C, BTx/D, BTx/E, BTx/F, BTx/G, and a non-Clostridial botulinum-like toxin.

In one embodiment, the clostridial neurotoxin L-chain is selected from the L-chains of the clostridial neurotoxins provided in Table 1. In one embodiment, the clostridial neurotoxin L-chain is selected from SEQ. ID. NOS: 20-28.

In another aspect, provided herein is a fusion protein comprising (a) a disulfide-containing peptide toxin which is capable of blocking ion channels in a nociceptor neuron; and (b) a targeting moiety (TM) that is capable of binding to a binding site on the nociceptor neuron, wherein the nociceptor neuron expresses the ion channels therein (e.g., sodium or calcium or both sodium and calcium channels). In other words, the disulfide-containing peptide toxin here blocks ion channels in a nociceptor neuron and the TM binds to a binding site on the nociceptor neuron.

In another aspect, provided herein is a fusion protein comprising: (a) a disulfide-containing peptide toxin which is capable of blocking sodium or calcium or both sodium and calcium channels in a nociceptor neuron; and (b) a protein capable of binding to an anthrax toxin protective antigen (PA) or a PA fragment that binds a receptor expressed on the nociceptor neuron. In other words, the disulfide-containing peptide toxin here blocks sodium or calcium or both types of channels in a nociceptor neuron and the part (b) is a protein that binds to an anthrax toxin protective antigen (PA) or a PA fragment that binds a receptor expressed on the nociceptor neuron.

In one embodiment, the disulfide-containing peptide toxin comprised by a fusion protein described herein comprises a cysteine knot motif.

In one embodiment, the disulfide-containing peptide toxin comprised by a fusion protein described herein is a conotoxin, an agatoxin, a delta paulutoxin, a huwentotoxin or a ProTx II toxin.

In one embodiment, the PA-binding receptor expressed on the nociceptor neuron is ANTXR2 (CMG2).

In one embodiment, the PA or C-terminal receptor-binding domain of PA binds the ANTXR2 (CMG2) receptor expressed on the nociceptor neuron.

In one embodiment, the TM is selected from the group consisting of: (i) an anthrax toxin protective antigen (PA); (ii) a C-terminal receptor-binding domain of PA; and (iii) a nociceptor neuron-binding protein.

In one embodiment, the PA is a mutant PA that is resistant to furin cleavage.

In one embodiment, the C-terminal receptor-binding domain of PA is PA63 or PAd4.

In one embodiment, the PAd4, the PA or PA fragment thereof, or a C-terminal receptor binding domain of PA that binds ANTXR2 is modified or mutated.

In one embodiment, the PAd4, the PA or PA fragment thereof, or a C-terminal receptor binding domain of PA that binds ANTXR2 is resistant to cleavage by a protease, such as Lys C.

In one embodiment, the nociceptor neuron-binding protein is an antibody.

In one embodiment, the antibody specifically binds to the nerve growth factor (NGF) receptor, the ANTXR2 receptor, or an ion-channel protein present on nociceptor neurons.

In one embodiment, the ion-channel protein is selected from Nav1.7, Nav1.8 or Nav1.9.

In one embodiment, the protein capable of binding to PA is an anthrax toxin lethal factor (LF) or an anthrax toxin edema factor (EF). In other words, the protein here binds PA and is an LF or EF.

In one embodiment, the PA binding domain of LF is the N-terminal domain of LF, (abbreviated as LFPABD or LFn).

In one embodiment, the PA binding domain of EF is the N-terminal domain of EF, (abbreviated as EFPABD or EFn).

In another aspect, provided herein is a fusion protein comprising: (a) an AB toxin; (b) an anthrax toxin protective antigen (PA) or a fragment thereof, wherein the PA or fragment thereof binds a receptor expressed on a nociceptor neuron; and (c) a translocation domain (TL) that is capable of translocating the toxin (a protease) from within an endosome, across the endosomal membrane and into the cytosol of the nociceptor neuron. In other words, the TL translocates the toxin into the cytosol of the nociceptor neuron.

In one embodiment, the AB toxin is selected from Ricin toxin, Cholera toxin A-part and B-part; *Pseudomonas aeruginosa* Exotoxin A A-part and B-part; Shiga toxin A-part and B-part; and Diphtheria toxin A-part and B-part.

In one embodiment, the PA-binding receptor expressed on the nociceptor neuron is ANTXR2 (CMG2).

In one embodiment, the PA fragment is a C-terminal receptor-binding domain of PA.

In one embodiment, the TL is a translocation domain derived from a clostridial neurotoxin, or is a holotoxin; or is a mutant form of the holotoxin that has been modified (e.g., chemically) or mutated to negate the toxin receptor-binding function of the AB toxin.

In another aspect, provided herein is a fusion protein comprising a botulinum neurotoxin (BTx) moiety comprising an N-terminal enzymatic domain (LC or L chain) and an intermediate pore-forming/translocation-domain ($H_N$) of the BTx, linked to a C-terminal receptor-binding domain of anthrax toxin protective antigen (PA). The C-terminal receptor-binding domain of anthrax toxin protective antigen can be, for example, a PAd4 domain.

In one embodiment, the fusion protein further comprises a linker peptide between the BTx moiety and the C-terminal receptor-binding domain of anthrax toxin protective antigen or PAd4 domain.

In another aspect, provided herein is a fusion protein comprising: (a) a botulinum neurotoxin N-terminal enzymatic domain of a botulinum neurotoxin (BTx) moiety, and (b) an N-terminal domain of anthrax toxin lethal factor (LFn), which domain binds to oligomeric forms of PA63, the proteolytically activated form of anthrax PA; or the N-terminal domain of anthrax toxin edema factor (EFn), which domain binds to oligomeric forms of PA63, the proteolytically activated form of anthrax PA, wherein part (a) is linked N-terminally or C-terminally or both N-terminally and C-terminally to part (b).

In one embodiment of any of the fusion proteins including a BTx moiety, the fusion protein can further comprise an amino acid sequence defining a belt corresponding to the N-terminal part of the BTx $H_N$ domain, wherein the $H_N$ of the BTx is located at the C-terminal side of the BTx moiety. The presence of the belt stabilizes the L chain.

In one embodiment of any of the fusion proteins including a BTx moiety, wherein the BTx moiety comprises, consist essentially of, or consists of the L chain and the $H_N$ domain of BTx, the S-S bridge between the L chain and the $H_N$ domain is not reduced.

In one embodiment of any of the fusion proteins including a BTx moiety, wherein the BTx moiety comprises, consist essentially of, or consists of the L chain and not the $H_N$ domain of BTx, the Cys residues in the L chain and the belt corresponding to the N-terminal part of the BTx $H_N$ domain, if present, can be mutated to Ala, Ser, or Thr.

In one embodiment, for a fusion protein comprising a BTx L moiety and an LFn or EFn domain, the fusion protein further comprises a linker peptide between the BTx L moiety and the LFn or EFn domain.

In another aspect, provided herein is a fusion protein comprising anthrax toxin protective antigen (PA), an anthrax toxin protective antigen C-terminal receptor binding domain (PAd4), or a nociceptor neuron-binding protein, linked to a disulfide-containing peptide toxin. In one embodiment, the disulfide-containing peptide toxin is an inhibitor cysteine knot toxin.

In one embodiment, the fusion protein further comprises a linker peptide between the PA, PAd4 or nociceptor-binding protein and the disulfide-containing peptide toxin (e.g., the inhibitor cysteine knot toxin).

In another aspect, provided herein is a fusion protein comprising a disulfide-containing peptide toxin operably linked N-terminally or C-terminally or both N-terminally and C-terminally, or chemically crosslinked at one or more sites, to the N-terminal domain (LFn) of anthrax toxin lethal factor, which domain binds to oligomeric forms of PA63, the proteolytically activated form of anthrax PA; or the N-terminal domain (EFn) of anthrax toxin edema factor, which domain binds to oligomeric forms of PA63.

In one embodiment of any fusion protein described in which a toxin is fused to LFn or EFn, the fusion protein further comprises a linker peptide between the LFn and the toxin or the EFn and the toxin.

In another aspect, provided herein is a fusion protein comprising an AB toxin fused to a linker peptide linked to a C-terminal receptor-binding domain of anthrax toxin protective antigen (PAd4 domain), wherein the fusion protein further comprises a translocation domain, a holotoxin, or a mutant form of the holotoxin that have been modified (e.g., chemically) or mutated to negate the toxin receptor-binding function of the AB toxin.

In one embodiment of any fusion protein including an AB toxin, the AB toxin is selected from Ricin toxin, Cholera toxin A-part and B-part, *Pseudomonas aeruginosa* Exotoxin A A-part and B-part, Shiga toxin A-part and B-part, and Diphtheria toxin A-part and B-part.

In another aspect, provided herein is a fusion protein comprising an N-terminal enzymatic domain (Chain A) together with a translocation/pore-forming domain from a Clostridial neurotoxin or a non-Clostridial botulinum-like toxin, linked to a C-terminal receptor-binding domain of anthrax toxin protective antigen (PAd4 domain). Examples of a Clostridial neurotoxin is tetanus neurotoxin (frequently abbreviated as TTx or TeNT in scientific literatures).

In one embodiment, the fusion protein further comprises a linker peptide between the TTx moiety and the PAd4 domain.

In one embodiment of any fusion protein described as having a linker, the linker peptide is 1-20 amino acids long.

In one embodiment of any fusion protein described as having a linker, the linker peptide is stable in human serum for at least 1 minute.

In one embodiment of any fusion protein described as having a linker, the linker peptide comprises at least one amino acid that is Gly or Ser.

In one embodiment of any fusion protein described as having a linker, the linker peptide does not comprise Lys and/or Arg.

In one embodiment of any fusion protein described that includes a BTx moiety, the BTx moiety is selected from the BTx light chain and heavy chain domains of any one of BTx/A, BTx/B, BTx/C, BTx/D, BTx/E, BTx/F, BTx/G. For examples, the the BTx light chain and heavy chain domains are selected from SEQ ID NO: 29-31 or Table 1 described herein. It is specifically contemplated that a non-Clostridial botulinum-like toxin can also be used.

In one embodiment of any fusion protein described as including a PAd4 domain, the fusion protein comprises 2-10 PAd4 domains in tandem.

In one embodiment of any fusion protein described as including a PAd4 domain and a BTx moiety, about 1-60 consecutive amino acids from the N-terminal side of PA adjacent to the native PAd4 domain are further incorporated between the BTx moiety and the PAd4.

In one embodiment of any fusion protein described as including a PAd4 domain and an AB toxin, about 1-60 consecutive amino acids from the N-terminal side of PA adjacent to the native PAd4 domain are further incorporated between the AB toxin and the PAd4.

In one embodiment of any fusion protein described as including a PAd4 domain, e.g., a PAd4, a PA or a C-terminal receptor binding domain of PA, one or more of the Lys residues in the PAd4 domain at positions 594, 613, 633, 637, 653, 673, 679, 680, 684, 695, 703, 722, 723, 729, and 730 has been replaced by Arg or His, wherein the numbering refers to that of SEQ ID NO:1 after minusing the 29 aa signal peptide in SEQ. ID. NO:1.

In one embodiment of any fusion protein described as including a PAd4 domain, e.g., a PA or a C-terminal receptor binding domain of PA, one or more of the Lys residues in the PAd4 domain at positions 623, 642, 662, 666, 682, 702, 708, 709, 713, 724, 732, 751, 752, 758, and 759 in SEQ. ID. NO: 1 has been replaced, for example, by Arg or His.

In one embodiment of any fusion protein described as including an entire PA protein, the furin cleavage site of PA comprising amino acid residues $^{164}$RKKR$^{167}$ of SEQ ID NO: 1 (minus the 29 aa signal peptide in SEQ. ID. NO:1) has been replaced by a furin-resistant amino acid sequence. In one embodiment, the furin-resistant amino acid sequence is SSSR (SEQ ID NO: 32) or SSSS (SEQ ID NO: 33).

In one embodiment of any fusion protein described as including a PAd4 domain, one or more of the Asn residues in the PAd4 domain at position 601, 713, 719 of SEQ ID NO:1 (minus the 29 aa signal peptide in SEQ. ID. NO:1) has been replaced by Asp.

In one embodiment of any fusion protein described herein, the fusion protein further comprises at least one D-amino acid at the N-terminus of the fusion protein.

In one embodiment of any fusion protein that includes all or part of a BTx L chain and H chain, the residue corresponding to an L chain junction of BTx with an H chain of BTx has been cleaved.

In one embodiment of any fusion protein that includes a nociceptor neuron-binding protein, the nociceptor neuron-binding protein is an antibody. In one embodiment, the antibody specifically binds to NGF receptor or an ion-channel protein present on nociceptor neurons. In one embodiment, the ion-channel protein is selected from Nav1.7, Nav1.8 or Nav1.9.

In another aspect, provided herein is a composition comprising any one of the fusion proteins described in the preceding paragraphs. In one embodiment, the composition further comprises a pharmaceutically acceptable carrier, excipient or diluent.

In one embodiment of any composition described, the composition further comprises a native anthrax toxin protective antigen (PA). In one embodiment, the PA is an oligomeric PA. In one embodiment, the oligomeric PA is bound to the fusion protein.

In another aspect, provided herein is a nucleic acid encoding any of the fusion proteins described herein.

In another aspect, provided herein is a vector comprising the nucleic acid described in the preceding paragraph. For examples, the vector is a plasmid, a bacteriaphage or a viral vector. For example, the plasmid is an expression plasmid for recombinant protein expression in a bacteria, e.g., *Escherichia coli*. In another aspect, provided herein is a viral particle comprising a vector comprising a nucleic acid described in the preceding paragraph. In another aspect, provided herein is a viral particle comprising a a nucleic acid described in the preceding paragraph.

In another aspect, provided herein is a cell comprising the nucleic acid described herein or the vector of described herein. For example, an *E. coli* carrying a plasmid that comprises a nucleic acid encoding a fusion protein described herein. For example, for the recombinant protein expression of the a fusion protein encoded in the nucleic acid. In another aspect, provided herein is a cell comprising a viral particle comprising a vector comprising a nucleic acid described in the preceding paragraph. In another aspect, provided herein is a cell comprising a viral particle comprising a a nucleic acid described in the preceding paragraph.

In another aspect, provided herein is a method of producing a fusion protein, the method comprising culturing the cell described herein above under conditions such that the fusion protein is expressed, and recovering the fusion protein.

In another aspect, provided herein is a fusion protein produced by the method described in the preceding paragraph.

In one embodiment, any of the fusion proteins described herein, or a fusion protein produced by a method described herein, is glycosylated. In another embodiment, any of the fusion proteins described herein, or a fusion protein produced by a method described herein, is non-glycosylated.

In one embodiment of the method described for producing a fusion protein, the cell is a prokaryotic cell such as bacteria. In one embodiment of the method described for producing a fusion protein, the cell is a bacteria cell. In one embodiment, the bacteria is *Escherichia coli* (*E. Coli*). In another embodiment, the bacteria is an attenuated *Bacillus anthracis* strains, e.g., CDC 684. In one embodiment of the method described for producing a fusion protein, the cell is a yeast cell. In one embodiment, the yeast is *Saccharomyces cerevisiae*.

In one embodiment of the method described for producing a fusion protein, the yeast cell is glycosylation deficient.

In one embodiment of the method described for producing a fusion protein, the yeast cell is glycosylation and protease deficient.

In one embodiment of the method described for producing a fusion protein, the cell is a mammalian cell. In one embodiment, the mammalian cell is a COS cell, a CHO cell, or an NSO cell.

In one embodiment, provided herein is the use of any of the fusion proteins described herein for the treatment of pain.

In one embodiment, provided herein is the use of any of the fusion proteins described herein for the manufacture of medicament for the treatment of pain.

In another aspect, provided herein is an engineered fusion protein comprising an anthrax toxin Protective-Antigen (PA) moiety or its receptor binding domain (PAd4) fused with an inhibitor cysteine knot (ICK) toxin, e.g., a Conotoxin (CTx).

In another aspect, provided herein is an engineered fusion protein comprising an anthrax toxin lethal factor domain (LFn) fused with an inhibitor cysteine knot (ICK) toxin and a Protective-Antigen (PA) moiety. In another aspect, provided herein is an engineered fusion protein comprising an anthrax toxin lethal factor domain (LFn) fused with a L chain of a Clostridial neurotoxin and a Protective-Antigen (PA) moiety. In one embodiment, this fusion protein can further comprise the belt of the H chain of the Clostridial neurotoxin, the belt is the N-terminal segment of the H chain. In another aspect, provided herein is an engineered fusion protein comprising an anthrax toxin lethal factor domain (LFn) fused with an intracellur acting toxin (e.g., an AB type toxin) and a Protective-Antigen (PA) moiety.

In another aspect, provided herein is an engineered fusion protein comprising a mutant anthrax protective antigen (mPA) moiety that has been altered to block its native receptor-binding function, fused with a molecule capable of specifically targeting a nociceptor surface receptor or a nociceptor ion channel receptor, and an anthrax lethal factor domain (LFn) fused to an intracellularly acting toxin catalytic domain. ANTXR2 is the native receptor for PA. In other words, the molecule specifically targets a nociceptor surface receptor or a nociceptor ion channel receptor.

In another aspect, provided herein is an engineered fusion protein comprising an anthrax protective antigen (PA) moiety fused with a molecule capable of specifically targeting a nociceptor surface receptor or a nociceptor ion channel receptor, and an anthrax lethal factor domain (LFn) fused to an intracellularly acting toxin catalytic domain. ANTXR2 is the native receptor for PA. In some embodiments of any of the aspects described herein, PA can be further engineered to enhance binding to one or more receptors. In other words, the molecule specifically targets a nociceptor surface receptor or a nociceptor ion channel receptor.

In one embodiment, the molecule capable of specifically targeting or the molecule that specifically targets a nociceptor surface receptor or a nociceptor ion channel receptor is selected from an antibody, or antibody mimetic, that specifically binds to the NGF receptor, or an antibody or antibody mimetic that specifically binds to Nav1.7, Nav1.8 or Nav1.9. In some embodiments of any of the aspects described herein, molecule capable of specifically targeting a nociceptor surface receptor or a nociceptor ion channel can be further engineered to enhance binding to one or more receptors.

In one embodiment, wherein the intracellularly acting toxin catalytic domain is selected from diphtheria toxin (DTx), *Pseudomonas aeruginosa* exotoxin A (PTx), botulinium toxin (BTx), tetanus toxin (TTx), shiga toxin, ricin toxin, anthrax lethal toxin (lethal factor, LF), and/or anthrax edema toxin (edema factor, EF).

In another aspect, provided herein is an engineered fusion protein comprising a native protective antigen (PA) or a mutant PA (mPA), wherein the mPA has been modified (e.g., chemically) or mutated so as to block its native receptor-binding function, and a molecule that can target nociceptor neuron surface molecules, specifically in combination with anthrax toxin edema factor (EF) and/or anthrax lethal factor (LF).

In one embodiment of an engineered fusion protein of any of the preceding paragraphs, the PA or mPA is in a covalent or noncovalent oligomeric form. In one embodiment, the oligomeric form is bound to the molecule, e.g., covalently or noncovalently.

In another aspect, provided herein is a composition comprising an engineered fusion protein comprising an anthrax toxin Protective-Antigen (PA) moiety or its receptor binding domain (PAd4) fused with an inhibitor cysteine knot (ICK) toxin, e.g. a Conotoxin (CTx).

In another aspect, provided herein is a composition comprising an engineered fusion protein comprising an anthrax toxin lethal factor domain (LFn), fused with an inhibitor cysteine knot (ICK) toxin (e.g., a conotoxin (CTx)) and a Protective-Antigen (PA) moiety.

In another aspect, provided herein is a composition comprising an engineered mutant anthrax protective antigen (mPA) moiety that has been altered to block its native receptor-binding function, fused with a molecule capable of specifically targeting a nociceptor surface receptor, or a nociceptor ion channel and an anthrax lethal factor domain (LFn), fused to an intracellularly acting toxin catalytic domain.

In another aspect, provided herein is a composition comprising an engineered fusion protein comprising an anthrax protective antigen (PA) moiety fused with a molecule capable of specifically targeting a nociceptor surface receptor or a nociceptor ion channel receptor, and an anthrax lethal factor domain (LFn) fused to an intracellularly acting toxin catalytic domain. ANTXR2 is the native receptor for PA. In some embodiments of any of the aspects described herein, PA can be further engineered to enhance binding to one or more receptors.

In one embodiment, the molecule capable of specifically targeting a nociceptor surface receptor or a nociceptor ion channel is selected from a NGF, and an antibody that specifically binds to Nav1.7, Nav1.8 or Nav1.9. In some embodiments of any of the aspects described herein, molecule capable of specifically targeting a nociceptor surface receptor or a nociceptor ion channel can be further engineered to enhance binding to one or more receptors.

In another embodiment, the intracellularly acting toxin catalytic domain is selected from diphtheria toxin (DTx), *Pseudomonas aeruginosa* exotoxin A (PTx), botulinium toxin (BTx) tetanus toxin (TTx), Shiga toxin, ricin toxin, anthrax lethal toxin (lethal factor, LF), and/or anthrax edema toxin (edema factor, EF).

In another aspect, provided herein is a composition comprising an engineered fusion protein comprising a native protective antigen (PA) or a mutant PA (mPA), wherein the mPA has been modified (e.g., chemically) or mutated so as to block its native receptor-binding function, and a molecule that can target nociceptor neuron surface molecules specifically in combination with anthrax toxin edema factor (EF).

In one embodiment, the PA or mPA is in an oligomeric form. In one embodiment, the oligomeric form is bound to the molecule.

In one embodiment, a fusion protein-comprising composition further comprises a pharmaceutically acceptable carrier or excipient.

In another aspect, provided herein is a method for treatment of pain, the method comprising administering to a subject in need thereof a composition comprising a fusion protein as described herein.

In another aspect, provided herein is a method of treating pain, the method comprising administering to a subject in need thereof a native mature anthrax toxin protective antigen (PA) and anthrax toxin edema factor (EF), anthrax toxin lethal factor (LF) or any combination thereof.

In another aspect, provided herein is a method for the treatment of nerve, joint, skin, visceral, bladder, or muscle pain, comprising administering peripherally by intradermal injection, subcutaneous injection, intramuscular injection, intraneural injection, or intra-articular injection to a subject in need thereof a composition comprising a fusion protein as described herein.

In another aspect, described herein is a method for treatment of diabetic neuropathic pain, cancer pain, fibromyalgia or other systemic pain disorders, comprising administering by epidural injection, intrathecal infusion or intra-cerebroventricular infusion into the central nervous system of a subject in need thereof a composition comprising a fusion protein as described herein.

In another aspect, described herein is a method for treatment of pain, the method comprising administering to a subject in need thereof an effective, pain reducing amount of a composition comprising an engineered fusion protein comprising an anthrax toxin Protective-Antigen (PA) moiety or its receptor binding domain (PAd4) fused to an intracellularly acting toxin catalytic domain, wherein the engineered fusion protein is delivered to nociceptor neurons and results in decreased intracellular signaling events in the nociceptor neurons or decreased neurotransmitter release from the nociceptor neurons.

In one embodiment, the intracellularly acting toxin catalytic domain is selected from diphtheria toxin (DTx), *Pseudomonas aeruginosa* exotoxin A (PTx), botulinium toxin (BTx) tetanus toxin (TTx), Shiga toxin, ricin toxin, anthrax lethal toxin (lethal factor), and/or anthrax edema toxin (edema factor)

In some aspects, any compositions described in the preceding paragraphs or any compositions comprising a fusion protein described in the preceding paragraphs is use for the treatment of pain. Treatment of pain can include administering more than one, i.e., several, of the different compositions described in the preceding paragraphs.

In another aspect, described herein is a method for treatment of pain, the method comprising administering to a subject in need thereof an effective, pain reducing amount of a composition comprising an engineered fusion protein comprising an anthrax toxin Protective-Antigen (PA) moiety or its receptor binding domain (Pad4) fused with an inhibitor cysteine knot (ICK) toxin (e.g., a Conotoxin (CTx)).

In another aspect, described herein is a method for treatment of pain, the method comprising administering to a subject in need thereof an effective amount of a composition comprising an engineered fusion protein comprising an anthrax toxin lethal factor (LFn) fused with an inhibitor cysteine knot (ICK) toxin (e.g., a Conotoxin (CTx)) and a Protective-Antigen (PA) moiety. Alternately, treatment of pain is carried out by administering to a subject in need thereof an effective amount of a composition comprising an engineered fusion protein comprising an anthrax toxin lethal factor domain (LFn) fused with a L chain of a Clostridial neurotoxin and a Protective-Antigen (PA) moiety, or an engineered fusion protein comprising an anthrax toxin lethal factor domain (LFn) fused with an intracellur acting toxin (e.g., an AB type toxin) and a Protective-Antigen (PA) moiety. In one embodiment, the fusion protein comprising the L chain of a Clostridial neurotoxin can further comprise the belt of the H chain of the Clostridial neurotoxin, the belt is the N-terminal segment of the H chain.

In another aspect, described herein is a method for treatment of pain, the method comprising administering to a subject in need thereof an effective, pain reducing amount of an engineered mutant anthrax protective antigen (mPA) moiety that has been altered to block its native receptor-binding function fused with a molecule capable of specifically targeting a nociceptor surface receptor or an ion channel receptor and an anthrax lethal factor domain (LFn) fused to an intracellularly acting toxin catalytic domain.

In one embodiment, the molecule is selected from an antibody that specifically binds to the NGF receptor and an antibody that specifically binds to Nav1.7, Nav1.8 or Nav1.9.

In another embodiment, the intracellularly acting toxin catalytic domain is selected from diphtheria toxin (DTx), *Pseudomonas aeruginosa* exotoxin A (PTx), botulinium toxin (BTx), tetanus toxin (TTx), Shiga toxin, ricin toxin, anthrax lethal toxin (lethal factor), and/or anthrax edema toxin (edema factor).

In another aspect, described herein is a method of treating pain in a subject in need thereof comprising administering to the subject an engineered fusion protein comprising a native protective antigen (PA) or a mutant PA (mPA), wherein the mPA has been modified (e.g., chemically) or mutated so as to block its native receptor-binding function and a molecule that can target nociceptor surface molecules specifically in combination with anthrax toxin edema factor (EF) and/or anthrax lethal factor (LF).

In one embodiment, the PA or mPA is administered in an oligomeric form, wherein the oligomeric PA or mPA is formed from proteolytically activated PA or mPA (or mutant thereof) to achieve increased avidity for receptor-bearing cells. In one embodiment, the oligomeric form is bound to the molecule before administering.

In one embodiment, the composition is administered separately before, simultaneously, or after administering a composition comprising an anthrax protective antigen (PA), in a pharmaceutically acceptable carrier, excipient or diluent.

In one embodiment, the administering is performed by intrathecal infusion or intra-cerebroventricular infusion or by an epidural injection into the central nervous system, or by peripheral administration using intradermal injection, subcutaneous injection, intramuscular injection, intraneural injection, or intra-articular injection.

In another embodiment, the pain is selected from diabetic neuropathic pain, cancer pain, fibromyalgia, other systemic pain disorders, nerve, joint, skin, visceral, bladder, and muscle pain.

In another aspect, provided herein is a method of manufacture of a pharmaceutical composition comprising one or more of the fusion proteins described in the preceding paragraphs and a pharmaceutically acceptable carrier or excipient.

In another aspect, provided herein is a fusion protein described in the preceding paragraphs for use in the manufacture of medicament for the treatment of pain. In one embodiment, the fusion protein is formulated with at least one pharmaceutically acceptable carrier or excipient.

In another aspect, provided herein is a fusion protein described in the preceding paragraphs for use in the treatment of pain. In one embodiment, the fusion protein is formulated with at least one pharmaceutically acceptable carrier or excipient.

BRIEF DESCRIPTION OF THE DRAWINGS

Figure 1A:
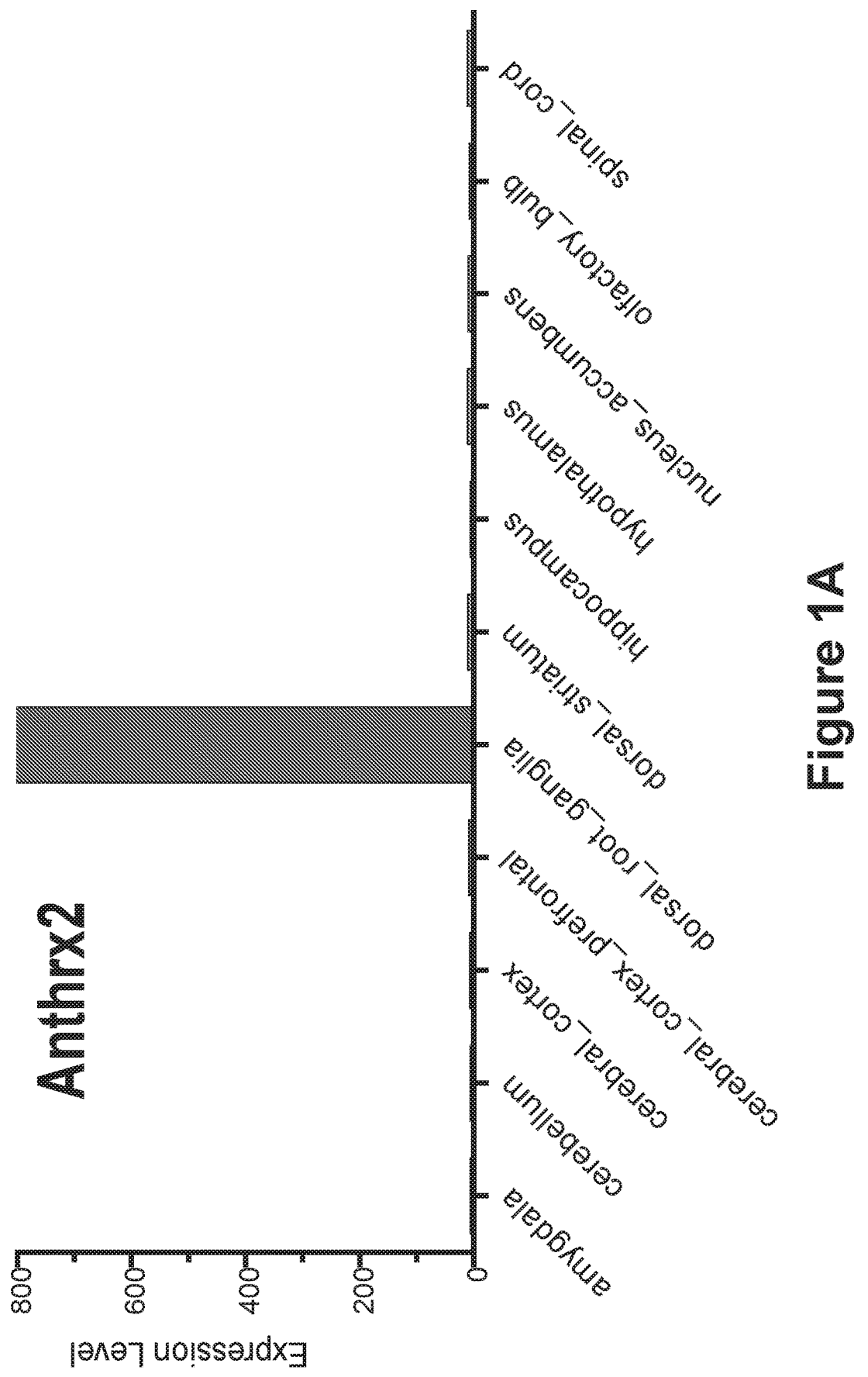

FIGS. 1A-1B demonstrate that Anthrax Toxin Receptor is specifically expressed in the dorsal root ganglia compared to other nervous system tissues. (FIG. 1A) Expression profiling data of 11 nervous tissue types showing that Antxr2 transcript expression is only present in dorsal root ganglia tissues, where nociceptor neurons are found. (FIG. 1B) In situ hybridization image for Antxr2 showing strong expression in dorsal root ganglia but not surrounding tissues or spinal cord.

FIG. 5 shows that protein synthesis inhibition in neurons by the fusion protein LFn-DTX is dependent on the presence of PA and that LFn-DTX is able to block protein synthesis intracellularly in nociceptor neurons at picomolar concentrations.

FIG. 7A shows the modular construction of embodiments of BoTX-PA fusion proteins using various domains of BoTX protein and different PA-derived proteins. The PA-derived protein is the Pad4 domain or PA that is resistant to cleavage by a protease, such as furin protease.

FIG. 7B shows the modular construction of embodiments of TTX-PA fusion proteins using various domains of TTX protein and different PA-derived proteins. The PA-derived protein is the Pad4 domain or PA that is resistant to cleavage by a protease, such as furin protease.

FIG. 8A shows the modular construction of embodiments of a fusion proteins comprising BoTX and the PA-binding domains LFn or EFn. The fusion proteins are made using the light chain/catalytic domain from various BoTX serotypes with the PA-binding domain of the two PA-binding proteins, LF and EF. These BoTX-PA-binding fusion proteins are to be used in conjuction with the native PA protein for the treatment of pain.

FIG. 8B shows the modular construction of embodiments of a fusion proteins comprising TTX or other intracellular acting toxins and the PA-binding domains LFn or EFn. These fusion proteins are made using the light chain/catalytic domain of TTX protein or various other intracellular acting toxins, with the PA-binding domain of the two PA-binding proteins, LF and EF.

FIG. 9 shows the modular construction of embodiments of a fusion proteins comprising small disulfide containing toxins or inhibitor cysteine knots (ICK) toxins and a PA-derived protein. The PA-derived protein is the Pad4 domain or the PA that is resistant to by a protease, such as furin protease.

DETAILED DESCRIPTION OF THE INVENTION

Figure 1B:
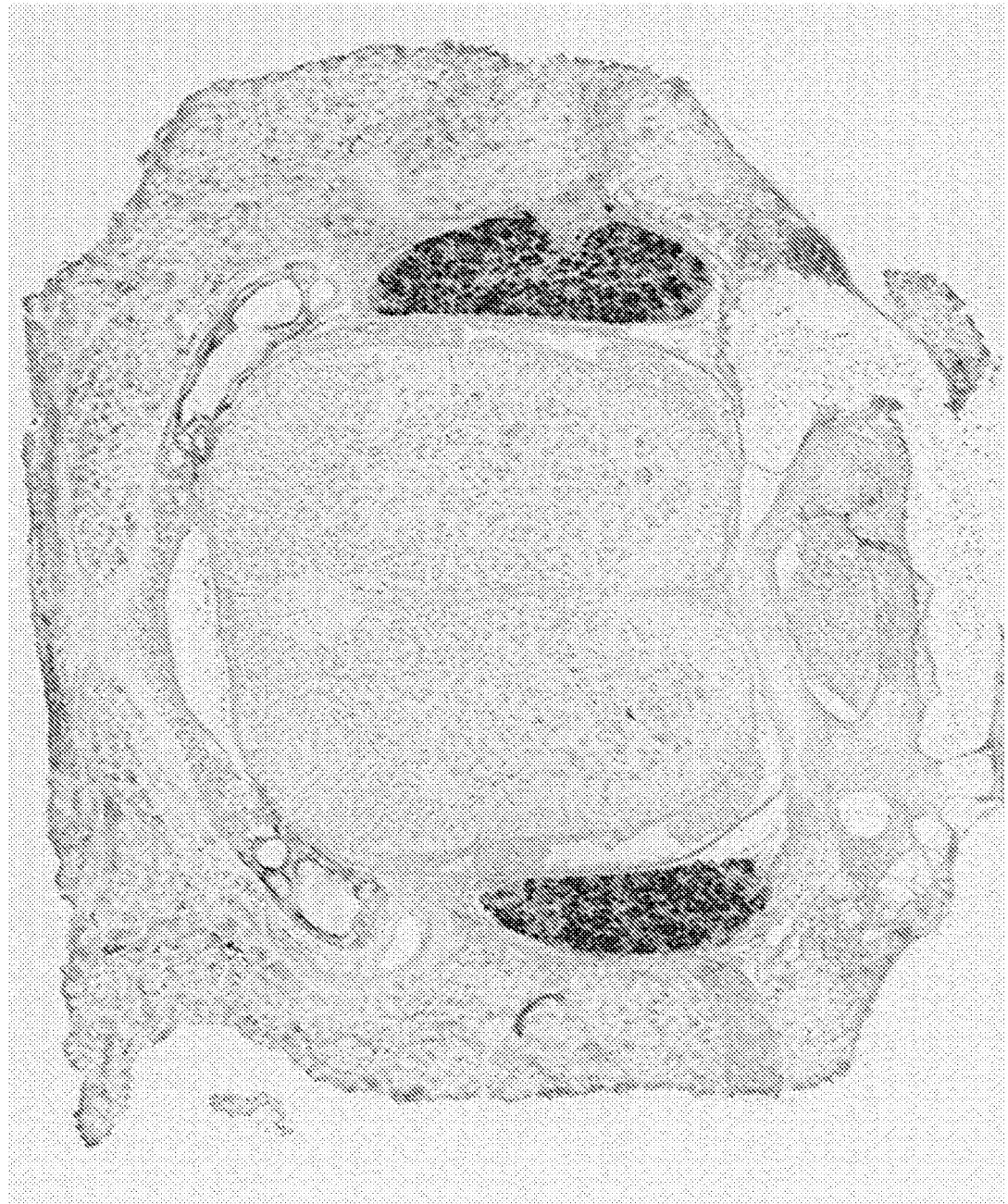

Abbreviations: ANTXR2 (CMG2)=a cell surface receptor for the anthrax toxin; PA=anthrax toxin Protective-Antigen, 83 kDa; PA63=active 63 kDa of fragment of PA derived from furin cleavage, self-assembles into a ring-shaped heptamer or octamer to form a receptor-bound prepore, PA63 prepore binds up to three or four EF, LF, LFn or EFn, forming complexes that are then endocytosed; PAd1=an LF/EF binding component or fragment of PA; PAd2=a membrane translocation component or fragment of PA, an anthrax-derived translocation domain or peptide; PAd3=an oligomerisation component or fragment of PA; PAd4=the host cell receptor binding domain of PA to ANTXR1 and ANTXR2 receptors, PA's native receptors; PA$^{furin-}$=a furin resistant PA with modified or mutated furin-protease recognition site, is incapable of multimerisation and translocation, no binding to LFn or EFn but can still bind host cell receptor; ICK=inhibitor cysteine knot; LFn=N-terminal PA binding domain of anthrax toxin lethal factor, an "anthrax toxin translocation peptide"; EFn=N-terminal PA binding domain of anthrax toxin edema factor, also an "anthrax translocation signal peptide"; LF=anthrax lethal toxin (lethal factor); EF=anthrax edema toxin (edema factor); mPA=a mutant anthrax protective antigen moiety that has been altered to block its native receptor-binding function; Nav1.7, Nav1.8 or Nav1.9=ion channel proteins; DTx=diphtheria toxin including A and B components of the toxin, DTA=diphtheria toxin only the A components of the toxin, the enzymatic component, the component that is the intracellur acting toxin; PE or PTx=*Pseudomonas aeruginosa* exotoxin A; BTx or BoTX or BoNT=botulinium toxin; TTx=tetanus toxin; CTx=Conotoxin; CNT=clostridial neurotoxin family; LC or L=50 kDa light chain of of a neurotoxin member of the clostridial neurotoxin family, L functions as a zinc-dependent endopeptidase; HC=heavy chain (HC=$H_N$ HO contains two functional domains, each of ~50 kDa; $H_N$=N-terminal half of HC, is the translocation domain of a neurotoxin member of the clostridial neurotoxin family. $H_N$ is known to form ion channels in lipid bilayers. $H_C$=C-terminal half of HC, is the receptor binding domain of a neurotoxin member of the clostridial neurotoxin family; $LH_N$=L+$H_N$.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012

(ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

We have identified a novel way to treat pain utilizing pain-sensing nociceptor-specific delivery of molecules that quell pain.

Skin lesions caused by *Bacillus anthracis*, the causative agent of anthrax, are characteristically painless. We discovered that pain-sensing nociceptor neurons specifically express high levels of ANTXR2, the receptor for anthrax toxin, while this receptor is not expressed or substantially expressed by other neuron subtypes. Anthrax toxin receptor is also expressed by hematopoietic lineage cells (macrophages, osteoclasts, osteoblasts) involved in joint remodeling. Without wishing to be bound by a theory, we submit that anthrax toxin silences pain during infection by acting through ANTXR2 on nociceptor sensory neurons, and that it can also be used to target immune cells involved in joint remodeling.

We have previously described a system of targeted delivery of antigens (U.S. Patent Application Publication No. 20030202989) and proteins (WO2012096926) using different anthrax toxin-based delivery systems, including a system in which anthrax receptor binding to its native target receptor has been ablated (U.S. Patent Application Publication No. 20150044210). In these systems, the pore-forming ability of anthrax toxin was exploited to permit entry of a reagent into a cell. The receptor-binding portion of anthrax toxin was ablated in order to permit engineering of cell-binding specificity as desired by the user.

In short, the receptor-binding component of anthrax toxin, termed Protective Antigen (PA), binds to ANTXR2, is endocytosed, and subsequently translocates either anthrax Lethal Factor (LF) or anthrax Edema Factor (EF), or both, across the endosomal membrane to the cytosol. As described herein, the inventors have made the surprising discovery that the major anthrax toxin receptor ANTXR2 is highly specific in expression within nociceptive neurons amongst all nervous tissues, i.e., anthrax toxin is preferentially targeted to nociceptive neurons via binding to ANTXR2. The discovery of this preferential binding of the native anthrax toxin permits the use of anthrax toxin and its cytosolic delivery mechanisms to specifically target nociceptive neurons to produce highly specific and efficacious pain blockade. In some embodiments of any of the aspects described herein, no receptor binding modifications are needed, as the target neurons express the receptor the anthrax system naturally binds to. In some aspects of any of the embodiments, specificity can be increased and side effects reduced by use of additional ligand-receptor interactions, in concert with the anthrax toxin-ANTXR2 interaction. Here we utilized anthrax toxin as a platform to specifically block chronic pain, silence muscle spasticity, and to target and prevent both pain and joint destruction in osteoarthritis. The methods and compositions described herein diverge from earlier anthrax-toxin delivery systems in utilizing the receptor-binding portion of anthrax toxin to direct delivery to a specific cell type, instead of using only the pore-forming activity of the toxin to permit entry of a reagent to a cell targeted by means independent of any native anthrax toxin binding activity.

Chronic pain is a major socio-economic burden in society for which few targeted treatments are available. Nociceptor sensory neurons mediate the detection of noxious/injurious stimuli, resulting in pain sensations and avoidance behavior. Sustained activation of nociceptors during inflammation or following nerve injury leads to chronic pain. We provide uses of proteinaceous toxins to create new targeted molecular entities to treat pain.

We have found that the anthrax toxin receptor ANTXR2 is highly expressed on nociceptors and specific to these neurons compared to other neuronal subtypes. This finding suggests that we can use the Protective Antigen (PA) moiety of anthrax toxin or its receptor-binding domain (PAd4) as a cellular specificity determinant for creating constructs to kill nociceptors or otherwise block their ability to transmit signals to the central nervous system (CNS).

The advantage of this surprising strategy is the specificity of targeting peripheral pain-sensing neurons compared to other pain treatments, which often have off-target effects on other neuronal subtypes.

We describe engineering intracellularly acting toxins such as anthrax toxin, disulfide-containing peptide toxins such as inhibitor cysteine knot (ICK) toxins, AB type toxins such as diphtheria toxin (DT), and SNARE targeting toxins such as tetanus toxin (TTx), and/or botulinum toxins (BTx) for use as a targeted painkiller. In some embodiments, these toxins depend on PA mediated delivery of the intracellular enzymatic activity of these toxins into nociceptor neurons.

Toxins and their Components, Parts and Fragments Useful for the Modular Construction of Engineered Fusion (Chimeric) Proteins Anthrax Toxin Anthrax toxin is a trimeric complex of three protein components secreted by virulent strains of the bacterium, *Bacillus anthracis*. The three protein components are Protective Antigen (PA), Edema Factor (EF), and Lethal Factor (LF). PA is an 83 kDa protein that mediates specific receptor targeting and binding. Upon binding to its receptor, either Tumor Endothelium Marker-8 (TEM8 or "ANTRX1") or Capillary Morphogenesis Protein 2 (CMG2 or "ANTXR2"), PA83 is proteolytically activated by furin or other furin-like proteases, removing an N-terminal piece (PA20) and leaving the remaining piece (PA63) bound to the receptor. This activates PA enabling it to multimerise to form heptamers/octamers that bind up to 4 EF/LF molecules. PA63 spontaneously oligomerizes to form ring-shaped heptameric or octameric "prepores", which contain binding sites capable of binding LF or EF with high nM affinity. LF and EF (each ~90 kDa) have homologous, ~260-residue N-terminal domains that bind the prepores; the enzymatic moieties of LF and EF are C-terminal. The resulting complexes are internalised by endocytosed and under low pH of the endosome, the PA63 prepore changes conformation, inserts into the membrane and transports bound cargo molecules (LF/EF) to the cytosol, where they refold and catalyze their respective reactions. The LF is zinc dependent endopeptidase that catalyzes the hydrolysis (cleavage) of certain mitogen-activated protein kinase kinases (MAP Kinase/ERK Kinase; also known as MAP Kinase Kinase), and this leads to the disruption of many cellular signalling pathways, which eventually leads to cell death. EF is a calmodulin and calcium dependent adenylate cyclase that increases cAMP to extraordinary levels in cells. Changes in intracellular cAMP affect membrane permeability and may account for edema. In macrophages and neutrophils, an additional effect is the depletion of ATP reserves which are needed for the engulfment process. This is a list of the possible combinations that can occur with the Anthrax Toxin: PA+LF leads to lethal activity; EF+PA leads to edema; EF+LF has no toxic effects on cells; and PA+LF+EF leads to lethal activity and edema in an affected cell. LF consists of an N-terminal PA binding domain (abbreviated herein as "LFPABD" or "LFn") and a C-terminal proteolytic component. LF acts by cleaving mitogen-activated protein (MAP) kinase kinases. EF consists of an N-terminal PA binding domain (abbreviated herein as "EFPABD" or "EFn"), a central enzymatic component, and a C-terminal calmodulin binding component. EF is a calcium dependent adenylate cyclase that elevates cellular cAMP levels. MAP kinase and cAMP signalling have both been found to be critical in mediating nociceptor signalling.

PA possesses four major functions distributed across four structurally distinct domains—an LF/EF binding component (PAd1), a membrane translocation component (PAd2), an oligomerisation component (PAd3), and a host cell receptor binding component (PAd4).

As used herein, "anthrax toxin protective antigen" or "PA" refers to a polypeptide that, in oligomeric form, binds specifically and selectively to the ANTXR2 receptors, subsequently forming a pore in the cell membrane and translocating cargo toxins. The sequence of PA is known in the art, e.g., (NCBI Gene ID No: 3361714 (SEQ ID NO: 1; the 29 amino acid residue peptide sequence is the signal peptide: MKKRKVLIPLMALSTILVSSTGNLEVIQA (SEQ ID NO: 34) at the N-terminus (NCBI Ref Seq: NP 052806; UNI-PROT P13423). The numbering of the amino acid residues can be with reference to SEQ. ID. NO: 1 that has the signal peptide. Alternatively, the numbering of the amino acid residues can be with reference to the PA sequence without the signal peptide. PA binds to host cell surface ANTXR2 receptors and is cleaved by a furin-family protease to an active 63 kDa PA form (PA63) that self-assembles into a ring-shaped heptamer or octamer to form a receptor-bound prepore. The PA63 prepore binds up to three or four molecules of, e.g., anthrax lethal factor, forming complexes that are then endocytosed. Upon acidification of the endosome, protective antigen prepore undergoes a conformational rearrangement to form a membrane-spanning, ion-conductive pore, which transports anthrax lethal factor and/or anthrax edema factor from the endosome to the cytosol. LFn, the N-terminal domain of anthrax lethal factor, has nanomolar binding affinity for the pore, and this domain (or the corresponding EF domain, EFn) alone can be used for translocation of chemical moieties.

The furin-family protease cleavage site in $^{164}$RKKR$^{167}$, and cleavage occurs between $^{167}$RS$^{168}$, the amino acid residue numbering is referenced against SEQ. ID. NO: 1 minus the 29 amino acid signal peptide. To remove the furin site in order to make a furin-resistant PA, RKKR (residues 164-167 of SEQ ID NO: 1 minus the 29 aa signal peptide in SEQ ID NO:1) can be replaced with SSSR (SEQ ID NO: 32) or SSSS (SEQ ID NO: 33) (to eliminate all basic residues). Removal of the furin cleavage site to produce furin resistant PA (PA$^{furin-}$) will prevent multimerization and translocation.

As used herein, "anthrax toxin edema factor" or "EF" refers to a calmodulin- and Ca2+-dependent adenylyl cyclase, which elevates the level of cAMP within the cell. The sequence of EF is known, e.g. NCBI Gene ID: 3361726; SEQ ID NO: 6.

As used herein, "anthrax toxin lethal factor" or "LF" refers to a metalloprotease that cleaves most members of the MAP kinase family. The sequence of LF is known, e.g., NCBI Gene ID: 3361711; SEQ ID NO: 7. For further discussion of EF and LF, see, e.g., Leppla, 79 PNAS, 3162 (1982); Duesbery et al., 280 Science 734 (1998); Vitale et al., 248 Biochem. Biophys. Res. Commn. 706 (1998); each of which is incorporated by reference herein in its entirety.

As used herein, "anthrax translocation signal peptide" or "anthrax toxin translocation peptide" refers to a anthrx-derived domain or peptide that, when comprised by and/or linked to a polypeptide, causes that polypeptide to bind to PA or mPA (optionally to PA or mPA in an oligomeric complex) and be translocated by the mature PA/mPA pore to the cytoplasm of a target cell. In some embodiments, the anthrax toxin translocation peptide can be LFn (e.g., amino acids 34-267, 34-293, or 34-297 of SEQ ID NO:7, the full-length LF with its N-terminal signal peptide), EFn (e.g., amino acids 59-277 or 34-290 of SEQ. ID. NO:6), or variants thereof.

In some embodiments of all the aspects described herein, a small positively charged peptide segment that mimics LFn or EFn can be used to aid in translocating cargo molecules through a PA or mPA pore. These mimics may be composed of at least one non-natural amino acid and are described in more detail in, e.g., International Patent Publication WO 2012/096926; U.S. Pat. No. 9,079,952, and US Patent Application Publications No: US 2013/0336974 and US 2015/0267186, each of which is incorporated by reference herein in its entirety.

As used herein, "PAd4" or "protective antigen domain 4" refers to the domain of PA that recognizes and binds to host cell cellular receptors (e.g. ANTXR1 and/or ANTXR2). PAd4 can comprise the sequence from about amino acid 621 to about amino acid 764 of SEQ ID NO: 1 (PAd4 sequence inclusive of the signal peptide). In some embodiments of all the aspects described herein, PAd4 can comprise amino acids 621-764 of SEQ ID NO: 1, which is the amino acid sequence of PA with the signal peptide. In some embodiments of all the aspects described herein, PAd4 can comprise amino acids 596-735 of SEQ ID NO: 1. In one embodiment of all the aspects described herein, PAd4 can comprise amino acids 625-764 of SEQ ID NO: 1. In another embodiment of all the aspects described herein, PAd4 can comprise amino acids 616-764 of SEQ ID NO: 1. In another embodiment of all the aspects described herein, PAd4 can comprise amino acids 609-764 of SEQ ID NO: 1. In one embodiment of all the aspects described herein, the PAd4 comprises

```
                                            (SEQ ID NO: 35)
REHYDRNNIAVGADESVVKEAHREVINSSTEGLLLNIDKDIRKDILS

GYIVEIEDTEGLKEVINDRYDMLNISSLRQGKTFIDEKKYNDKLPLY

ISNPNYKVNVYAVTKENTIINPSENGDTSTNGIKKILIFSKKGYEIG.
```

In one embodiment of all the aspects described herein, PAd4 consist essentially of

```
                                            (SEQ ID NO: 36)
REHYDRNNIAVGADESVVKEAHREVINSSTEGLLLNIDKDIRKILSG

YIVEIEDTEGLKEVINDRYDMLNISSLRQDGKTFIDEKKYNDKLPLY

ISNPNYKVNVYAVTKENTIINPSENGDTSTNGIKKILIFSKKGYEIG.
```

In one embodiment of all the aspects described herein, the PAd4 comprises

```
                                            (SEQ ID NO: 37)
FHYDRNNIAVGADESVVKEAHREVINSSTEGLLLNIDKDIRKILSGY

IVEIEDTEGLKEVINDRYDMLNISSLRQDGKTFIDEKKYNDKLPLYI

SNPNYKVNVYAVTKENTIINPSENGDTSTNGIKKILIFSKKGYEIG.
```

In one embodiment of all the aspects described herein, PAd4 consist essentially of

```
                                            (SEQ ID NO: 38)
FHYDRNNIAVGADESVVKEAHREVINSSTEGLLLNIDKDIRKILSGY

IVEIEDTEGLKEVINDRYDMLNISSLRQDGKTFIDEKKYNDKLPLYI

SNPNYKVNVYAVTKENTIINPSENGDTSTNGIKKILIFSKKGYEIG.
```

In one embodiment of all the aspects described herein, the PAd4 comprises

```
                                            (SEQ ID NO: 39)
GLKEVINDRYDMLNISSLRQDGKTFIDFKKYNDKLPLYISNPN

YKVNVYAVTKENTIINPSENGDTSTNGIKKILIFSKKGYEIG.
```

In one embodiment of all the aspects described herein, the PAd4 consist essentially of

```
                                            (SEQ ID NO: 40)
GLKEVINDRYDMLNISSLRQDGKTFIDFKKYNDKLPLYISNPNY

KVNVYAVTKENTIINPSENGDTSTNGIKKILIFSKKGYEIG.
```

In one embodiment of all aspects of the fusion proteins described herein, the PAd4 is fused or joined to the other protein or toxin by a linker peptide. Examples of linker peptide include:

```
                                            (SEQ ID NO: 41)
        FHYDRNNIAVGADESVVKEAHREVINSS

TEGLLLNIDKDIRKILSGYIVEIEDTE, (SEQ ID NO: 42)
        VEIEDTE, (SEQ ID NO: 43)
        KDIRKILSGYIVEIEDTE, (SEQ ID NO: 44)
        STEGLLLNIDKDIRKILSGYIVEIEDTE,
and
                                            (SEQ ID NO: 45)
        VGADESVVKEAHREVINSSTEGLLLNID

KDIRKILSGYIVEIEDTE.
```

Examples of linker peptides attached to the N-terminus of PAd4 are shown as follows where the linker peptide sequences are shown in bold:

```
                                            (SEQ ID NO: 46)
    FHYDRNNIAVGADESWKEAHREVINSSTEGLLLNIDKDIRK

ILSGYIVEIEDTEGLKEVINDRYDMLNISSLRQDGKTFIDF

KKYNDKLPLYISNPNYKVNVYAVTKENTIINPSENGDTSTN

GIKKILIFSKKGYEIG (SEQ ID NO: 47)
    VEIEDTEGLKEVINDRYDMLNISSLRQDGKTFIDFKKYNDK

LPLYISNPNYKVNVYAVTKENTIINPSENGDTSTNGIKKIL

IFSKKGYEIG
```

-continued (SEQ ID NO: 48)
KDIRKILSGYIVEIEDTEGLKEVINDRYDMLNISSLRQDGK

TFIDFKKYNDKLPLYISNPNYKVNVYAVTKENTIINPSENG

DTSTNGIKKILIFSKKGYEIG (SEQ ID NO: 49)
STEGLLLNIDKDIRKILSGYIVEIEDTEGLKEVINDRYDML

NISSLRQDGKTFIDFKKYNDKLPLYISNPNYKVNVYAVTKE

NTIINPSENGDTSTNGIKKILIFSKKGYEIG (SEQ ID NO: 50)
VGADESWKEAHREVINSSTEGLLLNIDKDIRKILSGYIVEI

EDTEGLKEVINDRYDMLNISSLRQDGKTFIDFKKYNDKLPL

YISNPNYKVNVYAVTKENTIINPSENGDTSTNGIKKILIFS

KKGYEIG

SNARE-Targeting Toxins (Including BTx and TTx)

Botulinum neurotoxin (BTx, also abbreviated as BoTX or BoNT) causes botulism which is characterized by descending flaccid paralysis as a result of inhibition of acetylcholine release at the neuromuscular junction. There are seven botulinum neurotoxin serotypes (A-G) produced by bacteria of the genus Clostridium. In addition, botulinum-like neurotoxin from non-Clostridium sp. Weissella oryzae SG25T has recently been discovered (Nature Scientific Repo. Rts|6: 30257|DOI: 10.1038/srep30257). BTx, with tetanus neurotoxin (TTx) produced by Clostridium tetani, make up the clostridial neurotoxin (CNT) family. TTx exhibits a high degree of sequence and structural homology to the BTxs, in particular to BTx/B, and is the causative agent of tetanus, which is characterized by spastic paralysis. Although differing in clinical manifestation, the fundamental mode of action—inhibition of neurotransmission—is common to all CNTs. Inhibition of neurotransmitter release by the CNTs is caused by the specific cleavage of a group of proteins integral to the exocytotic process, the SNARE proteins (soluble NSF-attachment protein receptors). Cleavage of one or more of the SNARE proteins leads to a block in the release of vesicular contents to the extracellular environment.

These SNARE targeting toxins share a similar basic CNT structure. CNTs are synthesized as single-chain polypeptides of ~150 kDa (a holotoxin) and are subsequently cleaved to form di-chain molecules made of the light (LC) and heavy chains (HC) that are linked by a single disulfide bond. The 50-kDa LC acts as a zinc-dependent endopeptidase. The heavy chain contains two functional domains, each of ~50 kDa. The N-terminal half ($H_N$) is the translocation domain, known to form ion channels in lipid bilayers, and the C-terminal half ($H_C$) is the ganglioside and protein binding domain, which has a key role in binding to the target cell membrane and internalization of the toxin molecules into cholinergic neurons. The three functional domains are structurally distinct and arranged in a linear fashion, such that there is no contact between the LC and HC domains. Overall, BTxs and TTx share ~35% sequence identity. The BTx catalytic LC domains share up to 36% sequence identity [2], and the LC domains of BTx/B and TTx have over 50% identity. (See Review "Botulinum and tetanus neurotoxins: structure, function and therapeutic utility" by K. Turton et al., Trends in Biochemistry, 2002, 27:552-558). Proteases suitable for cleaving the holotoxin to form a di-chain toxin include but are not limited to lysyl peptidase, trypsin, Enterokinase, clostripain, elastase, thermolysin, endoproteinase Lys-C, and endoproteinase Arg-C.

BTx, a neurotoxic protein produced by the bacterium Clostridium botulinum, is expressed as a large, single polypeptide molecule that has three distinct domains—a 50 kDa proteolytic N-terminal end (LC), a 50 kDa translocation domain located in the middle ($H_N$), and a 50 kDa host cell receptor binding C-terminal end ($H_C$). For the toxin to be functional, it must first be proteolytically cleaved to yield a di-chain protein consisting of a light chain (LC) and heavy chain (HC=$H_N H_C$), held together by a single disulfide bond. Proteolytic activation is crucial because after receptor binding and internalisation by endocytosis, subsequent acidification of the endosome is believed to cause a conformational change in the protein, leading to insertion of the $H_N$ domain into the endosomal membrane, formation of a translocation pore and delivery of the LC into the cytoplasm, where the disulphide bond is reduced and the LC released. The LC is a zinc-dependant protease with a highly specific substrate specificity. There are multiple BTx serotypes (A to G) and sub-serotypes (up to 12 for any given serotype). A serotype is based upon the ability of neutralising antibodies to neutralise botulinum neurotoxin. To date there are 7 serotypes of botulinum neurotoxin that have been identified, labelled A through to G (BTx/A to BTx/G). With the advent of next generation sequencing it has been identified that within serotypes there are subtypes of BoNT, these are defined as toxins with a sequence difference from other toxins of >2.5% at the protein level. To date over 40 subtypes of BoNT have been identified across the seven serotypes. Different serotypes have different substrate specificities—BTx/A and BTx/E cleave SNAP-25, serotypes/B, /D, /F and/G cleave synaptobrevin/VAMP. BTx/C cleaves both SNAP-25 and syntaxin 1A. These substrates are SNARE (SNAP (Soluble NSF Attachment Protein) Receptor) proteins that play a critical role in neurotransmitter release at the pre-synaptic nerve terminal and are critical to vesicular secretion from all eukaryotic cells.

The three domains of BTx (LC, $H_N$, $H_C$) are functionally and structurally distinct and the boundaries of each domain for each sub-serotype have been defined in the art. (See Review "Botulinum and tetanus neurotoxins:structure, function and therapeutic utility" by K. Turton et al., Trends in Biochemistry, 2002, 27:552-558; this literature reference is hereby incorporated by reference in its entirety). Each of the 50 kDa domains can function independently from each other, for example, in a chimeric protein. The $H_N$ domain has a "belt" region that wraps around the LC—this is believed to behave as a pseudo-inhibitor and have a chaperone function during LC translocation. The belt regions of the HN of BTx of various serotypes or of TTx are shown in Table 1.

Derivation of Botulinum Neurotoxin sequences

For BTx and TTx molecules with no published structure, the structural homology modelling tool LOOPP, available at the website of the loopp organization, was used to obtain a predicted structure based on BTx/A1 (3BTA.pdb). From this, as well as a sequence alignment of all BTx subserotypes by Clustal Omega, it was possible to determine the transition point between domains. Clustal BTx sequence alignments are provided at the end of this document for those BTx sero- and sub-types identified to date.

$LH_N$=Botulinum neurotoxin catalytic domain (LC)+translocation domain ($H_N$)

The $LH_N$ domain for each subserotype are known in the art, e.g., L $H_N$/A1 (residues 1-872) and $LH_N$/B1 (residues 1-859).

LC or L=Botulinum neurotoxin catalytic domain, (50 kDa, pI~6.3-8.1)

The LC domain for each subserotype has previously been defined in US 2007/0166332 (hereby incorporated by reference in its entirety), e.g., LC/A1 (residues 1-448) and LC/B1 (residues 1-441), and are summarized in Table 1 below.

TABLE 1

| Neurotoxin | Accession Number | LC | Belt | H$_N$ |
| --- | --- | --- | --- | --- |
| BoNT/A1 | A5HZZ9 | 1-448 | 449-546 | 449-872 |
| BoNT/A2 | X73423 | 1-448 | 449-546 | 449-872 |
| BoNT/A3 | DQ185900 | 1-444 | 445-542 | 445-869 |
| BoNT/A4 | EU341307 | 1-448 | 449-546 | 449-872 |
| BoNT/A5 | EU679004 | 1-448 | 449-546 | 449-872 |
| BoNT/A6 | FJ981696 | 1-448 | 449-546 | 449-872 |
| BoNT/A7 | JQ954969 | 1-448 | 449-546 | 449-872 |
| BoNT/A8 | KM233166 | 1-448 | 449-546 | 449-872 |
| BoNT/B1 | B1INP5 | 1-440 | 441-533 | 441-859 |
| BoNT/B2 | AB084152 | 1-440 | 441-533 | 441-859 |
| BoNT/B3 | EF028400 | 1-440 | 441-533 | 441-859 |
| BoNT/B4 | EF051570 | 1-440 | 441-533 | 441-859 |
| BoNT/B5 | EF033130 | 1-440 | 441-533 | 441-859 |
| BoNT/B6 | AB302852 | 1-440 | 441-533 | 441-859 |
| BoNT/B7 | JQ354985 | 1-440 | 441-533 | 441-859 |
| BoNT/B8 | JQ964806 | 1-440 | 441-533 | 441-859 |
| BoNT/C1 | P18640 | 1-441 | 442-542 | 442-867 |
| BoNT/CD | AB200360 | 1-441 | 442-542 | 442-867 |
| BoNT/DC | AB745660 | 1-445 | 446-538 | 446-863 |
| BoNT/D | P19321 | 1-445 | 446-538 | 446-863 |
| BoNT/E1 | Q00496 | 1-422 | 423-515 | 423-846 |
| BoNT/E2 | EF028404 | 1-422 | 423-515 | 423-846 |
| BoNT/E3 | EF028403 | 1-422 | 423-515 | 423-846 |
| BoNT/E4 | AB088207 | 1-422 | 423-515 | 423-846 |
| BoNT/E5 | AB037711 | 1-422 | 423-515 | 423-846 |
| BoNT/E6 | AM695759 | 1-422 | 423-515 | 423-846 |
| BoNT/E7 | JN695729 | 1-422 | 423-515 | 423-846 |
| BoNT/E8 | JN695730 | 1-422 | 423-515 | 423-846 |
| BoNT/E9 | JX424534 | 1-422 | 423-515 | 423-846 |
| BoNT/E10 | KF861917 | 1-422 | 423-515 | 423-846 |
| BoNT/E11 | KF861875 | 1-422 | 423-515 | 423-846 |
| BoNT/E12 | KM370319 | 1-425 | 426-518 | 426-849 |
| BoNT/F1 | Q57236 | 1-439 | 440-534 | 440-865 |
| BoNT/F2 | GU213209 | 1-439 | 440-534 | 440-865 |
| BoNT/F3 | GU213227 | 1-439 | 440-534 | 440-865 |
| BoNT/F4 | GU213214 | 1-439 | 440-534 | 440-865 |
| BoNT/F5 | GU213211 | 1-438 | 439-531 | 439-862 |
| BoNT/F6 | M92906 | 1-439 | 440-534 | 440-864 |
| BoNT/F7 | GU213233 | 1-431 | 432-524 | 432-856 |
| BoNT/G | Q60393 | 1-441 | 442-538 | 442-864 |
| BoNT/"H" | KGO15617 | 1-434 | 435-528 | 435-860 |
| TeNT | P04958 | 1-457 | 458-556 | 458-880 |

The above-identified reference sequences should be considered a guide, as slight variations may occur according to sub-serotypes. By way of example, US 2007/0166332 (hereby incorporated by reference in its entirety) cites slightly different clostridial sequences:

LC (has the catalytic or enzymatic activity against SNAREs):
Botulinum type A neurotoxin: amino acid residues M1-K448
Botulinum type B neurotoxin: amino acid residues M1-K441
Botulinum type C1 neurotoxin: amino acid residues M1-K449
Botulinum type D neurotoxin: amino acid residues M1-R445
Botulinum type E neurotoxin: amino acid residues M1-R422
Botulinum type F neurotoxin: amino acid residues M1-K439
Botulinum type G neurotoxin: amino acid residues M1-K446

Tetanus neurotoxin: amino acid residues M1-A457
H$_N$ domain:
Botulinum type A neurotoxin: amino acid residues A449-K871
Botulinum type B neurotoxin: amino acid residues A442-S858
Botulinum type C1 neurotoxin: amino acid residues T450-N866
Botulinum type D neurotoxin: amino acid residues D446-N862
Botulinum type E neurotoxin: amino acid residues K423-K845
Botulinum type F neurotoxin: amino acid residues A440-K864
Botulinum type G neurotoxin: amino acid residues S447-S863
Tetanus neurotoxin: amino acid residues S458-V879

Inhibitor Cysteine Knot (ICK) Toxins

As used herein, "inhibitor cysteine knot toxin" or "ICK toxin" refers to a toxin comprising the cysteine knot motif and which modulates the activity of a receptor and/or ion channel target. An inhibitor cysteine knot (ICK) is a protein structural motif containing three disulfide bridges. Along with the sections of polypeptide between them, two disulfides form a loop through which the third disulfide bond (linking the 3rd and 6th cysteine in the sequence) passes, forming a knot (thus the alternate name knottin). The motif is common in invertebrate toxins such as those from arachnids and molluscs. The motif is also found in some inhibitor proteins found in plants, but the plant and animal motifs are thought to be a product of convergent evolution. The ICK motif is a very stable protein structure which is resistant to heat denaturation and proteolysis. ICK peptide components of venoms target voltage-gated ion channels but members of the family also act as antibacterial and haemolytic agents. Plant ICK proteins are often protease inhibitors. ICK toxins are typically found in the venom of, e.g., cone snails, spiders, and scorpions. In some embodiments, ICK toxins are disulfide-containing peptide toxins. These disulfide-containing peptide toxins have between 30-70 amino acid residue. In some embodiments of any of the aspects described herein, the ICK toxin is a conotoxin, an agatoxin, a delta-palutoxin, a huwentotoxin or a ProTx II toxin.

Huwentotoxins are 7 types of ICK toxins (HWTX-1, HWTX-III, HWTX-IV, HWTX-X, HWTX-II, HWTX-VII, HWTX-VIII) from Chinese bird spiders that act against voltage-gated calcium channels.

Delta-palutoxins consist of 4 types of ICK Toxins (IT1, IT2, IT3, IT4) from spiders that act against voltage-gated sodium channels.

Conotoxins are small, 10-30 residue peptide ICK toxins from cone snails which act on voltage gated calcium and sodium channels. Some of these toxins are known to act extracellularly to modulate the activity of ion channels. Examples, W-conotoxin GVIA and W-conotoxin MVIIC.

As used herein, "conotoxin" refers to a toxin produced by the marine cone snail (e.g. the genus Conus). Some conotoxins can modulate ion channel activity. In some embodiments of all the aspects described herein, the conotoxin can be an ion channel modulator. Non-limiting examples of conotoxins can include δ-conotoxin (e.g. NCBI ID: AKD43185; SEQ ID NO: 10; for further discussion see, e.g., Leipold et al. FEBS Letters 2005 579:3881-4, which is incorporated by reference herein in its entirety), which is known to block voltage-dependent sodium channels, μ-conotoxin (e.g. Swiss-Prot ID: P15472.1; SEQ ID NO: 9; for further discussion, see, e.g., Li and Tomaselli. Toxicol.

2004 44:117-122; which is incorporated by reference herein in its entirety) which also blocks voltage-dependent sodium channels, or co-conotoxin M VII A (e.g. NCBI ID: ADB93081; SEQ ID NO: 8; for further discussion see, e.g., Nielsen et al. Molecular Recognition 2000 13:55-70, which is incorporated by reference herein in its entirety) (e.g. ziconotide), which is known to block N-type voltage-dependent calcium channels. Additional non-limiting examples of ICK toxins include, e.g., psalmotoxin-1, β-TRTX-Tp2a, and purotoxin-1 and are described in the literature (see, e.g., US Patent Publications 20120277166; 20120220539; 20120087969, 20050214903, and 20050143560; Craik et al. Toxicon 2001 39:43-60; Zhu et al. FASEB Journal 2003 17:1765-7; Daly and Craik. Current Opinion in Chemical Biology 2011 15:362-368; Grishin. European Journal of Biochemistry 1999 264: 276-280; Liang et al. Toxicon 2004 43:575-585; Kolmar FEBS Journal 2008 275: 2684-2690; Saez et al. Toxins 2010 2:2851-2871; Vetter et al. Amino Acids 2011 40:15-28; Alewood et al. Australian Journal of Chemistry 2003 56:769-774; King. Expert Opinion on Biological Therapy 2011 11:1469-1484; King et al. Toxicon 2008 52:264-276; Herzig et al. Nucl. Acids Res 2010; Szeto et al. FEBS Letters 2000 470: 203-299; and Bergeron and Bingham. Toxins 2012 4:1082-1119; each of which is incorporated by reference herein in its entirety).

The following are examples of cysteine knot sequences from ICK toxins that can attach to PAd4, mPA, PA$^{furin-}$, LFn, EFn, or other nociceptor-binding protein etc for delivery to nociceptor neurons.

```
W-conotoxin GVIA:
                                   (SEQ ID NO: 51)
CKSXGSSCSXTSYNCCRSCNXYTKRCY
(Modifications: X = Hyp, Disulfide bridge
between 1-16, 8-19, 15-26, Tyr-27 = C-terminal
amide)

W-conotoxin MVIIC:
                                   (SEQ ID NO: 52)
CKGKGAPCRKTMYDCCSGSCGRRGKC
(Modifications: Disulfide bridge between
1-16, 8-20, 15-26, Cys-26 = C-terminal amide)

W-Agatoxin IVA:
                                   (SEQ ID NO: 53)
KKKCIAKDYGRCKWGGTPCCRGRG CICSIMGTNCECKPRLIMEGLGLA
(Modifications: Disulfide bridge between
4-20, 12-25, 19-36, 27-34)

W-Agatoxin TK:
                                   (SEQ ID NO: 54)
EDNCIAEDYGKCTWGGTKCCRGRP CRCSMIGTNCECTPRLIMEGLSFA
(Modifications: Disulfide bridge between
4-20, 12-25, 19-36, 27-34)

Huwentotoxin IV:
                                   (SEQ ID NO: 55)
ECLEIFKACNPSNDQCCKSSKLVCSRKTRWCKYQI
(Modifications: Disulfide bridge: 2-17, 9-24,
16-31) (Modifications: Ile-35 = C-terminal
amide)

ProTx II:
                                   (SEQ ID NO: 56)
YCQKWMWTCDSERKCCEGMVCRLWCKKKLW
(Modifications: Disulfide bridge: 2-16, 9-21,
15-25)
```

The AB Toxins

The AB toxins are two-component protein complexes secreted by a number of pathogenic bacteria. They are named AB toxins due to their components: the "A" component is usually the "active" portion, and the "B" component is usually the "binding" portion. The "A" subunit possesses enzyme activity, where the catalytic domain or activity is found, and is transferred to the host cell following a conformational change in the membrane-bound transport "B" subunit. Among the toxins produced by certain *Clostridium* spp. are the binary exotoxins. These proteins consist of two independent polypeptides, which correspond to the A/B subunit moieties. The enzyme component (A) enters the cell through endosomes produced by the oligomeric binding/translocation protein (B), and prevents actin polymerisation through ADP-ribosylation of monomeric G-actin.

Examples of the "A" component of the binary toxin family include *C. perfringens* iota toxin Ia, *C. botulinum* C2 toxin CI, and *Clostridium difficile* ADP-ribosyltransferase. Other homologous proteins have been found in *Clostridium spiroforme*.

Examples of the of the "B" component (aka binding or transport component) binary toxin family include the *Bacillus anthracis* protective antigen (PA) protein described herein.

The Diphteria toxin (DT) also is an AB toxin. It inhibits protein synthesis in the host cell through phosphorylation of the eukaryotic elongation factor 2, which is an essential component for protein synthesis. The exotoxin A of *Pseudomonas aeruginosa* is another example of an AB toxin that targets the eukaryotic elongation factor 2.

Engineered Fusion Chimeric Proteins

BTx/TTx-PAd4/PA Fusion Proteins

Encompassed herein is a BTx or TTx fused to PAd4 to allow redirecting the action of TTx or one or another BTx to nociceptors via PAd4 binding. This encompasses a BTx in which the receptor binding domain is replaced by the receptor binding function of anthrax PA. In this construct we replace the C-terminal domain of BTx with the C-terminal receptor-binding domain of PA, PAd4 or PA63, or any PA fragment that can still bind the receptor ANTXR2. The BTx Light chain (enzymatic moiety is encompassed in the L-chain) and translocation domain ($H_N$) are linked to a receptor binding domain of PA. (See FIG. 7A) The C-terminal receptor-binding domain of PA, e.g., PAd4, will bind the construct/fusion protein to the ANTXR2 receptor on nociceptors and mediate trafficking to the endosome, at which point the BTx pore forming domain ($H_N$) would insert into the membrane and mediate translocation of the BTx L-chain to the cytosol, where it would cleave a SNARE and block neurotransmitter release. PA will target its receptor ANTXR2 (CMG2), and botulinum toxin $H_N$ domain will trigger pore-formation, translocation, and enzymatic moieties to block synaptic function. In some embodiments, this strategy requires botulinum or tetanus toxins to act both extracellularly and intracellularly. In some embodiments, this strategy requires the pre-activation of the toxins by Lys-C enzyme. This approach could apply similarly to the translocation domain in the heavy chain and light chain domains of tetanus toxin. (See FIG. 7B). Other proteases suitable for cleaving the junction include but are not limited to lysyl peptidase, trypsin, Enterokinase, clostripain, elastase, thermolysin, endoproteinase Lys-C, and endoproteinase Arg-C.

Accordingly, in one aspect, the engineered fusion protein comprises (a) PAd4 and (b) a BTx or TTx, wherein the PAd4 is fused or linked with the BTx or TTx. BTx or TTx are SNARE-targeting proteases. In one embodiment, the engineered fusion protein comprises (a) a PAd4 and (b) a SNARE-targeting protease, wherein the PAd4 is fused or linked with the SNARE-targeting protease. In one embodiment of the engineered fusion protein, the PAd4 domain is replaced with PA. In one embodiment, the PA is a variant PA mutant form that is resistant to cleavage by furin. In another aspect, we provide a composition comprising an engineered fusion protein comprises (a) a PAd4 and (b) a SNARE-targeting protease, wherein the PAd4 is fused or linked with the SNARE-targeting protease. In one embodiment, provided herein is a composition comprising an engineered fusion protein that comprises (a) PAd4 and (b) a BTx or TTx, wherein the PAd4 is fused or linked with the BTx or TTx. In another embodiment of the composition, the PAd4 domain of the engineered fusion protein includes PA, instead of PAd4. In one embodiment, the PA is a variant PA mutant form that is resistant to cleavage by furin. In another embodiment of any of the fusion polypeptide compositions described herein, the composition further comprises a pharmaceutically acceptable carrier or excipient.

In one embodiment of a fusion protein or composition described herein, the PAd4 or PA is linked with the TTx, BTx, or SNARE targeting protease with a peptide linker. In one embodiment of a fusion protein or composition, the linker peptide is 1-20 amino acids long. In one embodiment of a fusion protein or composition, the PAd4 or PA can replace the native receptor binding domain of the BTx or TTx neurotoxin, or is fused to a form of one of the BTx or TTx neurotoxins in which the native receptor-binding function had been ablated by mutation. In one embodiment of a fusion protein or composition, the TTx or BTx or SNARE-targeting protease comprises the entire protein, i.e., the holotoxin, wherein the native receptor-binding function had been ablated by mutation. In one embodiment of a fusion protein or composition, the TTx or BTx or SNARE-targeting protease consist essentially of the entire protein, i.e., the holotoxin, wherein the native receptor-binding function had been ablated by mutation. In one embodiment of a fusion protein or composition, the TTx or BTx or SNARE-targeting protease consists of the entire protein, i.e., the holotoxin, wherein the native receptor-binding function had been ablated by mutation. In one embodiment of a fusion protein or composition, the TTx or BTx or SNARE-targeting protease comprises, consist essentially of, or consists of only a part of the protein, rather than the holotoxin, e.g., one or two domains of the holotoxin protein. For example, the TTx or BTx or SNARE-targeting protease element can consist essentially of the LC and $H_N$ ($LH_N$) of a TTx, BTx or SNARE-targeting protease.

In another aspect, described herein is a fusion protein comprising (a) a botulinum neurotoxin (BTx) moiety comprising an N-terminal enzymatic domain (LC), and (b) an intermediate pore-forming/translocation-domain ($H_N$) of the BTx, and (c) a C-terminal receptor-binding domain of anthrax toxin protective antigen (PAd4 domain), wherein the parts (a)-(c) are linked together, e.g., linked together by linker peptides as described herein. In other words, an L $H_N$ of a BTx is fused to a PAd4 domain of PA by a linker peptide, wherein PAd4 is the C-terminal receptor-binding domain of anthrax toxin protective antigen. In one embodiment of a fusion protein, PA is included instead of the PAd4. In one embodiment, the PA is a variant PA mutant form that is resistant to cleavage by furin. In another aspect, described herein is a composition comprising a fusion protein comprising (a) a botulinum neurotoxin (BTx) moiety comprising an N-terminal enzymatic domain (LC), and (b) an intermediate pore-forming/translocation-domain ($H_N$) of the BTx, and (c) a C-terminal receptor-binding domain of anthrax toxin protective antigen (PAd4 domain), wherein the parts (a)-(c) are linked together. In one embodiment, the composition includes PA in place of the PAd4 domain in the fusion protein. In another embodiment, the PA is a variant PA mutant form that is resistant to cleavage by furin. In another embodiment of all the aspects described herein, a composition as described herein can further comprise a pharmaceutically acceptable carrier or excipient.

In one embodiment of a fusion protein or composition described herein, the BTx moiety is selected from the BTx light chain (LC) and heavy chain (HC) domains of any one of Clostridial BTx serotypes: BTx/A, BTx/B, BTx/C, BTx/D, BTx/E, BTx/F, BTx/G, and a non-Clostridial botulinum-like toxin.

In another aspect, described herein is a fusion protein comprising (a) an N-terminal enzymatic domain (LC) of tetanus neurotoxin (TTx), (b) a translocation/pore-forming domain ($H_N$) of TTx, and (c) a C-terminal receptor-binding domain of anthrax toxin protective antigen (PAd4 domain), wherein the parts (a)-(c) of fusion protein are linked together, e.g., operably linked together by linker peptides described herein. In other words, a $LH_N$ of a TTx is fused to to a PAd4 domain of PA by a linker peptide, wherein PAd4 is the C-terminal receptor-binding domain of anthrax toxin protective antigen. In one embodiment, described herein is a composition comprising a fusion protein comprising (a) an N-terminal enzymatic domain (LC) of tetanus neurotoxin (TTx), (b) a translocation/pore-forming domain ($H_N$) of TTx, and (c) a C-terminal receptor-binding domain of anthrax toxin protective antigen (PAd4 domain), wherein the parts (a)-(c) of the fusion protein are linked together. In some embodiments of all the aspects described herein, a composition as described herein can further comprise a pharmaceutically acceptable carrier or excipient. In another embodiment of a fusion protein or composition, the amino acid residues corresponding to the junction between the light chain of TTx and the heavy chain of TTx has been cleaved.

In one embodiment of a fusion protein or composition described herein, the amino acid residues corresponding to the LC junction with the HC of the BTx (serotypes included) or with TTx has been cleaved. In one embodiment of a fusion protein or composition described herein, the amino acid residues corresponding to the LC junction with the $H_N$ of the BTx (serotypes included) or TTx has been cleaved. The cleavage is carried out by a protease, such as but is not limited to, lysyl peptidase, trypsin, Enterokinase, clostripain, elastase, thermolysin, endoproteinase Lys-C, and endoproteinase Arg-C.

In one embodiment of any of the fusion proteins including a BTx moiety, the BTx moiety comprises a BTx or TTx enzymatic moiety and a translocation peptide/domain. In one embodiment, the enzymatic moiety and a translocation peptide/domain are linked by a linker peptide. In one embodiment of any of the fusion proteins including a BTx moiety comprising a BTx or TTx enzymatic moiety and a translocation peptide/domain, the enzymatic moiety and a translocation peptide/domain are separated by cleavage with a protease, e.g., Lys-C. In one embodiment of any of the fusion proteins including a BTx moiety comprising a BTx or TTx enzymatic moiety and a translocation peptide/domain linked by a linker peptide, the enzymatic moiety and a translocation peptide/domain are separated by cleavage, e.g., with a protease, e.g., Lys-C. Cleavage functions to activate the enzymatic moiety and a translocation peptide/domain in the fusion protein.

In one embodiment of any of the fusion proteins including a BTx moiety, wherein the BTx moiety comprises, consist essentially of, or consists of an L chain and a $H_N$ domain of the BTx, the S-S bridge between the L chain and the $H_N$ domain is not reduced. In one embodiment of any of the fusion proteins including a BTx moiety, wherein the BTx moiety comprises, consist essentially of, or consists of an L chain and not a $H_N$ domain of the BTx, the Cys residues in the L-chain and the belt corresponding to the N-terminal part of the BTx $H_N$ domain in the holotoxin, if present, can be changed to Ala, Ser, or Thr. In one embodiment of a fusion protein or composition described herein, the fusion protein further comprises at least one D-amino acid at the N-terminus of the fusion protein. The D-amino acid residues in the N-terminus serve to]decrease potential immunogenicity of the fusion protein.

In one embodiment of a fusion protein or composition described herein, the PAd4 is linked with the $LH_N$ with a peptide linker. In one embodiment, the linker peptide is 1-20 amino acids long. In one embodiment, about 1-60 consecutive amino acids from the N-terminal side of PA adjacent to the native PAd4 domain are further incorporated between the enzymatic/pore-forming domains of the fusion protein and the receptor binding PAd4 fusion partner. In one embodiment of fusion protein or composition, the PAd4 is located at the C-terminus of the fusion protein, and the $LH_N$ is at the N-terminus of the fusion protein. In one embodiment of a fusion protein or composition, the PAd4 is located at the N-terminus of the fusion protein. In another embodiment of a fusion protein or composition, the PAd4 is located both at the N-terminus and the C-terminus of the fusion protein, with the $LH_N$ (LC and $H_N$) sandwiched between two PAd4 domains. In another embodiment of a fusion protein or composition, there are more than one PAd4 domain in the fusion protein, e.g., two to ten PAd4 domains, one to five PAd4 domains, or two to five PAd4 domains. In one embodiment of a fusion protein or composition described herein, where multiple PAd4 domains are present, the multiple PAd4 domains are arranged in tandem. In one embodiment of a fusion protein or composition described herein, the multiple PAd4 domains are linked by peptide linkers. In one embodiment, the linker peptide is 1-20 amino acids long.

BTx/TTx-LFn/EFn Fusion Proteins

Native PA and a fusion protein comprising LFn fused to the catalytic domain of TTx or the catalytic domain of one or another of the various forms/serotypes of BTx, when used in combination can be directed to disrupt intracellular signaling in the nociceptor neurons or block synaptic transmission via neurotransmitters. (See FIGS. 8A and 8B) These constructs make use of the proteolytic activities of the catalytic domains to cleave SNARE proteins and thereby block neurotransmitter release without killing nociceptors or bystander cells. The TTx or one or another of the various forms/serotypes of BTx or CNT family of toxins are SNARE-targeting proteases. Accordingly, in one aspect, the engineered fusion protein comprises (a) an LFn and (b) a SNARE-targeting protease. In one embodiment, the engineered fusion protein comprises (a) an LFn and (b) a TTx or a BTx. In one embodiment of a fusion protein described herein, LFn is linked with the TTx, BTx, or SNARE targeting protease with a peptide linker. In one embodiment, provided herein is a composition comprising a engineered fusion protein comprising (a) an LFn and (b) a TTx or a BTx. It one embodiment, provided herein is a composition comprising an engineered fusion protein comprising (a) an LFn and (b) a SNARE-targeting protease. In one embodiment of all the aspects described herein, a fusion protein composition can further comprise a pharmaceutically acceptable carrier or excipient. In one embodiment of a fusion protein or composition described herein, LFn is linked with the TTx, BTx, or SNARE targeting protease with a peptide linker. In one embodiment, the linker peptide is 1-20 amino acids long. In one embodiment of an engineered fusion protein or composition described herein, the LFn is located at the N-terminus of the fusion protein. In one embodiment of an engineered fusion protein or composition described herein, the LFn is located at the C-terminus of the fusion protein. In one embodiment of an engineered fusion proteins described herein, the LFn is located both at the N-terminus and C-terminus of the fusion protein, with the TTx or BTx or SNARE-targeting protease sandwiched between the two LFns. In another embodiment of an engineered fusion protein or composition described herein, EFn is included instead of LFn. In one embodiment of a fusion protein or composition described herein, the TTx or BTx or SNARE-targeting protease comprises the entire protein, i.e., the holotoxin. In one embodiment of a fusion protein or composition, the TTx or BTx or SNARE-targeting protease consist essentially of the entire protein, i.e., the holotoxin. In one embodiment of a fusion protein or composition, the TTx or BTx or SNARE-targeting protease consists of the entire protein, i.e., the holotoxin. The fusion protein containing the holotoxin would need to be activated by proteolytic cleavage. Proteases suitable activating the holotoxin include but are not limited to lysyl peptidase, trypsin, Enterokinase, clostripain, elastase, thermolysin, endoproteinase Lys-C, and endoproteinase Arg-C. Proteases suitable for cleaving the junction include but are not limited to lysyl peptidase, trypsin, Enterokinase, clostripain, elastase, thermolysin, endoproteinase Lys-C, and endoproteinase Arg-C. In one embodiment of a fusion protein or composition, the TTx or BTx or SNARE-targeting protease comprises, consist essentially of, or consists of only a part of the protein, not the holotoxin, e.g., a domain of the holotoxin. For example, the TTx or BTx or SNARE-targeting protease can consist essentially of LC or LC and $H_N$ ($LH_N$) of the TTx or BTx or SNARE-targeting protease. For example, the TTx or BTx or SNARE-targeting protease can consist essentially of LC plus the belt segment located at the N-terminus of the holotoxin, the belt segment is found between the L chain and the $H_N$ chain. In one embodiment of a fusion protein or composition described, the BTx is selected from the BTx light chain (LC) and heavy chain (HC) domains of any one of serotypes: BTx/A, BTx/B, BTx/C, BTx/D, BTx/E, BTx/F, BTx/G, and a non-Clostridial botulinum-like toxin. In one embodiment of a fusion protein or composition described, the BTx is selected from BTx light chain (LC) and heavy chain (HC) domains from Table 1, as non-limiting examples, see SEQ. ID. NOS: 29-31.

Accordingly, in one aspect, provided herein is a fusion protein comprising (a) an enzymatic moiety of a botulinum neurotoxin (BTx) or an an enzymatic moiety of a tetanus neurotoxin (TTx), and (b)(i) the N-terminal domain (LFn) of anthrax toxin lethal factor; or (b)(ii) the N-terminal domain (EFn) of anthrax toxin edema factor. The enzymatic moiety of BTx is located at the N-terminal of botulinum neurotoxin holotoxin. In one embodiment, provided herein is a composition comprising a fusion protein comprising (a) an enzymatic moiety of a botulinum neurotoxin (BTx) or an an enzymatic moiety of a tetanus neurotoxin (TTx), and (b)(i) the N-terminal domain (LFn) of anthrax toxin lethal factor; or (b)(ii) the N-terminal domain (EFn) of anthrax toxin edema factor. In one embodiment of all the aspects described herein, the composition further comprises a pharmaceutically acceptable carrier or excipient.

In one aspect, provided herein is a fusion protein comprising: (a) a non-cytotoxic protease, which protease is capable of cleaving a SNARE protein in a nociceptor neuron; and (b) a protein capable of binding to an anthrax toxin protective antigen (PA) or a fragment thereof, wherein the PA or PA fragment binds a receptor expressed on the nociceptor neuron. In one embodiment, provided herein is a fusion protein comprising: (a) a non-cytotoxic protease, which protease is capable of cleaving a SNARE protein in a nociceptor neuron; and (b) a protein capable of binding to an anthrax toxin protective antigen (PA) or a PA fragment thereof, wherein the PA or PA fragment binds a receptor expressed on the nociceptor neuron. In some embodiments of all the aspects described herein, the composition as described herein further comprise a pharmaceutically acceptable carrier or excipient.

In one embodiment of a fusion protein or composition as described herein, the non-cytotoxic protease comprises a clostridial neurotoxin L-chain (LC) or a non-Clostridial botulinum-like toxin L-chain. In one embodiment of a fusion protein or composition, the clostridial neurotoxin L-chain (LC) or a non-Clostridial botulinum-like toxin L-chain is the enzymatic moiety. In one embodiment of a fusion protein or composition, the non-cytotoxic protease is selected from the group consisting of the BTx light chain domains of any one of BTx/A, BTx/B, BTx/C, BTx/D, BTx/E, BTx/F, BTx/G, a first non-Clostridial botulinum-like toxin, and a TTx. For example, the non-cytotoxic protease can be selected from the group consisting of BTx/A LC (a.a. 1-448), BTx/B LC (a.a. 1-441), BTx/C LC (a.a. 1-449), BTx/D LC (a.a. 1-442), BTx/E LC (a.a. 1-422), BTx/F LC (a.a. 1-436), and BTx/GLC (a.a. 1-442). For examples, the the BTx light chain can be selected from SEQ ID NO: 20-28 or Table 1 described herein.

In one embodiment of a fusion protein or composition, the clostridial neurotoxin is BTx or TTx.

In one embodiment of a fusion protein or composition, the PA-binding receptor expressed on the nociceptor neuron is ANTXR2 (CMG2).

In one embodiment of a fusion protein or composition, the protein capable of binding to PA is: (i) an anthrax toxin lethal factor (LF); or (ii) an anthrax toxin edema factor (EF).

In one embodiment of a fusion protein or composition, the PA binding domain of LF is the N-terminal domain of LF, (abbreviated as LFPABD or LFn).

In one embodiment of a fusion protein or composition, the PA binding domain of EF is the N-terminal domain of EF, (abbreviated as EFPABD or EFn).

In one embodiment of a fusion protein or composition, the LFn and EFn are domains that bind to oligomeric forms of PA63, the proteolytically activated form of anthrax PA. In one embodiment of a fusion protein or composition, the enzymatic domain is the LC of the BTx or TTx described herein. In one embodiment of a fusion protein or composition, the enzymatic domain is linked N-terminally or C-terminally or both N-terminally and C-terminally, to LFn or EFn. In one embodiment of a fusion protein or composition described herein, the LFn or EFn is linked with the enzymatic domain or the LC of the BTx or TTx by way of a peptide linker. In one embodiment, the linker peptide is 1-20 amino acids long. In one embodiment of an engineered fusion protein or composition described herein, the LFn or EFn is located at the N-terminus of the fusion protein. In one embodiment of an engineered fusion protein or composition described herein, the LFn or EFn is located at the C-terminus of the fusion protein. In one embodiment of an engineered fusion protein described herein, the LFn or EFn is located both at the N-terminus and C-terminus of the fusion protein, with the N-terminal enzymatic domain or the LC of the BTx or TTx sandwiched between the two LFns or EFns. In one embodiment of a fusion protein or composition described herein, the fusion protein can further comprise an amino acid sequence defining a belt corresponding to the N-terminal part of the BTx $H_N$ domain, wherein the $H_N$ domain is located at the C-terminal side of the BTx.

In one embodiment of a fusion protein or composition described herein, where the fusion protein comprises both the L and $H_N$ of a BTx or TTx, e.g., amino acids 1-872 (SEQ. ID. NO:29), the amino acid residues corresponding to the LC junction with the $H_N$ of BTx have been cleaved. Proteases suitable for cleaving the junction include but are not limited to lysyl peptidase, trypsin, Enterokinase, clostripain, elastase, thermolysin, endoproteinase Lys-C, and endoproteinase Arg-C. In one embodiment of any of the fusion proteins including a BTx moiety, wherein the BTx moiety comprises, consist essentially of, or consists of an L chain and a $H_N$ domain of BTx, the S-S bridge between the L chain and the $H_N$ domain is not reduced. In one embodiment of any of the fusion proteins including a BTx moiety, wherein the BTx moiety comprises, consist essentially of, or consists of an L chain and not a $H_N$ domain of BTx, the Cys residues in the L-chain and the belt corresponding to the N-terminal part of the BTx $H_N$ domain in the holotoxin, if present, have been changed to Ala, Ser, or Thr. In one embodiment of a fusion protein or composition described herein, the fusion protein further comprises at least one D-amino acid at the N-terminus of the fusion protein. The D-amino acid can be added by a Sortase reaction and are described in more detail in, e.g., International Patent Publication WO 2012/096926; U.S. Pat. No. 9,079,952, and US Patent Application Publications No: US 2013/0336974 and US 2015/0267186, each of which is incorporated by reference herein in its entirety.

In one embodiment of a fusion protein described herein that comprises an LFn or EFn, or LF or EF, these fusion proteins are used together with non-fused PA, or used together with a second fusion protein comprising (a) PA or PA fragment capable of binding LFn or EFn, and (b) a nociceptor neuron-binding protein, where the PA or PA fragment is fused to a nociceptor neuron-binding protein, and the nociceptor neuron-binding protein directs the toxin to nociceptor neurons to treat pain. In other words, in one embodiment, the fusion protein described herein comprising an LFn or EFn, or LF or EF is co-administered with a separate, non-fused PA polypeptide to a subject to treat pain. In another embodiment, the fusion protein described herein comprising an LFn or EFn, or LF or EF is co-administered with a second fusion protein to a subject to treat pain. The second fusion protein comprises (a) PA or a PA fragment capable of binding LFn or EFn, and (b) a nociceptor neuron-binding protein, where the PA or PA fragment is fused to a nociceptor neuron-binding protein, and the nociceptor neuron-binding protein directs the first fusion protein containing the toxin to nociceptor neurons to treat pain. In some embodiments of the second fusion protein, the PA is a variant (mPA), a modified or mutated form that does not bind the ANTXR2 receptor as described herein.

In one aspect, then, provided herein is a composition comprising:

(I) a first fusion protein comprising (a) a botulinum neurotoxin N-terminal enzymatic domain of a botulinum neurotoxin (BTx) moiety, the enzymatic domain, or tetanus neurotoxin (TTx) moiety, the enzymatic domain and (b)(i)

the N-terminal domain (LFn) of anthrax toxin lethal factor or (b)(ii) the N-terminal domain (EFn) of anthrax toxin edema factor, and (II) a second protein comprising (c) PA or PA fragment capable of binding LFn or EFn, and optionally (d) nociceptor neuron-binding protein, wherein the parts (a) and (b) are joined by a peptide linker, and wherein the parts (c) and (d) are also joined by a peptide linker, when part (d) is present. In one embodiment of the composition described, when the second protein is a fusion protein, the PA is a mutant variant of PA, an mPA.

In one embodiment of any of the toxin proteins, toxin fusion proteins or fusion protein compositions described herein, the composition further comprises a pharmaceutically acceptable carrier or excipient. In one embodiment of a composition comprising a linker peptide, the linker peptide is 1-20 amino acids long. An non-limiting example of a PA fragment capable of binding LFn or EFn is PA63. In one embodiment, the PA protein is an oligomeric PA. In one embodiment, the PA is a native anthrax toxin protective antigen (PA) protein. In one embodiment of a composition described herein, the PA is an oligomeric PA, which can be bound to the fusion protein. In one embodiment, this composition is useful for the treatment of pain such as nerve, joint, skin, visceral, bladder, or muscle pain, and diabetic neuropathic pain, cancer pain, fibromyalgia or other systemic pain disorders. In another embodiment, this composition is useful in the manufacture of medicament for the treatment of pain.

AB Toxin-LFn/EFn Fusion Proteins

Native PA and a fusion protein LFn-DT in combination can be directed to nociceptor neurons using the catalytic domain (aka the "A" component or "A" part) of diphtheria toxin (DT) to block protein synthesis. DT is an AB type toxin. Accordingly, in one aspectt, an engineered fusion protein comprises (a) an LFn and (b) a DT. In one embodiment, provided herein is a composition comprising an engineered fusion protein comprising (a) an LFn and (b) a DT. In one embodiment of a fusion protein, LFn is linked to the DT with a peptide linker. In one embodiment of a fusion protein, DT comprises both the A part and the B part found in SEQ. ID. NO: 2. In one embodiment, DT is DTA, comprising the A part (the active, catalytic/enzymatic domain) found in SEQ ID NO: 2. The DTA amino acid sequence includes residues 1-193 of the diphtheria toxin. In one embodiment of an engineered fusion protein comprising LFn, the LFn is located at the N-terminus of the fusion protein. In another embodiment of an engineered fusion protein comprising LFn, the LFn is located at the C-terminus of the fusion protein. In another embodiment of an engineered fusion protein comprising LFn, the LFn is located both at the N-terminus and C-terminus of the fusion protein, with DT sandwiched between the two LFns. In another embodiment, the LFn is replaced with EFn. Accordingly, in one embodiment, the engineered fusion protein comprises (a) an EFn and (b) a DT. In one embodiment, provided herein is a composition comprising an engineered fusion protein comprising (a) an EFn and (b) a DT. In some embodiments of all the aspects described herein, a composition as described herein can further comprise a pharmaceutically acceptable carrier or excipient.

In some embodiments of an engineered fusion protein or composition described herein, the catalytic domains of other intracellularly acting toxins, such as the plant toxin, ricin, or a disulfide-containing peptide toxin such as the ICK toxin could be fused to LFn in place of DT, giving an engineered fusion protein such as LFn-PE (PTx), LFn-conotoxin, LFn-ricin, LFn-Cholera toxin, LFn-agatoxin, LFn-delta-palutoxin, LFn-huwentotoxin, LFn-scorpion long-chain toxin, and/or LFn-Shiga toxin. Accordingly, in one embodiment of an engineered fusion protein or composition described herein, the LFn is linked with one other toxin, the other toxin being an intracellularly acting toxin. In one embodiment of a fusion protein or composition, the intracellularly acting toxin is selected from the group consisting of ricin, PE, conotoxin, Cholera toxin, agatoxin, delta-palutoxin, huwentotoxin, Shiga toxin, scorpion long-chain toxin, and scorpion short-chain toxin. In one embodiment of a fusion protein or composition, LFn is linked to the other toxin with a peptide linker. In another embodiment of an engineered fusion protein or composition described herein, the LFn is linked with at least one other toxin that is not derived from the anthrax toxin. In another embodiment of an engineered fusion protein or composition described herein, the LFn is linked to the A component or active, catalytic or enzymatic domain of an AB toxin, e.g., the A component residues between amino acid residues 364-613 of PE, the A part residues are 1-193 of the DT.

In one embodiment of an engineered fusion protein or composition described herein, LFn is located at the N-terminus of the fusion protein. In another embodiment of an engineered fusion protein or composition described herein, LFn is located at the C-terminus of the fusion protein. In one embodiment of an engineered fusion protein or composition described herein, LFn is located both at the N-terminus and C-terminus of the fusion protein, with the intracellularly acting toxin sandwiched between the two LFns. In another embodiment of an engineered fusion protein or composition described herein, EFn is included instead of LFn. For example, this provides an engineered fusion protein such as EFn-PE (PTx), EFn-conotoxin, EFn-ricin, EFn-Cholera toxin, EFn-agatoxin, EFn-delta-palutoxin EFn-huwentotoxin, or EFn-Shiga toxin.

In some embodiments of a fusion protein described herein comprising a LFn or EFn, or LF or EF, these fusion proteins are used together with non-fused or separate PA, or used together with a second fusion protein to treat pain. In other words, in one embodiment, the fusion protein described herein comprising an LFn or EFn, or LF or EF polypeptide is co-administered with PA to a subject to treat pain. In another embodiment, the fusion protein described herein comprising an LFn or EFn, or LF or EF is co-administered with a second fusion protein to a subject to treat pain. The second fusion protein comprises (a) PA or PA fragment capable of binding LFn or EFn, and (b) a nociceptor neuron-binding protein, where the PA or PA fragment is fused to a nociceptor neuron-binding protein, and the nociceptor neuron-binding protein directs the first fusion protein containing the toxin to nociceptor neurons to treat pain. In some embodiments of the second fusion protein, the PA is a mutant variant of the native PA (mPA), a form that does not bind the ANTXR2 receptor as described herein.

In one aspect, provided herein is a composition comprising:

(I) a first fusion protein comprising (a) a DT, an intracellularly acting toxin, an ICK toxin or a disulfide-containing peptide toxin, and (b)(i) the N-terminal domain (LFn) of anthrax toxin lethal factor or (b)(ii) the N-terminal domain (EFn) of anthrax toxin edema factor, and (II) a second protein comprising (c) PA or PA fragment capable of binding LFn or EFn, and optionally (d) a nociceptor neuron-binding protein, wherein the parts (a) and (b) are joined by a peptide linker, and wherein the parts (c) and (d) are also joined by a peptide linker when (d) is present. In one embodiment of the composition described, when the second protein is a fusion protein, the PA is a mutant variant of PA, a mPA.

In one embodiment of the composition, the linker peptides are 1-20 amino acids long. A non-limiting example of PA fragment capable of binding LFn or EFn is PA63. In one embodiment of a composition described herein which includes a PA protein, the PA protein is an oligomeric PA. In another embodiment, the PA is a native anthrax toxin protective antigen (PA) protein. In another embodiment, the oligomeric PA is bound to the fusion protein.

In one embodiment, compositions described herein which include toxins and/or toxin fusions are useful for the treatment of pain such as nerve, joint, skin, visceral, bladder, or muscle pain, diabetic neuropathic pain, cancer pain, fibromyalgia or other systemic pain disorders. In another embodiment, these compositions are useful in the manufacture of medicament for the treatment of pain.

AB toxin-PAd4/PA fusion proteins

In another aspect, provided herein is a fusion protein comprising an AB toxin fused to a linker peptide that is then linked to a PAd4 domain of PA, wherein PAd4 is the C-terminal receptor-binding domain of anthrax toxin protective antigen, wherein the fusion protein further comprises a translocation domain, a holotoxin or a mutant form of the holotoxin that has been modified (e.g., chemically) or mutated to negate the toxin receptor-binding function of the AB toxin. In one embodiment of a fusion protein, PA is used instead of a PAd4 domain. In one embodiment, the PA is a variant PA mutant form that is resistant to cleavage by furin, (PA$^{furin-}$).

In one embodiment, provided herein is a composition comprising an AB toxin fused to a linker peptide operably linked to a PAd4 domain of PA, wherein Pad4 is the C-terminal receptor-binding domain of anthrax toxin protective antigen, wherein the fusion protein further comprises a translocation domain, a holotoxin or a mutant form of the holotoxin that has been modified (e.g., chemically) or mutated to negate the toxin receptor-binding function of the AB toxin. In one embodiment of a fusion protein, PA is used instead of a PAd4 domain. In one embodiment, the PA is a variant PA mutant form that is resistant to cleavage by furin, (PA$^{furin-}$). In some embodiments of all the aspects described herein, a composition as described herein can further comprise a pharmaceutically acceptable carrier or excipient.

In one aspect, provided herein is a fusion protein comprising: (a) an AB toxin; (b) an anthrax toxin protective antigen (PA) or a PA fragment thereof, wherein the PA or fragment binds a receptor expressed on the nociceptor neuron; and (c) a translocation domain (TL) that is capable of translocating the protease from within an endosome, across the endosomal membrane and into the cytosol of the nociceptor neuron.

In one embodiment, provided herein is a composition comprising a fusion protein comprising: (a) an AB toxin; (b) an anthrax toxin protective antigen (PA) or a PA fragment thereof, wherein the PA or fragment binds a receptor expressed on the nociceptor neuron; and (c) a translocation domain (TL) that is capable of translocating the toxin, a protease, from within an endosome, across the endosomal membrane and into the cytosol of the nociceptor neuron. In some embodiments of all the aspects described herein, a composition as described herein can further comprise a pharmaceutically acceptable carrier or excipient.

In one embodiment of a fusion protein or composition described herein, the AB toxin is selected from Ricin toxin, Cholera toxin A-part and B-part; *Pseudomonas aeruginosa* Exotoxin A A-part and B-part; Shiga toxin A-part and B-part; and Diphtheria toxin A-part and B-part.

In one embodiment of a fusion protein or composition described herein, the PA-binding receptor expressed on the nociceptor neuron is ANTXR2 (CMG2).

In one embodiment of a fusion protein or composition described herein, the PA fragment is a C-terminal receptor-binding domain of PA, e.g., PA63, PAd2 and PAd4, or PAd4 as non-limiting examples.

In one embodiment of a fusion protein or composition described herein, the C-terminal receptor-binding domain of PA comprises, consist essentially of, or consists of a domain having the amino acid sequence of SEQ ID NO: 35-40. In one embodiment of a fusion protein or composition described herein, the PA fragment comprises, consist essentially of, or consists of a domain having the amino acid sequence of SEQ ID NO: 35-40.

In one embodiment of a fusion protein or a composition described herein, the C-terminal receptor-binding domain of PA comprises the PAd2 that is involved in membrane insertion and heptamerization. In one embodiment, PAd2 is located at residues 259-487 of PA (SEQ. ID. NO:1). In one embodiment of a fusion protein or a composition described herein, the C-terminal receptor-binding domain of PA comprises the PAd4 that is involved in host cell receptor binding. In one embodiment, PAd4 is located at residues 595-735 of PA (SEQ. ID. NO:1).

In one embodiment of a fusion protein or a composition described herein, the C-terminal receptor-binding domain of PA comprises, consists of, or consist essentially of the PAd2 and the PAd4domain of PA. For example, the C-terminal receptor-binding domain of PA comprises, consists of, or consist essentially of the residues 259-487 and 488-735 of PA (SEQ. ID. NO:1). Alternately, the C-terminal receptor-binding domain of PA comprises, consists of, or consist essentially of the residues 259-487 and 488-764 of PA (SEQ. ID. NO:1).

In one embodiment of a fusion protein or composition described herein, the PAd4 or PA fragment is linked with the AB toxin with a peptide linker. In one embodiment, the linker peptide is 1-20 amino acids long. In one embodiment of a fusion protein or composition described, approximately about 1-60 consecutive amino acids from the N-terminal side adjacent to the native PAd4 domain are further incorporated between the AB toxin and the PAd4. In one embodiment of a fusion protein or composition, the PAd4 is located at the C-terminus of the fusion protein, and the AB toxin is at the C-terminus of the fusion protein. In one embodiment of a fusion protein or composition, the PAd4 is located at the N-terminus of the fusion protein. In another embodiment of a fusion protein or composition, the PAd4 is located both at the N-terminus and the C-terminus of the fusion protein, with the AB toxin sandwiched between the two PAd4 domains. In another embodiment of a fusion protein or composition, there are more than one PAd4 domain in the fusion protein, e.g., 2-10 PAd4 domains, 1-5 PAd4 domains, 2-5 PAd4 domains, in tandem. In one embodiment of a fusion protein or composition described herein, where multiple PAd4 domains are present, the multiple PAd4 domains are arranged in tandem. In one embodiment of a fusion protein or composition described herein, the multiple PAd4 domains are linked by peptide linkers. In one embodiment of a fusion protein or composition described herein, the TL, translocation domain; a holotoxin; or a mutant form of the holotoxin is sandwiched between the AB toxin and PAd4 or PA fragment.

In one embodiment of a fusion protein or composition described herein, the AB toxin is selected from Ricin toxin, Cholera toxin A-part and B-part; *Pseudomonas aeruginosa* Exotoxin A A-part and B-part; Shiga toxin A-part and B-part; and Diphtheria toxin A-part and B-part. In one embodiment of a fusion protein or composition described herein, the TL is a clostridial neurotoxin translocation domain; a holotoxin; or a mutant form of the holotoxin that have been modified (e.g., chemically) or mutated to negate the toxin receptor-binding function of the AB toxin. In some embodiments of a fusion protein or composition described herein, the translocation domain is derived from BTx or TTx, e.g., the $H_N$ of BTx or TTx as disclosed in Table 1 (a clostridial neurotoxin translocation domain), or the translocation domain is derived from the anthrax toxin, e.g., LFn or EFn, or a polycationic sequence described herein. In some embodiments of the fusion proteins or compositions described herein, the holotoxin or a mutant form of the holotoxin is selected from Ricin toxin, Cholera toxin, PE; Shiga toxin, DT; and scorpion long—or short—chain toxins. In some embodiments of a fusion protein or composition described herein, the holotoxin or a mutant form of the holotoxin is PA, mPA, or PA$^{furin-}$, e.g., for an entire PA protein, the furin cleavage site comprising amino acid residues RKKR (residues 164-167 of SEQ ID NO: 1 minus the 29 aa signal peptide in SEQ ID NO:1) has been replaced by a furin-resistant amino acid sequence such as SSSR (SEQ ID NO: 32) or SSSS (SEQ ID NO: 33).

In some embodiments of a fusion protein described herein comprising a LFn or EFn, or LF or EF, these fusion proteins can be used together with non-fused or separate PA, or used together with a second fusion protein comprising (a) PA or PA fragment capable of binding LFn or EFn, and (b) a nociceptor neuron-binding protein, where the PA or PA fragment is fused to a nociceptor neuron-binding protein, and the nociceptor neuron-binding protein directs the toxin to nociceptor neurons to treat pain. In other words, in one embodiment, the fusion protein described herein comprising a LFn or EFn, or LF or EF is co-administered with PA alone to a subject to treat pain. In another embodiment, the fusion protein described herein comprising an LFn or EFn, or LF or EF is co-administered with a second fusion protein to a subject to treat pain. In such instances, the second fusion protein comprises (a) PA or PA fragment capable of binding LFn or EFn, and (b) a nociceptor neuron-binding protein, where the PA or PA fragment is fused to a nociceptor neuron-binding protein, and the nociceptor neuron-binding protein directs the first fusion protein containing the toxin to nociceptor neurons to treat pain. In some embodiments of the second fusion protein, the PA is a variant, modified (e.g., chemically) or mutated form (mPA) that does not bind the ANTXR2 receptor as described herein.

In one aspect, provided herein is a composition comprising:

(I) a first fusion protein comprising (a) AB toxin and (b)(i) the N-terminal domain (LFn) of anthrax toxin lethal factor or (b)(ii) the N-terminal domain (EFn) of anthrax toxin edema factor, and (II) a second protein comprising (c) PA or PA fragment capable of binding LFn or EFn, and optionally (d) nociceptor neuron-binding protein, wherein the parts (a) and (b) are joined by a peptide linker, and wherein the parts (c) and (d) are also joined by a peptide linker, when part (d) is present. In one embodiment of the composition described, when the second protein is a fusion protein, the PA is a mutant variant of PA, an mPA.

In one embodiment of the composition, the linker peptides are 1-20 amino acids long. An example of PA fragment capable of binding LFn or EFn is PA63. In one embodiment of any one composition described herein, the PA protein is an oligomeric PA. In one embodiment of any one composition described herein, the PA is a native anthrax toxin protective antigen (PA) protein. In one embodiment, the PA is the oligomeric PA. In one embodiment, the oligomeric PA is bound to the fusion protein. In one embodiment, this composition is useful for the treatment of pain such as nerve, joint, skin, visceral, bladder, or muscle pain, and diabetic neuropathic pain, cancer pain, fibromyalgia or other systemic pain disorders. In another embodiment, this composition is useful in the manufacture of medicament for the treatment of pain.

ICK Toxin-PAd4/PA Fusion Proteins

Also described herein is the engineering of anthrax toxin components with an inhibitor cysteine knot (ICK) toxin (e.g., a Conotoxin (CTx)). Because some ICK toxins are known to modulate the activity of ion channels, they have been used to treat pain but effects on cell-types other than nociceptors have hampered systemic treatment. If these toxins are fused to, or otherwise used to decorate, PAd4 or native PA, they can be targeted specifically to nociceptors. (See FIG. 9) Accordingly, in one aspect, an engineered fusion protein comprises (a) PAd4 or native PA or receptor-binding fragment thereof, and (b) an ICK toxin. In another embodiment, provided herein is a composition comprising an engineered fusion protein that comprises (a) PAd4 or native PA or receptor-binding fragment thereof, and (b) an ICK toxin. In some embodiments of all the aspects described herein, a composition as described herein can further comprise a pharmaceutically acceptable carrier or excipient. The PAd4 or native PA or receptor-binding fragment thereof can be fused to the ICK toxin by a peptide linker. In one embodiment, the linker peptide is 1-20 amino acids long.

ICK Toxin—LFn/EFn Fusion Proteins

Alternatively, the ICK toxin can be fused to LFn or EFn, or a fusion protein containing LFn or EFn, which can then be used in combination with PA, or a modified (e.g., chemically) or mutated form of PA, to affect nociceptors specifically. Accordingly, in one aspect, provided herein is an engineered fusion protein comprising (a) LFn and (b) an ICK toxin. In another aspect, provided herein is an engineered fusion protein comprising (a) EFn, and (b) an ICK-toxin. In another aspect, provided herein is an engineered fusion protein comprising (a) an ICKtoxin, and (b) a nociceptor neuron-binding protein. In one embodiment, provided herein is a composition comprising an engineered fusion protein comprising (a) LFn and (b) an ICK toxin. In another embodiment, provided herein is a composition comprising an engineered fusion protein comprising (a) EFn, and (b) an ICKtoxin. In another embodiment, provided herein is a composition comprising an engineered fusion protein comprising (a) an ICKtoxin, and (b) a nociceptor neuron-binding protein. The nociceptor neuron-binding protein helps direct the ICK toxin specifically to the nociceptor neuron. Similarly, the LFn or EFn, together with PA or variant forms of PA or receptor-binding fragments thereof, helps deliver the toxin directly to nociceptor neurons and into the cytosol. In one embodiment of an engineered fusion protein or composition described herein, the LFn, EFn, or nociceptor neuron-binding protein is fused to the ICK toxin by a peptide linker. In one embodiment, the linker peptide is 1-20 amino acids long. In one embodiment of an engineered fusion protein or composition described herein, the LFn, EFn, or nociceptor neuron-binding protein is located at the N-terminus of the fusion protein. In one embodiment of an engineered fusion protein or composition described herein, the LFn, EFn, or nociceptor neuron-binding protein is located at the C-terminus of the fusion protein. In another embodiment, the LFn, EFn, or nociceptor neuron-binding protein is located at both the N-terminus and the C-terminus of the fusion protein, with the ICKtoxin sandwiched between the LFn, EFn, or Nociceptor Neuron-Binding Protein.

Disulfide-Containing Peptide Toxin—LFn/EFn Fusion Proteins

In another aspect, provided herein is a fusion protein comprising (a) a disulfide-containing peptide toxin and (b)(i) the N-terminal domain (LFn) of anthrax toxin lethal factor or (b)(ii) the N-terminal domain (EFn) of anthrax toxin edema factor. In one embodiment, a composition is provided comprising a fusion protein comprising (a) a disulfide-containing peptide toxin and (b)(i) the N-terminal domain (LFn) of anthrax toxin lethal factor or (b)(ii) the N-terminal domain (EFn) of anthrax toxin edema factor. In one embodiment of all the aspects described herein, a composition as described herein can further comprise a pharmaceutically acceptable carrier or excipient.

In one embodiment of a fusion protein or composition described, the disulfide-containing peptide toxin is linked N-terminally or C-terminally or both N-terminally and C-terminally, or chemically crosslinked at one or more sites to LFn or EFn. In one embodiment of a fusion protein or composition described herein, the disulfide-containing peptide toxin is linked to LFn or EFn. LFn is a domain of anthrax toxin lethal factor which binds to oligomeric forms of PA63, the proteolytically activated form of anthrax PA. EFn is a domain of anthrax toxin edema factor, which domain binds to oligomeric forms of PA63. In one embodiment of a fusion protein or composition described herein, the disulfide-containing peptide toxin is an inhibitor cysteine knot toxin (ICK) toxin. In one embodiment of a fusion protein or composition described herein, the disulfide-containing peptide toxin is a conotoxin, an agatoxin, a delta-palutoxin, a huwentotoxin or a ProTx II toxin. In one embodiment of a fusion protein or composition, part (a) is fused with part (b) with a linker peptide. In one embodiment, the linker peptide is 1-20 amino acids long. In one embodiment of a fusion protein or composition described herein, the LFn or EFn is located at the N-terminus of the fusion protein. In one embodiment of a fusion protein or composition described herein, the LFn or EFn is located at the C-terminus of the fusion protein. In another embodiment of a fusion protein or composition, the LFn or EFn is located at both the N-terminus and the C-terminus of the fusion protein, with the disulfide-containing peptide toxin sandwiched between the two LFns or EFns.

In one aspect, described herein is a fusion protein comprising: (a) a disulfide-containing peptide toxin and (b) a protein capable of binding to an anthrax toxin protective antigen (PA) or a fragment thereof, wherein the fragment binds a receptor expressed on a nociceptor neuron. In one embodiment, the disulfide-containing peptide toxin is a channel blocking toxin having a cysteine-knot motif that is capable of blocking sodium or calcium or both sodium and calcium channels in a nociceptor neuron. In one embodiment, a composition is provided comprising a fusion protein comprising: (a) a disulfide-containing peptide toxin and (b) a protein capable of binding to an anthrax toxin protective antigen (PA) or a fragment thereof, wherein the PA fragment binds a receptor expressed on the nociceptor neuron. In some embodiments of all the aspects described herein, a composition as described herein can further comprise a pharmaceutically acceptable carrier or excipient.

In all of the above aspects and embodiments of a fusion protein or composition described, the disulfide-containing peptide toxin can comprise a cysteine knot motif.

In all of the above aspects and embodiments of a fusion protein or composition described, the disulfide-containing peptide toxin can be a conotoxin, an agatoxin, a delta-palutoxin, a huwentotoxin or a ProTx II toxin.

In all of the above aspects and embodiments of a fusion protein or composition described, the PA-binding receptor expressed on the nociceptor neuron can be ANTXR2 (CMG2).

In all of the above aspects and embodiments of a fusion protein or composition described, the protein capable of binding to PA can be: (i) an anthrax toxin lethal factor (LF); or (ii) an anthrax toxin edema factor (EF).

In all of the above aspects and embodiments of a fusion protein or composition described, the PA binding domain of LF is the N-terminal domain of LF, (abbreviated as LFPABD or LFn).

In all of the above aspects and embodiments of a fusion protein or composition described, the PA binding domain of EF is the N-terminal domain of EF, (abbreviated as EFPABD or EFn).

In some embodiments of a fusion protein described herein comprising a LFn or EFn, or LF or EF, these fusion proteins are used or administered together with unfused PA, or used or administered together with a second fusion protein comprising (a) PA or PA fragment capable of binding LFn or EFn, and (b) a nociceptor neuron-binding protein, where the PA or PA fragment is fused to a nociceptor neuron-binding protein, and the nociceptor neuron-binding protein directs the toxin to nociceptor neurons to treat pain. In other words, in one embodiment, the fusion protein described herein comprising an LFn or EFn, or LF or EF is co-administered with unfused or native PA to a subject to treat pain. In another embodiment, the fusion protein described herein comprising an LFn or EFn, or LF or EF is co-administered with a second fusion protein to a subject to treat pain. The second fusion protein comprises (a) PA or PA fragment capable of binding LFn or EFn, and (b) a nociceptor neuron-binding protein, where the PA or PA fragment is fused to a nociceptor neuron-binding protein, and the nociceptor neuron-binding protein directs the first fusion protein containing the toxin to nociceptor neurons to treat pain. In some embodiments of the second fusion protein, the PA is a modified (e.g., chemically) or mutated variant form (mPA), that does not bind the ANTXR2 receptor as described herein.

In one aspect, described herein is a composition comprising:

(I) a first fusion protein comprising (a) a disulfide-containing peptide toxin and (b)(i) the N-terminal domain (LFn) of anthrax toxin lethal factor or (b)(ii) the N-terminal domain (EFn) of anthrax toxin edema factor, and (II) a second protein comprising (c) PA or PA fragment capable of binding LFn or EFn, and optionally (d) nociceptor neuron-binding protein, wherein the parts (a) and (b) are joined by a peptide linker, and wherein the parts (c) and (d) are also joined by a peptide linker. In one embodiment of the composition described, when the second protein is a fusion protein, the PA is a mutant variant of PA, an mPA. In one embodiment of all the aspects described herein, a composition as described herein can further comprise a pharmaceutically acceptable carrier or excipient.

In one embodiment, the linker peptides are 1-20 amino acids long. A non-limiting example of a PA fragment capable of binding LFn or EFn is PA63. In one embodiment of a composition described herein, the PA protein is an oligomeric PA. In one embodiment of a composition described herein, the PA is a native anthrax toxin protective antigen (PA) protein. In one embodiment of a composition described herein, the PA is an oligomeric PA, which can be bound to the fusion protein. In one embodiment, such a composition is useful for the treatment of pain such as nerve, joint, skin, visceral, bladder, or muscle pain, and diabetic neuropathic pain, cancer pain, fibromyalgia or other systemic pain disorders. In another embodiment, this composition is useful in the manufacture of medicament for the treatment of pain.

Disulfide-Containing Peptide Toxin—PAd4/PA Fusion Proteins

In one aspect, provided herein is a fusion protein comprising (a) a disulfide-containing peptide toxin, and (b)(i) an anthrax toxin protective antigen (PA) or (b)(ii) an anthrax toxin protective antigen C-terminal receptor binding domain (PAd4); or (b)(iii) a nociceptor neuron-binding protein. (See FIG. 9) In one embodiment, a composition is provided comprising a fusion protein comprising (a) a disulfide-containing peptide toxin, and (b)(i) an anthrax toxin protective antigen (PA) or (b)(ii) an anthrax toxin protective antigen C-terminal receptor binding domain (PAd4); or (b)(iii) a nociceptor neuron-binding protein. In one embodiment of a fusion protein or composition, part (a) is fused to part (b) with a linker peptide. In one embodiment, the linker peptide is 1-20 amino acids long. In one embodiment of a fusion protein or composition described herein, the disulfide-containing peptide toxin is located at the N-terminus of the fusion protein. In one embodiment of a fusion protein or composition described herein, the disulfide-containing peptide toxin is located at the C-terminus of the fusion protein. In another embodiment, the PA, PAd4 or nociceptor neuron-binding protein is located at both the N-terminus and the C-terminus of the fusion protein, such that the disulfide-containing peptide toxin is sandwiched by the two PA, PAd4 or nociceptor neuron-binding proteins. In one embodiment of a fusion protein or composition described herein, the disulfide-containing peptide toxin is an inhibitor cysteine knot toxin (ICK) toxin. In one embodiment of a fusion protein or composition described herein, the disulfide-containing peptide toxin is a conotoxin, an agatoxin, a delta-palutoxin, a huwentotoxin or a ProTx II (PE) toxin. In one embodiment of a fusion protein or composition described herein, the fusion protein comprises a linker peptide between the PA, PAd4 or nociceptor-binding protein and the inhibitor cysteine knot toxin.

In another aspect, provided herein is a fusion protein comprising: (a) a disulfide-containing peptide toxin that is capable of blocking sodium or calcium or both sodium and calcium channels in a nociceptor neuron; and (b) a targeting moiety (TM) that is capable of binding to a binding site on the nociceptor neuron, wherein the nociceptor neuron expresses sodium or calcium or both sodium and calcium channels. In one embodiment, the disulfide-containing peptide toxin is a channel blocking toxin having a cysteine-knot motif that is capable of blocking sodium or calcium or both sodium and calcium channels in a nociceptor neuron. In another embodiment, provided herein is a composition comprising a fusion protein comprising: (a) a disulfide-containing peptide toxin that is capable of blocking sodium or calcium or both sodium and calcium channels in a nociceptor neuron; and (b) a targeting moiety (TM) that is capable of binding to a binding site on the nociceptor neuron, wherein the nociceptor neuron expresses the sodium or calcium or both sodium and calcium channels therein. In some embodiments of all the aspects described herein, a composition as described herein can further comprise a pharmaceutically acceptable carrier or excipient.

In all of the above aspects and embodiments of a fusion protein or composition described, the disulfide-containing peptide toxin can comprises a cysteine knot motif.

In all of the above aspects and embodiments of a fusion protein or composition described, the disulfide-containing peptide toxin can be, for example, a conotoxin, an agatoxin, a delta-palutoxin, a huwentotoxin or a ProTx II toxin.

In all of the above aspects and embodiments of a fusion protein or composition described, the TM can be selected, for example, from the group consisting of: (i) an anthrax toxin protective antigen (PA); (ii) a C-terminal receptor-binding domain of PA; or (iii) a PA fragment thereof, e.g., PAd4; or (iv) a nociceptor neuron-binding protein.

In one embodiment of each of the fusion protein or composition described, the TM, PA or C-terminal receptor-binding domain of PA, or a PA fragment or the nociceptor neuron-binding protein can bind the ANTXR2 (CMG2) receptor expressed on the nociceptor neuron. In one embodiment, the nociceptor neuron-binding protein is an antibody that specifically binds the ANTXR2 receptor. In one embodiment, the antibody is an antibody fragment that can bind the ANTXR2 receptor. In another embodiment, the antibody specifically binds to the NGF receptor, or an ion-channel protein present on nociceptor neurons. In some embodiments, the ion-channel protein is selected from Nav1.7, Nav1.8 or Nav1.9.

In all of the above aspects and embodiments of a fusion protein or composition described, the PA can be, for example, a mutant PA resistant to furin cleavage as described herein and known in the art. For example, the furin cleavage site comprising amino acid residues RKKR can be replaced by a furin-resistant amino acid sequence such as SSSR (SEQ ID NO: 32) or SSSS (SEQ ID NO: 33). RKKR are the residues 164-167 of SEQ ID NO: 1 minus the 29 amino acid signal peptide in SEQ ID NO:1.

In all of the above aspects and embodiments of a fusion protein or composition described, the C-terminal receptor-binding domain of PA can be, for example, PA63 or PAd4.

In all of the above aspects and embodiments of a fusion protein or composition described, the PAd4, the PA or the C-terminal receptor binding domain of PA can be modified or mutated, for example, to be resistant to cleavage by a protease. For example, one or more, up to and including each of the Lys residues at positions 594, 613, 633, 637, 653, 673, 679, 680, 684, 695, 703, 722, 723, 729, and 730 of SEQ ID NO: 1 (minus the 29 aa signal peptide in SEQ. ID. NO:1) can be replaced, for example, by Arg or His. In other words, one or more, up to and including each of the Lys residues in the PAd4 domain of the PA at positions 623, 642, 662, 666, 682, 702, 708, 709, 713, 724, 732, 751, 752, 758, and 759 in SEQ. ID. NO:1 can be replaced, for example, by Arg or His. Other examples of proteases which the PAd4, the PA or the C-terminal receptor binding domain of PA can be made resistant to but are not limited to are lysyl peptidase, trypsin, Enterokinase, clostripain, elastase, chymotrypsin, thermolysin, endoproteinase Lys-C, and endoproteinase Arg-C.

(mPA—Nociceptor-Binding Protein) Fusion Protein

Further described herein is the engineering of mPA, a variant modified (e.g., chemically) or mutated PA, so as to block its native receptor-binding function, as described, e.g., in U.S. Patent Application Publication No. 20150044210, incorporated herein by reference in its entirety) to be fused with molecules that can target nociceptor surface receptors or ion channels specifically. Accordingly, in one aspect, the engineered fusion protein comprises (a) an engineering mPA, and (b) a nociceptor-binding protein. In one embodiment, provided herein is a composition comprising a engineered fusion protein comprises (a) an engineering mPA, and (b) a nociceptor-binding protein. As examples, the nociceptor-binding protein can be a non-PA protein capable of binding the ANTRAX receptor on the nociceptor, or an antibody that binds a receptor or ion channel proteins on the cell surface of the nociceptor, or a protein ligand of a receptor on the cell surface of the nociceptor. As examples of the described engineered fusion protein, the mPA can be fused to NGF which targets and binds the NGF receptor, or mPA can be fused to antibodies or antibody fragments that specifically bind the Nav1.7 channel which creates sodium ion pores on nociceptors. Nav1.7 is usually expressed at high levels in two types of neurons, the nociceptive (pain) neurons at dorsal root ganglion (DRG) and trigeminal ganglion, and sympathetic ganglion neurons, which are part of the autonomic (involuntary) nervous system. When such a fusion protein comprising an mPA fused to nociceptor-binding protein is used in conjunction with another fusion protein comprising LFn or EFn or EF or LF, e.g., LFn fused to BTx, or LFn fused to TTx, or EFn fused to BTx, or EFn fused to the TTx, and when the mPA/LFn or EFn interaction occurs between the first fusion protein and the second fusion protein, the toxins are specifically directed to nociceptors by the nociceptor-binding protein of the fusion protein, and the toxin enters the cytosol by way of the mPA/LFn or EFn interaction.

Also provided herein are native PA or mutant PA (mPA, which denotes a variant PA modified (e.g., chemically) or mutated, that has its native receptor-binding function blocked), fused with molecules that can target nociceptor surface molecules in combination with LF or EF. In some embodiments, the fusion protein comprising an mPA fused to a nociceptor-binding protein is used specifically in conjunction with LF or EF. MAP kinases and their signaling pathways have been shown to be important for chronic pain development in mouse models. LF specifically inhibits MAP kinase signaling. In one embodiment, PA or mPA in combination with LF can be used to specifically target MAP kinase signaling in nociceptors to block pain. EF activates adenylate cyclase, which has also been linked to pain development. One can also target adenylate cyclase in pain by using PA or mPA in combination with EF.

Nav1.8 and Nav1.9 can also be used as target receptors for the nociceptor-binding protein of a fusion protein as described herein. In other embodiments of the engineered fusion protein described herein, the nociceptor-binding protein part of the fusion protein binds Nav1.8 or Nav1.9.

In any of the above aspects and embodiments of a fusion protein or composition described herein comprising an LFn or EFn, or LF or EF, and embodiments of a fusion protein or composition described herein comprising PA or PA fragments, an oligomeric form of PA formed from proteolytically activated PA (e.g., PA63) or mPA can be substituted for monomeric PA to increase avidity for receptor-bearing cells. The toxin effector moiety can be bound to the PA oligomeric form before administering, or injected separately.

In another aspect, described herein is an engineered fusion protein comprising:
a first domain comprising a polypeptide selected from the group consisting of:
  i) an anthrax toxin protective antigen (PA) moiety; or
  ii) a mutant anthrax toxin protective antigen (mPA) moiety that has been altered to block its native receptor-binding function, fused with a molecule capable of specifically targeting a nociceptor surface receptor or an ion channel receptor; and
a second domain comprising a polypeptide selected from the group consisting of:
  iii) an inhibitor cysteine knot (ICK) toxin (e.g., a Conotoxin (CTx)) optionally fused with an anthrax toxin translocation peptide;
  iv) an intracellularly acting toxin catalytic domain optionally fused with an anthrax toxin translocation peptide; or
  v) an anthrax toxin edema factor (EF) and/or anthrax toxin lethal factor (LF).

In one embodiment, the first domain and the second domain are fused together with a linker peptide. In one embodiment, the linker peptide is 1-20 amino acids long. In another embodiment, the linker peptide is stable in human serum for at least 1 minute.

In another embodiment, the first domain of the fusion protein serves as the targeting moiety (TM) of the fusion protein. The targeting moiety functions to direct the toxin to the nociceptor neuron via a cell surface marker enriched on the nociceptor. Non-limiting examples include, but are not limited to the abundant ANTXR2 receptor, NGF receptor, and/or the Nav1.7, Nav1.8, or Nav1.9 ion channels expressed on the surface of nociceptors. In one embodiment, the targeting moiety is one that is capable of binding to a binding site on the nociceptor neuron, which binding site is capable of undergoing endocytosis to be incorporated into an endosome within the nociceptor neuron, and wherein the nociceptor neuron expresses a SNARE protein which is subsequently proteolytically cleaved by the toxin of the second domain. In another embodiment, the targeting moiety is one that is capable of binding to a binding site on the nociceptor neuron, wherein the nociceptor neuron expresses sodium or calcium, or both sodium and calcium, ion channels (e.g., Nav1.7, Nav1.8, and Nav1.9 ion channels), or expresses ANTXR2 receptor or NGF receptor. In one embodiment, the binding site on the nociceptor neuron is, accordingly, ANTXR2 receptor, NGF receptor, Nav1.7, Nav1.8, or Nav1.9 ion channel.

The molecule capable of specifically targeting a nociceptor surface receptor, such as ANTXR2, or an ion channel receptor can be, e.g. a polynucleotide (e.g. an aptamer), a polypeptide, an antibody or antigen-binding fragment thereof, or an affibody. Affibody molecules are small proteins engineered to bind to a large number of target proteins or peptides with high affinity, imitating monoclonal antibodies, and are therefore a member of the family of antibody mimetics. In some embodiments, the molecule can be an antibody reagent, e.g. an antibody, monoclonal antibody, and/or antigen-binding portion thereof. Nociceptor surface receptors and/or nociceptor ion channel receptors are known in the art and are described in, e.g., Gohar. Modulator 2005 19:9-13; Bennaroch. Neurology 2015 10; Simon et al. The Nociceptive Membrane. Academic Press 2011; each of which is incorporated by reference herein in its entirety. Non-limiting examples of nociceptor surface receptors and/or nociceptor ion channel receptors include, e.g., NGF receptor (NGFR) (e.g. NCBI Gene ID: 4804) Nav1.7 (e.g. NCBI Gene ID: 6335), Nav1.8 (e.g. NCBI Gene ID: 6336), or Nav1.9 (e.g. NCBI Gene ID: 11280). All database sequences as referred herein and throughout the specification by sequence reference numbers are incorporated herein by reference in their entirety. The database reference numbers and sequences are as set forth in the databases on the filing date of this application. In one embodiment of any aspect involving a molecule capable of specifically targeting a nociceptor surface receptor, the molecule can be an antibody reagent that specifically binds to the NGF receptor and/or an antibody reagent that specifically binds to Nav1.7, Nav1.8 or Nav1.9. In some embodiments of any such aspect, in order to decrease off-target effects, multiple molecules capable of specifically targeting a nociceptor surface receptor or an ion channel receptor can be present in the same fusion protein and/or composition. The composition may also comprise two, three or more fusion proteins with different targeting moieties.

In one embodiment of any of the aspects described herein that involve a PA polypeptide, the pore-forming ability of the PA is desired to be targeted without using PA's ability to specifically bind ANTXR2. Accordingly, in one embodiment of any aspect involving a PA polypeptide, the composition can comprise a mutant anthrax toxin protective antigen (mPA) moiety that has been altered to block its native ANTXR2-binding function, fused with a molecule capable of specifically targeting a nociceptor surface receptor or an ion channel receptor. By way of non-limiting example, the PAd4 domain of PA can be deleted and/or altered to block the receptor-binding function. By way of further non-limiting example, mPA can comprise N682A and/or D683A (relative to the sequence of SEQ ID NO: 1 after the removal of the signal peptides at aa 1-29 residues) (see, e.g., Rosovitz M J, et al. 2003. Alanine-scanning mutations in domain 4 of anthrax toxin protective antigen (PAd4) reveal residues important for binding to cellular receptor and to a neutralizing monoclonal antibody. J. Biol. Chem. 278:30936-30944; which is incorporated by reference herein in its entirety). Various methods of altering polypeptide sequences and/or engineering proteins to comprise desired mutations are known in the art, and examples of them are described elsewhere herein.

In one embodiment of an engineered fusion protein described herein, the second domain of the fusion protein is the toxin effector moiety of the fusion protein. Depending upon the toxin protein, the toxin effector moiety functions to disrupt cell signaling on the nociceptors and/or blocks the release of neurotransmitters from the nociceptors or kills the nociceptors. The toxin effector moiety can be a non-cytotoxic protease that targets one or more SNARE proteins in vesicles (e.g., BTx and TTx), MAP kinases (EF and LF), etc.

As described herein, the inventors have discovered that the anthrax protective antigen can selectively target nociceptor neurons, binding to them and forming a pore capable of membrane transport. By coupling (either physically or functionally), an anthrax toxin protective antigen and an appropriate toxin, the nociceptor neurons can be killed and/or disabled or the pain signal can be blocked. Such compositions can be used, e.g. to treat pain, e.g., by disabling cell signaling or synaptic transmission in nociceptor neurons without substantial off-target effects on the rest of the nervous system. Moreover, use of this system allows a pain treatment without the debilitating side effect of substance abuse.

In certain aspects, the fusion proteins described herein can comprise a toxin. As used herein, "toxin" refers to a compound produced by an organism which causes or initiates the development of a noxious, poisonous or deleterious effect in a host cell presented with the toxin. Such deleterious conditions may include inhibition of key cellular functions, inhibition of cell metabolism, and/or cell death.

In some embodiments of all the aspects described herein involving a toxin, the toxin can be an inhibitor cysteine knot (ICK) toxin, e.g., a conotoxin (CTx).

In some embodiments of all the aspects described herein involving a toxin, the toxin can be an intracellularly acting toxin and/or an intracellularly acting toxin catalytic domain. Suitable bacterial toxins can include those with proteolytic activity against, e.g. SNARE proteins to prevent neurotransmitter release, or toxins that are cytotoxic to neurons. Non-limiting examples of suitable toxins can include bacterial toxins such as, e.g., diphtheria toxin (DTx) (e.g. NCBI Gene ID: 2650491; SEQ ID NO: 2); *Pseudomonas aeruginosa* exotoxin A (PTx or PE) (e.g. NCBI Gene ID: 877850; SEQ ID NO: 3); botulinium toxin (BTx) (e.g. NCBI Gene ID: 5398487; SEQ ID NO: 4); tetanus toxin (TTx) (e.g. NCBI Gene ID: 17583237; SEQ ID NO: 5) shiga toxin (e.g. *Shigella* Stx (e.g., GenBank accession numbers CAC05622 and CAC05623) Stx-1 (e.g. GenBank accession numbers 32400300 and 32400299) and/or Stx-2 (e.g. GenBank accession numbers 161511882 and 161511883), anthrax lethal toxin (lethal factor), and/or anthrax edema toxin (edema factor). A further non-limiting example of a suitable toxin is ricin toxin (e.g. NCBI Gene ID: 8287993).

In some embodiments of all the aspects described herein, the toxin can be an anthrax toxin edema factor (EF) and/or anthrax toxin lethal factor (LF).

In some embodiments of all the aspects described herein, multiple toxins can be present in the same fusion protein and/or composition as described herein.

In some embodiments, an effector moiety includes a toxin that comprises a translocation domain (TL) therein. In one embodiment, the TL is capable of translocating the fusion protein from within an endosome, across the endosomal membrane and into the cytosol of a nociceptor neuron. In some embodiments, the TL is the anthrax translocation signal peptide (LFn or EFn), also referred to herein as the anthrax toxin translocation peptide, a $H_N$ domain of BTx (serotypes included) or the $H_N$ domain of TTx, or a polycationic sequence such as KKK, KKKKKK (SEQ ID NO: 59), KKKKKKKK (SEQ ID NO: 60), HHH, HHHHHH (SEQ ID NO: 61), HHHHHHHH (SEQ ID NO: 62), RRR, RRRRRR (SEQ ID NO: 63), or RRRRRRRR (SEQ ID NO: 64). See US Patent Application Publication No: US 2003/0202989, which is incorporated here by reference in its entirety. In other embodiments, the TL is a clostridial neurotoxin translocation domain, $H_N$, derived from a clostridial neurotoxin (CNT) family member protein. This includes the BTx serotypes, TTx and the newly discovered non-Clostridial botulinum-like toxin.

In some embodiments of all the aspects described herein, the toxin can be fused with an anthrax toxin translocation peptide, e.g., to enable the PA and/or mPA to recognize and transport the toxin into the nociceptor cell.

In some embodiments of all the aspects described herein, a translocation domain can be a polycationic sequence. Such sequences are discussed in the art; see, e.g., Blanke, Proc. Natl. Acad. Sci. USA 93, pp. 8437-8442, 1996, and US Patent Application Publication No: US 2003/0202989, each of which is incorporated here by reference in its entirety. A polycationic sequence can comprise at least 2 cationic amino acids, e.g., lysine, arginine, or histidine. In some embodiments of all the aspects described herein that employ a polycationic sequence for translocation function, the polycationic sequence can comprise at least about 3, about 6, or about 8 cationic amino acids. In some embodiments of all the aspects described herein that employ a polycationic sequence for translocation function, the polycationic sequence can comprise the sequence KKK, KKKKKK (SEQ ID NO: 59), or KKKKKKKK (SEQ ID NO: 60). In some embodiments of all the aspects described herein that employ a polycationic sequence for translocation function, the polycationic sequence can comprise the sequence HHH, HHHHHH (SEQ ID NO: 61), or HHHHHHHH (SEQ ID NO: 62). In some embodiments of all the aspects described herein that employ a polycationic sequence for translocation function, the polycationic sequence can comprise the sequence RRR, RRRRRR (SEQ ID NO: 63), or RRRRRRRR (SEQ ID NO: 64).

In some embodiments of toxin fusion proteins as described herein, a first fusion protein domain comprises an anthrax toxin protective antigen (PA) moiety and a second fusion protein domain comprises an anthrax toxin translocation peptide fused with an inhibitor cysteine knot (ICK) toxin (e.g., a Conotoxin (CTx)). In other embodiments of a first fusion protein domain, the the anthrax toxin translocation peptide is replaced with a clostridial neurotoxin translocation domain, $H_N$, or a polycationic sequence.

In some embodiments of toxin fusion proteins as described herein, the first domain comprises a mutant anthrax toxin protective antigen (mPA) moiety that has been altered to block its native receptor-binding function, fused with a molecule capable of specifically targeting a nociceptor surface receptor or an ion channel receptor, and the second domain comprises an anthrax toxin translocation peptide fused with an intracellularly-acting toxin catalytic domain. In other embodiments of a first fusion protein domain, the the anthrax toxin translocation peptide is replaced with a clostridial neurotoxin translocation domain, $H_N$, or a polycationic sequence.

In some embodiments of toxin fusion proteins as described herein, a first domain comprises: i) an anthrax toxin protective antigen (PA) moiety; or ii) a mutant anthrax toxin protective antigen (mPA) moiety that has been altered to block its native receptor-binding function, fused with a molecule capable of specifically targeting a nociceptor surface receptor or an ion channel receptor; and a second domain comprises an anthrax toxin edema factor (EF) and/or anthrax toxin lethal factor (LF).

In another aspect, described herein is an engineered fusion protein comprising an anthrax toxin Protective-Antigen (PA) moiety or its receptor binding domain (Pad4) fused with an inhibitor cysteine knot (ICK) toxin (e.g., a Conotoxin (CTx)).

In order to form a functional pore, PA and/or mPA must oligomerize. Accordingly, in some embodiments of any of the aspects described herein that involve a PA polypeptide, the PA or mPA can in an oligomeric form. In some embodiments of any of the aspects described herein that involve a PA polypeptide, the PA or mPA can be in an oligomeric form prior to administration to a subject and/or prior to coming in contact with a nociceptor cell.

Linkers

A linker may be used to connect two or more domains or portions of a polypeptide as described herein. Linker molecules ("linkers") may be peptides, which consist of one to multiple amino acids, or non-peptide molecules. Examples of peptide linker molecules useful in the polypeptides described herein include glycine-rich peptide linkers (see, e.g., U.S. Pat. No. 5,908,626), wherein more than half of the amino acid residues are glycine. Preferably, such glycine-rich peptide linkers consist of about 20 or fewer amino acids.

Linker molecules may also include non-peptide or partial peptide molecules. For instance, the peptides can be linked to peptides or other molecules using well known cross-linking molecules such as glutaraldehyde or EDC (Pierce, Rockford, Ill.).

In some embodiments of the fusion proteins described herein, the various domains and moieties, TM, TL, PAd4, PA fragments, LF, LFn, EF, EFn, mPA, various types of toxin (BTx including the various serotypes, TTx, AB toxins, Ricin toxin, Cholera toxin, PE, Shiga toxin, DT, conotoxin, an agatoxin, a delta-palutoxin, a huwentotoxin or a ProTx II toxin) etc. are joined together in the respective fusion protein with a linker peptide. Examples of linker peptide include, but are not limited to:

```
                                    (SEQ ID NO: 65)
FHYDRNNIAVGADESVVKEAHREVINSS

TEGLLLNIDKDIRKILSGYIVEIEDTE;

(SEQ ID NO: 66)
VEIEDTE, (SEQ ID NO: 67)
KDIRKILSGYIVEIEDTE;

(SEQ ID NO: 68)
STEGLLLNIDKDIRKILSGYIVEIEDTE, (SEQ ID NO: 69)
EVKQENRLLNESES;
and (SEQ ID NO: 70)
VGADESVVKEAHREVINSSTEGLLLN

IDKDIRKILSGYIVEIEDTE.
```

Flexible linkers are generally composed of small, non-polar or polar residues such as Gly, Ser and Thr. In one embodiment of a fusion protein described herein that includes a linker, the linker peptide comprises at least one amino acid that is Gly or Ser. In one embodiment of a fusion protein described herein that includes a linker, the linker is a flexible polypeptide between 1 and 25 residues in length. Common examples of flexible peptide linkers include $(GGS)_n$, where n=1 to 8, or (Gly4Ser)n repeat where n=1-8 (SEQ ID NO:57), preferably, n=3, 4, 5, or 6, that is (Gly-Gly-Gly-Gly-Ser)n, where n indicates the number of repeats of the motif. For example, the flexible linker is $(GGS)_2$, GGSGGS (SEQ ID NO: 58).

In one embodiment of a fusion protein described herein that includes a linker, the linker peptide is 1-20 amino acids long. In one embodiment, the linker peptide is stable in human serum for at least 1 minute. In one embodiment, the linker peptide does not comprise Lys and/or Arg.

In one embodiment of a fusion protein including a linker and PAd4, the linker appended to the N-terminus of PAd4 is less than 20 amino acids in length and is comprised of at least three amino acids Gly, Ser, and Ala.

In one embodiment of a fusion protein including a linker and PAd4, the linker appended to the N-terminus of PAd4 is less than 20 amino acids in length and is comprised of at least four amino acids Gly, Ser, Thr, and Ala.

In one embodiment of a fusion protein including a linker, the linker is stable in human serum for at least 1 minute and is less than 20 amino acids in length.

Bifunctional cross-linking molecules are linker molecules that possess two distinct reactive sites. For example, one of the reactive sites of a bifunctional linker molecule may be reacted with a functional group on a peptide to form a covalent linkage and the other reactive site may be reacted with a functional group on another molecule to form a covalent linkage. General methods for cross-linking molecules have been reviewed (see, e.g., Means and Feeney, Bioconjugate Chem., 1: 2-12 (1990)).

Homobifunctional cross-linker molecules have two reactive sites which are chemically the same. Examples of homobifunctional cross-linker molecules include, without limitation, glutaraldehyde; N,N'-bis(3-maleimido-propionyl-2-hydroxy-1,3-propanediol (a sulfhydryl-specific homobifunctional cross-linker); certain N-succinimide esters (e.g., discuccinimyidyl suberate, dithiobis(succinimidyl propionate), and soluble bis-sulfonic acid and salt thereof (see, e.g., Pierce Chemicals, Rockford, Ill.; Sigma-Aldrich Corp., St. Louis, Mo.).

Preferably, a bifunctional cross-linker molecule is a heterobifunctional linker molecule, meaning that the linker has at least two different reactive sites, each of which can be separately linked to a peptide or other molecule. Use of such heterobifunctional linkers permits chemically separate and stepwise addition (vectorial conjunction) of each of the reactive sites to a selected peptide sequence. Heterobifunctional linker molecules useful in the invention include, without limitation, m-maleimidobenzoyl-N-hydroxysuccinimide ester (see, Green et al., Cell, 28: 477-487 (1982); Palker et al., Proc. Natl. Acad. Sci (USA), 84: 2479-2483 (1987)); m-maleimido-benzoylsulfosuccinimide ester; maleimidobutyric acid N-hydroxysuccinimide ester; and N-succinimidyl 3-(2-pyridyl-dithio)propionate (see, e.g., Carlos et al., Biochem. J., 173: 723-737 (1978); Sigma-Aldrich Corp., St. Louis, Mo.).

PAd4 domains—In one embodiment of a fusion protein comprising a PAd4 domain described herein, the fusion protein comprises about 2-10 PAd4 domains in tandem, or 1-5 PAd4 domains, or 2-5 PAd4 domains, etc., in tandem. In one embodiment of a fusion protein, approximately 1-60 consecutive amino acids from the N-terminal side of PA adjacent to the native PAd4 domain are further incorporated between the toxin moiety (e.g., BTx moiety, TTx moiety, disulfide-containing peptide toxin moiety, AB toxin moiety, etc., and the PAd4 domain(s).

In one embodiment of a fusion protein comprising a PAd4 domain or a composition comprising a PAd4 domain described herein, the fusion protein further comprises domain 2 of PA (PAd2). The PAd2 domain can be found at amino acid residues 259-487 of the PA sequence (SEQ. ID. NO:1). In one embodiment of a fusion protein or a composition described herein, the fusion protein comprises, consists of, or consist essentially of the PAd2 and the PAd4domain of PA. For example, the fusion protein comprises, consists of, or consist essentially of the residues 259-487 and 488-764 of PA (SEQ. ID. NO:1).

In one embodiment of a fusion protein comprising a PAd4 domain or a composition comprising a PAd4 domain described herein, the fusion protein further comprises a variant form of intact PA in which the furin cleavage site has been ablated by mutation (M), so that the PA is resistant to proteolytic activation and hence does not oligomerize.

In one embodiment of a fusion protein comprising a PA, or a PA fragment thereof, or a C-terminal receptor binding domain of PA that binds ANTXR2 as described herein, or a composition comprising a fusion protein including a PA or PA fragment thereof, or a C-terminal receptor binding domain of PA that binds ANTXR2 as described herein, the PA or PA fragment thereof, or a C-terminal receptor binding domain of PA that binds ANTXR2, the PA-derived protein is modified or mutated.

In one embodiment, the PAd4, the PA or PA fragment thereof, or a C-terminal receptor binding domain of PA that binds ANTXR2 is resistant to cleavage by a protease, such as Lys C. Other examples of proteases that the PA can be made resistant to include but are not limited to lysyl peptidase, trypsin, Enterokinase, clostripain, elastase, thermolysin, endoproteinase Lys-C, and endoproteinase Arg-C.

In one embodiment of any fusion protein described as including a PAd4 domain, one or more of the Lys residues in the PAd4 domain at positions 594, 613, 633, 637, 653, 673, 679, 680, 684, 695, 703, 722, 723, 729, and 730 has been replaced by Arg or His, wherein the numbering refers to that of SEQ ID NO:1 after minusing the 29 aa signal peptide in SEQ. ID. NO:1. This includes any C-terminal receptor binding domain of a PA.

In one embodiment of any fusion protein described as including a PAd4 domain, one or more of the Lys residues in the PAd4 domain at positions 623, 642, 662, 666, 682, 702, 708, 709, 713, 724, 732, 751, 752, 758, and 759 in SEQ. ID. NO: 1 has been replaced, for example, by Arg or His.

In one embodiment, one or more of the Asn residues in the PAd4 domain at position 630, 742, and/or 748 of SEQ ID NO: 1 has been replaced by Asp.

PA In one embodiment of a fusion protein described herein comprising a PA domain or a composition comprising such a fusion protein, the PA is a variant or mutant form of PA that is resistant to furin cleavage ($PA^{furin-}$) or is mutated to block its native receptor-binding function (mPA). In one embodiment, the PA furin cleavage site comprising amino acid residues RKKR has been replaced by a furin-resistant amino acid sequence. RKKR are the residues 164-167 of SEQ ID NO: 1 minus the 29 amino acid signal peptide in SEQ ID NO:1. In one embodiment, the furin-resistant amino acid sequence is SSSR (SEQ ID NO: 32) or SSSS (SEQ ID NO: 33). In one embodiment, PA has one or two mutations that block the receptor-binding function of PA, N711A and/or D712A; the amino acid numbering is according to SEQ ID NO:1, the entire PA including the 29 residue signal peptide. The two mutations are N682A/D683A in the PA sequence numbered without the 29 residue signal peptide.

In one embodiment of a fusion protein described herein comprising a PA, the PA is modified or mutated, for example, to be resistant to cleavage by a protease, such as Lys-C or furin. For example, the one or more of the Lys residues in the PAd4 domain of the PA at positions 594, 613, 633, 637, 653, 673, 679, 680, 684, 695, 703, 722, 723, 729, and 730 can be replaced by Arg or His. (SEQ ID NO: 1 after the removal of the N-terminal the 29 aa signal peptide) (This sequence is P13423 with the 29 aa signal peptide). In other words, one or more, up to and including each of the Lys residues in the PAd4 domain of PA, at positions 623, 642, 662, 666, 682, 702, 708, 709, 713, 724, 732, 751, 752, 758, and 759 in SEQ. ID. NO:1 can be replaced, for example, by Arg or His.

In one embodiment of a fusion protein described herein, the fusion protein further comprises at least one D-amino acid at the N-terminus of the fusion protein.

In one embodiment of a fusion protein described herein, the fusion protein is glycosylated.

In one embodiment of a fusion protein described herein, the fusion protein is non-glycosylated.

Production of Engineered Fusion Protein

The various polypeptides (e.g. fusion polypeptides or first or second polypeptides) described herein can be purified from natural sources and/or produced recombinantly using any method that is known in the art. For examples, the engineered fusion proteins described herein can be produced by recombinant molecular cloning that is known in the art. By way of non-limiting example, PA can be purified from the Sterne strain of *B. anthracis* or synthesized by other known means. In *B. anthracis*, the gene for PA is located on a plasmid referred to as pXO1 (Milne et al., 1994, J. of Biol. Chem. 269(32):20607-20612; which is incorporated by reference herein in its entirety). Methods of recombinant expression are well-known in the art. In some embodiments, PA63 can be substituted for full-length PA. The PA63 fragment may be purified from trypsin-treated PA by anion exchange chromatography (Milne et al., 1994, supra). PA encoding gene has been cloned and sequenced (Vodkin, et al., 1983, Cell 34:693-697; which is incorporated by reference herein in its entirety) and may be used to obtain purified PA polypeptide.

The fusion of two polypeptide moieties is effected either by recombinant DNA technology, or using a sortase reaction (see e.g., WO 2012096926, WO2013177231, WO2014088928; U.S. Pat. No. 9,079,952, and US Patent Application Publications No: US 2013/0336974 and US 2015/0267186, each of which is incorporated by reference herein in its entirety.), or other method of chemical linking/ biochemical conjugation that is known in the art.

Recombinant DNA and molecular biology techniques can be use to produce the described engineered fusion protein. The process of cloning the cDNA segments and sequences that encode the respective protein domains and moieties, e.g., TM, TL, PAd4, PA fragments, LF, LFn, EF, EFn, mPA, various types of toxin (BTx, TTx, AB toxins, Ricin toxin, Cholera toxin, PE, Shiga toxin, DT, conotoxin, an agatoxin, a delta-palutoxin, a huwentotoxin or a ProTx II toxin) etc., the production of DNA sequences encoding the various peptide linkers, the ligation of different cDNA sequences, the construction of the expression vectors (e.g., plasmid, bacteriophage, phagmid, or viral vector) for the various engineered fusion proteins, and the protein expression and purification of various recombinant engineered fusion proteins can be performed by conventional recombinant molecular biology and protein biochemistry techniques such as described in Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005, which are all incorporated by reference herein in their entireties.

The engineered fusion proteins and peptide linkers can be produced by any method known in the art for the synthesis of a fusion protein, in particular, by chemical synthesis or by recombinant expression techniques.

The engineered fusion proteins of the invention can be produced by any method known in the art for the expression and purification of recombinant proteins.

Recombinant expression of engineered fusion proteins requires construction of an expression vector containing a polynucleotide that encodes the engineered fusion protein described herein. The polynucleotide can further sequences that encode additional amino acids for the purpose of protein purification or identifying or locating the engineered fusion protein in the expression system or during the protein purification process. Once a polynucleotide encoding an engineered fusion protein has been obtained, the vector for the production of the fusion protein can be produced by recombinant DNA technology using techniques well known in the art. Thus, methods for preparing a protein by expressing a polynucleotide containing a fusion protein-encoding nucleotide sequence are described herein. Methods which are well known to those skilled in the art can be used to construct expression vectors containing protein coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding a fusion protein of the invention, operably linked to a promoter. The expression vector is transferred to a host cell by conventional techniques and the transfected cells are then cultured by conventional techniques to produce an engineered fusion protein of the invention. Thus, the invention includes host cells containing a polynucleotide encoding a fusion protein, operably linked to a heterologous promoter.

A variety of host-expression vector systems can be utilized to express the fusion proteins of the invention. Such host-expression systems represent vehicles by which the coding sequences of interest can be produced and subsequently purified, but also represent cells which can, when transformed or transfected with the appropriate nucleotide coding sequences, express the fusion protein of the invention in situ. These include but are not limited to microorganisms such as prokaryotic bacteria (e.g., attenuated *Bacillus anthracis* strains, *E. coli*, *B. subtilis*) transformed with recombinant bacteriophage DNA, plasmid DNA or cosmid DNA expression vectors containing the fusion protein coding sequences; yeast (e.g., *Saccharomyces*, *Pichia*) transformed with recombinant yeast expression vectors containing the fusion protein coding sequences; insect cell systems infected with recombinant virus expression vectors (e.g., baculovirus) containing the fusion protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the fusion protein coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *E. coli* and attenuated *B. anthracis* strains are especially useful for the expression of the fusion proteins described herein.

In bacterial systems, a number of expression vectors can be advantageously selected depending upon the use intended for the fusion protein being expressed. For example, when a large quantity of such a protein is to be produced, for the generation of pharmaceutical compositions of a fusion protein, vectors which direct the expression of high levels of a fusion protein products that are readily purified can be desirable. Such vectors include, but are not limited, to the *E. coli* expression vector pUR278 (Ruther et al., EMBO J., 2:1791 (1983)), in which the fusion protein coding sequence can be ligated individually into the vector in frame with the lacZ coding region so that a fusion protein is produced; pIN vectors (Inouye & Inouye, Nucleic Acids Res., 13:3101-3109 (1985); Van Heeke & Schuster, J. Biol. Chem., 24:5503-5509 (1989)); and the like pGEX vectors can also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety. Alternately, the pET expression vectors can be used for producing histidine-tagged recombinant proteins, where the histidine-tagged recombinant proteins can be affinity purified by a nickel column. Expression of recombinant proteins in *Pichia pastoris* is described by Holliger, P. (2002) *Meth. Mol. Biol.*, 178:349-57, and is hereby incorporated by reference. Examples of recombinant expression and purification of engineered anthrax containing fusion proteins and BTx- or TTx-containing fusion proteins are known in the art, and are described in more detail in, e.g., International Patent Publication WO 2012/096926 ani WO 2015/166242; U.S. Pat. Nos. 9,079,952, 9,234,011, 9,243,301, and US Patent Application Publications No: US 2013/0336974, US 2015/0267186, US 2015/0044210, each of which is incorporated by reference herein in its entirety.

In an insect system, *Autographa californica* nuclear polyhedrosis virus (AcNPV) is used as a vector to express foreign genes. The virus grows in *Spodoptera frugiperda* cells. The fusion protein coding sequence can be cloned individually into non-essential regions (for example the polyhedrin gene) of the virus and placed under control of an AcNPV promoter (for example the polyhedrin promoter).

Large scale expression of heterologous proteins in the algae *Chlamydomonas reinhardtii* are described by Griesbeck C. et. al. 2006 Mol. Biotechnol. 34:213-33; Manuell A L et. al. 2007 Plant Biotechnol J. Eprint; Franklin SE and Mayfield SP, 2005, Expert Opin Biol Ther. February; 5(2): 225-35; Mayfield SP and Franklin SE, 2005 Vaccine March 7; 23(15):1828-32; and Fuhrmann M. 2004, Methods Mol Med. 94:191-5. Foreign heterologous coding sequences are inserted into the genome of the nucleus, chloroplast and mitochodria by homologous recombination. The chloroplast expression vector p64 carrying the most versatile chloroplast selectable marker aminoglycoside adenyl transferase (aadA), which confers resistance to spectinomycin or streptomycin, can be used to express foreign protein in the chloroplast. Biolistic gene gun method is used to introduce the vector in the algae. Upon its entry into chloroplasts, the foreign DNA is released from the gene gun particles and integrates into the chloroplast genome through homologous recombination.

In mammalian host cells, a number of viral-based expression systems can be utilized. In cases where an adenovirus is used as an expression vector, the coding sequence of fusion protein can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the fusion protein in infected hosts. See, e.g., Logan & Shenk, Proc. Natl. Acad. Sci. USA, 81:355-359 (1984). Specific initiation signals can also be required for efficient translation of inserted fusion protein coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, Bittner et al., Methods in Enzymol., 153: 51-544 (1987)).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERY, BHK, Hela, COS, MDCK, NSO, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the fusion protein can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the fusion protein. Such engineered cell lines can be particularly useful in screening and evaluation of compounds that interact directly or indirectly with the fusion protein.

A number of selection systems can be used, including but not limited to the herpes simplex virus thymidine kinase (Wigler et al., Cell, 11:223 (1977)), hypoxanthine-guanine phosphoribosyltransferase (Szybalska & Szybalski, Proc. Natl. Acad. Sci. USA, 48:202 (1992)), and adenine phosphoribosyltransferase (Lowy et al., Cell, 22:817 (1980)) genes can be employed in tk-, hgprt- or aprt-cells, respectively. Also, anti-metabolite resistance can be used as the basis of selection for the following genes: dhfr, which confers resistance to methotrexate (Wigler et al., Proc. Natl. Acad. Sci. USA, 77:357 (1980); O'Hare et al., Proc. Natl. Acad. Sci. USA, 78:1527 (1981)); gpt, which confers resistance to mycophenolic acid (Mulligan & Berg, Proc. Natl. Acad. Sci. USA, 78:2072 (1981)); neo, which confers resistance to the aminoglycoside G-418; Wu and Wu, Biotherapy, 3:87-95 (1991); Tolstoshev, Ann. Rev. Pharmacol. Toxicol., 32:573-596 (1993); Mulligan, Science, 260:926-932 (1993); and Morgan and Anderson, Ann. Rev. Biochem., 62:191-217 (1993); Can, 1993, TIB TECH 11(5):155-215); and hygro, which confers resistance to hygromycin (Santerre et al., Gene, 30:147 (1984)). Methods commonly known in the art of recombinant DNA technology can be routinely applied to select the desired recombinant clone, and such methods are described, for example, in Current Protocols in Molecular Biology, Ausubel et al., eds. (John Wiley & Sons, NY 1993); Kriegler, Gene Transfer and Expression, A Laboratory Manual (Stockton Press, NY 1990); and Current Protocols in Human Genetics, Dracopoli et al., eds. (John Wiley & Sons, NY 1994), Chapters 12 and 13; Colberre-Garapin et al., J. Mol. Biol., 150:1 (1981), which are incorporated by reference herein in their entireties.

The expression levels of an engineered fusion protein described herein can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing the fusion protein is amplifiable, increase in the level of inhibitor present in culture of host cell will increase the number of copies of the marker gene. Since the amplified region is associated with the nucleic acid sequence encoding the engineered fusion protein described herein, production of the engineered fusion protein will also increase (Crouse et al., Mol. Cell. Biol., 3:257 (1983)).

The host cell can be co-transfected with two expression vectors of the invention, the first vector encoding a first fusion protein and the second vector encoding a second fusion protein. The two vectors can contain identical selectable markers which enable equal expression of a fusion polypeptides. Alternatively, a single vector can be used which encodes, and is capable of expressing, both fusion polypeptides. A bi-cistronic expression cassette encoding both fusion polypeptides is inserted into the expression vector (Proudfoot, Nature, 322:52 (1986); Kohler, Proc. Natl. Acad. Sci. USA, 77:2197 (1980)).

Once a fusion protein of the invention has been produced by an animal or recombinantly expressed, it can be purified by any method known in the art for protein purification for example, by chromatography (e.g., ion exchange, affinity, particularly by affinity for the specific antigen after Protein A, and sizing column chromatography), centrifugation, differential solubility, or by any other standard technique for the purification of proteins. In addition, the engineered fusion protein described herein can be fused to heterologous polypeptide sequences described herein or otherwise known in the art, to facilitate purification.

For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (QIAGEN®) useful with histidine-tagged fusion proteins. Tags can also facilitate the detection of the expressed recombinant fusion proteins. Examples of such tags include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation.

Accordingly, in one embodiment, encompassed herein is a nucleic acid sequence encoding any one of the fusion proteins described herein.

In one embodiment, provided herein is a vector comprising a nucleic acid sequence encoding any one of the fusion protein described herein. For examples, the vector can be a plasmid, a bacteriophage, a phagmid, a cosmid, a viral vector, or a viral particle. These vectors are known in the art. In one embodiment, provided herein is a plasmid comprising a nucleic acid sequence encoding any one of the fusion protein described herein. For example, the plasmid is a bacterial plasmid. In one embodiment of a vector described, the vector is an expression vector. For example, the plasmid (vector) is an expression plasmid for the recombinant protein expression in a bacteria, e.g., *Escherichia coli*. In one embodiment of an expression vector described, the expression vector is a bacterial expression vector. In one embodiment of an expression vector described, the expression vector is a prokaryotic expression vector. In one embodiment of an expression vector described, the expression vector is an eukaryotic expression vector. In one embodiment of an expression vector described, the expression vector is a mammalian expression vector. In one embodiment, the expression vector is a yeast expression vector.

In another embodiment, provided herein is a viral particle comprising a vector comprising a nucleic acid described in the preceding paragraph. In another aspect, provided herein is a viral particle comprising a a nucleic acid described in the preceding paragraph.

In one embodiment, provided herein is a cell comprising a nucleic acid sequence encoding any one of the fusion proteins described herein or a vector comprising a nucleic acid sequence encoding any one of the fusion proteins described herein. The cell can be a bacteria, a yeast cell, a mammalian cell etc. For example, an *E. coli* carrying a plasmid that comprises a nucleic acid encoding a fusion protein described herein. For example, for the recombinant protein expression of the a fusion protein encoded in the nucleic acid.

In another aspect, provided herein is a cell comprising a viral particle comprising a vector comprising a nucleic acid sequence encoding any one of the fusion proteins described herein. In another aspect, provided herein is a cell comprising a plasmid comprising a nucleic acid sequence encoding any one of the fusion proteins described herein. In another aspect, provided herein is a cell comprising a viral particle comprising a nucleic acid sequence encoding any one of the fusion proteins described herein.

In one embodiment, provided herein is a method of producing any one of the fusion proteins described herein, comprising (a) culturing a cell comprising a nucleic acid sequence encoding any one of the fusion proteins described herein, or a vector (e.g., a plasmid) comprising a nucleic acid sequence encoding any one of the fusion proteins described herein, or a viral particle comprising a vector comprising a nucleic acid sequence encoding any one of the fusion proteins described, or a viral particle comprising a nucleic acid sequence encoding any one of the fusion proteins described herein herein, wherein the culturing is performed under conditions such that the fusion protein described is expressed; and (b) recovering the fusion protein.

In one embodiment, provided herein is a fusion protein produced by the method described herein, specifically, the method comprising (a) culturing a cell comprising a nucleic acid sequence encoding any one of the fusion proteins described herein or a vector (e.g., a plasmid) comprising a nucleic acid sequence encoding any one of the fusion proteins described herein, or a viral particle comprising a vector comprising a nucleic acid sequence encoding any one of the fusion proteins described, or a viral particle comprising a nucleic acid sequence encoding any one of the fusion proteins described herein herein, wherein the culturing is performed under conditions such that the fusion protein described is expressed; and (b) recovering the fusion protein.

In one embodiment of the method described for producing a fusion protein, the cell is a prokaryotic cell such as bacteria. In one embodiment of the method described for producing a fusion protein, the cell is a bacteria cell. In one embodiment, the bacteria is *Escherichia coli* (*E. Coli*). In another embodiment, the bacteria is an attenuated *B. anthracis* strains (e.g. CDC 684).

In one embodiment of a method of producing a fusion protein described herein, the cell is a yeast cell. In one embodiment, the yeast is *Saccharomyces cerevisiae*. In one embodiment, the yeast is cell glycosylation deficient.

In one embodiment of a method of producing a fusion protein described herein, the yeast is glycosylation and protease deficient. In one embodiment, the protease is furin or furin-like protease.

In one embodiment of a method of producing a fusion protein described herein, the cell is a mammalian cell. In one embodiment, the mammalian cell is a COS cell, a CHO cell, or an NSO cell.

Compositions

In one aspect, described herein is a composition comprising at least one engineered fusion protein as described herein. In one embodiment, the composition further comprises a pharmaceutically acceptable carrier, excipient or diluent.

In some aspects, any compositions described in the preceding paragraphs or any compositions comprising a fusion protein described in the preceding paragraphs is use for the treatment of pain. Treatment of pain can include administering more than one, i.e., several, of the different compositions described in the preceding paragraphs. For example, compositions comprising fusion proteins comprising LFn, LF, EFn, or EF, and where there is noceiceptor receptor binding protein present in the fusion protein, the composition would preferably be used in combination with a composition comprising a PA, a PA fragment, a PAd4 containing fragment of PA, or a C-terminal receptor binding domain of PA of PA.

In some embodiments, the composition can comprise two or more different engineered fusion proteins, e.g., fusion proteins with different first and/or second domains. Such mixtures of proteins can, e.g. reduce off-target effects and/or provide multiple mechanisms of inhibiting nociceptors to increase efficacy. In some embodiments, the two or more different engineered fusion proteins can be in oligomeric form such that the oligomeric complex comprises at least two different engineered fusion proteins. In some embodiments, a first engineered fusion protein has a first domain comprising an anthrax toxin protective antigen (PA) moiety; and a second engineered fusion protein has a first domain comprising a mutant anthrax toxin protective antigen (mPA) moiety that has been altered to block its native receptor-binding function fused with a molecule capable of specifically targeting a nociceptor surface receptor or an ion channel receptor. In some embodiments, a composition as described herein can further comprise a pharmaceutically acceptable carrier or excipient.

When a polypeptide comprises an anthrax toxin translocation peptide, the translocation peptide can cause the polypeptide to be bound by and translocated across a membrane by PA and/or mPA present. Accordingly, the PA and/or mPA and the polypeptide to be translocated (e.g. a toxin) can be present as separate polypeptides. In one aspect then, described herein is a composition comprising:

(I) a first polypeptide selected from the group consisting of:
  a) an anthrax toxin protective antigen (PA) moiety; and optionally
  b) a mutant anthrax toxin protective antigen (mPA) moiety that has been altered to block its native receptor-binding function, fused with a molecule capable of specifically targeting a nociceptor surface receptor or an ion channel receptor; and (II) a second polypeptide selected from the group consisting of:
  c) an anthrax translocation signal peptide fused with an inhibitor cysteine knot (ICK) toxin (e.g., a Conotoxin (CTx));
  d) an anthrax translocation signal peptide fused with an intracellularly-acting toxin catalytic domain; and/or
  e) an anthrax toxin edema factor (EF) and/or anthrax toxin lethal factor (LF).

In one embodiment of such a composition, the first polypeptide comprises an anthrax toxin protective antigen (PA) moiety and the second polypeptide comprises an anthrax toxin translocation peptide fused with an inhibitor cysteine knot (ICK) toxin (e.g., a Conotoxin (CTx)).

In another embodiment of such a composition, the first polypeptide comprises a mutant anthrax toxin protective antigen (mPA) moiety that has been altered to block its native receptor-binding function, fused with a molecule capable of specifically targeting a nociceptor surface receptor or an ion channel receptor, and the second polypeptide comprises an anthrax toxin translocation peptide fused with an intracellularly-acting toxin catalytic domain. In other embodiments of a second polypeptide, the the anthrax toxin translocation peptide is replaced with a clostridial neurotoxin translocation domain, $H_N$, or a polycationic sequence.

In another embodiment of such a composition, the first polypeptide comprises: i) an anthrax toxin protective antigen (PA) moiety; or ii) a mutant anthrax toxin protective antigen (mPA) moiety that has been altered to block its native receptor-binding function fused with a molecule capable of specifically targeting a nociceptor surface receptor or an ion channel receptor; and the second polypeptide comprises an anthrax toxin edema factor (EF) and/or anthrax toxin lethal factor (LF).

In another embodiment of such a composition comprising a first and second polypeptide, the PA or mPA is in an oligomeric form. In another embodiment of such a composition comprising first and second polypeptides, the composition comprises both i) an anthrax toxin protective antigen (PA) moiety and ii) a mutant anthrax toxin protective antigen (mPA) moiety that has been altered to block its native receptor-binding function, fused with a molecule capable of specifically targeting a nociceptor surface receptor or an ion channel receptor. In one embodiment, the i) anthrax toxin protective antigen (PA) moiety and ii) mutant anthrax toxin protective antigen (mPA) moiety that has been altered to block its native receptor-binding function fused, with a molecule capable of specifically targeting a nociceptor surface receptor or an ion channel receptor, two different first polypeptides are in oligomeric form such that the oligomeric complex comprises both polypeptides. In one embodiment, the composition further comprises a pharmaceutically acceptable carrier or excipient.

In one embodiment of any of the aspects described herein, the composition further comprises a native anthrax toxin protective antigen (PA) protein. In one embodiment, the PA protein is an oligomeric PA. In another embodiment, the oligomeric PA is bound to the fusion protein.

In one embodiments of any of the compositions comprising LFn, LF, EF or EFn-containing fusion proteins described herein, the composition further comprises a native anthrax toxin protective antigen (PA) protein. In one embodiment, the PA protein is an oligomeric PA. In another embodiment, the oligomeric PA is bound to the fusion protein.

Uses of Engineered Fusion Proteins and Compositions for Pain Treatment

Any compositions comprising a fusion protein described herein, used individually or in combinations, can be used for the treatment of pain. Similarly, any fusion protein described herein can be used for the treatment of pain. Moreover, it is envisioned that various combinations of the described compositions or various combinations of the described engineered fusion proteins would be used in the treatment of pain. The fusion proteins and compositions described herein can selectively bind to nociceptors and deliver toxins that kill and/or inhibit the nociceptor cells. In some embodiments, other neurons are not affected by the fusion proteins and/or compositions described herein.

In another aspect, provided herein is a method of manufacture of a pharmaceutical composition comprising one or more of the fusion proteins described in the preceding paragraphs and a pharmaceutically acceptable carrier or excipient.

In another aspect, provided herein is a fusion protein described in the preceding paragraphs for use in the manufacture of medicament for the treatment of pain. In one embodiment, the fusion protein is formulated with at least one pharmaceutically acceptable carrier or excipient.

In another aspect, provided herein is a fusion protein described in the preceding paragraphs for use in the treatment of pain. In one embodiment, the fusion protein is formulated with at least one pharmaceutically acceptable carrier or excipient.

Accordingly, in one aspect, described herein is a method for treatment of pain, the method comprising administering to a subject in need thereof an effective, pain reducing amount of a composition as described herein. More than one composition can be administered, either stimultaneously or sequentially. For example, compositions comprising fusion proteins comprising LFn, LF, EFn, or EF, and where there is no noceiceptor receptor binding protein present in the fusion protein, the composition would preferably be used in combination with a composition comprising a PA, a PA fragment, a PAd4 containing fragment of PA, or a C-terminal receptor binding domain of PA of PA.

In another aspect, described herein is a method for treatment of pain, the method comprising administering to a subject in need thereof an effective, pain reducing amount of a fusion protein comprising: (a) a botulinum neurotoxin (BTx) or a tetanus neurotoxin (TTx), and (b) an anthrax toxin protective antigen (PA), or a C-terminal receptor-binding domain of PA, wherein part (a) and (b) are linked or fused together, or a composition comprising the fusion protein.

In another aspect, described herein is a method for treatment of pain, the method comprising administering to a subject in need thereof an effective, pain reducing amount of a fusion protein comprising: (a) a non-cytotoxic protease, which protease is capable of cleaving a SNARE protein in a nociceptor neuron; and (b) a protein capable of binding to an anthrax toxin protective antigen (PA) or a fragment thereof, wherein the PA or PA fragment thereof binds a receptor expressed on the nociceptor neuron, or a composition comprising the fusion protein.

In another aspect, described herein is a method for treatment of pain, the method comprising administering to a subject in need thereof an effective, pain reducing amount of a fusion protein comprising (a) a disulfide-containing peptide toxin which is capable of blocking ion channels in a nociceptor neuron; and (b) a targeting moiety (TM) that is capable of binding to a binding site on the nociceptor neuron, wherein the nociceptor neuron expresses the ion channels therein, or a composition comprising the fusion protein.

In another aspect, described herein is a method for treatment of pain, the method comprising administering to a subject in need thereof an effective, pain reducing amount of a fusion protein comprising: (a) a disulfide-containing peptide toxin which is capable of blocking sodium or calcium or both sodium and calcium channels in a nociceptor neuron; and (b) a protein capable of binding to an anthrax toxin protective antigen (PA) or a PA fragment that binds a receptor expressed on the nociceptor neuron, or a composition comprising the fusion protein.

In another aspect, described herein is a method for treatment of pain, the method comprising administering to a subject in need thereof an effective, pain reducing amount of a fusion protein comprising: (a) an AB toxin; (b) an anthrax toxin protective antigen (PA) or a fragment thereof, wherein the PA or fragment thereof binds a receptor expressed on a nociceptor neuron; and (c) a translocation domain (TL) that is capable of translocating the toxin (a protease) from within an endosome, across the endosomal membrane and into the cytosol of the nociceptor neuron, or a composition comprising the fusion protein.

In another aspect, described herein is a method for treatment of pain, the method comprising administering to a subject in need thereof an effective, pain reducing amount of a fusion protein comprising a botulinum neurotoxin (BTx) moiety comprising an N-terminal enzymatic domain (LC or L chain) and an intermediate pore-forming/translocation-domain ($H_N$) of the BTx, linked to a C-terminal receptor-binding domain of anthrax toxin protective antigen (PA), or a composition comprising the fusion protein.

In another aspect, described herein is a method for treatment of pain, the method comprising administering to a subject in need thereof an effective, pain reducing amount of a fusion protein comprising: (a) a botulinum neurotoxin N-terminal enzymatic domain of a botulinum neurotoxin (BTx) moiety, and (b) an N-terminal domain of anthrax toxin lethal factor (LFn), which domain binds to oligomeric forms of PA63, the proteolytically activated form of anthrax PA; or the N-terminal domain of anthrax toxin edema factor (EFn), which domain binds to oligomeric forms of PA63, the proteolytically activated form of anthrax PA, wherein part (a) is linked N-terminally or C-terminally or both N-terminally and C-terminally to part (b), or a composition comprising the fusion protein.

In another aspect, described herein is a method for treatment of pain, the method comprising administering to a subject in need thereof an effective, pain reducing amount of a fusion protein comprising anthrax toxin protective antigen (PA), an anthrax toxin protective antigen C-terminal receptor binding domain (PAd4), or a nociceptor neuron-binding protein, linked to a disulfide-containing peptide toxin, or a composition comprising the fusion protein.

In another aspect, described herein is a method for treatment of pain, the method comprising administering to a subject in need thereof an effective, pain reducing amount of a fusion protein comprising a disulfide-containing peptide toxin operably linked N-terminally or C-terminally or both N-terminally and C-terminally, or chemically crosslinked at one or more sites, to the N-terminal domain (LFn) of anthrax toxin lethal factor, which domain binds to oligomeric forms of PA63, the proteolytically activated form of anthrax PA; or the N-terminal domain (EFn) of anthrax toxin edema factor, which domain binds to oligomeric forms of PA63, or a composition comprising the fusion protein.

In another aspect, described herein is a method for treatment of pain, the method comprising administering to a subject in need thereof an effective, pain reducing amount of a fusion protein comprising an AB toxin fused to a linker peptide linked to a C-terminal receptor-binding domain of anthrax toxin protective antigen (PAd4 domain), wherein the fusion protein further comprises a translocation domain, a holotoxin, or a mutant form of the holotoxin that have been modified (e.g., chemically) or mutated to negate the toxin receptor-binding function of the AB toxin, or a composition comprising the fusion protein.

In another aspect, described herein is a method for treatment of pain, the method comprising administering to a subject in need thereof an effective, pain reducing amount of a fusion protein comprising an N-terminal enzymatic domain (Chain A) together with a translocation/pore-forming domain from a Clostridial neurotoxin or a non-Clostridial botulinum-like toxin, linked to a C-terminal receptor-binding domain of anthrax toxin protective antigen (PAd4 domain), or a composition comprising the fusion protein.

In another aspect, described herein is a method for treatment of pain, the method comprising administering to a subject in need thereof an effective, pain reducing amount of an engineered fusion protein comprising a native protective antigen (PA) or a mutant PA (mPA), wherein the mPA has been modified (e.g., chemically) or mutated so as to block its native receptor-binding function, and a molecule that can target nociceptor neuron surface molecules, specifically in combination with anthrax toxin edema factor (EF) and/or anthrax lethal factor (LF), or a composition comprising the engineered fusion protein.

In another aspect, described herein is a method for treatment of pain, the method comprising administering to a subject in need thereof an effective, pain reducing amount of an engineered fusion protein comprising an anthrax protective antigen (PA) moiety fused with a molecule capable of specifically targeting a nociceptor surface receptor or a nociceptor ion channel receptor, and an anthrax lethal factor domain (LFn) fused to an intracellularly acting toxin catalytic domain. ANTXR2 is the native receptor for PA, or a composition comprising the engineered fusion protein.

In another aspect, described herein is a method for treatment of pain, the method comprising administering to a subject in need thereof an effective, pain reducing amount of an engineered fusion protein comprising a mutant anthrax protective antigen (mPA) moiety that has been altered to block its native receptor-binding function, fused with a molecule capable of specifically targeting a nociceptor surface receptor or a nociceptor ion channel receptor, and an anthrax lethal factor domain (LFn) fused to an intracellularly acting toxin catalytic domain. ANTXR2 is the native receptor for PA, or a composition comprising the engineered fusion protein.

In another aspect, described herein is a method for treatment of pain, the method comprising administering to a subject in need thereof an effective, pain reducing amount of an engineered fusion protein comprising an anthrax toxin Protective-Antigen (PA) moiety or its receptor binding domain (PAd4) fused with an inhibitor cysteine knot (ICK) toxin, e.g., a Conotoxin (CTx), or a composition comprising the engineered fusion protein.

In another aspect, described herein is a method for treatment of pain, the method comprising administering to a subject in need thereof an effective, pain reducing amount of an engineered fusion protein comprising an anthrax toxin lethal factor domain (LFn) fused with an inhibitor cysteine knot (ICK) toxin and a Protective-Antigen (PA) moiety, or a composition comprising the engineered fusion protein.

In another aspect, described herein is a method for treatment of pain, the method comprising administering to a subject in need thereof an effective, pain reducing amount of an engineered fusion protein comprising an anthrax toxin lethal factor domain (LFn) fused with a L chain of a Clostridial neurotoxin and a Protective-Antigen (PA) moiety, or a composition comprising the engineered fusion protein. In one embodiment, this fusion protein can further comprise the belt of the H chain of the Clostridial neurotoxin, the belt is the N-terminal segment of the H chain.

Non-limiting examples of pain that can be treated according to the methods described herein can include: chronic pain; chronic neuropathic pain; painful diabetic neuropathy (PDN), post-herpetic neuropathy (PHN); trigeminal neuralgia (TN); inflammatory pain; neuropathic pain; a channelopathy; primary erythermalgia (PE); paroxysmal extreme pain disorder (PEPD); spinal cord injury pain; multiple sclerosis pain; phantom limb pain; post-stroke pain; chronic back pain; osteoarthritis pain; cancer-associated pain; HIV-associated pain; chronic inflammatory pain; central neuropathy; peripheral neuropathy; anaesthesia dolorosa; hyperalgesia; hyperpathia; paresthesia; psychogenic pain; back pain; breakthrough pain; erythromelalgia; nerve compression and/or entrapment [e.g., carpal tunnel syndrome, tarsal tunnel syndrome, ulnar nerve entrapment, compression radiculopathy, radicular low back pain, spinal root lesions, spinal root compression, lumbar spinal stenosis, sciatic nerve compression, and/or intercostal neuralgia]; neuritis; pain from chemotherapy; chronic alcoholism (alcoholic polyneuropathy); rheumatoid arthritis pain; pain associated with burns; encephalitis pain; bone fracture pain; neuritis pain; autoimmune disease pain; postoperative pain; dental pain; pain associated with bacterial infection, e.g. a bacterial infection or viral infection; pain associated with radiotherapy; pain associated with gout and irritable bowel syndrome; pain from trauma (such as from lacerations, incisions, burns, foreign bodies or bullet and/or shrapnel injuries, spinal cord injury, brachial plexus avulsion, nerve crush and/or entrapment; nerve transection; visceral pain (such as renal or ureteral colic, irritable bowel syndrome, angina or cardiac pain, cardiac arrhythmia, period pain, interstitial cystitis, rectal pain, pain associated with diarrhoea, appendicitis, cholecystitis and pancreatitis); uremia pain; pain associated with hypothyroidism; pain associated with vitamin deficiency; headache pain (e.g., tension headache, migraine and cluster headache); idiopathic pain (e.g., trigeminal neuralgia, a complex regional pain syndrome [e.g. complex regional pain syndrome I and/or complex regional pain syndrome II], allodynia or fibromyalgia); respiratory pain (e.g., pain associated with asthma, airway hyper-reactivity in asthma, chronic cough, e.g. in asthma and/or chronic obstructive pulmonary disorder); fibromyalgia; hormonal therapy pain; hypothyroidism pain; epileptic pain; ataxia; periodic paralysis; acute itch and/or chronic itch pain.

In one embodiment, the pain to treat by using any of the compositions described herein is selected from diabetic neuropathic pain, cancer pain, fibromyalgia and other systemic pain disorders.

In one embodiment, the pain to treat by using any of the compositions described herein is selected from nerve, joint, skin, visceral, bladder, and muscle pain.

In one embodiment, the composition to be administered comprises a first polypeptide (or fusion protein) and a second polypeptide (or fusion protein), and the first polypeptide is bound to the second polypeptide before administration.

In another aspect, described herein is a method for treatment of pain, the method comprising administering to a subject in need thereof an effective, pain reducing amount of a first composition comprising
  a) an anthrax toxin protective antigen (PA) moiety; and/or
  b) a mutant anthrax toxin protective antigen (mPA) moiety that has been altered to block its native receptor-binding function fused with a molecule capable of specifically targeting a nociceptor surface receptor or an ion channel receptor; and
  c) a second composition comprising:
    (i) an anthrax toxin translocation signal peptide fused with an inhibitor cysteine knot (ICK) toxin (e.g., a Conotoxin (CTx));
    (ii) an anthrax toxin translocation peptide fused with an intracellularly-acting toxin catalytic domain; and/or
    (iii) an anthrax toxin edema factor (EF) and/or anthrax toxin lethal factor (LF).

In any of the aspects drawn to a method of treating pain, the administering can be performed by intrathecal infusion, intra-cerebroventricular infusion, an epidural injection into the central nervous system, or by peripheral administration using intradermal injection, subcutaneous injection, intramuscular injection, intraneural injection, or intra-articular injection.

Accordingly, in one embodiment, described herein is a method for treatment of nerve, joint, skin, visceral, bladder, or muscle pain comprising administering peripherally by intradermal injection, subcutaneous injection, intramuscular injection, intraneural injection, or intra-articular injection to a subject in need thereof an effective, pain reducing amount of a composition as described herein.

In another embodiment, described herein is a method for treatment of diabetic neuropathic pain, cancer pain, fibromyalgia or other systemic pain disorders comprising administering by epidural injection, intrathecal infusion or intra-cerebroventricular infusion into the central nervous system of a subject in need thereof an effective, pain reducing amount of a composition as described herein.

In one embodiment of any of the methods of treating pain described herein, the effective, pain reducing amount of a composition as described herein is administered separately before, simultaneously, or after administering a composition comprising an anthrax protective antigen (PA) in a pharmaceutically acceptable carrier, excipient or diluent.

In one embodiment of a method of treating pain described herein, the method comprises administering to a subject in need thereof, native mature anthrax toxin protective antigen (PA) and anthrax toxin edema factor (EF), anthrax toxin lethal factor (LF) or any combination thereof.

In one embodiment of an aspect described herein in which PA is part of the fusion protein or part of the composition that is administered for pain treatment, the PA or mPA is administered in an oligomeric form. In one embodiment, the oligomeric PA or mPA is formed from proteolytically activated PA or mPA (or mutant thereof) to achieve increased avidity for receptor-bearing cells. By way of non-limiting example, PA can be treated with trypsin to nick and then separate the two fragments (e.g. PA63 and PA20) on an ion exchange column. PA63 will elute as an oligomer (e.g. a heptamer) and will remain in the proteolytically activated prepore state if the pH is kept above about pH 8.0. Preparation of oligomeric and/or proteolytically activated PA is described in the art, e.g., in Milne et al, JBC 269: 20607-20612, 1994; which is incorporated by reference herein in its entirety.

In one embodiment of an aspect involving administering a first and second composition, the first composition comprises both i) an anthrax toxin protective antigen (PA) moiety and ii) a mutant anthrax toxin protective antigen (mPA) moiety that has been altered to block its native receptor-binding function, fused with a molecule capable of specifically targeting a nociceptor surface receptor or an ion channel receptor. In another embodiment including administration of a first composition comprising i) anthrax toxin protective antigen (PA) moiety and ii) mutant anthrax toxin protective antigen (mPA) moiety that has been altered to block its native receptor-binding function, fused with a molecule capable of specifically targeting a nociceptor surface receptor or an ion channel receptor, the two different first polypeptides are in oligomeric form such that the oligomeric complex comprises both polypeptides. In one embodiment, the first composition is administered in a separate injection before, simultaneously or after administering the second composition.

The compositions and methods described herein can be administered to a subject having or diagnosed as having pain. Thus, the methods described herein encompass administering an effective amount of a composition described herein to a subject in order to alleviate pain. As used herein, "alleviating pain" is ameliorating any condition or symptom associated with the pain. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of the composition that is sufficient to provide a particular anti-pain effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

In some embodiments of all the aspects described herein, the technology described herein relates to a pharmaceutical composition as described herein, and optionally combined with a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments of all the aspects described herein, the carrier inhibits the degradation of the active agent, e.g. a composition as described herein.

In one embodiment of any aspect described herein involving a pharmaceutical composition, the pharmaceutical composition can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a composition as disclosed herein can also be incorporated into the parenteral dosage forms of the disclosure, including conventional and controlled-release parenteral dosage forms.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments of all the aspects described herein, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B 1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. Non-limiting examples of a second agent and/or treatment can include pain relievers, anti-inflammatories, and other medications that treat pain and/or a condition causing pain.

In one embodiment of any aspect described herein involving the administration of an effective dose of a composition, an effective dose of a composition as described herein can be administered to a patient once. In another embodiment, an effective dose of a composition can be administered to a patient repeatedly. For systemic administration, subjects can be administered a therapeutic amount of a composition as described herein, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In one embodiments of any of the aspects described herein involving administration of a composition for the treatment of pain, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. pain by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the composition. The desired dose or amount of activation can be administered at one time or divided into subdoses, e.g., 2-4 subdoses and administered over a period of time, e.g., at appropriate intervals through the day or other appropriate schedule. In some embodiments of all the aspects described herein, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition can be administered over a period of time, such as over a 5 minute, 10 minute, 15 minute, 20 minute, or 25 minute period.

The dosage ranges for the administration of a composition as described herein, according to the methods described herein depend upon, for example, the form of the active ingredient, its potency, and the extent to which symptoms, markers, or indicators of a condition described herein are desired to be reduced, for example the percentage reduction desired for pain. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a composition in, e.g. the treatment of a condition described herein, or to induce a response as described herein (e.g. a reduction of pain) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of a mouse model of pain. When using an experimental animal model, efficacy of treatment is evidenced when a statistically significant change in a marker is observed, e.g. responses to or avoidance of stimuli in the affected area.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

Definitions

For convenience, certain terms employed herein, in the specification, examples and appended claims are collected here.

As used herein, the term "capable of" when used with a verb, encompasses or means the action of the corresponding verb. For example, "capable of blocking" also means blocks, "capable of cleaving" also means cleaves, "capable of binding" also means binds, "capable of translocating" also means translocates, and "capable of specifically targeting . . . " also means specifically targets.

As used herein, a "nociceptor neuron-binding protein" or "nociceptor-binding protein" when used in reference with a fusion protein described herein refers to a polypeptide targeting moiety (TM) that is capable of binding to a binding site on the nociceptor neuron, wherein the interaction results in that binding site of the neuron undergoing endocytosis to be incorporated into an endosome within the nociceptor neuron. In one embodiment, the nociceptor neuron-binding protein is an antibody or antibody fragment thereof that binds a receptor or ion channel expressed on the cell surface of the nociceptor neuron, e.g., the nerve grow factor receptor or the ANTXR2 or Nav1.7, Nav1.8, and Nav1.9 ion channel proteins. In one embodiment, the nociceptor neuron-binding protein is a ligand for a cell surface receptor of the nociceptor neuron, e.g., the nerve grow factor ligand for the nerve grow factor receptor. In one embodiment, the nociceptor neuron-binding protein is a PA or a variant form of PA or PA fragments thereof that is capable of binding to its receptor, ANTXR2. In one embodiment, the TM targets binds to the ANTXR2 (CMG2) receptor expressed on the nociceptor neuron.

In one embodiment, a variant form of PA that is capable of binding or binds to its receptor is resistant to furin protease and furin-like proteases. In one embodiment, a variant form of PA is modified (e.g., chemically) or mutated at the furin cleavage site. In some embodiments, the $PA^{furin-}$ is mutated at the furin cleavage site $^{164}RKKR^{167}$ to amino acid residues SSSR (SEQ ID NO: 32) or SSSS (SEQ ID NO: 33). The amino acid numbering is with reference to a PA polypeptide without the 29 residue signal peptide at the N-terminus. In one embodiment, PA fragments thereof that is capable of binding to its receptor are PA63, the fragment produced by furin cleavage of the full-length PA protein, and PAd4, the C-terminal receptor binding part of the full-length native PA. In one embodiment, the PA fragments thereof that is capable of binding to its receptor is PAd4 plus at least 1-60 consecutive amino acid residues N-terminal to PAd4 domain in the native PA, meaning the estimated PAd4 sequence plus additional upstream sequence is the C-terminal receptor binding section of PA.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments of all the aspects described herein, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments of all the aspects described herein, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of pain. A subject can be male or female.

A subject can be one who has been previously diagnosed with or identified as suffering from or having a condition in need of treatment (e.g. pain) or one or more complications related to such a condition, and optionally, have already undergone treatment for pain or the one or more complications related to pain. Alternatively, a subject can also be one who has not been previously diagnosed as having pain or one or more complications related to pain. For example, a subject can be one who exhibits one or more risk factors for pain or one or more complications related to pain or a subject who does not exhibit risk factors.

A "subject in need" of treatment for a particular condition can be a subject having that condition, diagnosed as having that condition, or at risk of developing that condition.

As used herein, "engineered" refers to the aspect of having been manipulated by the hand of man. For example, an fusion polypeptide is considered to be "engineered" when the sequence of the polypeptide and/or encoding nucleic acid sequence manipulated by the hand of man to differ from the sequence of a polypeptide as it exists in nature. As is common practice and is understood by those in the art, progeny and copies of an engineered polynucleotide and/or polypeptide are typically still referred to as "engineered" even though the actual manipulation was performed on a prior entity.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In some embodiments of all the aspects described herein, a polypeptide, e.g., a fusion polypeptide or portion thereof (e.g. a domain), can be a variant of a sequence described herein. In some embodiments of all the aspects described herein, the variant is a conservative substitution variant. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein, e.g., at least 50% of the wildtype reference protein. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or not, has more than 100% of the activity of wildtype, e.g. 110%, 125%, 150%, 175%, 200%, 500%, 1000% or more.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are known. Polypeptides comprising conservative amino acid substitutions can be tested in any one of the assays described herein to confirm that a desired activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure. Typically conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In one embodiment of any the aspects described herein involving administering a polypeptide, the polypeptide administered to a subject can comprise one or more amino acid substitutions or modifications. In one embodiment, the substitutions and/or modifications can prevent or reduce proteolytic degradation and/or prolong half-life of the polypeptide in the subject. In one embodiment, a polypeptide can be modified by conjugating or fusing it to other polypeptide or polypeptide domains such as, by way of non-limiting example, transferrin (WO06096515A2), albumin (Yeh et al., 1992), growth hormone (US2003104578AA); cellulose (Levy and Shoseyov, 2002); and/or Fc fragments (Ashkenazi and Chamow, 1997). The references in the foregoing paragraph are incorporated by reference herein in their entireties.

In one embodiment of any of the aspects described herein involving a polypeptide, a polypeptide as described herein can comprise at least one peptide bond replacement. A single peptide bond or multiple peptide bonds, e.g. 2 bonds, 3 bonds, 4 bonds, 5 bonds, or 6 or more bonds, or all the peptide bonds can be replaced. An isolated peptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In one embodiment of any of the aspects described herein involving a polypeptide, a polypeptide as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In one embodiment of any of the aspects described herein involving a polypeptide, a polypeptide as described herein can comprise alternative amino acids. Non-limiting examples of alternative amino acids include D-amino acids, beta-amino acids, homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In one embodiment of any of the aspects described herein involving a polypeptide, a polypeptide can be modified, e.g. by addition of a moiety to one or more of the amino acids comprising the peptide. In one embodiment, a polypeptide as described herein can comprise one or more moiety molecules, e.g. 1 or more moiety molecules per peptide, 2 or more moiety molecules per peptide, 5 or more moiety molecules per peptide, 10 or more moiety molecules per peptide or more moiety molecules per peptide. In some embodiments of all the aspects described herein, a polypeptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments of all the aspects described herein, an end-capping modification can comprise acetylation at the N-terminus, N-terminal acylation, and N-terminal formylation. In some embodiments of all the aspects described herein, an end-capping modification can comprise amidation at the C-terminus, introduction of C-terminal alcohol, aldehyde, ester, and thioester moieties. The half-life of a polypeptide can be increased by the addition of moieties, e.g. PEG or albumin.

In one embodiment of any of the aspects described herein involving administering a polypeptide (or administering a nucleic acid encoding a polypeptide), the polypeptide administered or encoded can be a functional fragment of one of the amino acid sequences described herein. As used herein, a "functional fragment" is a fragment or segment of a peptide which retains at least 50% of the wild-type reference polypeptide's activity according to the assays described below herein. A functional fragment can comprise conservative or non-conservative substitutions of the sequences disclosed herein.

Alterations of the original amino acid sequence can be accomplished by any of a number of techniques known to one of skill in the art. Amino acid substitutions can be introduced, for example, at particular locations by synthesizing oligonucleotides containing a codon change in the nucleotide sequence encoding the amino acid to be changed, flanked by restriction sites permitting ligation to fragments of the original sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. In some embodiments of all the aspects described herein, a polypeptide as described herein can be chemically synthesized and mutations can be incorporated as part of the chemical synthesis process.

As used herein an "antibody" refers to IgG, IgM, IgA, IgD or IgE molecules or antigen-specific antibody fragments thereof (including, but not limited to, a Fab, F(ab')2, Fv, disulfide linked Fv, scFv, single domain antibody, closed conformation multispecific antibody, disulfide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of the molecule.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of all the aspects described herein, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality. As used herein, the term "specific binding" refers to a chemical interaction between two molecules, compounds, cells and/or particles wherein the first entity binds to the second, target entity with greater specificity and affinity than it binds to a third entity which is a non-target. In some embodiments of all the aspects described herein, specific binding can refer to an affinity of the first entity for the second target entity which is at least 10 times, at least 50 times, at least 100 times, at least 500 times, at least 1000 times or greater than the affinity for the third nontarget entity.

Additionally, and as described herein, an antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to the target molecule.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. pain. The term "treating" includes reducing or alleviating at least one adverse effect or symptom of a condition, disease or disorder associated with pain. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

As used herein, a protease activity included in a fusion protein embraces all non-cytotoxic proteases that are capable of cleaving one or more proteins of the exocytic fusion apparatus in eukaryotic cells. The protease is preferably a bacterial protease (or fragment thereof). More preferably the bacterial protease is selected from the genera *Clostridium* or *Neisseria/Streptococcus* (e.g. a clostridial L-chain, or a neisserial IgA protease preferably from *N. gonorrhoeae* or *S. pneumoniae*). Another example of non-cytotoxic protease includes scorpion venom protease, such as those from the venom of the Brazilian scorpion Tityus serrulatus, or the protease antarease.

Protease activities also embrace the activities of variant non-cytotoxic proteases (i.e. variants of naturally-occurring protease molecules), so long as the variant proteases still demonstrate the requisite protease activity. By way of example, a variant may have at least 70%, preferably at least 80%, more preferably at least 90%, and most preferably at least 95% or at least 98% amino acid sequence homology with a reference protease sequence. Thus, the term variant includes non-cytotoxic proteases having enhanced (or decreased) endopeptidase activity—particular mention here is made to the increased Kcat/Km of BTx/A mutants Q161A, E54A, and K165L see Ahmed, S. A. (2008) Protein J. DOI 10.1007/s10930-007-9118-8, which is incorporated by reference thereto. The term fragment, when used in relation to a protease, typically means a peptide having at least 150, preferably at least 200, more preferably at least 250, and most preferably at least 300 amino acid residues of the reference protease. As with the TM 'fragment' component (discussed above), protease 'fragments' of the present invention embrace fragments of variant proteases based on a reference sequence.

In one embodiment of any of the aspects described herein, the protease activity included in a fusion protein demonstrates a serine or metalloprotease activity (e.g. endopeptidase activity). In one embodiment, the protease is specific for a SNARE protein (e.g. SNAP-25, synaptobrevin/VAMP, or syntaxin).

Particular mention is made to the protease domains of neurotoxins, for example the protease domains of bacterial neurotoxins. Thus, the various aspects described herein embrace the use of neurotoxin domains which occur in nature, as well as recombinantly prepared versions of such naturally-occurring neurotoxins.

Exemplary neurotoxins are produced by clostridia, and the term clostridial neurotoxin embraces neurotoxins produced by *C. tetani* (TTx), and by *C. botulinum* (BTx) serotypes A-G, as well as the closely related BTx-like neurotoxins produced by *C. baratii* and *C. butyricum*. The above-mentioned abbreviations are used throughout the present specification. For example, the nomenclature BTx/A denotes the source of neurotoxin as BTx (serotype A). Corresponding nomenclature applies to other BTx serotypes.

BTxs are the most potent toxins known, with median lethal dose (LD50) values for mice ranging from 0.5 to 5 ng/kg depending on the serotype. BTxs are adsorbed in the gastrointestinal tract, and, after entering the general circulation, bind to the presynaptic membrane of cholinergic nerve terminals and prevent the release of their neurotransmitter acetylcholine. BTx/B, BTx/D, BTx/F and BTx/G cleave synaptobrevin/vesicle-associated membrane protein (VAMP); BTx/C, BTx/A and BTx/E cleave the synaptosomal-associated protein of 25 kDa (SNAP-25); and BTx/C cleaves syntaxin.

BTxs share a common structure, being di-chain proteins of ~150 kDa, consisting of a heavy chain (H-chain) of ~100 kDa covalently joined by a single disulfide bond to a light chain (L-chain) of ~50 kDa. The H-chain consists of two domains, each of ~50 kDa. The C-terminal domain (H$_C$ is required for the high-affinity neuronal binding, whereas the N-terminal domain (H$_N$) is proposed to be involved in membrane translocation. The L-chain is a zinc-dependent metalloprotease responsible for the cleavage of the substrate SNARE protein.

The term L-chain fragment means a component of the L-chain of a neurotoxin, which fragment demonstrates a metalloprotease activity and is capable of proteolytically cleaving a vesicle and/or plasma membrane associated protein involved in cellular exocytosis.

Examples of suitable protease (reference) sequences include:

Botulinum type A neurotoxin-amino acid residues (1-448)

Botulinum type B neurotoxin-amino acid residues (1-440)

Botulinum type C neurotoxin-amino acid residues (1-441)

Botulinum type D neurotoxin-amino acid residues (1-445)

Botulinum type E neurotoxin-amino acid residues (1-422)

Botulinum type F neurotoxin-amino acid residues (1-439)

Botulinum type G neurotoxin-amino acid residues (1-441)

Tetanus neurotoxin-amino acid residues (1-457)

IgA protease-amino acid residues (1-959) Pohlner, J. et al. (1987). Nature 325, pp. 458-462, which is hereby incorporated by reference thereto.

In one embodiment of a fusion protein described herein having a non-cytotoxin protease, the non-cytotoxin protease can be an IgA protease or an Antarease described herein. In one embodiment of a fusion protein described herein having a non-cytotoxin protease, the non-cytotoxin protease can have a unique cleavage recognition sequence described in the following pages.

A variety of clostridial toxin fragments comprising the light chain can be useful in aspects of the present invention with the proviso that these light chain fragments can specifically target the core components of the neurotransmitter release apparatus and thus participate in executing the overall cellular mechanism whereby a clostridial toxin proteolytically cleaves a substrate. The light chains of clostridial toxins are approximately 420-460 amino acids in length and comprise an enzymatic domain. Research has shown that the entire length of a clostridial toxin light chain is not necessary for the enzymatic activity of the enzymatic domain. As a non-limiting example, the first eight amino acids of the BTx/A light chain are not required for enzymatic activity. As another non-limiting example, the first eight amino acids of the TTx light chain are not required for enzymatic activity. Likewise, the carboxyl-terminus of the light chain is not necessary for activity. As a non-limiting example, the last 32 amino acids of the BTx/A light chain (residues 417-448) are not required for enzymatic activity. As another non-limiting example, the last 31 amino acids of the TTx light chain (residues 427-457) are not required for enzymatic activity. Thus, aspects of this embodiment can include clostridial toxin light chains comprising an enzymatic domain having a length of, for example, at least 350 amino acids, at least 375 amino acids, at least 400 amino acids, at least 425 amino acids and at least 450 amino acids. Other aspects of this embodiment can include clostridial toxin light chains comprising an enzymatic domain having a length of, for example, at most 350 amino acids, at most 375 amino acids, at most 400 amino acids, at most 425 amino acids and at most 450 amino acids.

Further examples of suitable non-cytotoxic proteases are described in detail in WO 2007/106115, which is hereby incorporated in its entirety by reference thereto.

In one embodiment, the non-cytotoxic protease cleaves a non-neuronal SNARE protein such as a SNAP-23 protein. In one embodiment, the non-cytotoxic protease is a modified botulinum toxin L-chain capable of cleaving SNAP-23. An example of such a modified L-chain is described by Chen and Barbieri, PNAS, vol. 106, no. 23, p9180-9184, 2009.

In one embodiment, the non-cytotoxic protease is a BTx/A, BTx/C or BTx/E protease, and the preferred SNARE motif is a SNAP (e.g. SNAP 25) motif.

In another embodiment, the non-cytotoxic protease is a BTx/B, BTx/D, BTx/F or BTx/G or tetanus neurotoxin (TTx) protease, and the preferred SNARE motif is a VAMP motif.

In another embodiment, the non-cytotoxic protease is a BTx/C1 protease, and the preferred SNARE motif is a syntaxin motif.

The non-cytotoxic proteases of the engineered fusion proteins described herein recognise different cleavage site sequences and thus have slightly different cleavage specificities.

| Non-cytotoxic Protease | \multicolumn{7}{c}{Cleavage site recognition sequence: P4-P3-P2-P1-↓-P1'-P2'-P3'} | |
|---|---|---|---|---|---|---|---|---|
| | P4 | P3 | P2 | P1 | P1' | P2' | P3' | |
| BTx/A | E | A | N | Q | R | A | T | (SEQ ID NO: 71) |
| BTx/B | G | A | S | Q | F | E | T | (SEQ ID NO: 72) |
| BTx/C | A | N | Q | R | A | T | K | (SEQ ID NO: 73) |
| BTx/C | D | T | K | K | A | V | K | (SEQ ID NO: 74) |
| BTx/D | R | D | Q | K | L | S | E | (SEQ ID NO: 75) |
| BTx/E | Q | I | D | R | I | M | E | (SEQ ID NO: 76) |
| BTx/F | E | R | D | Q | K | L | S | (SEQ ID NO: 77) |
| BTx/G | E | T | S | A | A | K | I | (SEQ ID NO: 78) |
| TTx | G | A | S | Q | F | E | T | (SEQ ID NO: 79) |
| IgA protease | S | T | P | P | T | P | S | (SEQ ID NO: 80) |
| Antarease | I | K | R | K | Y | W | W | (SEQ ID NO: 81) |

By way of further example, reference is made to the following recognition sequences and cleavage sites:

| Non-cytotoxic Protease | \multicolumn{7}{c}{Cleavage site recognition sequence: P4-P3-P2-P4-↓-P1'-P2'-P3'} | |
|---|---|---|---|---|---|---|---|---|
| | P4 | P3 | P2 | P1 | P1' | P2' | P3' | |
| BTx/A | E | A | N | Q | R | A | T | (SEQ ID NO: 82) |
| | A | N | Q | R | A | T | K | (SEQ ID NO: 83) |
| | E | A | N | Q | R | A | T | (SEQ ID NO: 84) |
| | F | A | N | Q | R | A | T | (SEQ ID NO: 85) |
| | E | A | N | Q | R | A | T | (SEQ ID NO: 86) |
| | E | A | N | Q | R | A | I | (SEQ ID NO: 87) |
| | E | A | N | K | A | T | K | (SEQ ID NO: 88) |
| | E | A | N | K | H | A | T | (SEQ ID NO: 89) |
| | E | A | N | K | H | A | N | (SEQ ID NO: 90) |
| | Q | R | | | | | | |
| | K | H | | | | | | |
| BTx/C | D | E | A | N | Q | R | A | (SEQ ID NO: 91) |
| | E | A | N | Q | R | A | T | (SEQ ID NO: 92) |
| | A | N | Q | R | A | T | K | (SEQ ID NO: 93) |
| | N | Q | R | A | T | K | M | (SEQ ID NO: 94) |
| | A | N | Q | R | A | I | K | (SEQ ID NO: 95) |
| | A | N | Q | R | A | H | Q | (SEQ ID NO: 96) |
| | D | T | K | K | A | V | K | (SEQ ID NO: 97) |
| | K | T | K | K | A | V | K | (SEQ ID NO: 98) |
| | E | T | K | K | A | I | K | (SEQ ID NO: 99) |
| | E | T | K | R | A | M | K | (SEQ ID NO: 100) |
| | D | T | K | K | A | V | R | (SEQ ID NO: 101) |
| | D | T | K | K | A | L | K | (SEQ ID NO: 102) |
| | D | T | K | K | A | M | K | (SEQ ID NO: 103) |
| | E | S | K | K | A | V | K | (SEQ ID NO: 104) |
| | E | T | K | K | A | M | K | (SEQ ID NO: 105) |
| | E | T | K | K | A | V | K | (SEQ ID NO: 106) |
| | | | | K | A | | | |
| | | | | R | A | | | |

-continued

| Non-cytotoxic Protease | Cleavage site recognition sequence: P4-P3-P2-P4-↓-P1'-P2'-P3' | | | | | | | |
|---|---|---|---|---|---|---|---|---|
| | P4 | P3 | P2 | P1 | P1' | P2' | P3' | |
| BTx/E | Q | I | D | R | I | M | E | (SEQ ID NO: 107) |
| | Q | I | Q | K | I | T | E | (SEQ ID NO: 108) |
| | Q | I | D | R | I | V | E | (SEQ ID NO: 109) |
| | Q | F | D | R | I | M | D | (SEQ ID NO: 110) |
| | Q | F | D | R | I | M | E | (SEQ ID NO: 111) |
| | Q | L | D | R | I | H | D | (SEQ ID NO: 112) |
| | Q | I | D | R | I | M | D | (SEQ ID NO: 113) |
| | Q | V | D | R | I | Q | Q | (SEQ ID NO: 114) |
| | | | | R | I | | | |
| | | | | K | I | | | |
| BTx/B | G | A | S | Q | F | E | T | (SEQ ID NO: 115) |
| | A | G | A | S | Q | F | E | (SEQ ID NO: 116) |
| | G | A | S | Q | F | E | S | (SEQ ID NO: 117) |
| | Q | A | S | Q | F | E | S | (SEQ ID NO: 118) |
| | G | A | S | Q | G | E | T | (SEQ ID NO: 119) |
| | G | A | S | Q | F | E | Q | (SEQ ID NO: 120) |
| | Q | A | S | Q | F | E | A | (SEQ ID NO: 121) |
| | G | A | S | Q | F | Q | Q | (SEQ ID NO: 122) |
| | G | A | S | Q | F | E | A | (SEQ ID NO: 123) |
| | | | | Q | F | | | |
| BTx/D | R | D | Q | K | L | S | E | (SEQ ID NO: 124) |
| | R | D | Q | K | I | S | E | (SEQ ID NO: 125) |
| | K | D | Q | K | L | A | E | (SEQ ID NO: 126) |
| | | | | K | L | | | |
| BTx/F | E | R | D | Q | K | L | S | (SEQ ID NO: 127) |
| | V | L | E | R | D | Q | K | (SEQ ID NO: 128) |
| | E | R | D | Q | K | I | S | (SEQ ID NO: 129) |
| | E | R | D | Q | A | L | S | (SEQ ID NO: 130) |
| | E | K | D | Q | K | L | A | (SEQ ID NO: 131) |
| | | | | Q | K | | | |
| BTx/G | E | S | S | A | A | K | I | (SEQ ID NO: 132) |
| | E | T | S | A | A | K | I | (SEQ ID NO: 133) |
| | E | S | S | A | A | K | L | (SEQ ID NO: 134) |
| | E | T | S | A | A | K | L | (SEQ ID NO: 135) |
| | | | | A | A | | | |
| TTx | G | A | S | Q | F | E | T | (SEQ ID NO: 136) |
| | G | A | S | Q | G | E | T | (SEQ ID NO: 137) |
| | G | A | S | Q | F | E | Q | (SEQ ID NO: 138) |
| | Q | A | S | Q | F | E | A | (SEQ ID NO: 139) |
| | G | A | S | Q | F | E | S | (SEQ ID NO: 140) |
| | Q | A | S | Q | F | E | S | (SEQ ID NO: 141) |
| | G | A | S | Q | F | Q | Q | (SEQ ID NO: 142) |
| | G | A | S | Q | F | E | A | (SEQ ID NO: 143) |
| | | | | Q | F | | | |
| IgA protease | S | T | P | P | T | P | S | (SEQ ID NO: 144) |
| Antarease | I | K | R | K | Y | W | W | (SEQ ID NO: 145) |

A targeting moiety (TM) means any chemical structure that functionally interacts with a Binding Site to cause a physical association between a fusion polypeptide as described herein and the surface of a target cell. In the context of the present invention, the target cell is a nociceptor neuron. The term TM embraces any molecule (i.e. a naturally occurring molecule, or a chemically/physically modified variant thereof) that is capable of binding to a Binding Site on the target cell, which Binding Site is capable of internalization (e.g. endosome formation)—also referred to as receptor-mediated endocytosis. The TM may possess an endosomal membrane translocation function, in which case separate TM and Translocation Domain components need not be present in an agent of the present invention. Throughout the preceding description, specific TMs have been described. Reference to the TMs is merely exemplary, and the present invention embraces all variants and derivatives thereof, which retain the basic binding (i.e. targeting) ability of the exemplified TMs.

A TM according to the present invention includes antibodies (e.g. antibody fragments) and binding scaffolds; especially commercially available antibodies/fragments and scaffolds designed for the purpose of binding (e.g. specifically) to target cells.

Protein scaffolds represent a new generation of universal binding frameworks to complement the expanding repertoire of therapeutic monoclonal antibodies and derivatives such as scFvs, Fab molecules, dAbs (single-domain antibodies), camelids, diabodies and minibodies, each of which may be employed as a TM of the present invention. Scaffold systems create or modify known protein recognition domains either through creation of novel scaffolds or modification of known protein binding domains. Such scaffolds include but are not limited to:

(i) protein A based scaffolds-affibodies (Nord, K. et al 1997 "Binding proteins selected from combinatorial libraries of an alpha-helical bacterial receptor domain". Nat Biotechnol 15, 772-777);

(ii) lipocalin based scaffolds—anticalins (Skerra 2008 "Alternative binding proteins: anticalins—harnessing the structural plasticity of the lipocalin ligand pocket to engineer novel binding activities". FEBS J. 275:2677-83);

(iii) fibronectin based scaffolds—adnectin (Dineen et al 2008 "The Adnectin CT-322 is a novel VEGF receptor 2 inhibitor that decreases tumour burden in an orthotropic mouse model of pancreatic cancer". BMC Cancer 8:352);

(iv) avimers (Silverman et al 2005 "Multivalent avimer proteins evolved by exon shuffling of a family of human receptor domains". Nat Biotechnol 23:1556-61);

(v) ankyrin based scaffolds—darpins (Zahnd et al 2006 "Selection and characterization of Her2 binding-designed ankyrin repeat proteins". J Biol Chem. 281: 35167-75); and (vi) centyrin scaffolds—based on a protein fold that has significant structural homology to Ig domains with loops that are analogous to CDRs. Ig domains are a common module in human proteins and have been widely applied as alternative scaffold proteins. Each of the above 'scaffold' publications is hereby incorporated (in its entirety) by reference thereto.

Binding scaffolds can be used to target particular cell types via interaction with specific cell surface proteins, receptors or other cell surface epitopes such as sugar groups. Such modified scaffolds can be engineered onto recombinant non-cytotoxic protease based polypeptides of the present invention.

The TM of the present invention binds (preferably specifically binds) to a nociceptor neuron target cell in question. The term "specifically binds" preferably means that a given TM binds to the target cell with a binding affinity (Ka) of $10^6$ $M^{-1}$ or greater, preferably $10^7$ $M^{-1}$ or greater, more preferably $10^8 M^{-1}$ or greater, and most preferably, $10^9 M^{-1}$ or greater. The term "specifically binds" can also mean that a given TM binds to a given receptor, e.g., ANTXR2 or NGFR, or Nav1.7. 1.8 and 1.9 ion channels found on nociceptor, with a binding affinity (Ka) of $10^6$ $M^{-1}$ or greater, preferably $10^7$ $M^{-1}$ or greater, more preferably $10^8 M^{-1}$ or greater, and most preferably, $10^9$ M–1 or greater.

Reference to TM in the present specification embraces fragments and variants thereof, which retain the ability to bind to the target cell in question. By way of example, a variant may have at least 80%, preferably at least 90%, more preferably at least 95%, and most preferably at least 97 or at least 99% amino acid sequence homology with the reference TM (e.g. any SEQ ID NO presented in the present specification which defines a TM). Thus, a variant may include one or more analogues of an amino acid (e.g. an unnatural amino acid), or a substituted linkage. Also, by way of example, the term fragment, when used in relation to a TM, means a peptide having at least ten, preferably at least twenty, more preferably at least thirty, and most preferably at least forty amino acid residues of the reference TM. The term fragment also relates to the above-mentioned variants. Thus, by way of example, a fragment of the present invention may comprise a peptide sequence having at least 10, 20, 30 or 40 amino acids, wherein the peptide sequence has at least 80% sequence homology over a corresponding peptide sequence (of contiguous) amino acids of the reference peptide.

It is routine to confirm that a TM binds to the selected target cell. For example, a simple radioactive displacement experiment may be employed in which tissue or cells representative of a target cell in question are exposed to labelled (e.g. tritiated) TM in the presence of an excess of unlabelled TM. In such an experiment, the relative proportions of non-specific and specific binding may be assessed, thereby allowing confirmation that the TM binds to the target cell. Optionally, the assay may include one or more binding antagonists, and the assay may further comprise observing a loss of TM binding. Examples of this type of experiment can be found in Hulme, E. C. (1990), Receptor-binding studies, a brief outline, pp. 303-311, In Receptor biochemistry, A Practical Approach, Ed. E. C. Hulme, Oxford University Press.

In the context of the present invention, reference to a peptide TM embraces peptide analogues thereof, so long as the analogue binds to the same receptor as the corresponding 'reference' TM.

The fusion proteins (also referred to herein as polypeptides) described herein may lack a functional HC (heavy chain) or $H_C$ domain (C-terminal moiety of the HC) of a clostridial neurotoxin. In one embodiment, the polypeptides lack the last 50 C-terminal amino acids of a clostridial neurotoxin holotoxin. In another embodiment, the polypeptides lack the last 100, 150, 200, 250, or 300 C-terminal amino acid residues of a clostridial neurotoxin holotoxin. Alternatively, the HC binding activity may be negated/reduced by mutagenesis—by way of example, referring to BTx/A for convenience, modification of one or two amino acid residue mutations (W1266 to L and Y1267 to F) in the ganglioside binding pocket causes the HC region to lose its receptor binding function. Analogous mutations may be made to non-serotype A clostridial peptide components, e.g. a construct based on botulinum B with mutations (W1262 to L and Y1263 to F) or botulinum E (W1224 to L and Y1225 to F). Other mutations to the active site achieve the same ablation of HC receptor binding activity, e.g. Y1267S in botulinum type A toxin and the corresponding highly conserved residue in the other clostridial neurotoxins. Details of this and other mutations are described in Rummel et al (2004) (Molecular Microbiol. 51:631-634), which is hereby incorporated by reference thereto.

The HC peptide of a native clostridial neurotoxin comprises approximately 400-440 amino acid residues, and consists of two functionally distinct domains of approximately 25 kDa each, namely the N-terminal region (commonly referred to as the $H_N$ peptide or domain) and the C-terminal region (commonly referred to as the $H_C$ peptide or domain). Moreover, it has been well documented that the C-terminal region ($H_C$), which constitutes the C-terminal 160-200 amino acid residues, is responsible for binding of a clostridial neurotoxin to its natural cell receptors, namely to nerve terminals at the neuromuscular junction. Thus, reference throughout this specification to a clostridial heavy-chain lacking a functional heavy chain HC peptide (or domain) such that the heavy-chain is incapable of binding to cell surface receptors to which a native clostridial neurotoxin binds means that the clostridial heavy-chain simply lacks a functional $H_C$ peptide. In other words, the Hc peptide region is either partially or wholly deleted, or otherwise modified (e.g. through conventional chemical or proteolytic treatment) to inactivate its native binding ability for nerve terminals at the neuromuscular junction.

Thus, in one embodiment, a clostridial $H_N$ peptide lacks part of a C-terminal peptide portion ($H_C$) of a clostridial neurotoxin and thus lacks the HC binding function of native clostridial neurotoxin. By way of example, in one embodiment, the C-terminally extended clostridial $H_N$ peptide lacks the C-terminal 40 amino acid residues, or the C-terminal 60 amino acid residues, or the C-terminal 80 amino acid residues, or the C-terminal 100 amino acid residues, or the C-terminal 120 amino acid residues, or the C-terminal 140 amino acid residues, or the C-terminal 150 amino acid residues, or the C-terminal 160 amino acid residues of a clostridial neurotoxin heavy-chain. In another embodiment, the clostridial $H_N$ peptide of the present invention lacks the entire C-terminal peptide portion ($H_C$) of a clostridial neurotoxin and thus lacks the HC binding function of native clostridial neurotoxin. By way of example, in one embodiment, the clostridial $H_N$ peptide lacks the C-terminal 165 amino acid residues, or the C-terminal 170 amino acid residues, or the C-terminal 175 amino acid residues, or the C-terminal 180 amino acid residues, or the C-terminal 185 amino acid residues, or the C-terminal 190 amino acid residues, or the C-terminal 195 amino acid residues of a clostridial neurotoxin heavy-chain. By way of further example, the clostridial $H_N$ peptide of the present invention lacks a clostridial $H_C$ reference sequence selected from the group consisting of:

Botulinum type A neurotoxin-amino acid residues (Y1111-L1296)

Botulinum type B neurotoxin-amino acid residues (Y1098-E1291)

Botulinum type C neurotoxin-amino acid residues (Y1112-E1291)

Botulinum type D neurotoxin-amino acid residues (Y1099-E1276)

Botulinum type E neurotoxin-amino acid residues (Y1086-K1252)

Botulinum type F neurotoxin-amino acid residues (Y1106-E1274)

Botulinum type G neurotoxin-amino acid residues (Y1106-E1297)

Tetanus neurotoxin-amino acid residues (Y1128-D1315).

A Translocation Domain is a molecule or protein domain that enables translocation of a protease into a target cell such that a functional expression of protease activity occurs within the cytosol of the target cell. Whether any molecule (e.g. a protein or peptide) possesses the requisite translocation function of the present invention may be confirmed by any one of a number of conventional assays.

For example, Shone C. (1987) describes an in vitro assay employing liposomes, which are challenged with a test molecule. Presence of the requisite translocation function is confirmed by release from the liposomes of K+ and/or labelled NAD, which may be readily monitored [see Shone C. (1987) Eur. J. Biochem; vol. 167(1): pp. 175-180].

A further example is provided by Blaustein R. (1987), which describes a simple in vitro assay employing planar phospholipid bilayer membranes. The membranes are challenged with a test molecule and the requisite translocation function is confirmed by an increase in conductance across the membranes [see Blaustein (1987) FEBS Letts; vol. 226, no. 1: pp. 115-120].

Additional methodology to enable assessment of membrane fusion and thus identification of Translocation Domains suitable for use in the present invention are provided by Methods in Enzymology Vol 220 and 221, Membrane Fusion Techniques, Parts A and B, Academic Press 1993.

The present invention also embraces variant translocation domains, so long as the variant domains still demonstrate the requisite translocation activity. By way of example, a variant may have at least 70%, preferably at least 80%, more preferably at least 90%, and most preferably at least 95% or at least 98% amino acid sequence homology with a reference translocation domain. The term fragment, when used in relation to a translocation domain, means a peptide having at least 20, preferably at least 40, more preferably at least 80, and most preferably at least 100 amino acid residues of the reference translocation domain. In the case of a clostridial translocation domain, the fragment preferably has at least 100, preferably at least 150, more preferably at least 200, and most preferably at least 250 amino acid residues of the reference translocation domain (e.g. $H_N$ domain). As with the TM 'fragment' component (discussed above), translocation 'fragments' of the present invention embrace fragments of variant translocation domains based on the reference sequences.

The Translocation Domain is preferably capable of formation of ion-permeable pores in lipid membranes under conditions of low pH. Preferably it has been found to use only those portions of the protein molecule capable of pore-formation within the endosomal membrane.

The Translocation Domain may be obtained from a microbial protein source, in particular from a bacterial or viral protein source. Hence, in one embodiment, the Translocation Domain is a translocating domain of an enzyme, such as a bacterial toxin or viral protein.

It is well documented that certain domains of bacterial toxin molecules are capable of forming such pores. It is also known that certain translocation domains of virally expressed membrane fusion proteins are capable of forming such pores. Such domains may be employed in the present invention.

The Translocation Domain may be of a clostridial origin, such as the $H_N$ domain (or a functional component thereof). $H_N$ means a portion or fragment of the H-chain of a clostridial neurotoxin approximately equivalent to the amino-terminal half of the H-chain, or the domain corresponding to that fragment in the intact H-chain. In this regard, should it be desired to remove the HC cell-binding function, this may be done by deletion of the HC or $H_C$ amino acid sequence (either at the DNA synthesis level, or at the post-synthesis level by nuclease or protease treatment). Alternatively, the HC function may be inactivated by chemical or biological treatment.

Examples of suitable (reference) Translocation Domains include:

Botulinum type A neurotoxin-amino acid residues (449-871)

Botulinum type B neurotoxin-amino acid residues (441-858)

Botulinum type C neurotoxin-amino acid residues (442-866)

Botulinum type D neurotoxin-amino acid residues (446-862)

Botulinum type E neurotoxin-amino acid residues (423-845)

Botulinum type F neurotoxin-amino acid residues (440-864)

Botulinum type G neurotoxin-amino acid residues (442-863)

Tetanus neurotoxin-amino acid residues (458-879)

The above-identified reference sequence should be considered a guide, as slight variations may occur according to sub-serotypes. By way of example, US 2007/0166332 (hereby incorporated by reference thereto) cites slightly different clostridial sequences:

Botulinum type A neurotoxin-amino acid residues (A449-K871)
Botulinum type B neurotoxin-amino acid residues (A442-S858)
Botulinum type C neurotoxin-amino acid residues (T450-N866)
Botulinum type D neurotoxin-amino acid residues (D446-N862)
Botulinum type E neurotoxin-amino acid residues (K423-K845)
Botulinum type F neurotoxin-amino acid residues (A440-K864)
Botulinum type G neurotoxin-amino acid residues (S447-S863)
Tetanus neurotoxin-amino acid residues (S458-V879)

Further examples of suitable translocation domains are described in detail in WO 2007/106115, which is hereby incorporated in its entirety by reference thereto.

In the context of the present invention, a variety of clostridial toxin $H_N$ regions comprising a translocation domain can be useful in aspects of the present invention with the proviso that these active fragments can facilitate the release of a non-cytotoxic protease (e.g. a clostridial L-chain) from intracellular vesicles into the cytoplasm of the target cell and thus participate in executing the overall cellular mechanism whereby a clostridial toxin proteolytically cleaves a substrate. The $H_N$ regions from the heavy chains of clostridial toxins are approximately 410-430 amino acids in length and comprise a translocation domain. Research has shown that the entire length of a $H_N$ region from a clostridial toxin heavy chain is not necessary for the translocating activity of the translocation domain. Thus, embodiments can include clostridial toxin $H_N$ regions comprising a translocation domain having a length of, for example, at least 350 amino acids, at least 375 amino acids, at least 400 amino acids and at least 425 amino acids. Other embodiments can include clostridial toxin $H_N$ regions comprising translocation domain having a length of, for example, at most 350 amino acids, at most 375 amino acids, at most 400 amino acids and at most 425 amino acids.

For further details on the genetic basis of toxin production in *Clostridium botulinum* and *C. tetani*, we refer to Henderson et al (1997) in The Clostridia: Molecular Biology and Pathogenesis, Academic press.

The term $H_N$ embraces naturally-occurring neurotoxin $H_N$ portions, and modified $H_N$ portions having amino acid sequences that do not occur in nature and/or synthetic amino acid residues, so long as the modified $H_N$ portions still demonstrate the above-mentioned translocation function.

Alternatively, the Translocation Domain may be of a non-clostridial origin. Examples of non-clostridial translocation domain origins include, but not be restricted to, the translocation domain of diphtheria toxin [O=Keefe et al., Proc. Natl. Acad. Sci. USA (1992) 89, 6202-6206; Silverman et al., J. Biol. Chem. (1993) 269, 22524-22532; and London, E. (1992) Biochem. Biophys. Acta., 1112, pp. 25-51], the translocation domain of *Pseudomonas* exotoxin type A [Prior et al. Biochemistry (1992) 31, 3555-3559], the translocation domains of anthrax toxin [Blanke et al. Proc. Natl. Acad. Sci. USA (1996) 93, 8437-8442], a variety of fusogenic or hydrophobic peptides of translocating function [Plank et al. J. Biol. Chem. (1994) 269, 12918-12924; and Wagner et al (1992) PNAS, 89, pp. 7934-'7938], and amphiphilic peptides [Murata et al (1992) Biochem., 31, pp. 1986-1992]. The Translocation Domain may mirror the Translocation Domain present in a naturally-occurring protein, or may include amino acid variations so long as the variations do not destroy the translocating ability of the Translocation Domain.

Particular examples of viral translocation domains suitable for use in the compositions and methods described herein include certain translocating domains of virally expressed membrane fusion proteins. For example, Wagner et al. (1992) and Murata et al. (1992) describe the translocation (i.e. membrane fusion and vesiculation) function of a number of fusogenic and amphiphilic peptides derived from the N-terminal region of influenza virus haemagglutinin. Other virally expressed membrane fusion proteins known to have the desired translocating activity are a translocating domain of a fusogenic peptide of Semliki Forest Virus (SFV), a translocating domain of vesicular stomatitis virus (VSV) glycoprotein G, a translocating domain of SER virus F protein and a translocating domain of Foamy virus envelope glycoprotein. Virally encoded Aspike proteins have particular application in the context of the present invention, for example, the E1 protein of SFV and the G protein of the G protein of VSV.

Use of the translocation domains listed in Table 2 (below) includes use of sequence variants thereof. A variant may comprise one or more conservative nucleic acid substitutions and/or nucleic acid deletions or insertions, with the proviso that the variant possesses the requisite translocating function. A variant may also comprise one or more amino acid substitutions and/or amino acid deletions or insertions, so long as the variant possesses the requisite translocating function.

TABLE 2

| Translocation Domain source | Amino acid residues | References |
| --- | --- | --- |
| Diphtheria toxin | 194-380 | Silverman et al., 1994, J. Biol. Chem. 269, 22524-22532 London E., 1992, Biochem. Biophys. Acta., 1113, 25-51 |
| Domain II of pseudomonas exotoxin | 405-613 | Prior et al., 1992, Biochemistry 31, 3555-3559 Kihara & Pastan, 1994, Bioconj Chem. 5, 532-538 |
| Influenza virus haemagglutinin | GLFGAIAGFIENGW EGMIDGWYG, and Variants thereof | Plank et al., 1994, J. Biol. Chem. 269, 12918-12924 Wagner et al., 1992, PNAS, 89, 7934-7938 Murata et al., 1992, Biochemistry 31, 1986-1992 |
| Semliki Forest virus fusogenic protein | Translocation domain | Kielian et al., 1996, J Cell Biol. 134(4), 863-872 |
| Vesicular Stomatitis virus glycoprotein G | 118-139 | Yao et al., 2003, Virology 310(2), 319-332 |
| SER virus F protein | Translocation domain | Seth et al., 2003, J Virol 77(11) 6520-6527 |
| Foamy virus envelope glycoprotein | Translocation domain | Picard-Maureau et al., 2003, J Virol. 77(8), 4722-4730 |

The polypeptides of the compositions and methods described herein may further comprise a translocation facilitating domain. This domain facilitates delivery of the non-cytotoxic protease into the cytosol of the target cell and are described, for example, in WO 08/008803 and WO 08/008805, each of which is herein incorporated by reference thereto.

By way of example, suitable translocation facilitating domains include an enveloped virus fusogenic peptide domain, for example, suitable fusogenic peptide domains include influenza virus fusogenic peptide domain (e.g. influenza A virus fusogenic peptide domain of 23 amino acids), alphavirus fusogenic peptide domain (e.g. Semliki Forest virus fusogenic peptide domain of 26 amino acids), vesiculovirus fusogenic peptide domain (e.g. vesicular stomatitis virus fusogenic peptide domain of 21 amino acids), respirovirus fusogenic peptide domain (e.g. Sendai virus fusogenic peptide domain of 25 amino acids), morbiliivirus fusogenic peptide domain (e.g. Canine distemper virus fusogenic peptide domain of 25 amino acids), avulavirus fusogenic peptide domain (e.g. Newcastle disease virus fusogenic peptide domain of 25 amino acids), henipavirus fusogenic peptide domain (e.g. Hendra virus fusogenic peptide domain of 25 amino acids), metapneumovirus fusogenic peptide domain (e.g. Human metapneumovirus fusogenic peptide domain of 25 amino acids) or spumavirus fusogenic peptide domain such as simian foamy virus fusogenic peptide domain; or fragments or variants thereof.

By way of further example, a translocation facilitating domain may comprise a Clostridial toxin $H_N$ domain or a fragment or variant thereof. In more detail, a Clostridial toxin $H_N$ translocation facilitating domain may have a length of at least 200 amino acids, at least 225 amino acids, at least 250 amino acids, at least 275 amino acids. In this regard, a Clostridial toxin $H_N$ translocation facilitating domain preferably has a length of at most 200 amino acids, at most 225 amino acids, at most 250 amino acids, or at most 275 amino acids. Specific examples include:

Botulinum type A neurotoxin-amino acid residues (872-1110)
Botulinum type B neurotoxin-amino acid residues (859-1097)
Botulinum type C neurotoxin-amino acid residues (867-1111)
Botulinum type D neurotoxin-amino acid residues (863-1098)
Botulinum type E neurotoxin-amino acid residues (846-1085)
Botulinum type F neurotoxin-amino acid residues (865-1105)
Botulinum type G neurotoxin-amino acid residues (864-1105)
Tetanus neurotoxin-amino acid residues (880-1127)

The above sequence positions may vary somewhat according to serotype/sub-type, and further examples of suitable (reference) Clostridial toxin $H_N$ domains include:

Botulinum type A neurotoxin-amino acid residues (874-1110)
Botulinum type B neurotoxin-amino acid residues (861-1097)
Botulinum type C neurotoxin-amino acid residues (869-1111)
Botulinum type D neurotoxin-amino acid residues (865-1098)
Botulinum type E neurotoxin-amino acid residues (848-1085)
Botulinum type F neurotoxin-amino acid residues (867-1105)
Botulinum type G neurotoxin-amino acid residues (866-1105)
Tetanus neurotoxin-amino acid residues (882-1127)

Any of the above-described facilitating domains may be combined with any of the previously described translocation domain peptides that are suitable for use in the present invention. Thus, by way of example, a non-clostridial facilitating domain may be combined with non-clostridial translocation domain peptide or with clostridial translocation domain peptide. Alternatively, a Clostridial toxin $H_N$ translocation facilitating domain may be combined with a non-clostridial translocation domain peptide. Alternatively, a Clostridial toxin $H_N$ facilitating domain may be combined or with a clostridial translocation domain peptide, examples of which include:

Botulinum type A neurotoxin-amino acid residues (449-1110)
Botulinum type B neurotoxin-amino acid residues (442-1097)
Botulinum type C neurotoxin-amino acid residues (450-1111)
Botulinum type D neurotoxin-amino acid residues (446-1098)
Botulinum type E neurotoxin-amino acid residues (423-1085)
Botulinum type F neurotoxin-amino acid residues (440-1105)
Botulinum type G neurotoxin-amino acid residues (447-1105)
Tetanus neurotoxin-amino acid residues (458-1127)

The above-identified reference sequences should be considered a guide, as slight variations may occur according to sub-serotypes.

Sequence Homology

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics: 1428-1435 (2004).

Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

Alignment scores for determining sequence identity

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The percent identity is then calculated as:

$$\left[\frac{\text{Total number of identical matches}}{\text{length of the longer sequence plus the number of gaps introduced into the longer sequence in order to align the two sequences}}\right] \times 100$$

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

Conservative Amino Acid Substitutions
Basic: arginine
lysine
histidine
Acidic: glutamic acid
aspartic acid
Polar: glutamine
asparagine
Hydrophobic: leucine
isoleucine
valine
Aromatic: phenylalanine
tryptophan
tyrosine
Small: glycine
alanine
serine
threonine
methionine In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for clostridial polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethyl cysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in *Xenopus* oocytes by microinjection of mutated mRNA and chemically aminoacylated suppressor tRNAs (Turcatti et al., J. Biol. Chem. 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

A limited number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, Science 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992. The identities of essential amino acids can also be inferred from analysis of homologies with related components (e.g. the translocation or protease components) of the polypeptides of the present invention.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenised polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Some embodiments of the technology described herein can be defined according to any of the following numbered paragraphs:

1. A fusion protein comprising: (i) a botulinum neurotoxin (BTx) or a tetanus neurotoxin (TTx), and (ii) an anthrax toxin protective antigen (PA), or a C-terminal receptor-binding domain of PA, wherein part (a) and (b) are linked or fused together.

2. The fusion protein of paragraph 1, wherein the BTx or TTx comprises a BTx or TTx enzymatic moiety and the translocation signal.
3. The fusion protein of paragraph 2, wherein the BTx enzymatic moiety or translocation signal is selected from the BTx light chain and heavy chain domains of any one of BTx/A, BTx/B, BTx/C, BTx/D, BTx/E, BTx/F, BTx/G, and a non-Clostridial botulinum-like toxin.
4. The fusion protein of paragraph 2, wherein the BTx or TTx enzymatic moiety or translocation signal is selected from the respective LC enzymatic moiety or $H_N$ translocation peptide found in Table 1.
5. The fusion protein of any one of paragraph 2-4, wherein the part (a) and (b), or the enzymatic moiety and translocation peptide are linked by a linker peptide.
6. The fusion protein of paragraph 5, wherein the linker peptide is 1-20 amino acids long.
7. The fusion protein of paragraph 5 or 6, wherein the linker peptide is stable in human serum for at least 1 minute.
8. The fusion protein of any one of paragraph 5-7, wherein the linker peptide comprises at least one amino amino acid that is Gly or Ser.
9. The fusion protein of any one of paragraph 5-8, wherein the linker peptide does not comprise Lys and/or Arg.
10. The fusion protein of any one of paragraph 1-9, wherein the C-terminal receptor-binding domain of PA comprises a PAd4 domain, a PAd2 and a PAd4 domain, or PA63.
11. The fusion protein of any one of paragraph 1-10, wherein the PA or the C-terminal receptor-binding domain of PA is resistant to cleavage by a protease.
12. The fusion protein of any one of paragraph 1-11, wherein the the PA or the C-terminal receptor-binding domain of PA is resistant to furin cleavage, or Lys C cleavage or both.
13. A fusion protein comprising: (a) a non-cytotoxic protease, which protease is capable of cleaving a SNARE protein in a nociceptor neuron; and (b) a protein capable of binding to an anthrax toxin protective antigen (PA) or a fragment thereof, wherein the PA or fragment binds a receptor expressed on the nociceptor neuron.
14. The fusion protein of paragraph 13, wherein the non-cytotoxic protease comprises a clostridial neurotoxin L-chain.
15. The fusion protein of paragraph 14, wherein the clostridial neurotoxin is botulinum neurotoxin (BTx) or tetanus neurotoxin (TTx).
16. The fusion protein of paragraph 14 or 15, wherein the clostridial neurotoxin L-chain is selected from Table 1.
17. The fusion protein of any one of paragraph 13-16, wherein the PA-binding receptor expressed on the nociceptor neuron is ANTXR2 (CMG2).
18. The fusion protein of any one of paragraph 13-16, wherein the protein capable of binding to PA is an anthrax toxin lethal factor (LF), or an anthrax toxin edema factor (EF).
19. The fusion protein of paragraph 18, wherein PA binding domain of LF is the N-terminal domain of LF, (abbreviated as LFPABD or LFn).
20. The fusion protein of paragraph 18, wherein PA binding domain of EF is the N-terminal domain of EF, (abbreviated as EFPABD or EFn).
21. A fusion protein comprising: (a) a disulfide-containing peptide toxin (these include the channel blocking toxins having a cysteine-knot motif), which is capable of blocking ion channels in a nociceptor neuron; and (b) a targeting moiety (TM) that is capable of binding to a binding site on the nociceptor neuron, wherein the nociceptor neuron expresses said ion channels therein (e.g., sodium or calcium or both sodium and calcium);

22. The fusion protein of paragraph 21, wherein the disulfide-containing peptide toxin comprises a cysteine knot motif 23. The fusion protein of paragraph 21 or 22, wherein the disulfide-containing peptide toxin is a conotoxin, an agatoxin, a delta-palutoxin, a huwentotoxin or a ProTx II toxin.

24. The fusion protein according to paragraph 21, 22, or 23, wherein the TM is selected from the group consisting of: an anthrax toxin protective antigen (PA); a C-terminal receptor-binding domain of PA; and a nociceptor neuron-binding protein.

25. The fusion protein according to paragraph 24, wherein the PA or C-terminal receptor-binding domain of PA interacts with and binds the ANTXR2 (CMG2) receptor expressed on the nociceptor neuron.

26. The fusion protein according to paragraph 24 or 25, wherein the PA is a mutant or variant PA that is resistant to furin cleavage.

27. The fusion protein according to paragraph 24, 25, or 26, wherein the C-terminal receptor-binding domain of PA is PA63 or PAd4 or comprises PAd2 and PAd4 domains.

28. The fusion protein according to paragraph 27, wherein the PAd4 is resistant to cleavage by a protease.

29. The fusion protein according to paragraph 28, wherein the protease is furin or Lys C.

30. The fusion protein of any one of paragraph 24-29, wherein the nociceptor neuron-binding protein is an antibody.

31. The fusion protein of paragraph 30, wherein the antibody specifically binds to nerve growth factor receptor, the ANTXR2 receptor, or an ion-channel protein present on nociceptor neurons.

32. The fusion protein of paragraph 31, wherein the ion-channel protein is selected from Nav1.7, Nav1.8 or Nav1.9.

33. A fusion protein comprising: (a) a disulfide-containing peptide toxin (this are channel blocking toxin having a cysteine-knot motif), which is capable of blocking sodium or calcium or both sodium and calcium channels in a nociceptor neuron; and (b) a protein capable of binding to an anthrax toxin protective antigen (PA) or a fragment thereof, wherein the fragment binds a receptor expressed on the nociceptor neuron.

34. The fusion protein of paragraph 33, wherein the disulfide-containing peptide toxin comprises a cysteine knot motif 35. The fusion protein of paragraph 33 or 34, wherein the disulfide-containing peptide toxin is a conotoxin, an agatoxin, a delta-palutoxin, a huwentotoxin or a ProTx II toxin.

36. The fusion protein of paragraph 33, 34 or 35, wherein the PA-binding receptor expressed on the nociceptor neuron is ANTXR2 (CMG2).

37. The fusion protein of any one of paragraph 33-37, wherein the protein capable of binding to PA is: an anthrax toxin lethal factor (LF); or an anthrax toxin edema factor (EF).

38. A fusion protein comprising: (a) an AB toxin; (b) an anthrax toxin protective antigen (PA) or a fragment thereof, wherein the PA or fragment binds a receptor expressed on the nociceptor neuron; and (c) a translocation domain (TL) that is capable of translocating the protease from within an endosome, across the endosomal membrane and into the cytosol of the nociceptor neuron.

39. The fusion protein of paragraph 38, wherein the AB toxin is selected from Ricin toxin, Cholera toxin A-part and B-part; *Pseudomonas aeruginosa* Exotoxin A A-part and B-part; Shiga toxin A-part and B-part; and Diphtheria toxin A-part and B-part.

40. The fusion protein of paragraph 38 or 39, wherein the PA-binding receptor expressed on the nociceptor neuron is ANTXR2 (CMG2).

41. The fusion protein of paragraph 38, 30, or 40, wherein the PA fragment is a C-terminal receptor-binding domain of PA.

42. The fusion protein of any one of paragraph 38-41, wherein the TL is a clostridial neurotoxin translocation domain; a holotoxin; or a variant form of the holotoxin that has the toxin receptor-binding function of the AB toxin negated.

43. A nucleic acid encoding a fusion protein according to any of the previous paragraphs.

44. A vector comprising the nucleic acid of paragraph 43.

45. The vector of paragraph 44, wherein the vector is a plasmid, a bacteriophage, a phagmid, a cosmid, a viral vector, or a viral particle.

46. A cell comprising the nucleic acid of paragraph 43 or the vector of paragraph 44 or 45.

47. A method of producing the fusion protein of any of the preceding claim comprising: culturing the cell of paragraph 46 in conditions such that the fusion protein is expressed; and recovering the fusion protein.

48. The fusion protein produced by the method of paragraph 47.

49. A composition comprising the fusion protein of any one of previous paragraphs.

50. A method for treatment of pain, the method comprising administering to a subject in need thereof the composition of any of the preceding paragraphs.

51. A method of treating pain comprising administering to a subject in need thereof, native mature anthrax toxin protective antigen (PA) and anthrax toxin edema factor (EF), anthrax toxin lethal factor (LF) or any combination thereof 52. A fusion protein comprising a botulinum neurotoxin (BTx) moiety comprising an N-terminal enzymatic domain (L chain) and an intermediate pore-forming/translocation-domain ($H_N$) of the BTx linked to a C-terminal receptor-binding domain of anthrax toxin protective antigen (PAd4 domain).

53. The fusion protein of paragraph 52 further comprising a linker peptide between the BTx moiety and the PAd4 domain.

54. The fusion protein of paragraph 53, wherein the linker peptide is 1-20 amino acids long.

55. The fusion protein of paragraph 53 or 54, wherein the linker peptide is stable in human serum for at least 1 minute.

56. The fusion protein of any one of paragraph 53-55, wherein the linker peptide comprises at least one amino amino acid that is Gly or Ser.

57. The fusion protein of any one of paragraph 53-56, wherein the linker peptide does not comprise Lys and/or Arg.

58. The fusion protein of any one of paragraph 52-57, wherein the BTx moiety is selected from the BTx light chain and heavy chain domains of any one of BTx/A, BTx/B, BTx/C, BTx/D, BTx/E, BTx/F, BTx/G, and first non-Clostridial botulinum-like toxin.

59. The fusion protein of any one of paragraph 52-58, wherein the fusion protein comprising 2-10 PAd4 domains in tandem.

60. The fusion protein of any one of paragraph 52-59, wherein 1-60 consecutive amino acids from the N-terminal side adjacent to the native PAd4 domain are further incorporated between the BTx moiety and the PAd4.

61. The fusion protein of any one of paragraph 52-60, wherein the one or more of the Lys residues in the PAd4 domain at positions 594, 613, 633, 637, 653, 673, 679, 680, 684, 695, 703, 722, 723, and 729, and 730 of SEQ ID NO:1 (minus the 29 aa signal peptide in SEQ. ID. NO:1) have been replaced by Arg or His.

62. The fusion protein of any one of paragraph 52-61, wherein one or more, up to and including each of the Lys residues in the PAd4 domain at positions 623, 642, 662, 666, 682, 702, 708, 709, 713, 724, 732, 751, 752, 758, and 759 in SEQ. ID. NO:1 have been replaced Arg or His.

63. The fusion protein of any one of paragraph 52-63 comprising an entire PA protein, wherein the furin cleavage site comprising amino acid residues RKKR has been replaced by a furin-resistant amino acid sequence, wherein RKKR are the residues 164-167 of SEQ ID NO: 1 minus the 29 amino acid signal peptide in SEQ ID NO:1.

64. The fusion protein of paragraph 63, wherein the furin-resistant amino acid sequence is SSSR (SEQ ID NO: 32) or SSSS (SEQ ID NO: 33).

65. The fusion protein of any one of paragraph 52-64, wherein one or more of the Asn residues in the PAd4 domain at position 601, 713, 719 of SEQ ID NO:1 (the numbering is that after minus the 29 aa signal peptide from SEQ. ID. NO:1) have been replaced by Asp.

66. The fusion protein of any one of paragraph 52-65, further comprising at least one D-amino acid at the N-terminus of the fusion protein.

67. The fusion protein of any one of paragraph 52-66, wherein the residue corresponding to the junction between the L chain of BTx with the $H_N$ chain of BTx has been cleaved.

68. A composition comprising the fusion protein of any one of paragraphs 52-67.

69. The composition of paragraph 68 further comprising a pharmaceutically acceptable carrier, excipient or diluent.

70. A fusion protein comprising: a botulinum neurotoxin N-terminal enzymatic domain of a botulinum neurotoxin (BTx) moiety (L chain of BTx), and a N-terminal domain (LFn) of anthrax toxin lethal factor, which domain binds to oligomeric forms of PA63, the proteolytically activated form of anthrax PA; or the N-terminal domain (EFn) of anthrax toxin edema factor, which domain binds to oligomeric forms of PA63, the proteolytically activated form of anthrax PA the enzymatic domain, wherein part (a) is linked N-terminally or C-terminally or both N-terminally and C-terminally to part (b).

71. The fusion protein of paragraph 70 further comprising an amino acid sequence defining a belt corresponding to the N-terminal part of the BTx $H_N$ domain which is located at C-terminal side of the BTx moiety, and the belt is linked to the L chain.

72. The fusion protein of paragraph 71, wherein the residue corresponding to the L chain junction with the belt of the BTx $H_N$ domain has been cleaved.

73. The fusion protein of paragraph 71 or 72, wherein the Cys residues in the BTx L chain and the belt corresponding to the N-terminal part of the BTx $H_N$ domain have been changed to Ala, Ser, or Thr.

74. The fusion protein of any one of paragraph 70-73, further comprising at least one D-amino acid at the N-terminus of the fusion protein.

75. The fusion protein of any one of paragraph 70-73, further comprising a linker peptide between the BTx L moiety and the LFn or EFn domain.

76. The fusion protein of paragraph 75, wherein the linker peptide is 1-20 amino acids long.

77. The fusion protein of paragraph 75 or 76, wherein the linker peptide is stable in human serum for at least 1 minute.

78. The fusion protein of any one of paragraph 75-78, wherein the linker peptide comprises at least one amino amino acid that is Gly or Ser.

79. The fusion protein of any one of paragraph 75-79, wherein the linker peptide does not comprise Lys or Arg.

80. A composition comprising any one of the fusion proteins of paragraphs 70-79.

81. The composition of claim 80 further comprising a pharmaceutically acceptable carrier, excipient or diluent.

82. The composition of paragraph 80 or 81 and a native anthrax toxin protective antigen (PA) protein.

83. The composition of paragraph 82, wherein the PA protein is an oligomeric PA.

84. The composition of paragraph 83, wherein the oligomeric PA is bound to the fusion protein.

85. The composition of any one of paragraphs 80-84 further comprising a pharmaceutically acceptable carrier excipient or diluent.

86. A fusion protein comprising: anthrax toxin protective antigen (PA); an anthrax toxin protective antigen C-terminal receptor binding domain (PAd4); or a nociceptor neuron-binding protein linked to, a disulfide-containing peptide toxin.

87. The fusion protein of paragraph 86, wherein the disulfide-containing peptide toxin is an inhibitor cysteine knot toxin.

88. The fusion protein of paragraph 86 or 87, wherein the disulfide-containing peptide toxin is a conotoxin, an agatoxin, a delta-palutoxin, a huwentotoxin or a ProTx II toxin.

89. The fusion protein of paragraph 86, 87 or 88, further comprising a linker peptide between the PA, PAd4 or nociceptor-binding protein and the inhibitor cysteine knot toxin.

90. The fusion protein of paragraph 89, wherein the linker peptide is stable in human serum for at least 1 minute.

91. The fusion protein of paragraph 89 or 90, wherein the linker peptide comprises at least one amino acid that is Gly or Ser.

92. The fusion protein of any of the preceding paragraph 89-91, wherein the linker peptide does not comprise Lys and/or Arg.

93. The fusion protein of any of the preceding paragraph 89-92, wherein the fusion protein comprises 2-10 PAd4 domains in tandem.

94. The fusion protein of any of the preceding paragraph 89-93, wherein the one or more of the Lys residues in PAd4 or PA at positions 594, 613, 633, 637, 653, 673, 679, 680, 684, 695, 703, 722, 723, 729, and 730 of SEQ ID NO:1 (minus the 29 aa signal peptide in SEQ. ID. NO:1) have been replaced by Arg or His.

95. The fusion protein of paragraph 94, wherein one or more, up to and including each of the Lys residues in the PAd4 domain at positions 623, 642, 662, 666, 682, 702, 708, 709, 713, 724, 732, 751, 752, 758, and 759 in SEQ. ID. NO:1 have been replaced Arg or His.

96. The fusion protein of any of the preceding paragraph 89-95 comprising an entire PA protein, wherein the furin cleavage site comprising amino acid residues $^{614}$RKKR$^{167}$ of SEQ ID NO: 1 has been replaced by a furin-resistant amino acid sequence, wherein RKKR are the residues 164-167 of SEQ ID NO: 1 minus the 29 amino acid signal peptide in SEQ ID NO:1.

97. The fusion protein of paragraph 96, wherein the furin-resistant amino acid sequence is SSSR or SSSS.

98. The fusion protein of any of the preceding paragraph 89-97, wherein one or more of the Asn residues in PAd4 or PA at position 601, 713, 719 of SEQ ID NO:1 (minus the 29 aa signal peptide in SEQ. ID. NO:1) have been replaced by Asp.

99. The fusion protein of any of the preceding paragraph 89-98, further comprising at least one D-amino acid at the N-terminus of the fusion protein.

100. The fusion protein of any of the preceding paragraph 89-99, wherein the nociceptor neuron-binding protein is an antibody.

101. The fusion protein of paragraph 100, wherein the antibody specifically binds to nerve growth factor receptor or an ion-channel protein present on nociceptor neurons.

102. The fusion protein of paragraph 101, wherein the ion-channel protein is selected from Nav1.7, Nav1.8 or Nav1.9.

103. A composition comprising the fusion protein of any one of the paragraphs 86-102.

104. The composition of claim 103 further comprising a pharmaceutically acceptable carrier, diluent or excipient.

105. A fusion protein comprising a disulfide-containing peptide toxin operably linked N-terminally or C-terminally or both N-terminally and C-terminally, or chemically crosslinked at one or more sites to the N-terminal domain (LFn) of anthrax toxin lethal factor, which domain binds to oligomeric forms of PA63, the proteolytically activated form of anthrax PA; or the N-terminal domain (EFn) of anthrax toxin edema factor, which domain binds to oligomeric forms of PA63, the proteolytically activated form of anthrax PA.

106. The fusion protein of paragraph 105, further comprising a linker peptide between the LFn and the toxin or the EFn and the toxin.

107. The fusion protein of paragraph 106, wherein the linker peptide is stable in human serum for at least 1 minute.

108. The fusion protein of paragraph 106 or 107, wherein the linker peptide comprises at least one amino acid that is Gly or Ser.

109. The fusion protein of paragraph 106, 107, or 108, wherein the linker peptide does not comprise Lys and/or Arg.

110. A composition comprising the fusion protein of any one of claims paragraphs 105-109.

111. The composition of paragraph 110 further comprising a pharmaceutically acceptable carrier excipient or diluent.

112. The composition of paragraph 110 or 111 further comprising a native anthrax toxin protective antigen (PA).

113. The composition of paragraph 112, wherein the PA is in an oligomeric PA.

114. The composition of paragraph 113, wherein the oligomeric PA is bound to the fusion protein.

115. The composition of any one of paragraphs 110-114 further comprising a pharmaceutically acceptable carrier excipient or diluent.

116. A fusion protein comprising an AB toxin fused to a linker peptide operably linked to a C-terminal receptor-binding domain of anthrax toxin protective antigen (PAd4 domain), wherein the fusion protein further comprises a translocation domain, a holotoxin or a mutant form of the holotoxin that has the toxin receptor-binding function of the AB toxin negated.

117. The fusion protein of paragraph 116, wherein the AB toxin is selected from Ricin toxin, Cholera toxin A-part and B-part; *Pseudomonas aeruginosa* Exotoxin A A-part and B-part; Shiga toxin A-part and B-part; and Diphtheria toxin A-part and B-part.

118. The fusion protein of paragraph 116 or 117, wherein the linker peptide is 1-20 amino acids long.

119. The fusion protein of any of the preceding paragraph 116-118, wherein the linker peptide is stable in human serum for at least 1 minute.

120. The fusion protein of any one of paragraphs 116-119, wherein the linker peptide comprises at least one amino acid that is Gly or Ser.

121. The fusion protein of any one of paragraphs 116-120, wherein the linker peptide does not comprise Lys and Arg.

122. The fusion protein of any of the preceding paragraph 116-121, wherein 1-60 consecutive amino acids from the N-terminal side adjacent to the native PAd4 domain are further incorporated between the AB toxin and the PAd4.

123. The fusion protein of any of the preceding paragraph 116-122, wherein one or more of the Asn residues in PAd4 domain at position 601, 713, 719 of SEQ ID NO: 1 (minus the 29 aa signal peptide in SEQ. ID. NO:1) have been replaced by Asp.

124. The fusion protein of any one of paragraphs 116-123, further comprising at least one D-amino acid at the N-terminus of the fusion protein.

125. The fusion protein of any one of paragraphs 116-124 comprising 2-10 PAd4 domains in tandem.

126. The fusion protein of any of the preceding paragraph 116-125, wherein the one or more of the Lys residues in PAd4 domain at positions 594, 613, 633, 637, 653, 673, 679, 680, 684, 695, 701, 713, 719, 722, 723, 729, and 730 of SEQ ID NO:1 (minus the 29 aa signal peptide in SEQ. ID. NO:1) (PAd4) have been replaced by Arg or His.

127. The fusion protein of any of the preceding paragraph 116-126, wherein one or more, up to and including each of the Lys residues in the PAd4 domain at positions 623, 642, 662, 666, 682, 702, 708, 709, 713, 724, 732, 751, 752, 758, and 759 in SEQ. ID. NO:1 have been replaced Arg or His.

128. The fusion protein of any of the preceding paragraph 116-127 comprising an entire PA protein, wherein the furin cleavage site comprising amino acid residues RKKR has been replaced by a furin-resistant amino acid sequence, wherein RKKR are the residues 164-167 of SEQ ID NO: 1 minus the 29 amino acid signal peptide in SEQ ID NO:1.

129. The fusion protein of paragraph 128, wherein the furin-resistant amino acid sequence is SSSR or SSSS.

130. A composition comprising the fusion protein of any one of paragraph s 114-129.

131. The composition of paragraph 130 further comprising a pharmaceutically acceptable carrier, excipient or diluent.

132. A fusion protein comprising an N-terminal enzymatic domain (Chain A) together with the translocation/pore-forming domain from a tetanus neurotoxin (TTx) operably linked to a C-terminal receptor-binding domain of anthrax toxin protective antigen (PAd4 domain).

133. The fusion protein of paragraph 132 further comprising a linker peptide between the TTx moiety and the PAd4 domain.

134. The fusion protein of paragraph 133, wherein the linker peptide is 1-20 amino acids long.

135. The fusion protein of paragraph 133 or 134, wherein the linker peptide is stable in human serum for at least 1 minute.

136. The fusion protein of paragraph 133, 134, or 135, wherein the linker peptide comprises at least one amino amino acid that is Gly or Ser.

137. The fusion protein of any of the preceding paragraph 133-136, wherein the linker peptide does not comprise Lys or Arg.

138. The fusion protein of any one of paragraphs 132-137 comprising two to ten PAd4 domains in tandem.

139. The fusion protein of any one of paragraphs 132-138, wherein 1-60 amino consecutive amino acids from the N-terminal side adjacent to the native PAd4 domain are further incorporated between the BTx moiety and the PAd4.

140. The fusion protein of any one of paragraphs 132-139, wherein the one or more of the Lys residues in the PAd4 domain at positions 594, 613, 633, 637, 653, 673, 679, 680, 684, 695, 701, 713, 719, 722, 723, 729, and 730 of SEQ ID NO:1 (minus the 29 aa signal peptide in SEQ. ID. NO:1) have been replaced by Arg or His.

141. The fusion protein of any one of paragraphs 132-140, wherein one or more, up to and including each of the Lys residues in the PAd4 domain at positions 623, 642, 662, 666, 682, 702, 708, 709, 713, 724, 732, 751, 752, 758, and 759 in SEQ. ID. NO:1 have been replaced Arg or His.

142. The fusion protein of any one of paragraphs 132-141, comprising an entire PA protein, wherein the furin cleavage site comprising amino acid residues RKKR has been replaced by a furin-resistant amino acid sequence, wherein RKKR are the residues 164-167 of SEQ ID NO: 1 minus the 29 amino acid signal peptide in SEQ ID NO:1.

143. The fusion protein of paragraph 142, wherein the furin-resistant amino acid sequence is SSSR or SSSS.

144. The fusion protein of any one of paragraphs 132-143, wherein one or more of the Asn residues in the PAd4 domain at position 601, 713, 719 of SEQ ID NO:1 (minus the 29 aa signal peptide in SEQ. ID. NO:1) have been replaced by Asp.

145. The fusion protein of any one of paragraphs 132-144, further comprising at least one D-amino acid at the N-terminus of the fusion protein.

146. The fusion protein of any one of paragraphs 132-145, wherein the residue corresponding to a light chain junction of TTx with a heavy chain of TTx has been cleaved.

147. A composition comprising the fusion protein of any one of paragraphs 132-146.

148. The composition of paragraph 147 further comprising a pharmaceutically acceptable carrier, excipient or diluent.

149. A nucleic acid encoding any of the fusion protein of any of the paragraphs 52-67, 70-79, 86-102, 105-109, 116-129, and 132-146.

150. A vector comprising the nucleic acid of paragraph 149.

151. The vector of paragraph 150, wherein the vector is a plasmid, a bacteriophage, a phagmid, a cosmid, a viral particle, or viral vector.

152. A cell comprising the nucleic acid of paragraph 149 or the vector of paragraph 150 or 151.

153. A method of producing the fusion protein of any of the preceding claim comprising: (i) culturing the cell of paragraph 152 in conditions such that the fusion protein is expressed; and (ii) recovering the fusion protein.

154. The fusion protein produced by the method of paragraph 153.

155. The fusion protein of any of the paragraphs 1-42, 52-67, 70-79, 86-102, 105-109, 116-129, and 132-146, which is glycosylated.

156. The fusion protein of any of the paragraphs 1-42, 52-67, 70-79, 86-102, 105-109, 116-129, and 132-146, which is non-glycosylated.

157. The method of paragraph 153, wherein the cell is a bacterial cell.

158. The method of paragraph 157, wherein the bacterial cell is an *Escherichia coli*.

159. The method of paragraph 153, wherein the cell is a yeast cell.

160. The method of paragraph 159, wherein the yeast is *Saccharomyces cerevisiae*.

161. The method of paragraph 159, wherein the yeast is cell glycosylation deficient.

162. The method of paragraph 159, wherein the yeast is glycosylation and protease deficient.

163. The method of paragraph 153, wherein said cell is a mammalian cell.

164. The method of paragraph 163, wherein said mammalian cell is a COS cell, a CHO cell, or a NSO cell.

165. A use of any of the fusion proteins of the preceding paragraphs for the treatment of pain.

166. A use of any of the fusion proteins of the preceding paragraphs for the manufacture of a medicament for the treatment of pain.

167. A method for treatment of pain, the method comprising administering to a subject in need thereof the composition selected from paragraphs 49, 68-69, 80-85, 103-104, 110-115, 130-131 and 147-148.

168. The method of paragraph 167, wherein the administering is performed by intrathecal infusion or intracerebroventricular infusion or by an epidural injection into the central nervous system, or by peripheral administration using intradermal injection, subcutaneous injection, intramuscular injection, intraneural injection, or intra-articular injection.

169. The method of paragraph 168, wherein the pain is selected from diabetic neuropathic pain, cancer pain, fibromyalgia and other systemic pain disorders.

170. A method for treatment of nerve, joint, skin, visceral, bladder, or muscle pain comprising administering peripherally by intradermal injection, subcutaneous injection, intramuscular injection, intraneural injection, or intra-articular injection to a subject in need thereof the composition selected from paragraphs 49, 68-69, 80-85, 103-104, 110-115, 130-131 and 147-148.

171. A method for treatment of diabetic neuropathic pain, cancer pain, fibromyalgia or other systemic pain disorders comprising administering by epidural injection, intrathecal infusion or intra-cerebroventricular infusion into the central nervous system of a subject in need thereof the composition selected from paragraphs 49, 68-69, 80-85, 103-104, 110-115, 130-131 and 147-148.

172. The method of any one of paragraphs 167-171, wherein the composition of claims 80-85 and 110-115 is administered separately before, simultaneously or after administering a composition comprising an anthrax protective antigen (PA) in a pharmaceutically acceptable carrier, excipient or diluent.

173. A method of treating pain comprising administering to a subject in need thereof, native mature anthrax toxin protective antigen (PA) and anthrax toxin edema factor (EF), anthrax toxin lethal factor (LF) or any combination thereof.

174. A method of manufacture of a pharmaceutical composition for the treatment of pain, wherein the pharmaceutical composition comprising one or more of the fusion proteins described in the preceding paragraphs and a pharmaceutically acceptable carrier or excipient.

175. An engineered fusion protein comprising an anthrax toxin Protective-Antigen (PA) moiety or its receptor binding domain (Pad4) fused with an inhibitor cysteine knot (ICK) toxin (e.g., a Conotoxin (CTx)).

176. An engineered fusion protein comprising an anthrax toxin lethal factor domain (LFn) fused with an inhibitor cysteine knot (ICK) toxin (e.g., a Conotoxin (CTx)) and a Protective-Antigen (PA) moiety.

177. An engineered fusion protein comprising an anthrax protective antigen (PA) moiety or a mutant anthrax protective antigen (mPA) moiety that has been altered to block its native receptor-binding function fused with a molecule capable of specifically targeting a nociceptor surface receptor or an ion channel receptor and an anthrax lethal factor domain (LFn) fused to an intracellularly acting toxin catalytic domain.

178. An engineered fusion protein comprising an anthrax protective antigen (PA) moiety or at anthrax protective antigen (mPA) moiety fused with a molecule capable of specifically targeting a nociceptor surface receptor or an ion channel receptor and an anthrax lethal factor domain (LFn) fused to an intracellularly acting toxin catalytic domain.

179. The engineered fusion protein of paragraph 177 or 178, wherein the molecule is selected from an antibody that specifically binds to the nerve growth factor receptor, or an antibody that specifically binds to Nav1.7, Nav1.8 or Nav1.9.

180. The engineered fusion protein of any of the preceding paragraphs, wherein the intracellularly acting toxin catalytic domain is selected from diphtheria toxin (DTx), *Pseudomonas aeruginosa* exotoxin A (PTx), botulinium toxin (BTx) tetanus toxin (TTx), shiga toxin, ricin toxin, lethal toxin (lethal factor), and/or Edema toxin (edema factor).

181. An engineered fusion protein comprising a native protective antigen (PA) or a modified (e.g., chemically) or mutant PA (mPA), wherein the mPA native receptor-binding function is blocked, and a molecule that can target nociceptor neuron surface molecules specifically in combination with anthrax toxin edema factor (EF) and/or lethal factor (LF).

182. The engineered fusion protein of any of the preceding paragraphs, wherein PA or mPA is in an oligomeric form.

183. The engineered fusion protein of paragraph 182, wherein the oligomeric form is bound to the molecule.

184. A composition comprising an engineered fusion protein comprising an anthrax toxin Protective-Antigen (PA) moiety or its receptor binding domain (Pad4) fused with an inhibitor cysteine knot (ICK) toxin (e.g., a Conotoxin (CTx)).

185. A composition comprising an engineered fusion protein comprising an anthrax toxin lethal factor domain (LFn) fused with an inhibitor cysteine knot (ICK) toxin (e.g., a Conotoxin (CTx)) and a Protective-Antigen (PA) moiety.

186. A composition comprising engineered fusion protein comprising a native protective antigen (PA) or a mutant PA (mPA), fused, with a molecule capable of specifically targeting a nociceptor surface receptor or an ion channel receptor and an anthrax lethal factor domain (LFn) fused to an intracellularly acting toxin catalytic domain, wherein the mPA has been modified (e.g., chemically) or mutated so that the PA native receptor-binding function is blocked.

187. The composition of paragraph 186, wherein the molecule is selected from a nerve growth factor, and an antibody that specifically binds to Nav1.7, Nav1.8 or Nav1.9.

188. The composition of paragraph 186 or 187, wherein the intracellularly acting toxin catalytic domain is selected from diphtheria toxin (DTx), *Pseudomonas aeruginosa* exotoxin A (PTx), botulinium toxin (BTx) tetanus toxin (TTx), Shiga toxin, ricin toxin, lethal toxin (lethal factor), and/or Edema toxin (edema factor).

189. A composition comprising an engineered fusion protein comprising a native protective antigen (PA) or a mutant PA (mPA), and a molecule that can target nociceptor neuron surface molecules specifically in combination with anthrax toxin edema factor (EF), wherein the mPA has been modified (e.g., chemically) or mutated so that the PA native receptor-binding function is blocked.

190. The composition of any of the preceding paragraphs, wherein PA or mPA is in an oligomeric form.

191. The composition of paragraph 190, wherein the oligomeric form is bound to the molecule.

192. The composition of any of the preceding paragraphs, the composition further comprising a pharmaceutically acceptable carrier or excipient.

193. A method for treatment of pain, the method comprising administering to a subject in need thereof an effective, pain reducing amount of a composition comprising an engineered fusion protein comprising an anthrax toxin Protective-Antigen (PA) moiety or its receptor binding domain (PAd4) fused to an intracellularly acting toxin catalytic domain, wherein the engineered fusion protein is delivered to nociceptor neurons and results in decreased intracellular signaling events in the nociceptor neurons or decreased neurotransmitter release from the nociceptor neurons.

194. The method of paragraph 193, wherein the intracellularly acting toxin catalytic domain is selected from diphtheria toxin (DTx), *Pseudomonas aeruginosa* exotoxin A (PTx), botulinium toxin (BTx) tetanus toxin (TTx), Shiga toxin, ricin toxin, lethal toxin (lethal factor), and/or Edema toxin (edema factor).

195. A method for treatment of pain, the method comprising administering to a subject in need thereof an effective, pain reducing amount of a composition comprising an engineered fusion protein comprising an anthrax toxin Protective-Antigen (PA) moiety or its receptor binding domain (PAd4) fused with an inhibitor cysteine knot (ICK) toxin (e.g., a Conotoxin (CTx)).

196. A method for treatment of pain, the method comprising administering to a subject in need thereof an effective amount of a composition comprising an engineered fusion protein comprising an anthrax toxin lethal factor (LFn) fused with an inhibitor cysteine knot (ICK) toxin (e.g., a Conotoxin (CTx)) and a Protective-Antigen (PA) moiety.

197. The composition of any of the preceding paragraphs, the composition further comprising a pharmaceutically acceptable carrier or excipient.

198. A method for treatment of pain, the method comprising administering to a subject in need thereof an effective, pain reducing amount of an engineered fusion protein comprising an anthrax protective antigen (PA) moiety or a mutant anthrax protective antigen (mPA) moiety that has been altered to block its native receptor-binding function fused with a molecule capable of specifically targeting a nociceptor surface receptor or an ion channel receptor and an anthrax lethal factor domain (LFn) fused to an intracellularly acting toxin catalytic domain.

199. The method of paragraph 198, wherein the molecule is selected from an antibody that specifically binds to the nerve growth factor receptor and an antibody that specifically binds to Nav1.7, Nav1.8 or Nav1.9.

200. The method of paragraph 198 or 199, wherein the intracellularly acting toxin catalytic domain is selected from diphtheria toxin (DTx), *Pseudomonas aeruginosa* exotoxin A (PTx), botulinium toxin (BTx) tetanus toxin (TTx), Shiga toxin, ricin toxin, lethal toxin (lethal factor), and/or Edema toxin (edema factor).

201. A method of treating pain in a subject in need thereof comprising administering to the subject an engineered fusion protein comprising a native protective antigen (PA) or a mutant PA (mPA), and a molecule that can target nociceptor surface molecules specifically in combination with anthrax toxin edema factor (EF) and/or lethal factor (LF), wherein the mPA has been modified (e.g., chemically) or mutated so that the PA native receptor-binding function is blocked.

202. The method of any of the preceding paragraphs, wherein the PA or mPA is administered in an oligomeric form, wherein the oligomeric PA or mPA is formed from proteolytically activated PA or mPA (or mutant thereof) to achieve increased avidity for receptor-bearing cells.

203. The method of paragraph 202, wherein the oligomeric form is bound to the molecule before administering.

204. The method of paragraph 202 or 203, wherein the oligomeric form is administered in a separate injection before, simultaneously or after administering the "effector molecule."

The technology described herein is further illustrated by the following examples which in no way should be construed as being further limiting.

EXAMPLES

Example 1

We have discovered that the major anthrax toxin receptor, ANTXR2, is highly and specifically expressed by nociceptor neurons compared to other neuronal subtypes and CNS tissues. By using the endosomal delivery mechanisms inherent to anthrax toxin, we can specifically deliver molecular cargo into nociceptors that would result in pain-specific block without causing other neurological side effects.

Based on this discovery, we provide: (1) pain-specific blockade and targeted analgesic mechanisms in chronic pain conditions. These conditions include osteoarthritis, spasticity, rheumatoid arthritis, chemotherapy induced neuropathy, and cancer pain. (2) Treatment of muscle spasticity. Pain is a major component of spastic disease conditions. Dysregulation of sensory-motor reflex circuits triggered by nociceptors could drive muscle spasticity. We hypothesize that anthrax toxin mediated nociceptor silencing may not only treat pain but also decrease muscle spasticity. (3) Treatment of osteoarthritic conditions. Joint pain and destruction is a major component of osteoarticular diseases and rheumatological diseases. Outside the nervous system (where it is specific to nociceptors), we find that ANTXR2 is highly expressed by macrophages, osteoblasts, and osteoclasts, which are key hematopoietic cells mediating joint. The anthrax toxin and their delivery mechanisms can used to specifically target joint pain through nociceptors without neurological side effects, as well as concurrently targeting the macrophages, osteoblasts and osteoclasts that mediate joint destruction.

To determine if anthrax toxin can be used to specifically target selected molecular cargo proteins into nociceptor neurons through its built in endosomal escape and cytosolic delivery mechanisms. We will further test if anthrax toxin can be used to silence chronic pain in several disease conditions (osteoarthritis, muscle injury, rheumatoid arthritis, chemotherapy induced neuropathy, cancer pain), and as well as joint destruction in osteoarthritis.

We recently discovered that ANTXR2 is highly expressed in nociceptor neurons, and is specific to these neurons compared to other neuronal subtypes, based on our detailed FACS purified somatosensory neuron expression databases, in situ hybridization databases, and tissue expression databases. ANTXR2 is also highly expressed in macrophages, osteoblasts, and osteoclasts, key cell-types in joint destruction. This expression potentially allows anthrax toxin to deliver cargo into these cells to slow joint destruction in osteoarthritis.

We are utilizing anthrax toxin or its delivery mechanisms to specifically block chronic pain or joint destruction in different disease conditions. In some applications we will use native anthrax toxin, consisting of protective antigen (PA), the receptor binding component, together with Lethal Factor (LF, which silences MAP kinases) or Edema Factor (EF, a calcium dependent adenylate cyclase). In other applications, we will use anthrax toxin as a platform to mediate cytoplasmic delivery of the enzymatic moieties of other bacterial toxins, including diphtheria toxin (DTA) or ricin (Rcn).

Native anthrax toxin (PA, LF, EF) to silence pain. Anthrax skin infections cause lesions that are painless. PA binding to ANTXR2 mediates the delivery of Lethal Factor (LF), which is known to block MAP kinases or edema factor (EF), which is an adenylate cyclase. Both MAP kinase and cAMP pathways mediate nociceptor sensitization and chronic pain, and their modulation could silence pain. Thus, we will utilize local subcutaneous or joint injections of combinations of PA+LF, PA+EF, or PA+LF+EF to induce pain blockade in different disease conditions.

Anthrax toxin mediated cytosolic delivery of enzymatic moieties of diphtheria toxin (DTA) or Ricin (Rcn) to silence pain and arthritic joint destruction: PA, the receptor binding and pore-forming subunit of anthrax toxin, will be used to specifically deliver the PA-binding domain of lethal factor (LFn) fused to the enzymatic domain of diphtheria toxin (DTA) or Ricin (Rcn) into ANTXR2+ cells in the joints, including nociceptor neurons, macrophages and osteoclasts. These toxins will be injected into osteoarthritic or rheumatoid arthritic joints to silence pain and joint destruction.

In mouse models, we will deliver locally subcutaneously or into the joints the above anthrax toxin molecules or molecular combinations to test the efficacy of pain blockade or joint preservation in animal models of: osteoarthritis (e.g., via monoiodoacetate injection), muscle injury (e.g., cardiotoxin induced damage), rheumatoid arthritis (e.g., K/BxN Serum transfer arthritis), chemotherapy induced neuropathy (e.g., Paclitaxel), and cancer pain (e.g., Ehrlich cell model) Pain behavioral testing will assay the effects on mechanical and/or thermal hyperalgesia. We will also perform electrophysiology on primary nociceptor neurons to detect delivery of intracellular toxins into neurons and neuronal activity block. Joint pathology will be analyzed by measures of inflammation and histological analysis.

Of note, we can also utilize this Anthrax Toxin platform to deliver the enzymatic moiety of Botulinum Toxin (BTx).

FIGS. 1A and 1B depict the specific and high level expression of the receptor for the major anthrax toxin receptor within the dorsal root ganglia compared to 11 other nervous tissue types.

Figure 2:
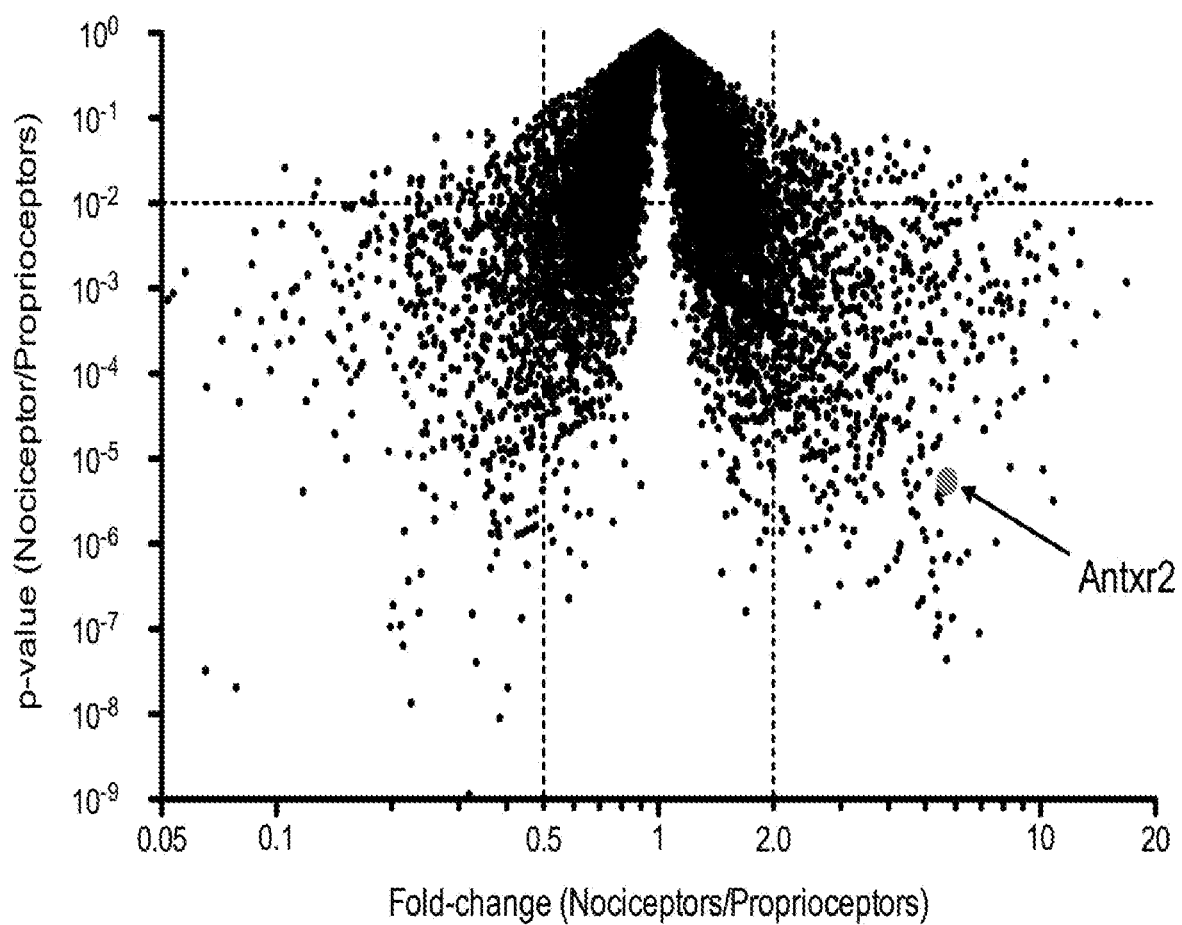
FIG. 2 demonstrates that Antxr2 is highly enriched in nociceptor neurons compared to proprioceptor sensory neurons (large dot and arrow). Volcano plot (P-value vs. fold-change of difference) shows Antxr2 is strongly enriched in nociceptor pain-sensing neurons compared to proprioceptor neurons.

FIG. 2 compares whole transcriptome data between purified mouse pain-sensing nociceptor neurons (Nav1.8-Cre/TdTomato+) vs. another somatosensory neuron subtype, proprioceptors (Parv-Cre/TdTomato+). Though they are related cell-types, pain-sensing Nav1.8+ nociceptor neurons show highly enriched expression of Antxr2 compared to proprioceptors. Antxr2 is >5-fold enriched in nociceptors vs. proprioceptor neurons (P-value<$10^{-5}$).

Taken together, these data from FIGS. 1 and 2 show that Antxr2, the receptor for anthrax toxin is highly enriched in nociceptor neurons compared to other CNS tissues and to proprioceptor neurons. This strongly indicates that Antxr2 can be utilized to target pain-sensing neurons specifically versus other neuronal subtypes.

Example 2—Assessment of In Vitro Efficacy (1)

We experimented to determine whether anthrax toxin components can be delivered to nociceptors in culture. This would be testing for the inhibition of protein synthesis in a mammalian cell in presense of the combination PA and the engineered fusion protein LFn-DTA, testing for the increase in intracellular cAMP levels in a mammalian cell in presense of the combination of PA and EF, and testing for the inhibition of MAPK signaling in a mammalian cell in presense of the combination PA and LF.

The A chain of diphtheria toxin (DTA) is used as the intracellular enzymatic toxin for proof of principle that the anthrax delivery system can be use to deliver toxins into neurons. DTA catalyzes the ADP-ribosylation of EF-2 and inhibits protein synthesis. The fusion protein, LFn-DTA, is frequently used to assay for PA-mediated translocation into the cytoplasm. Shown previously in Milne et al. Mol. Microbiol. February; 15(4):661-6, (1995) and in Liao et al. Chem. Bio. Chem., 15(16): 2458-2466, (2014), CHO-K1 cells treated with 20 nM PA together with the fusion protein, LFn-DTA or DTA-LFn, completely stopped protein synthesis at the femtomolar or picomolar concentration of a fusion proteins.

Figure 3:
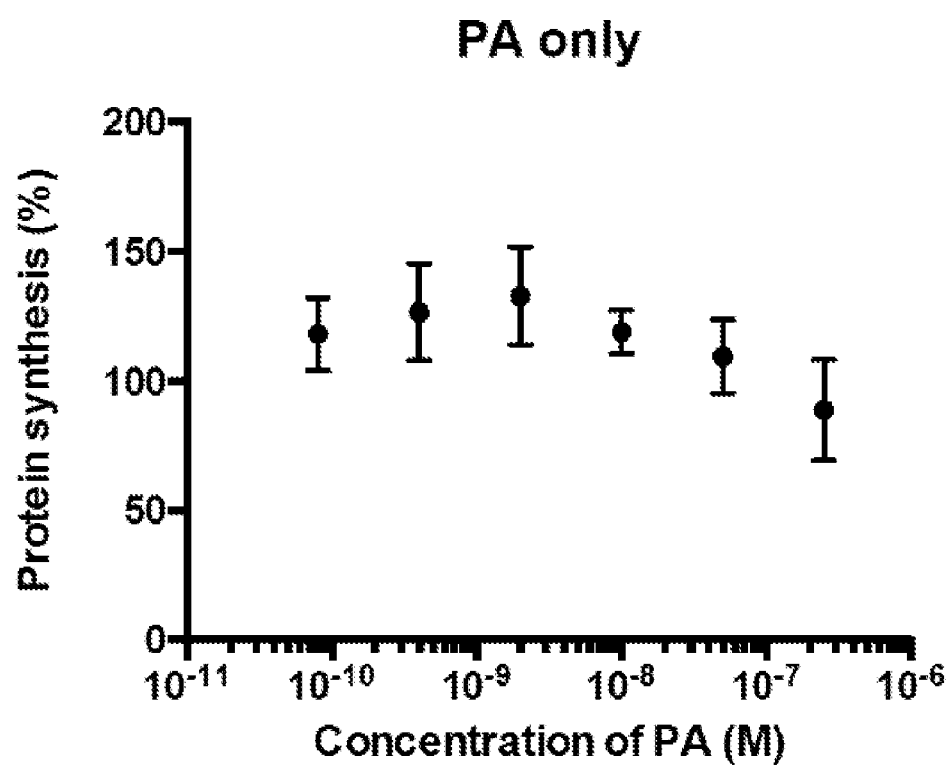
FIG. 3 shows that the Protective Antigen (PA) alone does not inhibit protein synthesis in neurons.
Figure 4:
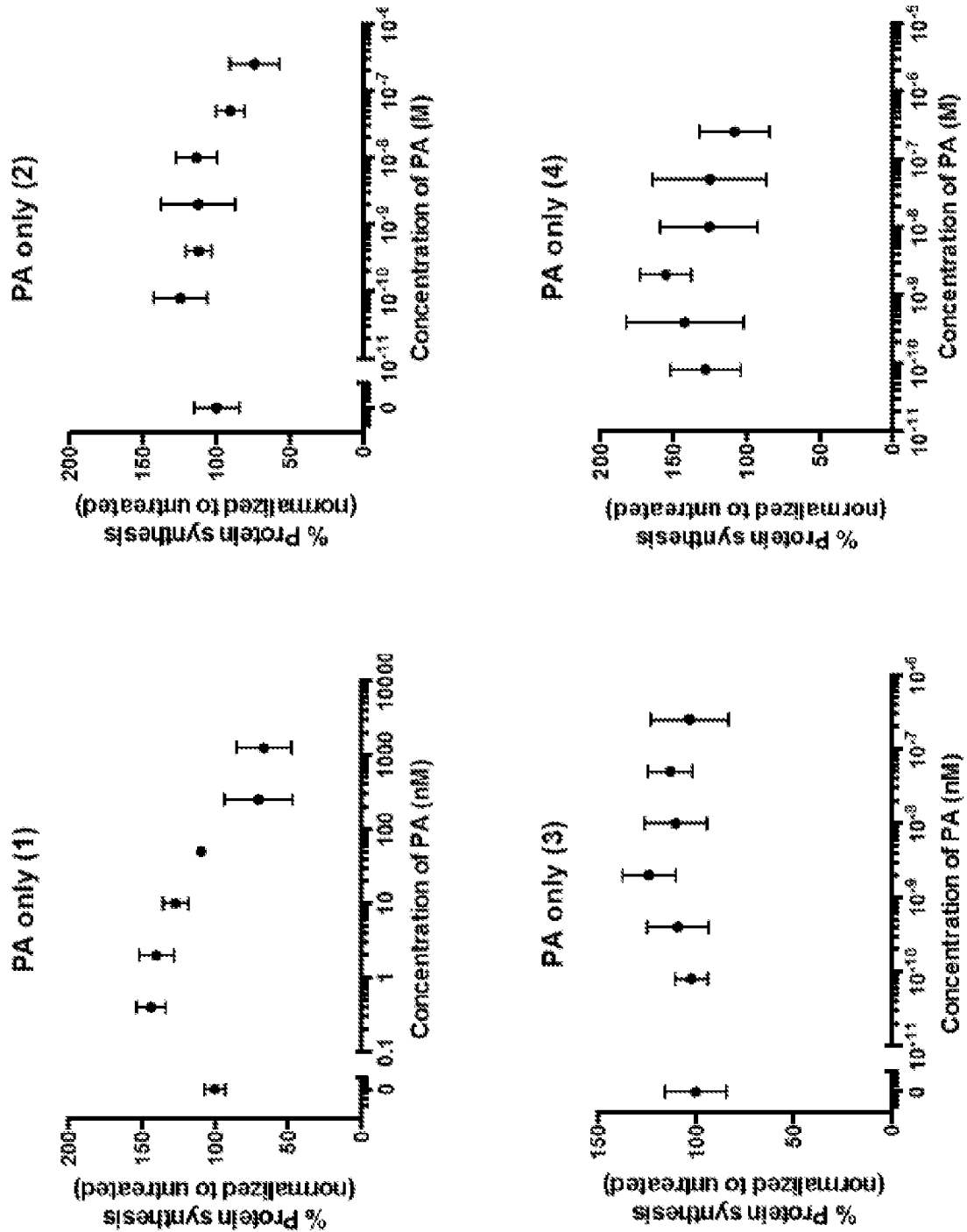
FIG. 4 shows that PA alone does not inhibit protein synthesis in neurons.
Figure 6:
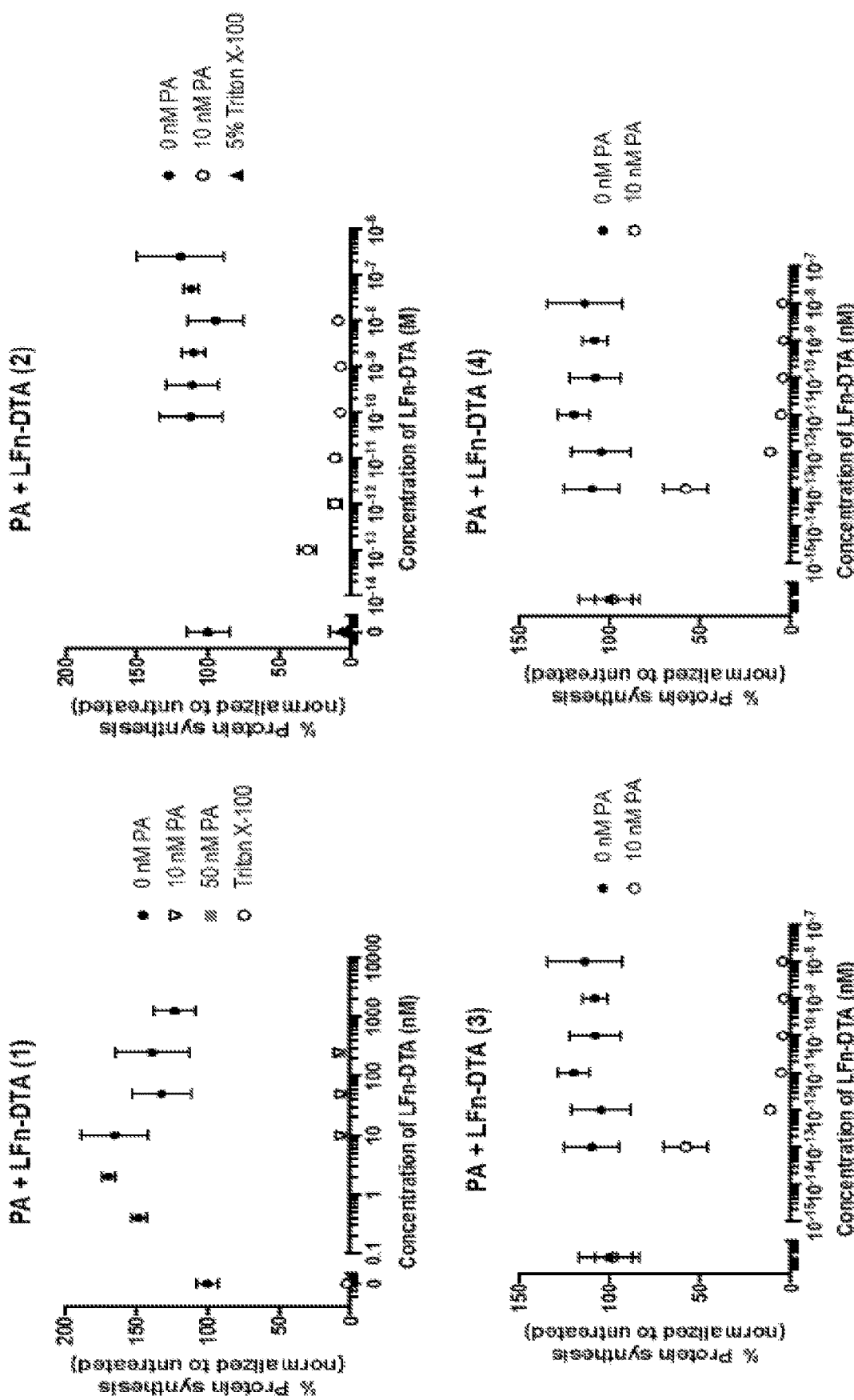
FIG. 6 shows that PA and the fusion protein LFn-DTX inhibit protein synthesis in neurons.

For our experiment, DRG neurons were harvested from wild-type B6 mice and cultured overnight at a cell density of ~2000 neurons/well. Cells were treated with varying concentrations of PA and LFn-DTA for 6 hrs at 37° C. in the presence of 3H-leu (400 nM). Protein synthesis was measured using radiolabeled leucine (3H-leu), newly synthesized protein would incorporate 3H-leu into the new protein. After the incubation period, the neurons were wash with F12K medium (leu-free), then incubated with 3H-leu in F12K medium (leu-free), followed by washing with PBS, and then finally lysed in scintillation fluid for the measurement of the incorporated 3H-leu radioactivity in newly synthesized protein. Control experiments were performed with PA but with no LFn-DTA added. Background 3H-leu radioactivity was subtracted from the experimental radioactivity, and the subtracted data was normalized to that of untreated neurons. No significant inhibition of protein synthesis was observed when the neurons were treated with PA alone (FIGS. 3 and 4). Therefore, PA alone does not affect protein synthesis in neurons. However, PA and LFn-DTA potently inhibits protein synthesis at nanomolar concentrations in cultured neurons. (FIGS. 5 and 6).

```
                          Sequence listings

SEQ ID NO: 1, PA, NCBI Ref Seq: NP_052806
    1 MKKRKVLIPL MALSTILVSS TGNLEVIQAE VKQENRLLNE SESSSQGLLG YYFSDLNFQA
   61 PMVVTSSTTG DLSIPSSELE NIPSENQYFQ SAIWSGFIKV KKSDEYTFAT SADNHVTMWV
  121 DDQEVINKAS NSNKIRLEKG RLYQIKIQYQ RENPTEKGLD FKLYWTDSQN KKEVISSDNL
  181 QLPELKQKSS NSRKKRSTSA GPTVPDRDND GIPDSLEVEG YTVDVKNKRT FLSPWISNIH
  241 EKKGLTKYKS SPEKWSTASD PYSDFEKVTG RIDKNVSPEA RHPLVAAYPI VHVDMENIIL
  301 SKNEDQSTQN TDSQTRTISK NTSTSRTHTS EVHGNAEVHA SFFDIGGSVS AGFSNSNSST
  361 VAIDHSLSLA GERTWAETMG LNTADTARLN ANIRYVNTGT APIYNVLPTT SLVLGKNQTL
  421 ATIKAKENQL SQILAPNNYY PSKNLAPIAL NAQDDFSSTP ITMNYNQFLE LEKTKQLRLD
  481 TDQVYGNIAT YNFENGRVRV DTGSNWSEVL PQIQETTARI IFNGKDLNLV ERRIAAVNPS
  541 DPLETTKPDM TLKEALKIAF GFNEPNGNLQ YQGKDITEFD FNFDQQTSQN IKNQLAELNA
  601 TNIYTVLDKI KLNAKMNILI RDKRFHYDRN NIAVGADESV VKEAHREVIN SSTEGLLLNI
  661 DKDIRKILSG YIVEIEDTEG LKEVINDRYD MLNISSLRQD GKTFIDFKKY NDKLPLYISN
  721 PNYKVNVYAV TKENTIINPS ENGDISTNGI KKILIFSKKG YEIG

SEQ ID NO: 2 Diptheria toxin NCBI Ref Seq: WP_003850266
    1 MSRKLFASIL IGALLGIGAP PSAHAGADDV VDSSKSFVME NFSSYHGTKP GYVDSIQKGI
   61 QKPKSGTQGN YDDDWKGFYS TDNKYDAAGY SVDNENPLSG KAGGVVKVTY PGLTKVLALK
```

```
    121 VDNAETIKKE LGLSLTEPLM EQVGTEEFIK RFGDGASRVV LSLPFAEGSS SVEYINNWEQ
    181 AKALSVELEI NFETRGKRGQ DAMYEYMAQA CAGNRVRRSV GSSLSCINLD WDVIRDKTKT
    241 KIESLKEHGP IKNKMSESPN KTVSEEKAKQ YLEEFHQTAL EHPELSELKT VTGTNPVFAG
    301 ANYAAWAVNV AQVIDSETAD NLEKTTAALS ILPGIGSVMG IADGAVHHNT EEIVAQSIAL
    361 SSLMVAQAIP LVGELVDIGF AAYNFVESII NLFQVVHNSY NRPAYSPGHK TQPFLHDGYA
    421 VSWNTVEDSI IRTGFQGESG HDIKITAENT PLPIAGVLLP TIPGKLDVNK SKTHISVNGR
    481 KIRMRCRAID GDVTFCRPKS PVYVGNGVHA NLHVAFHRSS SEKIHSNEIS SDSIGVLGYQ
    541 KTVDHTKVNS KLSLFFEIKS

SEQ ID NO: 3 Pseudomonas aeruginosa exotoxin A (PTx) NCBI Ref Seq: NP_249839
      1 MHLTPHWIPL VASLGLLAGG SFASAAEEAF DLWNECAKAC VLDDLKDGVRS SRMSVDPAIA
     61 DTNGQGVLHY SMVLEGGNDA LKLAIDNALS ITSDGLTIRL EGGVEPNKPV RYSYTRQARG
    121 SWSLNWLVPI GHEKPSNIKV FIHELNAGNQ LSHMSPIYTI EMGDELLAKL ARDATFFVRA
    181 HESNEMQPTL AISHAGVSVV MAQAQPRREK RWSEWASGKV LCLLDPLDGV YNYLAQQRCN
    241 LDDTWEGKIY RVLAGNPAKH DLDIKPTVIS HRLHFPEGGS LAALTAHQAC HLPLETFTRH
    301 RQPRGWEQLE QCGYPVQRLV ALYLAARLSW NQVDQVIRNA LASPGSGGDL GEAIREQPEQ
    361 ARLALTLAAA ESERFVRQGT GNDEAGAASA DVVSLTCPVA AGECAGPADS GDALLERNYP
    421 TGAEFLGDGG DISFSTRGTQ NWTVERLLQA HRQLEERGYV FVGYHGTFLE AAQSIVFGGV
    481 RARSQDLDAI WRGFYIAGDP ALAYGYAQDQ EPDARGRIRN GALLRVYVPR SSLPGFYRTG
    541 LTLAAPEAAG EVERLIGHPL PLRLDAITGP EEEGGRLETI LGWPLAERTV VIPSAIPTDP
    601 RNVGGDLDPS SIPDKEQAIS ALPDYASQPG KPPREDLK SEQ ID NO: 4 Botulinum toxin NCBI Ref Seq: YP_001386738
      1 MPFVNKQFNY KDPVNGVDIA YIKIPNAGQM QPVKAFKIHN KIWVIPERDT FTNPEEGDLN
     61 PPPEAKQVPV SYYDSTYLST DNEKDNYLKG VTKLFERIYS TDLGRMLLTS IVRGIPFWGG
    121 STIDTELKVI DTNCINVIQP DGSYRSEELN LVIIGPSADI IQFECKSFGH EVLNLTRNGY
    181 GSTQYIRFSP DFTFGFEESL EVDTNPLLGA GKFATDPAVT LAHELIHAGH RLYGIAINPN
    241 RVFKVNTNAY YEMSGLEVSF EELRTFGGHD AKFIDSLQEN EFRLYYYNKF KDIASTLNKA
    301 KSIVGTTASL QYMKNVFKEK YLLSEDTSGK FSVDKLKFDK LYKMLTEIYT EDNFVKFFKV
    361 LNRKTYLNFD KAVFKINIVP KVNYTIYDGF NLRNTNLAAN FNGQNTEINN MNFTKLKNFT
    421 GLFEFYKLLC VRGIITSKTK SLDKGYNKAL NDLCIKVNNW DLFFSPSEDN FTNDLNKGEE
    481 ITSDTNIEAA EENISLDLIQ QYYLTFNFDN EPENISIENL SSDIIGQLEL MPNIERFPNG
    541 KKYELDKYTM FHYLRAQEFE HGKSRIALTN SVNEALLNPS RVYTFFSSDY VKKVNKATEA
    601 AMFLGWVEQL VYDFTDETSE VSTTDKIADI TIIIPYIGPA LNIGNMLYKD DFVGALIFSG
    661 AVILLEFIPE IAIPVLGTFA LVSYIANKVL TVQTIDNALS KRNEKWDEVY KYIVTNWLAK
    721 VNTQIDLIRK KMKEALENQA EATKAIINYQ YNQYTEEKN NINFNIDDLS SKLNESINKA
    781 MININKFLNQ CSVSYLMNSM IPYGVKRLED FDASLKDALL KYIYDNRGTL IGQVDRLKDK
    841 VNNTLSTDIP FQLSKYVDNQ RLLSTFTEYI KNIIINTSILN LRYESNHLID LSRYASKINI
    901 GSKVNFDPID KNQIQLFNLE SSKIEVILKN AIVYNSMYEN FSTSFWIRIP KYFNSISLNN
    961 EYTIINCMEN NSGWKVSLNY GEIIWTLQDT QEIKQRVVFK YSQMINISDY INRWIFVTIT
   1021 NNRLNNSKIY INGRLIDQKP ISNLGNIHAS NNIMFKLDGC RDTHRYIWIK YFNLFDKELN
   1081 EKEIKDLYDN QSNSGILKDF WGDYLQYDKP YYMLNLYDPN KYVDVNNVGI RGYMYLKGPR
   1141 GSVMTTNIYL NSSLYRGTKF IIKKYASGNK DNIVRNNDRV YINVVVKNKE YRLATNASQA
   1201 GVEKILSALE IPDVGNLSQV VVMKSKNDQG ITNKCKMNLQ DNNGNDIGFI GFHQFNNIAK
   1261 LVASNWYNRQ IERSSRTLGC SWEFIPVDDG WGERPL SEQ ID NO: 5 Tetanus toxin NCBI Ref Seq: WP_023439719
      1 MPITINNFRY SDPVNNDTII MMEPPYCKGL DIYYKAFKIT DRIWIVPERY EFGTKPEDFN
     61 PPSSLIEGAS EYYDPNYLRT DSDKDRFLQT MVKLFNRIKN NVAGEALLDK IINAIPYLGN
    121 SYSLLDKFDT NSNSVSFNLS EQDPSGATTK SAMLTNLIIF GPGPVLNKNE VRGIVLRVDN
    181 KNYFPCRDGF GSIMQMAFCP EYIPTFDNVI ENITSLTIGK SKYFQDPALL LMHELIHVLH
    241 GLYGMQVSSH EIIPSKQEIY MQHTYPISAE ELFTFGGQDA NLISIDIKND LYEKTLNDYK
    301 AIANKLSQVT SCNDPNIDID SYKQIYQQKY QFDKDSNGQY IVNEDKFQIL YNSIMYGFTE
    361 IELGKKFNIK TRLSYFSMNH DPVKIPNLLD DTIYNDTEGF NIESKDLKSE YKGQNMRVNT
    421 NAFRNVDGSG LVSKLIGLCK KIIPPTNIRE NLYNRTASLT DLGGELCIKI KNEDLTFIAE
    481 KNSFSEEPFQ DETVSYNTKN KPLNFNYSLD KIILDYNLQS KITLPNDRTT PVTKGIPYAP
    541 KYKSNAASTI EIHNIDDNTI YQYLYAQKSP TTLQRITMTN SVDDALINST KIYSYFPSVI
    601 SKVNQGAQGI LFLQWVRDII DDFTNESSQK TTIDKISDVS TIVPYIGPAL NIVKQGYEGN
    661 FIGALETTGV VLLLEYIPEI TLPVIAALSI AESSTQKEKI IKTIDNFLEK RYEKWIEVYK
    721 LIKAKWLGTV NTQFQKRSYQ MYRSLEYQVD AIKKIIDYEY KIYSGPDKEQ IADEINNLKN
    781 KLEEKANKAM ININIFMRES SRSFLVNQMI NEAKKQLLER DTQSKNILMQ YIKANSKFIG
    841 ITELKKLESK INKVFSTPIP FSYSKNLDCW VDNEEDIDVI LKKSTILNLD INNDIISDIS
    901 GFNSSVITYP DAQLVPGING KAIHLVNNES SEVIVHKAMD IEYNDMFNNF TVSFWLRVPK
    961 VSASHLEQYG TNEYSIISSM KKYSLSIGSG WSVSLKGNNL IWTLKDSAGE VRQITFSDLS
   1021 DKFNAYLANK WVFITITNDR LSSANLYING VLMKNAEITG LGAIREDNNI TLKLDRCNNN
   1081 NQYVSIDKFR IFCKALNPKE IEKLYTSYLS ITFLRDFWGN PLRYDTEYYL IPVASSSKDV
   1141 QLKNITDYMY LTNAPSYTNG KLNIYYRRLY SGLKFIIKRY TPNNEIDSFV KSGDFIKLYV
   1201 SYNNNEHIVG YPKDGNAFNN LDRILRVGYN APGIPLYKKM EAVKLRDLKT YSVQLKLYDD
   1261 KNASLGLVGI RNGQIGNDPN RDILIASNWY FNHLKDKTLT CDWYFVPTDE GWTND SEQ ID NO: 6 Edema Factor NCBI Ref Seq: NP_052818
      1 MTRNKFIPNK FSIISFSVLL FAISSSQAIE VNAMNEHYTE SDIKRNHKTE KNKTEKEKFK
     61 DSINNLVKTE FTNETLDKIQ QTQDLLKKIP KDVLEIYSEL GGEIYFTDID LVEHKELQDL
    121 SEEEKNSMNS RGEKVPFASR FVFEKKRETP KLIINIKDYA INSEQSKEVY YEIGKGISLD
    181 IISKDKSLDP EFLNLIKSLS DDSDSSDLLF SQKFKEKLEL NNKSIDINFI KENLTEFQHA
    241 FSLAFSYYFA PDHRTVLELY APDMFEYMNK LEKGGFEKIS ESLKKEGVEK DRIDVLKGEK
    301 ALKASGLVPE HADAFKKIAR ELNTYILFRP VNKLATNLIK SGVATKGLNV HGKSSDWGPV
```

-continued

| Sequence listings |
|---|

361 AGYIPFDQDL SKKHGQQLAV EKGNLENKKS ITEHEGEIGK IPLKLDHLRI EELKENGIIL
421 KGKKEIDNGK KYLLLESNNQ VYEFRISDEN NEVQYKTKEG KITVLGEKFN WRNIEVMAKN
481 VEGVLKPLTA DYDLFALAPS LTEIKKQIPQ KEWDKVVNTP NSLEKQKGVT NLLIKYGIER
541 KPDSTKGTLS NWQKQMLDRL NEAVKYTGYT GGDVVNHGTE QDNEEFPEKD NEIFIINPEG
601 EFILTKNWEM TGRFIEKNIT GKDYLYYFNR SYNKIAPGNK AYIEWTDPIT KAKINTIPTS
661 AEFIKNLSSI RRSSNVGVYK DSGDKDEFAK KESVKKIAGY LSDYYNSANH IFSQEKKRKI
721 SIFRGIQAYN EIENVLKSKQ IAPEYKNYFQ YLKERITNQV QLLLTHQKSN IEFKLLYKQL
781 NFTENETDNF EVFQKIIDEK

SEQ ID NO: 7 Lethal Factor NCBI Ref Seq: NP_052803
1 MNIKKEFIKV ISMSCLVTAI TLSGPVFIPL VQGAGGHGDV GMHVKEKEKN KDENKRKDEE
61 RNKTQEEHLK EIMKHIVKIE VKGEEAVKKE AAEKLLEKVP SDVLEMYKAI GGKIYIVDGD
121 ITKHISLEAL SEDKKKIKDI YGKDALLHEH YVYAKEGYEP VLVIQSSEDY VENTEKALNV
181 YYEIGKILSR DILSKINQPY QKFLDVLNTI KNASDSDGQD LLFTNQLKEH PTDFSVEFLE
241 QNSNEVQEVF AKAFAYYIEP QHRDVLQLYA PEAFNYMDKF NEQEINLSLE ELKDQRMLSR
301 YEKWEKIKQH YQHWSDSLSE EGRGLLKKLQ IPIEPKKDDI IHSLSQEEKE LLKRIQIDSS
361 DFLSTEEKEF LKKLQIDIRD SLSEEEKELL NRIQVDSSNP LSEKEKEFLK KLKLDIQPYD
421 INQRLQDTGG LIDSPSINLD VRKQYKRDIQ NIDALLHQSI GSTLYNKIYL YENMNINNLT
481 ATLGADLVDS TDNIKINRGI FNEFKKNFKY SISSNYMIVD INERPALDNE RLKWRIQLSP
541 DTRAGYLENG KLILQRNIGL EIKDVQIIKQ SEKEYIRIDA KVVPKSKIDT KIQEAQLNIN
601 QEWNKALGLP KYTKLITFNV HNRYASNIVE SAYLILNEWK NNIQSDLIKK VTNYLVDGNG
661 RFVFTDITLP NIAEQYTHQD EIYEQVHSKG LYVPESRSIL LHGPSKGVEL RNDSEGFIHE
721 FGHAVDDYAG YLLDKNQSDL VTNSKKFIDI FKEEGSNLTS YGRTNEAEFF AEAFRLMHST
781 DHAERLKVQK NAPKTFQFIN DQIKFIINS SEQ ID NO: 8 ω-conotoxin M VII A NCBI Ref Seq: ADB93081
1 MKLTCVVIVA VLLLTACQLI TADDSRGTQK HRALRSTTKL SMSTRCKGKG AKCSRLMYDC
61 CTGSCRSGKC G SEQ ID NO: 9 μ-conotoxin Swiss-Prot: P15472.1
1 ACSGRGSRCP PQCCMGLRCG RGNPQKCIGA HEDV SEQ ID NO: 10 δ-conotoxin NCBI ID: AKD43185
1 LNKRCAGIGS FCGLPGLVDC CSGRCFIVCL P SEQ ID NO: 11, Shiga toxin A-part
KEFTLDFSTAKTYVDSLNVIRSAIGTPLQTISSGGTSLLMIDSGTGDNLFAVDVRGIDPEEGRFNNLRLIV
ERNNLYVTGFVNRTNNVFYRFADFSHVTFPGTTAVTLSGDSSYTTLQRVAGISRTGMQINRHSLTTSYLDLMSHSGT
SLTQSVARAMLRFVTVTAEALRFRQIQRGFRTTLDDLSGRSYVMTAEDVDLTLNWGRLSSVLPDYHGQDSVRVGRIS
FGSINAILGSVALILNCHHHASRVARMASDEFPSMCPADGRVRGITHNKILWDSSTLGAILMRRTISS SEQ ID NO: 12, Shiga toxin B-part:
TPDCVTGKVEYTKYNDDDTFTVKVGDKELFTNRWNLQSLLLSAQITGMTVTIKTNACHNGGGFSEVIFR Exotoxin A, A-part and B-part
SEQ ID NO: 13
AEEAFDLWNECAKACVLDLKDGVRSSRMSVDPAIADTNGQGVLHYSMVLEGGNDALKLAIDNALSITSDGL
TIRLEGGVEPNKPVRYSYTRQARGSWSLNWLVPIGHEKPSNIKVFIHELNAGNQLSHMSPIYTIEMGDELLAKLARD
ATFFVRAHESNEMQPTLAISHAGVSVVMAQAQPRREKRWSEWASGKVLCLLDPLDGVYNYLAQQRCNLDDTWEGKIY
RVLAGNPAKHDLDIKPTVISHRLHFPEGGSLAALTAHQACHLPLETFTRHRQPRGWEQLEQCGYPVQRLVALYLAAR
LSWNQVDQVIRNALASPGSGGDLGEAIREQPEQARLALTLAAAESERFVRQGTGNDEAGAANADVVSLTCPVAAGEC
AGPADSGDALLERNYPTGAEFLGDGGDVSFSTRGTQNWTVERLLQAHRQLEERGYVFVGYHGTFLEAAQSIVEGGVR
ARSQDLDAIWRGFYIAGDPALAYGYAQDQEPDARGRIRNGALLRVYVPRSSLPGFYRTSLTLAAPEAAGEVERLIGH
PLPLRLDAITGPEEEGGRLETILGWPLAERTVVIPSAIPTDPRNVGGDLDPSSIPDKEQAISALPDYASQPGKPPRE
DLK Cholera toxin
SEQ ID NO: 14, Cholera toxin, A1 component
NDDKLYRADSRPPDEIKQSGGLMPRGQSEYFDRGTQMNINLYDHARGTQTGFVRHDDGYVSTSISLRSAHL
VGQTILSGHSTYYLYVLATAPNMFNVNDVLGAYSPHPDEQEVSALGGIPYSQIYGWYRVHFGVLDEQLHRNRGYRDR
YYSNLDIAPAADGYGLAGFPPEHRAWREEPWIHHAPPGCGNAPRSS SEQ ID NO: 15, Cholera toxin, A2 component
MSNTCDEKTQSLGVKFLDEYQSKVKRQIFSGYQSDIDTHNRIKDEL SEQ ID NO: 16, Cholera toxin, B component
TPQNITDLCAEYHNTQIYTLNDKIFSYTESLAGKREMAIITFKNGAIFQVEVPSSQHID
SQKKAIERMKDTLRIAYLTEAKVEKLCTWNNKTPHAIAAISMAN SEQ ID NO: 17, Catalytic chain of tetanus (the L-chain sequence)
MPITINNFRYSDPVNNDTIIMMEPPYCKGLDIYYKAFKITDRIWIVPERYEFGTKPEDF
NPPSSLIEGASEYYDPNYLRTDSDKDRFLQTMVKLFNRIKNNVAGEALLDKIINAIPYLGNSYS
LLDKFDTNSNSVSFNLLEQDPSGATTKSAMLTNLIIFGPGPVLNKNEVRGIVLRVDNKNYFPCR
DGFGSIMQMAFCPEYVPTFDNVIENITSLTIGKSKYFQDPALLLMHELIHVLHGLYGMQVSSHE
IIPSKQEIYMQHTYPISAEELFTFGGQDANLISIDIKNDLYEKTLNDYKAIANKLSQVTSCNDP

| Sequence listings |
| --- |

NIDIDSYKQIYQQKYQFDKDSNGQYIVNEDKFQILYNSIMYGFTEIELGKKFNIKTRLSYFSMN
HDPVKIPNLLDDTIYNDTEGFNIESKDLKSEYKGQNMRVNTNAFRNVDGSGLVSKLIGLCKKII
PPTNIRENLYNRT

Ricin toxin
SEQ ID NO: 18, Ricin toxin, A component
IFPKQYPIINFTTAGATVQSYTNFIRAVRGRLTTGADVRHEIPVLPNRVGLPINQRFILVELSNHAELSVT
LALDVTNAYVVGYRAGNSAYFFHPDNQEDAEAITHLFTDVQNRYTFAFGGNYDRLEQLAGNLRENIELGNGPLEEAI
SALYYYSTGGTQLPTLARSFIICIQMISEAARFQYIEGEMRTRIRYNRRSAPDPSVITLENSWGRLSTAIQESNQGA
FASPIQLQRRNGSKFSVYDVSILIPIIALMVYRCAPPPSSQF SEQ ID NO: 19, Ricin toxin, B component
ADVCMDPEPIVRIVGRNGLCVDVRDGRFHNGNAIQLWPCKSNTDANQLWILKRDNTIRSNGKCLTTYGYSPGVYVMI
YDCNTAATDATRWQIWDNGTIINPRSSLVLAATSGNSGTTLTVQTNIYAVSQGWLPTNNTQPFVTTIVGLYGLCLQA
NSGQVWIEDCSSEKAEQQWALYADGSIRPQQNRDNCLTSDSNIRETVVKILSCGPASSGQRWMFKNDGTILNLYSGL
VLDVRASDPSLKQIILYPLHGDPNQIWLPLF SEQ ID NO: 20, BTx-A light chain (native): BTx-A Amino acids 1-448
MPFVNKQFNYKDPVNGVDIAYIKIPNVGQMQPVKAFKIHNKIWVIPERDTFTNPEEGDLNPPPEAKQVPVSYYDSTY
LSTDNEKDNYLKGVTKLFERIYSTDLGRMLLTSIVRGIPFWGGSTIDTELKVIDTNCINVIQPDGSYRSEELNLVII
GPSADIIQFECKSFGHEVLNLTRNGYGSTQYIRFSPDFTFGFEESLEVDTNPLLGAGKFATDPAVTLAHELIHAGHR
LYGIAINPNRVFKVNTNAYYEMSGLEVSFEELRTFGGHDAKFIDSLQENEFRLYYYNKFKDIASTLNKAKSIVGTTA
SLQYMKNVFKEKYLLSEDTSGKFSVDKLKFDKLYKMLTEIYTEDNFVKFFKVLNRKTYLNFDKAVFKINIVPKVNYT
IYDGFNLRNTNLAANFNGQNTEINNMNFTKLKNFTGLFEFYKLLCVRGIITSKTKSLDKGYNK SEQ ID NO: 21, BTx-A light chain Amino acids 1-430
MPFVNKQFNYKDPVNGVDIAYIKIPNVGQMQPVKAFKIHNKIWVIPERDTFTNPEEGDLNPPPEAKQVPVSYYDSTY
LSTDNEKDNYLKGVTKLFERIYSTDLGRMLLTSIVRGIPFWGGSTIDTELKVIDTNCINVIQPDGSYRSEELNLVII
GPSADIIQFECKSFGHEVLNLTRNGYGSTQYIRFSPDFTFGFEESLEVDTNPLLGAGKFATDPAVTLAHELIHAGHR
LYGIAINPNRVFKVNTNAYYEMSGLEVSFEELRTFGGHDAKFIDSLQENEFRLYYYNKFKDIASTLNKAKSIVGTTA
SLQYMKNVFKEKYLLSEDTSGKFSVDKLKFDKLYKMLTEIYTEDNFVKFFKVLNRKTYLNFDKAVFKINIVPKVNYT
IYDGFNLRNTNLAANFNGQNTEINNMNFTKLKNFTGLFEFYKLLC SEQ ID NO: 22, BTx-B light chain (native): BTx-B Amino acids 1-441
MPVTINNFNYNDPIDNNNIIMMEPPFARGTGRYYKAFKITDRIWIIPERYTFGYKPEDFNKSSGIFNRDVCEYYDPD
YLNTNDKKNIFLQTMIKLFNRIKSKPLGEKLLEMIINGIPYLGDRRVPLEEFNTNIASVTVNKLISNPGEVERKKGI
FANLIIFGPGPVLNENETIDIGIQNHFASREGEGGIMQMKFCPEYVSVFNNVQENKGASIFNRRGYFSDPALILMHE
LIHVLHGLYGIKVDDLPIVPNEKKFFMQSTDAIQAEELYTFGGQDPSIITPSTDKSIYDKVLQNFRGIVDRLNKVLV
CISDPNININIYKNKFKDKYKFVEDSEGKYSIDVESFDKLYKSLMFGFTETNIAENYKIKTRASYFSDSLPPVKIKN
LLDNEIYTIEEGFNISDKDMEKEYRGQNKAINKQAYEEISKEHLAVYKIQMCKSVK SEQ ID NO: 23, BTx-B Amino acids 1-437
MPVTINNFNYNDPIDNNNIIMMEPPFARGTGRYYKAFKITDRIWIIPERYTEGYKPEDFNKSSGIFNRDVCEYYDPD
YLNTNDKKNIFLQTMIKLFNRIKSKPLGEKLLEMIINGIPYLGDRRVPLEEFNTNIASVTVNKLISNPGEVERKKGI
FANLIIFGPGPVLNENETIDIGIQNHFASREGFGGIMQMKFCPEYVSVFNNVQENKGASIFNRRGYFSDPALILMHE
LIHVLHGLYGIKVDDLPIVPNEKKFFMQSTDAIQAEELYTEGGQDPSIITPSTDKSIYDKVLQNFRGIVDRLNKVLV
CISDPNININIYKNKFKDKYKFVEDSEGKYSIDVESFDKLYKSLMFGFTETNIAENYKIKTRASYFSDSLPPVKIKN
LLDNEIYTIEEGFNISDKDMEKEYRGQNKAINKQAYEEISKEHLAVYKIQMC SEQ ID NO: 24, BTx-C1 light chain (native): BoN/T-C1 Amino acids 1-449
MPITINNFNYSDPVDNKNILYLDTHLNTLANEPEKAFRITGNIWVIPDRFSRNSNPNLNKPPRVTSPKSGYYDPNYL
STDSDKDPFLKEIIKLFKRINSREIGEELIYRLSTDIPFPGNNNTPINTFDFDVDFNSVDVKTRQGNNWVKTGSINP
SVIITGPRENIIDPETSTFKLTNNTFAAQEGFGALSIISISPRFMLTYSNATNDVGEGRFSKSEFCMDPILILMHEL
NHAMHNLYGIAIPNDQTISSVTSNIFYSQYNVKLEYAEIYAFGGPTIDLIPKSARKYFEEKALDYYRSIAKRLNSIT
TANPSSFNKYIGEYKQKLIRKYRFVVESSGEVTVNRNKFVELYNELTQIFTEFNYAKIYNVQNRKIYLSNVYTPVTA
NILDDNVYDIQNGFNIPKSNLNVLFMGQNLSRNPALRKVNPENMLYLFTKFCHKAIDGRSLYNK SEQ ID NO: 25, BTx-D light chain (native): BoN/T-D Amino acids 1-442
MTWPVKDFNYSDPVNDNDILYLRIPQNKLITTPVKAFMITQNIWVIPERFSSDTNPSLSKPPRPTSKYQSYYDPSYL
STDEQKDTFLKGIIKLFKRINERDIGKKLINYLVVGSPFMGDSSTPEDTFDFTRHTTNIAVEKFENGSWKVTNIITP
SVLIFGPLPNILDYTASLTLQGQQSNPSFEGFGTLSILKVAPEFLLTTKDTNQSSAVLGKSIFCMDPILILMHEL
THSLHQLYGINIPSDKRIRPQVSEGFFSQDGPNVQFEELYTFGGLDVEIIPQIERSQLREKALGHYKDIAKRLNNIN
KTIPSSWISNIDKYKKIFSEKYNFDKDNTGNFVVNIDKFNSLYSDLTNVMSEVVYSSQYNVKNRTHYFSRHYLPVFA
NILDDNIYTIRDGFNLTNKGFNIENSGQNIERNPALQKLSSESVVDLFTKVCLRLTK SEQ ID NO: 26, BTx-E light chain (native): BTx-E Amino acids 1-422
MPTINSENYNDPVNNRTILYIKPGGCQQFYKSFNIMKNIWIIPERNVIGTIPQDFLPPTSLKNGDSSYYDPNYLQSD
QEKDKFLKIVTKIFNRINDNLSGRILLEELSKANPYLGNDNTPDGDFIINDASAVPIQFSNGSQSILLPNVIIMGAE
PDLFETNSSNISLRNNYMPSNHGFGSIAIVTFSPEYSFRFKDNSMNEFIQDPALTLMHELIHSLHGLYGAKGITTKY
TITQKQNPLITNIRGTNIEEFLTFGGTDLNIITSAQSNDIYTNLLADYKKIASKLSKVQVSNPLLNPYKDVFEAKYG
LDKDASGIYSVNINKFNDIFKKLYSFTEFDLATKFQVKCRQTYIGQYKYFKLSNLLNDSIYNISEGYNINNLKVNFR
GQNANLNPRIITPITGRGLVKKIIRFCKNIVSVKGIR SEQ ID NO: 27, BTx-F light chain (native): BTx-F Amino acids 1-436
MPVAINSFNYNDPVNDDTILYMQIPYEEKSKKYYKAFEIMRNVWIIPERNTIGTNPSDFDPPASLKNGSSAYYDPNY
LTTDAEKDRYLKTTIKLFKRINSNPAGKVLLQEISYAKPYLGNDHIPIDEFSPVTRTTSVNIKLSTNVESSMLLNLL
VLGAGPDIFESCCYPVRKLIDPDVVYDPSNYGFGSINIVTFSPEYEYTFNDISGGHNSSTESFIADPAISLAHELIH

Sequence listings

ALHGLYGARGVIYEETIEVKQAPLMIAEKPIRLEEFLTFGGQDLNIITSAMKEKIYNNLLANYEKIATRLSEVNSAP
PEYDINEYKDYFQWKYGLDKNADGSYTVNENKFNEIYKKLYSFTESDLANKFKVKCRNTYFIKYEFLKVPNLLDDDI
YTVSEGFNIGNLAVNNRGQSIKLNPKIIDSIPDKGLVEKIVKFCKSVIPRK

SEQ ID NO: 28, BTx-G light chain (native): BTx-G Amino acids 1-442
MPVNIKXFNYNDDPINNDDIIMMEPFNDPGPGTYYKAFRIIDRIWIVPERFTYGFQPDQFNASTGVFSKDVYEYYDPT
YLKTDAEKDKFLKTMIKLFNRINSKPSGQRLLDMIVDAIPYLGNASTPPDKFAANVANVSINKKIIQPGAEDQIKGL
MTNLIIFGPGPVLSDNFTDSMIMNGHSPISEGFGARMMIRFCPSCLNVFNNVQENKDTSIFSRRAYFADPALTLMHE
LIHVLHGLYGIKISNLPITPNTKEFFMQHSDPVQAEELYTFGGHDPSVISPSTDMNIYNKALQNFQDIANRLNIVSS
AQGSGIDISLYKQIYKNKYDFVEDPNGKYSVDKDKFDKLYKALMFGFTETNLAGEYGIKTRYSYFSEYLPPIKTEKL
LDNTIYTQNEGFNIASKNLKTEFNGQNKAVNKEAYEEISLEHLVIYRIAMCKPVMYK SEQ ID NO: 29, BTx-A (light chain and heavy chain translocation domain) Amino
acids 1-872
MPFVNKQFNYKDPVNGVDIAYIKIPNVGQMQPVKAFKIHNKIWVIPERDTFTNPEEGDLNPPPEAKQVPVS
YYDSTYLSTDNEKDNYLKGVTKLFERIYSTDLGRMLLTSIVRGIPFWGGSTIDTELKVIDTNCINVIQPDGSYRSEE
LNLVIIGPSADIIQFECKSFGHEVLNLTRNGYGSTQYIRFSPDFTFGFEESLEVDTNPLLGAGKFATDPAVTLAHEL
IHAGHRLYGIAINPNRVFKVNTNAYYEMSGLEVSFEELRTFGGHDAKFIDSLQENEFRLYYYNKFKDIASTLNKAKS
IVGTTASLQYMKNVFKEKYLLSEDTSGKFSVDKLKFDKLYKMLTEIYTEDNFVKFFKVLNRKTYLNFDKAVFKINIV
PKVNYTIYDGFNLRNTNLAANFNGQNTEINNMNFTKLKNFTGLFEFYKLLCVRGIITSKTKSLDKGYNKALNDLCIK
VNNWDLFFSPSEDNFTNDLNKGEEITSDTNIEAAEENISLDLIQQYYLTFNFDNEPENISIENLSSDIIGQLELMPN
IERFPNGKKYELDKYTMFHYLRAQEFEHGKSRIALTNSVNEALLNPSRVYTFFSSDYVKKVNKATEAAMFLGWVEQL
VYDFTDETSEVSTTDKIADITIIIPYIGPALNIGNMLYKDDFVGALIFSGAVILLEFIPEIAIPVLGTFALVSYIAN
KVLTVQTIDNALSKRNEKWDEVYKYIVTNWLAKVNTQIDLIRKKMKEALENQAEATKAIINYQYNQYTEEEKNNINF
NIDDLSSKLNESINKAMININKFLNQCSVSYLMNSMIPYGVKRLEDFDASLKDALLKYIYDNRGTLIGQVDRLKDKV
NNTLSTDIPFQLSKYVDNQRLLSTFTEYIKN SEQ ID NO: 30, BTx-A, (light chain and heavy chain translocation domain) Amino
acids 1-842
MPFVNKQFNYKDPVNGVDIAYIKIPNVGQMQPVKAFKIHNKIWVIPERDTFTNPEEGDLNPPPEAKQVPVS
YYDSTYLSTDNEKDNYLKGVTKLFERIYSTDLGRMLLTSIVRGIPFWGGSTIDTELKVIDTNCINVIQPDGSYRSEE
LNLVIIGPSADIIQFECKSFGHEVLNLTRNGYGSTQYIRFSPDFTFGFEESLEVDTNPLLGAGKFATDPAVTLAHEL
IHAGHRLYGIAINPNRVFKVNTNAYYEMSGLEVSFEELRTFGGHDAKFIDSLQENEFRLYYYNKFKDIASTLNKAKS
IVGTTASLQYMKNVFKEKYLLSEDTSGKFSVDKLKFDKLYKMLTEIYTEDNFVKFFKVLNRKTYLNFDKAVFKINIV
PKVNYTIYDGFNLRNTNLAANFNGQNTEINNMNFTKLKNFTGLFEFYKLLCVRGIITSKTKSLDKGYNKALNDLCIK
VNNWDLFFSPSEDNFTNDLNKGEEITSDTNIEAAEENISLDLIQQYYLTFNFDNEPENISIENLSSDIIGQLELMPN
IERFPNGKKYELDKYTMFHYLRAQEFEHGKSRIALTNSVNEALLNPSRVYTFFSSDYVKKVNKATEAAMFLGWVEQL
VYDFTDETSEVSTTDKIADITIIIPYIGPALNIGNMLYKDDFVGALIFSGAVILLEFIPEIAIPVLGTFALVSYIAN
KVLTVQTIDNALSKRNEKWDEVYKYIVTNWLAKVNTQIDLIRKKMKEALENQAEATKAIINYQYNQYTEEEKNNINF
NIDDLSSKLNESINKAMININKFLNQCSVSYLMNSMIPYGVKRLEDFDASLKDALLKYIYDNRGTLIGQVDRLKDKV
N SEQ ID NO: 31, BTx-B (light chain and heavy chain translocation domain) Amino
acids 1-863
MPVTINNFNY NDPIDNNNII MMEPPFARGT GRYYKAFKIT DRIWIIPERY TFGYKPEDFN KSSGIFNRDV
CEYYDPDYLN TNDKKNIFLQ TMIKLFNRIK SKPLGEKLLE MIINGIPYLG DRRVPLEEFN TNIASVTVNK
LISNPGEVER KKGIFANLII FGPGPVLNEN ETIDIGIQNH FASREGFGGI MQMKFCPEYV SVFNNVQENK
GASIFNRRGY FSDPALILMH ELIHVLHGLY GIKVDDLPIV PNEKKFFMQS TDAIQAEELY TFGGQDPSII
TPSTDKSIYD KVLQNFRGIV DRLNKVLVCI SDPNINININIY KNKFKDKYKF VEDSEGKYSI DVESFDKLYK
SLMFGFTETN IAENYKIKTR ASYFSDSLPP VKIKNLLDNE IYTIEEGFNI SDKMEKEYR GQNKAINKQA
YEEISKEHLA VYKIQMCKSV KAPGICIDVD NEDLFFIADK NSFSDDLSKN ERIEYNTQSN YIENDPPINE
LILDTDLISK IELPSENTES LTDFNVDVPV YEKQPAIKKI FTDENTIFQY LYSQTFPLDI RDISLTSSFD
DALLFSNKVY SFFSMDYIKT ANKVVEAGLF AGWVKQIVND FVIEANKSNT MDKIADISLI VPYIGLALNV
GNETAKGNFE NAFEIAGASI LLEFIPELLI PVVGAFLLES YIDNKNKIIK TIDNALTKRN EKWSDMYGLI
VAQWLSTVNT QFYTIKEGMY KALNYQAQAL EEIIKYRYNI YSEKEKSNIN IDFNDINSKL NEGINQAIDN
INNFINGCSV SYLMKKMIPL AVEKLLDFDN TLKKNLLNYI DENKLYLIGS AEYEKSKVNK YLKTIMPFDL
SIYTNDTILI EMFNKYNSEI LNN

The invention claimed is:

1. A nucleic acid encoding a fusion protein comprising:
   (a) a botulinum neurotoxin (BTx) moiety that comprises an enzymatic moiety and a translocation domain; and
   (b) a targeting moiety comprising a C-terminal receptor-binding domain of anthrax toxin protective antigen (PA), wherein the C-terminal receptor-binding domain of PA comprises a PAd4 domain,
   wherein part (a) and (b) are linked or fused together.

2. The nucleic acid of claim 1, wherein the enzymatic moiety or the translocation domain is selected from BTx light chain and heavy chain domains of any one of BTx/A, BTx/B, BTx/C, BTx/D, BTx/E, BTx/F, and BTx/G.

3. The nucleic acid of claim 1, wherein the enzymatic moiety and the translocation domain are linked by a linker peptide, optionally wherein the linker peptide:
   (i) is 1-20 amino acids long;
   (ii) is stable in human serum for at least 1 minute;
   (iii) comprises at least one amino acid that is Gly or Ser; and/or
   (iv) lacks a Lys, Arg, or both.

4. The nucleic acid of claim 1, wherein the BTx moiety and the targeting moiety are linked by a linker peptide, optionally wherein the linker peptide:
   (i) is 1-20 amino acids long;
   (ii) is stable in human serum for at least 1 minute;
   (iii) comprises at least one amino acid that is Gly or Ser; and/or
   (iv) lacks a Lys, Arg, or both.

5. The nucleic acid of claim 1, wherein:
   (i) the C-terminal receptor-binding domain of PA is resistant to cleavage by a protease; or
   (ii) the C-terminal receptor-binding domain of PA is resistant to furin cleavage or Lys C cleavage or both.

6. The nucleic acid of claim 1, wherein the C-terminal receptor-binding domain of PA comprises a furin cleavage site comprising amino acid residues RKKR that has been replaced by a furin-resistant amino acid sequence, wherein RKKR are residues 164-167 of SEQ ID NO: 1 minus the 29 amino acid signal peptide in SEQ ID NO: 1.

7. The nucleic acid of claim 6, wherein the furin-resistant amino acid sequence is SSSR (SEQ ID NO: 32).

8. The nucleic acid of claim 6, wherein the furin-resistant amino acid sequence is SSSS (SEQ ID NO: 33).

9. The nucleic acid of claim 1, wherein the C-terminal receptor-binding domain of PA further comprises a PAd2 or comprises PA63.

10. The nucleic acid of claim 1, wherein:
    (i) the fusion protein comprises 2-10 PAd4 domains in tandem; or
    (ii) 1-60 consecutive amino acids from the N-terminal side adjacent to the native PAd4 domain are incorporated between the BTx moiety and the PAd4.

11. The nucleic acid of claim 1, wherein:
    (i) the fusion protein further comprises an epitope tag; or
    (ii) the fusion protein further comprises an epitope tag selected from the group consisting of FLAG, influenza virus haemagglutinin (HA), c-myc, and His.

12. The nucleic acid of claim 1, wherein:
    (i) the fusion protein comprises an amino acid substitution at one or more cysteine residues; or
    (ii) the fusion protein comprises an amino acid substitution at one or more cysteine residues, wherein the one or more cysteine residues are substituted with serine.

13. A vector comprising the nucleic acid of claim 1.

14. The vector of claim 2, wherein the vector is a plasmid, a bacteriophage, a phagmid, a cosmid, a viral particle, or viral vector.

15. A cell comprising the vector of claim 13.

16. A method of producing a fusion protein comprising steps of:
 (a) culturing a cell comprising a nucleic acid sequence encoding a fusion protein comprising:
  (i) a botulinum neurotoxin (BTx) moiety that comprises an enzymatic moiety and a translocation domain; and
  (ii) a targeting moiety comprising a C-terminal receptor-binding domain of anthrax toxin protective antigen (PA), wherein the C-terminal receptor-binding domain of PA comprises a PAd4 domain,
  wherein part (i) and (ii) are linked or fused together; and
 (b) recovering the fusion protein.

17. The method of claim 16, wherein said cell is a bacterial cell.

18. The method of claim 17, wherein said bacterial cell is an *Escherichia coli*.

19. The method of claim 16, wherein said cell is a yeast cell.

20. The method of claim 19, wherein said yeast is *Saccharomyces cerevisiae*.

21. The method of claim 19, wherein said yeast is cell glycosylation deficient.

22. The method of claim 19, wherein said yeast is glycosylation and protease deficient.

23. The method of claim 16, wherein said cell is a mammalian cell.

24. The method of claim 23, wherein said mammalian cell is a COS cell, a CHO cell, or a NSO cell.

* * * * *